US008822467B2

United States Patent
McGuinness et al.

(10) Patent No.: US 8,822,467 B2
(45) Date of Patent: Sep. 2, 2014

(54) BIARYL OXYACETIC ACID COMPOUNDS

(71) Applicant: Ligand Pharmaceuticals Inc., San Diego, CA (US)

(72) Inventors: Brian F. McGuinness, Plainsboro, NJ (US); Koc-Kan Ho, Salt Lake City, UT (US); Suresh Babu, Pennington, NJ (US); Guizhen Dong, Dayton, NJ (US); Jingqi Duo, Paoli, PA (US); Thuy X. H. Le, Monmouth Junction, NJ (US); Kurt W. Saionz, Cranford, NJ (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 81 days.

(21) Appl. No.: 13/715,754

(22) Filed: Dec. 14, 2012

(65) Prior Publication Data

US 2013/0102609 A1 Apr. 25, 2013

Related U.S. Application Data

(63) Continuation of application No. 13/452,663, filed on Apr. 20, 2012, now abandoned, which is a continuation of application No. 13/254,626, filed as application No. PCT/US2010/026279 on Mar. 4, 2010, said application No. 13/452,663 is a continuation of application No. PCT/US2010/026279.

(60) Provisional application No. 61/157,686, filed on Mar. 5, 2009.

(51) Int. Cl.
*A61K 31/5377* (2006.01)
*A61K 31/497* (2006.01)
*A61K 31/44* (2006.01)
*A61K 31/47* (2006.01)

(Continued)

(52) U.S. Cl.
CPC ............ *C07C 311/18* (2013.01); *C07D 241/12* (2013.01); *C07C 311/37* (2013.01); *C07D 295/108* (2013.01); *C07D 213/42* (2013.01); *C07C 307/06* (2013.01); *C07D 271/12* (2013.01); *C07C 311/17* (2013.01); *C07C 311/19* (2013.01); *C07D 333/34* (2013.01); *C07C 2101/02* (2013.01); *C07D 261/10* (2013.01); *C07C 311/29* (2013.01); *C07D 471/04* (2013.01); *C07D 213/70* (2013.01); *C07D 217/02* (2013.01); *C07D 213/71* (2013.01); *C07D 213/26* (2013.01); *C07C 311/14* (2013.01); *C07D 213/85* (2013.01); *C07D 231/12* (2013.01); *C07D 213/89* (2013.01); *C07D 239/26* (2013.01); *C07D 333/38* (2013.01); *C07C 311/13* (2013.01); *C07C 317/32* (2013.01); *C07D 235/08* (2013.01); *C07D 333/04* (2013.01); *C07D 271/06* (2013.01); *C07D 215/36* (2013.01); *C07D 209/08* (2013.01); *C07C 317/14* (2013.01)
USPC ............. 514/237.5; 514/252.1; 514/256; 514/300; 514/311; 514/344; 514/347; 514/357; 514/364; 514/394; 514/415; 514/438; 514/445; 514/524; 514/562; 544/160; 544/335; 544/336; 546/121; 546/172; 546/286; 546/293; 546/335; 548/126; 548/304.4; 548/469; 549/61; 549/65; 558/413; 562/430

(58) Field of Classification Search
USPC ............ 514/237.5, 252.1, 256, 300, 311, 344, 514/347, 357, 364, 394, 415, 438, 445, 524, 514/562; 544/160, 335, 336; 546/121, 172, 546/286, 293, 335; 548/126, 304.4, 469; 549/61, 65; 558/413; 562/430
See application file for complete search history.

(56) References Cited

FOREIGN PATENT DOCUMENTS

| EP | 1170594 | 9/2002 |
|---|---|---|
| WO | WO 2004/089884 | 10/2004 |
| WO | WO 2005/102338 | 11/2005 |

OTHER PUBLICATIONS

Chevalier, Eric, Cutting Edge: Chemoattractant Receptor-Homologous Molecule Expressed on TH2 Cells Plays a Restricing Rold on IL-5 Production and Eosinophil Recruitment, J. Immunology, 2005, 175, 2056-2060.

(Continued)

*Primary Examiner* — Samantha Shterengarts
(74) *Attorney, Agent, or Firm* — Knobbe, Martens, Olson & Bear, LLP

(57) ABSTRACT

The present invention provides biaryl oxyacetic acid compounds which may be useful for treating inflammatory disorders, including disorders affecting the respiratory system and skin. The compounds provided include those of the general formula I:

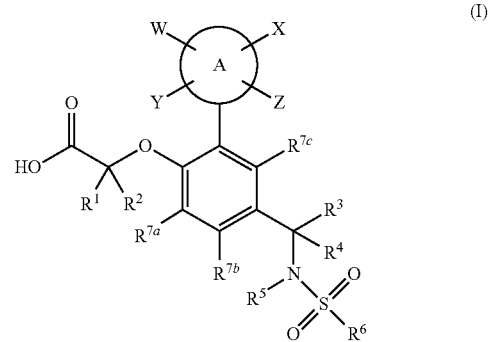

46 Claims, 1 Drawing Sheet

(51) Int. Cl.

| | | |
|---|---|---|
| A61K 31/41 | (2006.01) | |
| A61K 31/415 | (2006.01) | |
| A61K 31/404 | (2006.01) | |
| A61K 31/38 | (2006.01) | |
| A61K 31/275 | (2006.01) | |
| A61K 31/19 | (2006.01) | |
| C07D 241/12 | (2006.01) | |
| C07C 311/37 | (2006.01) | |
| C07D 295/108 | (2006.01) | |
| C07D 213/42 | (2006.01) | |
| C07C 307/06 | (2006.01) | |
| C07D 271/12 | (2006.01) | |
| C07C 311/17 | (2006.01) | |
| C07C 311/19 | (2006.01) | |
| C07D 333/34 | (2006.01) | |
| C07D 261/10 | (2006.01) | |
| C07C 311/29 | (2006.01) | |
| C07D 471/04 | (2006.01) | |
| C07D 213/70 | (2006.01) | |
| C07D 217/02 | (2006.01) | |
| C07D 213/71 | (2006.01) | |
| C07D 213/26 | (2006.01) | |
| C07C 311/14 | (2006.01) | |
| C07D 213/85 | (2006.01) | |
| C07D 231/12 | (2006.01) | |
| C07D 213/89 | (2006.01) | |
| C07D 239/26 | (2006.01) | |
| C07D 333/38 | (2006.01) | |
| C07C 311/13 | (2006.01) | |
| C07C 317/32 | (2006.01) | |
| C07D 235/08 | (2006.01) | |
| C07D 333/04 | (2006.01) | |
| C07C 311/18 | (2006.01) | |
| C07D 271/06 | (2006.01) | |
| C07D 215/36 | (2006.01) | |
| C07D 209/08 | (2006.01) | |
| C07C 317/14 | (2006.01) | |

(56) References Cited

OTHER PUBLICATIONS

Gervais, Francois, Selective modulation of chemokinesis degranulation, and apoptosis in eosinophils through the PGD receptors CRTHs and DP, J. Allergy Clin. Immunology, 2001, 108, 982-988.

Gyles, Shan, A dominant for chemoattractant receptor-homologous molecule expressed on T helper type 2 (Th 2) cells (CRTH2) in mediating chemotaxis of CRTH2+CD4+th2lymphocytes in response to mast cell supernatants, Immunology, 2006, 119, 362-368.

Maehr, Hubert, A Proposed New Convention for Graphic Presentation of Molecular Geometry and Topography, J. Chem. Ed. 62, 114-120, 1985.

Marchese, Adriano, Discovery of Three Novel Orphan G-Protein-Coupled Receptors, Genomics, 1999, 56, 12-21.

Nagata, Kinya, The second PGD2 receptor CRTH2: structure, properties, and functions in leukocytes Prostaglandins, Leukotrienes and Essential Fatty Acids, 2003, 69, 169-177.

Pettipher, Roy, Antagonism of the prostaglandin D2 receptors DP1 and CRTH2 as an approach to treat allergic diseases Nature Reviews Drug Discovery, 2007, 6, 313-325.

Tanaka, Kazuya, Effects of prostaglandin D2 on helper T cell functions, Biochem. Biophys res. Commun., 2004, 316, 1009-1014.

Uller, Lena, Antagonism of the prostaglandin D2 receptor CRTH2 attenuates asthma pathology in mouse eosinophilic airway inflammation, Respiratory Research, 2007, 8:16.

Yoshimura-Uchiyama, et al., Differential modulation of human basophil functions through prostaglandin D2 receptors DP and chemoattractant receptor-homologous molecule expressed on Th2 cells/DP2., Clin. Exp. Allergy, 2004, 34, 1283-1290.

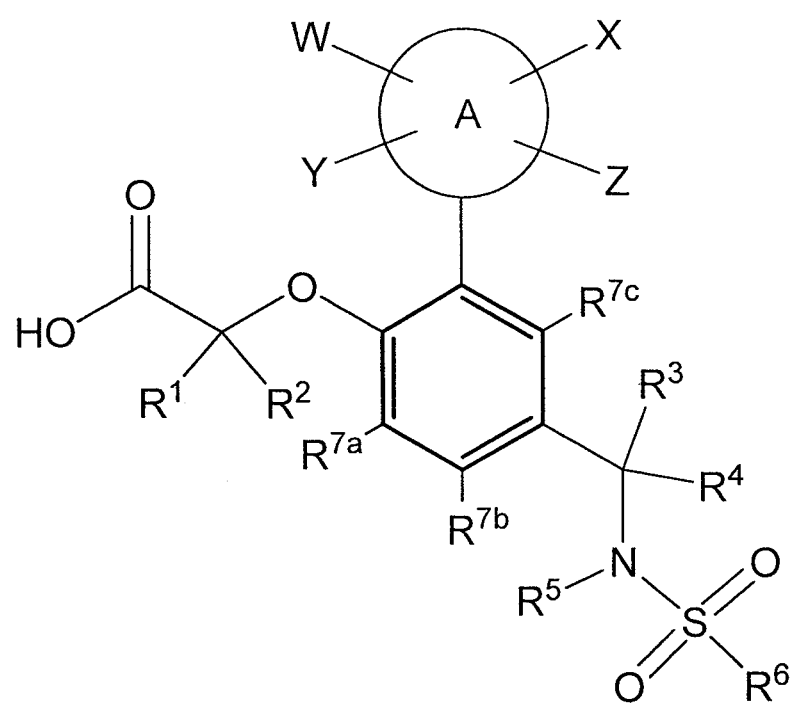
(I)

BIARYL OXYACETIC ACID COMPOUNDS

CROSS-REFERENCE TO RELATED APPLICATIONS

This application is a continuation of U.S. application Ser. No. 13/452,663 filed Apr. 20, 2012 which is a continuation of U.S. application Ser. No. 13/254,626 filed Sep. 2, 2011 which is the U.S. National Phase under 35 U.S.C. §371 of International Application No. PCT/US2010/026279, filed Mar. 4, 2010 which claims the benefit of U.S. Provisional Application No. 61/157,686, filed Mar. 5, 2009. U.S. application Ser. No. 13/452,663 is a continuation of International Application No. PCT/US2010/026279, filed Mar. 4, 2010 which claims priority to U.S. Provisional Application No. 61/157,686, filed Mar. 5, 2009. The entire contents of all the foregoing applications are hereby expressly incorporated herein by reference in their entireties.

FIELD OF THE INVENTION

The present invention relates to biaryl oxyacetic acid compounds that may be useful for treating inflammatory disorders, including disorders affecting the respiratory system and skin.

BACKGROUND OF THE INVENTION

CRTH2 (Chemoattractant Receptor-homologous molecule expressed on T Helper 2 cells, also known as DP2) is a G protein coupled receptor expressed on the major pro-inflammatory cells: eosinophils, T-Helper 2 (TH2), and basophils. The receptor's endogenous ligand Prostaglandin D2 (PGD2) is derived from arachidonic acid by sequential actions of cyclooxygenase and PGD2 synthases. It has been reported that CRTH2, upon activation by PGD2, leads to a number of inflammatory responses, which includes eosinophil shape change and degranulation (Gervais et al., 2001, J. Allergy Clin. Immunol. 108, 982-988), basophil degranulation (Yoshimura-Uchiyama et al., 2004, Clin. Exp. Allergy 34, 1283-1290), TH2 cell cytokine secretion (Tanaka et al., 2004, Biochem. Biophys. Res. Commun. 316, 1009-1014) and TH2 cell chemotaxis (Gyles et al., 2006, Immunology 119, 362-368. CRTH2 genetic knock-out data has been reported. CRTH2 knock-out mice show a significant decrease in antigen-induced lung inflammation (Chevalier et al., 2005, J. Immunolo. 175, 2056-2060). In addition to the knock-out data, Ramatroban, a marketed drug in Japan, has established efficacy against allergic rhinitis and is currently in clinical trial for treatment of asthma. Although the compound was first developed as a thromboxan antagonist, recent studies show that Ramatroban is also a potent CRTH2 antagonist (Pettipher et al., 2007, Nature Reviews Drug Discovery 6, 313-325). It has been suggested that the efficacy of Ramatroban in asthmatic and allergic reactions is in part mediated through CRTH2. A compound closely related to Ramatroban, TM30089, has been shown to reduce the pathology of asthma in vivo (Uller et al., 2007, Respiratory Research 8: 16).

Blockage of CRTH2, therefore, presents an attractive approach to treat various PGD2-mediated inflammatory diseases. Among disorders in which PGD2 is implicated are respiratory disorders, skin disorders, and other disorders related to allergic reactions. These disorders include allergic asthma, allergic rhinitis, atopic dermatitis, chronic obstructive pulmonary disorder, osteoarthritis, rheumatoid arthritis and inflammatory bowel disease.

CRTH2 is also expressed in the central nervous system (Nagata et al., 2003 Prostaglandins, Leukotrienes and Essential Fatty Acids 69, 169-177). CRTH2 mRNA was detected in various brain regions including the thalamus, frontal cortex, pons, hippocampus, hypothalamus, and caudate/putamen (Marchese et al., 1999 Genomics 56, 12-21). Corradini et al (WO2005/102338) disclosed that small molecule antagonists of the CRTH2 receptor are efficacious in two rat models: the chronic constrictive injury model and Seltzer model. The data established a link between CRTH2 and pain.

Blockage of CRTH2, therefore, presents an attractive approach to treat various pain conditions such as neuropathic pain.

SUMMARY OF THE INVENTION

The disclosed biaryl oxyacetic acid compounds may be useful for treating inflammatory disorders, including disorders affecting the respiratory system and skin. Some aspects relate to certain biaryl oxyacetic acid compounds which may be inhibitors of chemoattractant receptor-homologous molecule expressed on T helper 2 cells (CRTH2). In one aspect, there is provided a compound of general formula I or salt thereof:

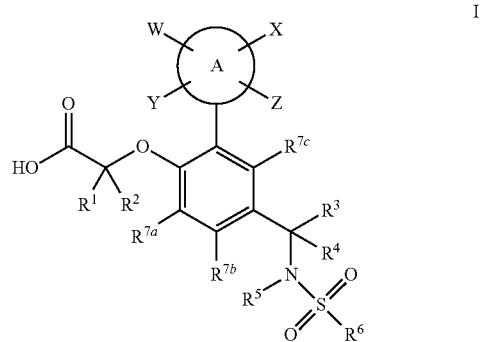

wherein
$R^1$, $R^2$, $R^3$ and $R^4$ are each independently selected from hydrogen and ($C_1$-$C_6$) alkyl;
$R^5$ is selected from hydrogen, ($C_1$-$C_6$) alkyl and ($C_3$-$C_8$) cycloalkyl;
$R^6$ is selected from:
a. ($C_1$-$C_4$) alkyl,
b. ($C_3$-$C_8$) cycloalkyl,
c. dialkylamino,
d. alkylamino, and
e. aryl, heteroaryl and arylalkyl, each optionally substituted with one to four substituents independently selected from halogen, cyano, ($C_1$-$C_6$) haloalkyl, ($C_1$-$C_6$) alkoxy, ($C_1$-$C_6$) haloalkoxy, ($C_1$-$C_6$) alkyl and ($C_1$-$C_6$) alkylsulfonyl;
$R^{7a}$ is selected from hydrogen and fluoro;
$R^{7b}$ is selected from hydrogen, fluoro and chloro;
$R^{7c}$ is selected from hydrogen, fluoro and chloro;
A is selected from aryl and heteroaryl; and
W, X, Y and Z are each independently selected from hydrogen, ($C_1$-$C_6$) alkyl, halogen, ($C_1$-$C_6$) haloalkyl, ($C_1$-$C_6$) haloalkoxy, hydroxy, ($C_1$-$C_6$) alkoxyalkyl, ($C_1$-$C_6$) alkylsulfonyl, ($C_1$-$C_6$) alkylaminosulfonyl, carboxamido, cyano, ($C_1$-$C_6$) alkoxy, ($C_1$-$C_6$) alkoxycarbonyl, aminosulfonyl, dialkylaminosulfonyl, alkylaminocarbonyl, dialkylaminocarbonyl, heterocyclylcarbonyl, heterocyclylacyl, heterocyclylalkyl and heterocyclyl optionally substituted with ($C_1$-$C_6$) alkyl;

with the proviso that, when A is substituted phenyl or pyridinyl substituted at the ortho position, any of W, X, Y and Z at said ortho position are each independently selected from hydrogen and halogen.

In another aspect, there is provided a compound of general formula I or salt thereof:

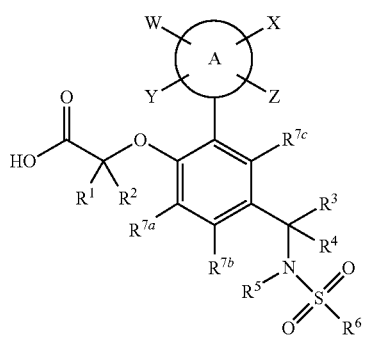

wherein $R^1$, $R^2$, $R^3$ and $R^4$ are each independently selected from hydrogen and ($C_1$-$C_6$) alkyl;

$R^5$ is selected from hydrogen and ($C_1$-$C_6$) alkyl;

$R^6$ is selected from:
a. ($C_1$-$C_4$) alkyl,
b. ($C_3$-$C_8$) cycloalkyl,
c. dialkylamino,
d. alkylamino, and
e. aryl, heteroaryl and arylalkyl, each optionally substituted with one to four substituents independently selected from halogen, cyano, ($C_1$-$C_6$) haloalkyl, ($C_1$-$C_6$) alkoxy, ($C_1$-$C_6$) haloalkoxy, ($C_1$-$C_6$) alkyl and ($C_1$-$C_6$) alkylsulfonyl;

$R^{7a}$ is selected from hydrogen and fluoro;

$R^{7b}$ is selected from hydrogen, fluoro and chloro;

$R^{7c}$ is selected from hydrogen, fluoro and chloro;

A is selected from aryl and heteroaryl; and

W, X, Y and Z are each independently selected from hydrogen, ($C_1$-$C_6$) alkyl, halogen, ($C_1$-$C_6$) haloalkyl, ($C_1$-$C_6$) haloalkoxy, hydroxy, ($C_1$-$C_6$) alkoxyalkyl, ($C_1$-$C_6$) alkylsulfonyl, ($C_1$-$C_6$) alkylaminosulfonyl, carboxamido, cyano, ($C_1$-$C_6$) alkoxy, ($C_1$-$C_6$) alkoxycarbonyl, aminosulfonyl, dialkylaminosulfonyl, alkylaminocarbonyl, dialkylaminocarbonyl, heterocyclylcarbonyl, heterocyclylacyl, heterocyclylalkyl and heterocyclyl optionally substituted with ($C_1$-$C_6$) alkyl;

with the proviso that, when A is substituted phenyl or pyridinyl substituted at the ortho position, any of W, X, Y and Z at said ortho position are each independently selected from hydrogen and halogen.

Some compounds provided herein are useful in inhibiting CRTH2 activity. In some embodiments, the compounds may be useful in indications where the suppression of the inflammatory response is desired.

In another aspect, the present invention relates to pharmaceutical compositions comprising a therapeutically effective amount of at least one compound of general formula I, or a pharmaceutically acceptable salt thereof, and a pharmaceutically acceptable carrier.

In another aspect, the present invention relates to a method for treating, preventing or ameliorating a disorder by altering a response mediated by CRTH2. The method comprises bringing into contact with CRTH2 at least one compound of general formula I, or a pharmaceutically acceptable salt thereof.

In yet another aspect the present invention relates to a method of suppressing the inflammatory response in a subject (for example, human) in need thereof comprising administering to the subject a therapeutically effective amount of at least one compound of general formula I, or a pharmaceutically acceptable salt thereof.

In still another aspect, the present invention relates to the use of at least one compound of general formula I, or a pharmaceutically acceptable salt thereof, for the treatment, prevention, or amelioration of a disorder responsive to inhibition of chemoattractant receptor-homologous molecule expressed on T helper 2 in a subject (for example human) in need thereof.

In a further aspect, the present invention relates to the use of at least one compound of general formula I, or a pharmaceutically acceptable salt thereof, in the manufacture of a medicament for the treatment, prevention or amelioration of a disorder responsive to inhibition of chemoattractant receptor-homologous molecule expressed on T helper 2 in a subject (for example human) in need thereof. Such disorders include asthma.

In another aspect, the present invention relates to at least one compound of general formula I, or a pharmaceutically acceptable salt thereof, for use in therapy.

In another aspect, the present invention relates to at least one compound of general formula I, or a pharmaceutically acceptable salt thereof, for use in any of asthma, rhinitis, chronic obstructive pulmonary disorder, bronchitis, dermatitis, psoriasis, urticaria, nasal polyposis, nasal congestion, farmer's lung, fibroid lung, cough, cutaneous eosinophilias, Lichen planus, pruritus, angiodermas, corneal ulcers, chronic skin ulcers, conjunctivitis, vasculitides, uveitis and erythemas.

In another aspect, the present invention relates to a compound of general formula I or a pharmaceutically acceptable salt thereof, for use in asthma.

Suppression of the inflammatory response is desirable for controlling the body's extreme reaction to internal or external stimuli, such as that found with inflammatory disorders, respiratory disorders, skin disorders and those disorders with an allergic component. Examples of such disorders include asthma, rhinitis, chronic obstructive pulmonary disorder, bronchitis, dermatitis, psoriasis, urticaria, nasal polyposis, nasal congestion, farmer's lung, fibroid lung, cough, cutaneous eosinophilias, Lichen planus, pruritus, angiodermas, corneal ulcers, chronic skin ulcers, conjunctivitis, vasculitides, uveitis and erythemas.

More indications in which the CRTH2 inhibitors are believed to be useful include osteoarthritis, rheumatoid arthritis, conjunctivitis, inflammatory bowel disease and pain.

BRIEF DESCRIPTION OF THE DRAWINGS

FIG. 1 shows general Formula I.

DETAILED DESCRIPTION OF THE INVENTION

In some embodiments, the present invention relates to compounds (and salts thereof) having general formula I:

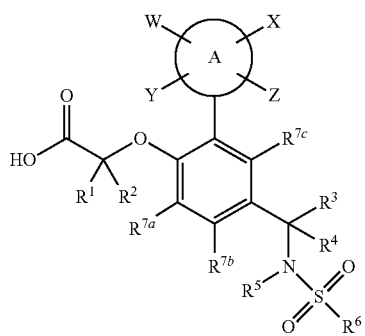

I

In certain embodiments, $R^1$, $R^2$, $R^3$ and $R^4$ are each independently selected from hydrogen and $(C_1-C_6)$ alkyl. In other embodiments, $R^1$, $R^2$, $R^3$ and $R^4$ are each selected from hydrogen and methyl. In further embodiments, $R^1$, $R^2$, $R^3$ and $R^4$ are each hydrogen.

In still more embodiments, $R^5$ is selected from hydrogen, $(C_1-C_6)$ alkyl and $(C_3-C_8)$ cycloalkyl. In yet other embodiments, $R^5$ is selected from hydrogen, methyl, ethyl, propyl and isopropyl. In further embodiments, $R^5$ is methyl.

In more embodiments, $R^6$ is selected from:
a. $(C_1-C_4)$ alkyl,
b. $(C_3-C_8)$ cycloalkyl,
c. dialkylamino,
d. alkylamino, and
e. aryl, heteroaryl and arylalkyl, each optionally substituted with one to four substituents independently selected from halogen, cyano, $(C_1-C_6)$ haloalkyl, $(C_1-C_6)$ alkoxy, $(C_1-C_6)$ haloalkoxy, $(C_1-C_6)$ alkyl and $(C_1-C_6)$ alkylsulfonyl.

In certain embodiments, $R^6$ is selected from aryl and heteroaryl, each optionally substituted with one to four substituents independently selected from halogen, cyano, $(C_1-C_6)$ haloalkyl, $(C_1-C_6)$ alkoxy, $(C_1-C_6)$ haloalkoxy, $(C_1-C_6)$ alkyl and $(C_1-C_6)$ alkylsulfonyl.

In more embodiments, $R^6$ is

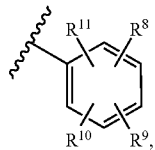

wherein $R^8$ is selected from hydrogen, halogen, $(C_1-C_6)$ alkyl, cyano, haloalkyl and $(C_1-C_6)$ alkoxy; $R^9$ is selected from hydrogen, halogen, $(C_1-C_6)$ alkyl, $(C_1-C_6)$ alkoxy, cyano, $(C_1-C_6)$ haloalkoxy, $(C_1-C_6)$ haloalkyl and $(C_1-C_6)$ alkylsulfonyl; $R^{10}$ is selected from hydrogen, halogen, $(C_1-C_6)$ alkoxy and $(C_1-C_6)$ alkyl; and $R^{11}$ is selected from hydrogen, halogen, $(C_1-C_6)$ alkoxy and $(C_1-C_6)$ alkyl.

In further embodiments, $R^6$ is

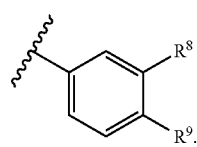

In some of these embodiments, $R^8$ is selected from hydrogen, methyl, fluoro, chloro, cyano, —$CF_3$ and methoxy; and $R^9$ is selected from hydrogen, fluoro, chloro, methyl, methoxy, cyano, —$CF_3$ and —$SO_2CH_3$, and in certain embodiments $R^8$ and $R^9$ are each independently selected from fluoro, chloro, methoxy and hydrogen.

In still more embodiments in which $R^6$ is

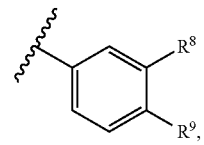

$R^8$ is hydrogen.

In some more embodiments, $R^6$ is

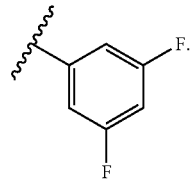 [SMILES: *c1cc(F)cc(F)c1]

In yet more embodiments, $R^6$ is selected from naphthyl, pyridinyl and quinolinyl, each optionally substituted with one to four substituents independently selected from halogen, cyano, $(C_1-C_6)$ haloalkyl, $(C_1-C_6)$ alkoxy, $(C_1-C_6)$ haloalkoxy, $(C_1-C_6)$ alkyl and $(C_1-C_6)$ alkylsulfonyl.

In some embodiments, $R^{7a}$ is selected from hydrogen and fluoro; $R^{7b}$ is selected from hydrogen, fluoro and chloro; and $R^{7c}$ is selected from hydrogen, fluoro and chloro. In other embodiments, $R^{7a}$ and $R^{7c}$ are each hydrogen.

In more embodiments, A is selected from aryl and heteroaryl. In yet more embodiments, A is selected from phenyl, pyridinyl, benzimidazolyl, quinolinyl, indolyl, pyrimidinyl and imidazopyridinyl. In still more embodiments A is phenyl or pyridinyl.

An example is shown below of the points of attachment for the phenyl and A ring. The asterisks indicate the points of attachment for determining substituent positions:

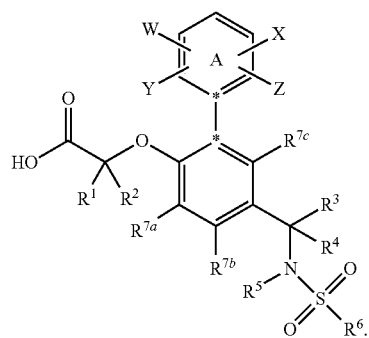

For example, if W is in the meta position, the following structure would result:

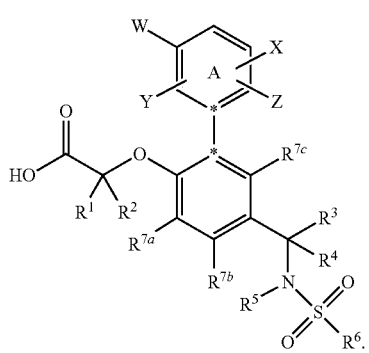

The same positional nomenclature is used when the A ring is pyridinyl; however, the skilled artisan will realize that the W, X, Y and Z substituents will not, unless otherwise specified, be substituents at the nitrogen-containing position on the ring:

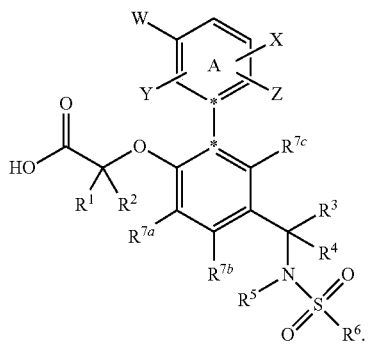

In certain embodiments, W, X, Y and Z are each independently selected from hydrogen, $(C_1-C_6)$ alkyl, halogen, $(C_1-C_6)$ haloalkyl, $(C_1-C_6)$ haloalkoxy, hydroxy, $(C_1-C_6)$ alkoxyalkyl, $(C_1-C_6)$ alkylsulfonyl, $(C_1-C_6)$ alkylaminosulfonyl, carboxamido, cyano, $(C_1-C_6)$ alkoxy, $(C_1-C_6)$ alkoxycarbonyl, aminosulfonyl, dialkylaminosulfonyl, alkylaminocarbonyl, dialkylaminocarbonyl, heterocyclylcarbonyl, heterocyclylacyl, heterocyclylalkyl and heterocyclyl optionally substituted with $(C_1-C_6)$ alkyl. In yet more embodiments, A is phenyl or pyridinyl; W is selected from hydrogen, $(C_1-C_6)$ alkyl, halogen and haloalkyl; X is selected from hydrogen, $(C_1-C_6)$ alkyl, halogen, haloalkyl, haloalkoxy, alkoxy, aminosulfonyl, alkoxycarbonyl, heterocyclylcarbonyl, hydroxy, alkoxyalkyl, alkylsulfonyl, alkylaminosulfonyl, carboxamido, cyano, and heterocyclyl optionally substituted with $(C_1-C_6)$ alkyl; and Y and Z are both hydrogen. In still more embodiments, W is selected from hydrogen, fluoro, chloro, methyl and trifluoromethyl and X is selected from hydrogen, trifluoromethyl, chloro, fluoro, bromo, methoxy, hydroxy, trifluoromethoxy, propyl, ethyl, methyl, methoxymethyl, cyano, carboxamido, heterocyclylcarbonyl, methylsulfonyl, ethylsulfonyl, propoxy, ethoxy, methoxy, methylaminocarbonyl, dimethylaminocarbonyl, dimethoxycarbonyl, aminosulfonyl, methylaminosulfonyl and dimethylaminosulfonyl.

In some embodiments, W and X are both substituted in the meta positions relative to the attachment of the ring A. In still other embodiments, W is substituted in the meta position and X is substituted in the para position relative to the attachment of the ring A.

In some embodiments, $R^1$, $R^2$, $R^3$ and $R^4$ are each hydrogen; $R^5$ is methyl; $R^6$ is phenyl optionally substituted with one to four substituents independently selected from halogen, cyano, haloalkyl, alkoxy, $(C_1-C_6)$ alkyl and alkylsulfonyl; $R^{7a}$ is hydrogen; $R^{7b}$ is selected from hydrogen, fluoro and chloro; $R^{7c}$ is hydrogen; and A is selected from phenyl and pyridinyl.

In some of these embodiments, $R^6$ is

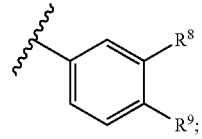

$R^8$ is selected from hydrogen, fluoro, chloro, methyl, cyano, $-CF_3$ and methoxy; $R^9$ is selected from hydrogen, fluoro, chloro, methyl, methoxy, cyano, $-CF_3$ and $-SO_2CH_3$; W is selected from hydrogen, $(C_1-C_6)$ alkyl, halogen and haloalkyl; X is selected from hydrogen, $(C_1-C_6)$ alkyl, halogen, haloalkyl, haloalkoxy, hydroxy, alkoxy, alkoxyalkyl, alkylsulfonyl, alkylaminosulfonyl, carboxamido, cyano, and heterocyclylalkyl; and Y and Z are each hydrogen. In more embodiments, $R^8$ is selected from hydrogen, fluoro, chloro and methyl; A is phenyl; W is selected from hydrogen and fluoro and is in the meta position in relation to the attachment of the ring A; and X is selected from alkylsulfonyl, fluoro, alkylaminosulfonyl and cyano and is in the meta position in relation to the attachment of the ring A.

In another embodiment, $R^1$, $R^2$, $R^3$ and $R^4$ are each independently selected from hydrogen and $(C_1-C_3)$ alkyl (for example methyl); $R^5$ is selected from hydrogen and $(C_1-C_3)$ alkyl (for example methyl); $R^6$ is selected from aryl (for example phenyl) and heteroaryl (for example thiophenyl) each optionally substituted with one or two substituents independently selected from halogen (for example fluorine and chlorine), $(C_1-C_3)$ haloalkyl (for example trifluoromethyl), $(C_1-C_6)$ alkoxy (for example methoxy), $(C_1-C_6)$ alkyl (for example methyl); $R^{7a}$ is selected from hydrogen and fluoro (for example hydrogen); $R^{7b}$ is selected from hydrogen, fluoro and chloro (for example hydrogen and chloro); $R^{7c}$ is selected from hydrogen, fluoro and chloro (for example hydrogen); A is selected from aryl (for example phenyl) and heteroaryl (for example benzoxadiazolyl); and W, X, Y and Z are each independently selected from hydrogen, $(C_1-C_3)$ alkyl (for example methyl), halogen (for example chloro and fluoro), (C1-C3) haloalkyl (for example trifluoromethyl), cyano, and (C1-C3) alkoxy (for example methoxy); with the proviso that any of W, X, Y and Z at the ortho position (in relation to the attachment of the ring A) must be hydrogen.

In certain embodiments, any of W, X, Y and Z at the para position (in relation to the attachment of the ring A) are hydrogen.

In more embodiments, the invention relates to compounds (or salts thereof) having general formula Ia:

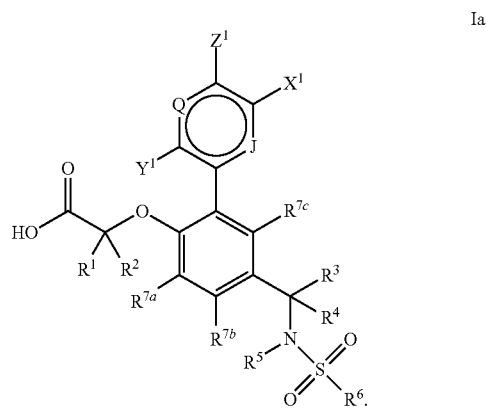

In certain embodiments, $R^1$, $R^2$, $R^3$ and $R^4$ are each independently selected from hydrogen and $(C_1-C_6)$ alkyl. In other embodiments, $R^1$, $R^2$, $R^3$ and $R^4$ are each independently selected from hydrogen and methyl. In further embodiments, $R^1$, $R^2$, $R^3$ and $R^4$ are each hydrogen.

In still more embodiments, $R^5$ is selected from hydrogen, $(C_1-C_6)$ alkyl and $(C_3-C_8)$ cycloalkyl. In yet more embodiments, $R^5$ is selected from hydrogen, methyl, ethyl, propyl and isopropyl. In further embodiments, $R^5$ is methyl.

In more embodiments, $R^6$ is selected from:
a. $(C_1-C_4)$ alkyl,
b. $(C_3-C_8)$ cycloalkyl,
c. dialkylamino,
d. alkylamino, and
e. aryl, heteroaryl and arylalkyl, each optionally substituted with one to four substituents independently selected from halogen, cyano, $(C_1-C_6)$ haloalkyl, $(C_1-C_6)$ alkoxy, $(C_1-C_6)$ haloalkoxy, $(C_1-C_6)$ alkyl and $(C_1-C_6)$ alkylsulfonyl.

In certain embodiments, $R^6$ is selected from aryl and heteroaryl, each optionally substituted with one to four substituents independently selected from halogen, cyano, $(C_1-C_6)$ haloalkyl, $(C_1-C_6)$ alkoxy, $(C_1-C_6)$ haloalkoxy, $(C_1-C_6)$ alkyl and $(C_1-C_6)$ alkylsulfonyl.

In more embodiments, $R^6$ is

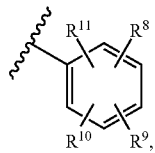

wherein $R^8$ is selected from hydrogen, halogen, $(C_1-C_6)$ alkyl, cyano, $(C_1-C_6)$ haloalkyl and $(C_1-C_6)$ alkoxy; $R^9$ is selected from hydrogen, halogen, $(C_1-C_6)$ alkyl, $(C_1-C_6)$ alkoxy, cyano, $(C_1-C_6)$ haloalkoxy, $(C_1-C_6)$ haloalkyl and $(C_1-C_6)$ alkylsulfonyl; $R^{10}$ is selected from hydrogen, halogen, $(C_1-C_6)$ alkoxy and $(C_1-C_6)$ alkyl; and $R^{11}$ is selected from hydrogen, halogen, $(C_1-C_6)$ alkoxy and $(C_1-C_6)$ alkyl.

In further embodiments, $R^6$ is

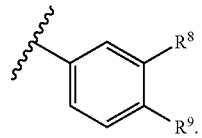

In some of these embodiments, $R^8$ is selected from hydrogen, methyl, fluoro, chloro, cyano, —$CF_3$ and methoxy; and $R^9$ is selected from hydrogen, fluoro, chloro, methyl, methoxy, cyano, —$CF_3$ and —$SO_2CH_3$, and in certain embodiments $R^8$ and $R^9$ are each independently selected from fluoro, chloro, methoxy and hydrogen.

In still more embodiments in which $R^6$ is

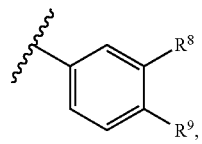

$R^8$ is hydrogen.

In some more embodiments, $R^6$ is

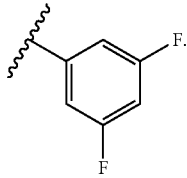

In yet more embodiments, $R^6$ is selected from naphthyl, pyridinyl and quinolinyl, each optionally substituted with one to four substituents independently selected from halogen, cyano, $(C_1-C_6)$ haloalkyl, $(C_1-C_6)$ alkoxy, $(C_1-C_6)$ haloalkoxy, $(C_1-C_6)$ alkyl and $(C_1-C_6)$ alkylsulfonyl.

In some embodiments, $R^{7a}$ is selected from hydrogen and fluoro; $R^{7b}$ is selected from hydrogen, fluoro and chloro; and $R^{7c}$ is selected from hydrogen, fluoro and chloro. In more embodiments, $R^{7a}$ and $R^{7c}$ are each hydrogen.

In more embodiments, Q is N. In some embodiments, Q is CX', and X' is selected from hydrogen, $(C_1-C_6)$ alkyl, halogen, $(C_1-C_6)$ haloalkyl, $(C_1-C_6)$ haloalkoxy, hydroxy, $(C_1-C_6)$ alkoxyalkyl, $(C_1-C_6)$ alkylsulfonyl, $(C_1-C_6)$ alkylaminosulfonyl, carboxamido, cyano, $(C_1-C_6)$ alkoxy, aminosulfonyl, dialkylaminosulfonyl, alkylaminocarbonyl, dialkylaminocarbonyl, heterocyclylcarbonyl, heterocyclylacyl, heterocyclylalkyl and heterocyclyl optionally substituted with $(C_1-C_6)$ alkyl. In certain embodiments, X' is selected from hydrogen, $(C_1-C_6)$ alkyl, halogen and haloalkyl. In still other embodiments, X' is selected from hydrogen and fluoro.

In some embodiments, J is N. In more embodiments, J is CY', and Y' is selected from hydrogen and halogen. In certain embodiments, Y' is hydrogen.

In some embodiments, Q is CX'; X' is selected from hydrogen, $(C_1-C_6)$ alkyl, halogen, $(C_1-C_6)$ haloalkyl, $(C_1-C_6)$ haloalkoxy, hydroxy, $(C_1-C_6)$ alkoxyalkyl, $(C_1-C_6)$ alkylsulfonyl, $(C_1-C_6)$ alkylaminosulfonyl, carboxamido, cyano, $(C_1-C_6)$ alkoxy, aminosulfonyl, dialkylaminosulfonyl, alkylaminocarbonyl, dialkylaminocarbonyl, heterocyclylcarbonyl, heterocyclylacyl, heterocyclylalkyl and heterocyclyl optionally substituted with $(C_1-C_6)$ alkyl; J is CY'; and Y' is selected from hydrogen and halogen. In further embodiments, X' is selected from hydrogen, $(C_1-C_6)$ alkyl, halogen and haloalkyl. In still more embodiments, X' is selected from hydrogen and fluoro. In yet other embodiments, Y' is hydrogen.

In some embodiments, X' is selected from hydrogen, $(C_1-C_6)$ alkyl, halogen, $(C_1-C_6)$ haloalkyl, $(C_1-C_6)$ haloalkoxy, hydroxy, $(C_1-C_6)$ alkoxyalkyl, $(C_1-C_6)$ alkylsulfonyl, $(C_1-C_6)$ alkylaminosulfonyl, carboxamido, cyano, $(C_1-C_6)$ alkoxy, aminosulfonyl, dialkylaminosulfonyl, alkylaminocarbonyl, dialkylaminocarbonyl, heterocyclylcarbonyl, heterocyclylacyl, heterocyclylalkyl and heterocyclyl optionally substituted with $(C_1-C_6)$ alkyl. In more embodiments, X' is selected from hydrogen, $(C_1-C_6)$ alkyl, halogen, haloalkyl, haloalkoxy, hydroxy, alkoxy, alkoxyalkyl, alkylsulfonyl, alkylaminosulfonyl, carboxamido, cyano, and heterocyclylalkyl. In further embodiments, X' is selected from alkylsulfonyl, fluoro, alkylaminosulfonyl and cyano.

In some embodiments of the invention, Y' is hydrogen. In other embodiments, Y' is halogen.

In some embodiments, $Z^1$ is selected from hydrogen, $(C_1-C_6)$ alkyl, halogen, $(C_1-C_6)$ haloalkyl, $(C_1-C_6)$ haloalkoxy, hydroxy, $(C_1-C_6)$ alkoxyalkyl, $(C_1-C_6)$ alkylsulfonyl, $(C_1-$ $C_6$) alkylaminosulfonyl, carboxamido, cyano, ($C_1$-$C_6$) alkoxy, aminosulfonyl, dialkylaminosulfonyl, alkylaminocarbonyl, dialkylaminocarbonyl, heterocyclylcarbonyl, heterocyclylacyl, heterocyclylalkyl and heterocyclyl optionally substituted with ($C_1$-$C_6$) alkyl. In more embodiments, $Z^1$ is selected from hydrogen, ($C_1$-$C_6$) alkyl, ($C_1$-$C_6$) alkylsulfonyl, halogen and haloalkyl. In further embodiments, Z' is selected from hydrogen, fluoro and methyl.

In some embodiments, the present invention relates to compounds of formula Ia in which $R^1$, $R^2$, $R^3$ and $R^4$ are each hydrogen, $R^5$ is methyl and $R^6$ is phenyl optionally substituted with one to four substituents independently selected from halogen, cyano, haloalkyl, alkoxy, ($C_1$-$C_6$) alkyl and alkylsulfonyl.

In some of these embodiments, $R^6$ is

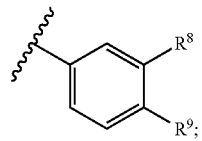

$R^8$ is selected from hydrogen, fluoro, chloro, methyl, cyano, —$CF_3$ and methoxy; $R^9$ is selected from hydrogen, fluoro, chloro, methyl, methoxy, cyano, —$CF_3$ and —$SO_2CH_3$; Q is CX'; X' is selected from hydrogen, ($C_1$-$C_6$) alkyl, halogen and haloalkyl; and X' is selected from hydrogen, ($C_1$-$C_6$) alkyl, halogen, haloalkyl, haloalkoxy, hydroxy, alkoxy, alkoxyalkyl, alkylsulfonyl, alkylaminosulfonyl, carboxamido, cyano, and heterocyclylalkyl. In further embodiments, $R^8$ is selected from hydrogen, fluoro, chloro and methyl; J is CY'; X' is selected from hydrogen and fluoro; X' is selected from alkylsulfonyl, fluoro, alkylaminosulfonyl and cyano; and Z' is selected from hydrogen, fluoro, chloro, ($C_1$-$C_6$) alkyl, alkylsulfonyl, and haloalkyl.

In some embodiments, Q is N and J is CY'. In further embodiments, Y' is hydrogen.

In some embodiments, the present invention relates to compounds disclosed herein in the form of a free base or as a salt thereof, for example as a pharmaceutically acceptable salt thereof.

In some embodiments, the present invention relates to a compound selected from 2-(3-fluoro-5-methoxyphenyl)-4-((3-chloro-4-fluoro-N-methylphenylsulfonamido)methyl) phenoxyacetic acid, 2-(3-cyano-5-fluorophenyl)-4-((3,4-dichloro-N-methylphenylsulfonamido)methyl) phenoxyacetic acid, 2-(3-cyanophenyl)-4-((3-chloro-4-fluoro-N-methylphenylsulfonamido)methyl)-5-chlorophenoxyacetic acid, 2-(3-cyano-5-fluorophenyl)-4-((3,4-difluoro-N-methylphenylsulfonamido)methyl) phenoxyacetic acid, 2-(3-cyano-5-fluorophenyl)-4-((3-chloro-N-methylphenylsulfonamido)methyl)phenoxyacetic acid, 2-(3-fluoro-5-methoxyphenyl)-4-((3,4-difluoro-N-methylphenylsulfonamido)methyl)phenoxyacetic acid, 2-(3-fluoro-5-methoxyphenyl)-4-((3-fluoro-4-methoxy-N-methylphenylsulfonamido)methyl)phenoxyacetic acid, 2-(3,5-difluorophenyl)-4-((3,4-dichloro-N-methylphenylsulfonamido)methyl)phenoxyacetic acid, 2-(3-cyano-5-fluorophenyl)-4-((4-fluoro-N-methylphenylsulfonamido)methyl)phenoxyacetic acid, 2-(3,5-difluorophenyl)-4-((3-chloro-4-fluoro-N-methylphenylsulfonamido)methyl)phenoxyacetic acid, 2-(3-cyanophenyl)-4-((3,5-difluoro-N-methylphenylsulfonamido)methyl)phenoxyacetic acid, 2-(3-trifluoromethylphenyl)-4-((4-fluoro-N-methylphenylsulfonamido)methyl)phenoxyacetic acid, 2-(5-benzo[c][1,2,5]oxadiazolyl)-4-((4-fluoro-N-methylphenylsulfonamido)methyl)phenoxyacetic acid, 2-(3-cyano-5-fluorophenyl)-4-((2,3-dichloro-5-methylthiophene-5-sulfonamido)methyl)phenoxyacetic acid, 2-(3-cyano-5-fluorophenyl)-4-((3,4-difluoro-phenyl-sulfonamido)methyl)phenoxyacetic acid, 2-(3-cyano-5-fluorophenyl)-4-((3-fluoro-4-methoxyphenylsulfonamido)methyl)phenoxyacetic acid, 2-(3-cyano-5-fluorophenyl)-(5-fluoro-4-((3-fluoro-4-methoxy-N-methylphenylsulfonamido)methyl)phenoxy)acetic acid, or a salt thereof such as a pharmaceutically acceptable salt. In certain embodiments, compounds are provided in the form of their free base.

It will be appreciated that the present invention extends to combinations of embodiments and example substituents described above.

Definitions

Terms and substituents are given their ordinary meaning unless defined otherwise, and may be defined when introduced and retain their definitions throughout unless otherwise specified, and retain their definitions whether alone or as part of another group unless otherwise specified.

Alkyl (whether alone or as part of another functional group) includes linear or branched hydrocarbon structures. The term can refer to alkyl of 10 or fewer carbons (for example, $C_1$, $C_2$, $C_3$, $C_4$, $C_5$, $C_6$, $C_7$, $C_8$, $C_9$, $C_{10}$). Lower alkyl refers to alkyl groups of 1, 2, 3, 4, 5 and 6 carbon atoms. Examples of lower alkyl groups include methyl, ethyl, propyl, isopropyl, butyl, s- and t-butyl and the like. Alkylene refers to linear or branched divalent hydrocarbon structures. The term can refer to a structure having 10 or fewer carbons. Lower alkylene are those of $C_6$ or below and includes methylene, ethylene, propylene (n-propylene and isopropylene), butylenes (n-butylene, isobutylene and t-butylene) and the like.

Cycloalkyl refers to cyclic hydrocarbon groups of 3, 4, 5, 6, 7, and 8 (for example, 3 to 6) carbon atoms. Examples of cycloalkyl groups include c-propyl, c-butyl, c-pentyl, c-hexyl, norbornyl, adamantyl and the like.

$C_1$- to $C_n$-Hydrocarbon (for example, $C_1$, $C_2$, $C_3$, $C_4$, $C_5$, $C_6$, $C_7$, $C_8$, $C_9$, $C_{10}$) includes alkyl, cycloalkyl, alkenyl, alkynyl, aryl and combinations thereof. Examples include benzyl, phenethyl, vinyl, allyl, cyclopropyl, cyclohexylmethyl, camphoryl and naphthylethyl. Hydrocarbon refers to any substituent comprised of hydrogen and carbon as the only elemental constituents. Saturated ($C_1$ to $C_n$) hydrocarbon is identical in meaning to ($C_1$ to $C_n$) alkyl or ($C_1$ to $C_n$) alkane as used herein. Whenever reference is made to $C_{0-n}$ alkyl, ($C_0$ to $C_n$) alkyl, or ($C_0$ to $C_n$) alkane when number of carbon atoms is 0, a direct bond is implied.

Alkoxy or alkoxyl refers to groups of from 1 to 8 carbon atoms of a linear, branched, or cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to six carbons, such as one to four carbon atoms. Similarly, aryloxy, cycloalkoxy and arylalkoxy are aryl, cycloalkyl and arylalkyl, respectively, bonded via an oxygen atom to the parent structure. For the purpose of this application, alkoxy and lower alkoxy include methylenedioxy and ethylenedioxy.

The term "halogen" or "halo" refers to fluorine, chlorine, bromine or iodine (for example fluorine or chlorine)

The terms "haloalkyl" and "haloalkoxy" mean alkyl or alkoxy, respectively, substituted with one or more (for example, 1, 2 or 3) halogen atoms. The terms "alkylcarbonyl" and "alkoxycarbonyl" mean —C(=O)alkyl or —C(=O)

alkoxy, respectively. It will usually be the case that no more than one Cl, Br or I will be present on each carbon. Commonly, there will not be more than three of these halogens in an alkyl or alkoxy residue. In the case of fluorine, all hydrogens in a residue could be replaced by fluorine atoms to provide a perfluoro alkyl residue. Examples of fluoroalkyl include fluoromethyl, difluoromethyl, trifluoromethyl, trifluoroethyl and pentafluoroethyl. Other examples of haloalkyl and haloalkoxy include trichloroethyl and trifluoromethoxy.

Acyl refers to formyl and to groups of 1, 2, 3, 4, 5, 6, 7 and 8 carbon atoms of a straight, branched or cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons. The double bonded oxygen, when referred to as a substituent itself, is called "oxo".

Amide refers to a substituent of formula —C(O)NR$^x$R$^y$, wherein R$^x$ and R$^y$ can each be hydrogen or $C_1$-$C_6$ alkyl.

Aryl and heteroaryl mean (i) a phenyl group (or benzene) or a monocyclic 5- or 6-membered heteroaromatic ring containing 1-4 heteroatoms selected from O, N, or S; (ii) a bicyclic 9- or 10-membered aromatic ring system or heteroaromatic ring system containing 1-4 heteroatoms selected from O, N, or S; or (iii) a tricyclic 13- or 14-membered aromatic ring system or heteroaromatic ring system containing 1-5 heteroatoms selected from O, N, or S. As commonly understood, when referring to aryl as a substituent, it is intended that the point of attachment is a ring carbon of the aryl group (or ring carbon or heteroatom of the heteroaryl). Aryl and heteroaryl refer to ring systems in which at least one ring, but not necessarily all rings, are fully aromatic. Thus aromatic 6- to 14-membered aryl rings include, for example, benzene, naphthalene, indane, tetralin, benzocycloheptane and fluorene and the 5- to 10-membered aromatic heteroaryl rings include, for example, imidazole, pyridine, indole, isoxazole, pyridine-N-oxide, imidazolepyridine, thiophene, benzooxadiazole, isoindoline, thiophene, benzopyranone, thiazole, furan, benzimidazole, quinoline, isoquinoline, tetrahydroisoquinoline, quinoxaline, tetrahydrocarboline, pyrimidine, pyrazine, tetrazole and pyrazole.

Arylalkyl means an alkyl residue attached to an aryl ring. As commonly understood, when referring to arylalkyl as a substituent, it is intended that the point of attachment is the alkyl group. Examples of arylalkyl are benzyl, phenethyl, phenylpropyl, naphthylethyl and the like. Heteroarylalkyl refers to a substituent in which a heteroaryl residue is attached to the parent structure through alkyl. Examples include pyridinylmethyl, pyrimidinylethyl and the like. In one embodiment, the alkyl group of an arylalkyl or a heteroarylalkyl is an alkyl group of from 1 to 6 carbons.

The term "heterocycle" means a monocyclic, bicyclic or tricyclic residue with 1 to 13 carbon atoms and 1 to 5 heteroatoms chosen from the group consisting of nitrogen, oxygen and sulfur. The nitrogen and sulfur heteroatoms may optionally be oxidized, and the nitrogen heteroatom may optionally be quaternized. As will be understood by a person with ordinary skill in the art, heterocycles include residues in which one or more carbon atoms may optionally be oxidized. Heterocycles also include spiroheterocycles. The heterocycle may be fused to an aromatic hydrocarbon radical. Suitable examples include 2-pyrrolinyl, 3-pyrrolinyl, pyrrolindinyl, 1,3-dioxolanyl, imidazolinyl, imidazolidinyl, pyrazolinyl, pyrazolidinyl, 2H-pyranyl, 4H-pyranyl, piperidinyl, 1,4-dithianyl, thiomorpholinyl, piperazinyl, and the like. A nitrogen heterocycle is a heterocycle containing at least one nitrogen in the ring; it may contain additional nitrogens, as well as other heteroatoms. Examples include piperidine, piperazine, morpholine, pyrrolidine and thiomorpholine. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolinyl, imidazolidinyl, oxazolidinyl, isoxazolidinyl, thiazolidinyl, quinuclidinyl, isothiazolidinyl, benzopyranyl, tetrahydrofuryl, tetrahydropyranyl, thiamorpholinyl, thiamorpholinylsulfoxide, thiamorpholinylsulfone, and tetrahydroquinolinyl.

Aminoalkyl means an amino group bound to a core structure via an alkyl group, for example, aminomethyl, aminoethyl, aminopenthyl, etc. The alkyl group, as defined above, could be linear or branched and, therefore, an aminoalkyl includes, for example, —$CH_2CH_2CH(CH_3)CH_2NH_2$, —$CH_2C(CH_3)_2CH_2NH_2$, etc. Alkylaminoalkyl means a secondary amine bound to a core structure via an alkyl group as defined above, for example, —$CH_2CH_2NHCH_3$, —$CH_2CH_2CH_2NHCH_2CH_3$, etc. Dialkylaminoalkyl means a tertiary amine bound to a core structure via an alkyl group, for example, —$CH_2N(CH_3)_2$, —$CH_2CH_2CH_2N(CH_3)CH_2CH_3$, etc.

Alkyl, aryl, heteroaryl, aryloxy, cycloalkyl, heterocyclyl, etc., when substituted refers to alkyl, aryl, heteroaryl, aryloxy, cycloalkyl or heterocyclyl wherein up to three (namely, 1 or 2 or 3) H atoms in each residue are replaced with halogen, alkyl, haloalkyl, haloalkoxy, haloalkoxyalkyl, haloalkylthio, perfluoroloweralkoxy, hydroxy, loweralkoxy (which for the purpose of the present disclosure includes methylene dioxy and ethylene dioxy), oxaalkyl, carboxy, carboalkoxy (also referred to as alkoxycarbonyl[-C(=O)O-alkyl]), carboxamido ([—C(=O)NH$_2$]), alkylaminocarbonyl [—C(=O) NH-alkyl]), alkoxycarbonylamino [HNC(=O)O-alkyl], hydroxyaminoalkylcarbonyl, hydroxyalkylaminocarbonyl, acyl, alkoxyalkyl, benzenesulfonyl, cyano, carbonyl, nitro, amino, hydroxyalkyl, alkylamino, dialkylamino, aminoalkyl, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, alkylsulfinyl, alkylsulfonyl, acylamino, acylaminoalkyl, acylaminoalkoxy, amidino, alkoxycarbonylamino, acetoxy, sulfoxide, sulfone, sulfonylamino, sulfonamido, aryl, phenyl, heterocyclyl, hydroxyimino, alkoxyimino, aminosulfonyl, trityl, amidino, guanidino, ureido, alkylaminosulfonyl, alkylureido, benzyloxyphenyl, benzyl, heteroaryl, heterocyclylalkyl, phenoxy, benzyloxy, or heteroaryloxy. "Oxo" is also included among the substituents referred to in "substituted"; it will be appreciated by persons of skill in the art that, because oxo is a divalent radical, there are circumstances in which it will not be appropriate as a substituent (for example, on phenyl). In one embodiment, 1, 2 or 3 hydrogen atoms are replaced with a specified radical. As used herein, the term "optionally substituted" may be used interchangeably with "unsubstituted or substituted".

As used herein, reference to "treatment" or "treating" a patient or subject means administration of a drug or pharmaceutical agent to elicit the biological or medical response of a tissue, system, animal or human that is being sought. Such biological or medical response may include, but is not limited to prevention or prophylaxis or amelioration of a disease, disorder, or side effect, or a decrease in the rate of advancement of a disease or disorder. The term also includes within its scope enhancement of normal physiological function.

The terms "preventing" or "prevention" as used herein refer to administering a medicament beforehand to forestall or obtund an acute episode or, in the case of a chronic condition, to diminish the likelihood or seriousness of the condition. Persons of ordinary skill in the medical art (to which the present use claims are directed) recognize that the term "prevent" is not an absolute term. In the medical art it is understood to refer to the prophylactic administration of a drug to diminish the likelihood or seriousness of a condition, and this is the sense intended.

More embodiments of the present invention include compounds and salts thereof that include isotopes, namely, compounds may contain one or more atoms containing an atomic mass or mass number different from the atomic mass or mass number usually found in nature. Isotopes include radioisotopes and non-radioisotopes. Examples of isotopes include isotopes of hydrogen, carbon, oxygen, nitrogen, phosphorus, sulfur and fluorine. Examples of radioisotopes of hydrogen, carbon, phosphorous, sulfur, and fluorine include $^{3}H$, $^{14}C$, $^{32}P$, $^{35}S$, and $^{18}F$, respectively. Tritiated H, namely, $^{3}H$, and carbon-14, namely, radioisotopes are useful for their ease in preparation and detectability. More examples of isotopes include deuterium ($^{2}H$), nitrogen-15, phosphorus-31, and the like.

Compounds and salts thereof containing isotopes, can generally be prepared by methods well known to those skilled in the art. For example, some compounds containing isotopes can be prepared by carrying out the procedures disclosed herein by substituting a non-isotopic reagent for a reagent containing an isotope. In one example, because of the high affinity for the CRTH2 enzyme active site, radiolabeled compounds of the invention are useful for CRTH2 assays.

As used herein, and as would be understood by the person of skill in the art, the references to "a compound" is intended to include the free base and salts thereof. It will be further appreciated that the invention extends to solvates and inclusion complexes of that compound as well as any stereoisomeric form, or a mixture of any such forms of that compound in any ratio, and polymorphic forms.

The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an anti-solvent. The solvate is typically dried or azeotroped under ambient conditions. Inclusion complexes are described in *Remington: The Science and Practice of Pharmacy* 19th Ed. (1995) volume 1, page 176-177, which is incorporated herein by reference in its entirety. The most commonly employed inclusion complexes are those with cyclodextrins, and all cyclodextrin complexes, natural and synthetic, are specifically encompassed within the claims.

The present invention includes compounds of formula I in the form of the free base or in the form of salts. Suitable salts include those formed with both organic and inorganic acids. Such salts will normally be pharmaceutically acceptable, although non-pharmaceutically acceptable salts may be of utility in the preparation and purification of the compound in question. The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, carbonic, citric, ethanedisulfonic, ethanesulfonic, ethylenediaminetetraacetic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, pamoic, pantothenic, phosphoric, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine.

Some of the compounds described herein contain one or more asymmetric centers and may thus give rise to enantiomers, diastereomers, and other stereoisometric forms which may be defined in terms of absolute stereochemistry as (R)- or (S)-. The present invention is meant to include all such possible diastereomers as well as their racemic and optically pure forms. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. For example, the graphic representation

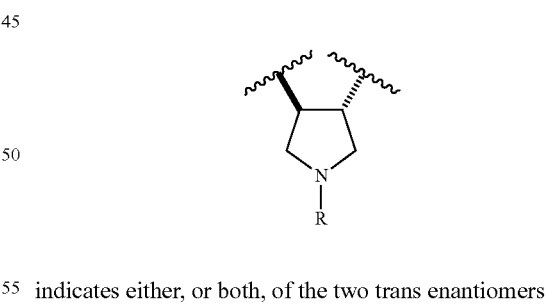

indicates either, or both, of the two trans enantiomers

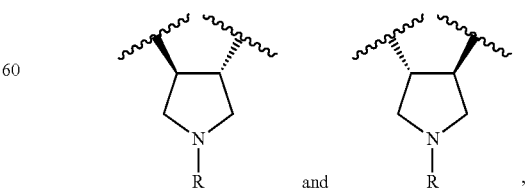

while the graphic representation

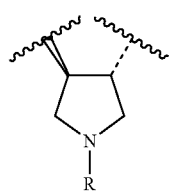

indicates a single diastereomer of unknown stereochemistry.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

Compounds of formula (I) may exist in different physical forms. Such forms are within the scope of the present invention. Thus, the compounds of formula (I) may be in a crystalline or amorphous state. Furthermore, if crystalline, the compounds of formula (I) may exist in one or more polymorphic forms, which are included in the scope of the present invention. The most thermodynamically stable polymorphic form, at room temperature, of compounds of formula (I) is of interest.

Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (ssNMR).

The variables are defined when introduced and retain that definition throughout. Thus, for example, $R^5$ is always selected from hydrogen, $(C_1-C_6)$ alkyl and cycloalkyl, although, according to standard patent practice, in dependent claims it may be restricted to a subset of these values.

The abbreviations Me, Et, Ph, Tf, Ts and Ms represent methyl, ethyl, phenyl, trifluoromethanesulfonyl, toluenesulfonyl and methanesulfonyl respectively. A comprehensive list of abbreviations utilized by organic chemists (namely, persons of ordinary skill in the art) appears in the first issue of each volume of the *Journal of Organic Chemistry*. The list, which is typically presented in a table entitled "Standard List of Abbreviations," is incorporated herein by reference.

Chemical Synthesis

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, for example in the case of suitably substituted phenoxyacetic esters, are either commercially available, synthesized as described in the examples or may be obtained by the methods well known to persons of skill in the art.

The present invention further provides pharmaceutical compositions comprising as active agents, the compounds described herein.

As used herein a "pharmaceutical composition" refers to a preparation of one or more of the compounds described herein, or pharmaceutically acceptable salts or solvates thereof, with other chemical components such as pharmaceutically suitable carriers and excipients.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

Compounds that modulate the function of CRTH2 can be formulated as pharmaceutical compositions and administered to a mammalian subject, such as a human patient in a variety of forms adapted to the chosen route of administration, namely, orally or parenterally, by intravenous, intramuscular, topical, transdermal or subcutaneous routes.

For purposes of the specification of this application, the term "formulation" is used interchangeably with the term "composition."

While it may be possible for the compounds of the invention to be administered as the raw chemical, it is possible to present them as a formulation. According to a further aspect, the present invention provides a composition comprising a compound of the invention (or a pharmaceutically acceptable salt thereof) with one or more pharmaceutically acceptable carriers thereof and optionally one or more other therapeutic ingredients. The carrier(s) must be "acceptable" in the sense of being compatible with the other ingredients of the composition and not deleterious to the recipient thereof.

The compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or nonaqueous techniques. "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation.

The compositions include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The compositions may conveniently be presented in unit dosage form and may be prepared by any of the methods well known in the art of pharmacy. All methods include the step of bringing into association a compound of the invention [or a pharmaceutically acceptable salt or solvate thereof ("active ingredient")] and a pharmaceutically acceptable carrier, which constitutes one or more accessory ingredients. In general, the compositions are prepared by uniformly and intimately bringing into association the active ingredient with liquid carriers or finely divided solid carriers or both and then, if necessary, shaping the product into the desired compositions.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar or alginic acid or a salt thereof such as sodium alginate.

In addition, enteric coating may be useful as it is may be desirable to prevent exposure of the compounds of the invention to the gastric environment.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added. All compositions for oral administration should be in dosages suitable for the chosen route of administration.

Compositions for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, or an appropriate fraction thereof, of the active ingredient.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Compositions for parenteral administration include aqueous and non-aqueous sterile injection solutions which may contain anti-oxidants, buffers, bacteriostats and solutes which render the formulation isotonic with the blood of the intended recipient.

Compositions for parenteral administration also include aqueous and non-aqueous sterile suspensions, which may include suspending agents and thickening agents. The compositions may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

For injection, the compounds of the invention may be formulated in aqueous solutions, preferably in physiologically compatible buffers such as Hank's or Ringer's solution or physiological saline buffer. For transmucosal and transdermal administration, penetrants appropriate to the barrier to be permeated may be used in the composition. Such penetrants, including for example DMSO or polyethylene glycol, are known in the art.

For administration by inhalation, the compounds for use according to the present invention are conveniently delivered in the form of an aerosol spray presentation from a pressurized pack or a nebulizer with the use of a suitable propellant, for example, dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

The compounds or salts of the present invention may also be formulated in rectal compositions such as suppositories or retention enemas, using, for example, conventional suppository bases such as cocoa butter or other glycerides.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The compounds of the invention may be administered orally or via injection at a dose from 0.001 mg/kg/day to 2500 mg/kg/day. The dose range for adult humans is generally from 0.005 mg/day to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

It should be understood that in addition to the ingredients particularly mentioned above, the compositions of this invention may include other agents conventional in the art having regard to the type of formulation in question, for example those suitable for oral administration may include flavoring agents.

The compositions may be presented in a packaging device or dispenser, which may contain one or more unit dosage forms containing the active ingredient. Examples of a packaging device include metal or plastic foil, such as a blister pack and a nebulizer for inhalation. The packaging device or dispenser may be accompanied by instructions for administration. Compositions comprising a compound of the present invention formulated in a compatible pharmaceutical carrier may also be placed in an appropriate container and labeled for treatment of an indicated condition.

Certain compounds of general formula (I) may be employed alone or in combination with other therapeutic agents. Combination therapies according to the present invention may thus comprise the administration of at least one compound of general formula (I) or a pharmaceutically acceptable salt thereof, and the use of at least one other pharmaceutically active agent. The compound(s) of the invention and the other pharmaceutically active agent(s) may be administered together in a single pharmaceutical composition or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect. Thus in a further aspect, there is provided a pharmaceutical composition comprising a compound of general formula (I) or a pharmaceutically acceptable salt thereof and at least one other pharmaceutically active agent. In one embodiment, there is provided combinations comprising one or two other therapeutic agents.

Suitable agents for use in the combinations of the invention include anti-inflammatory agents (including a steroid), anticholinergic agents (particularly an $M_1/M_2/M_3$ receptor antagonist), $\beta_2$-adrenoreceptor agonists, anti-allergy agents, antihistamines, leukotriene inhibitors and similar agents; FLAP inhibitors; kinase inhibitors for example P38 inhibitors, cytokine/chemokine receptor modulators, cytokine agonists or antagonists, TLR agonists and similar agents.

The invention thus provides, in a further aspect, a combination pharmaceutical product comprising a compound of formula (I) or a pharmaceutically acceptable salt thereof together with one or more other therapeutically active agents, for example selected from an anti-inflammatory agent such as a corticosteroid or an NSAID, an anticholinergic agent, a $\beta_2$-adrenoreceptor agonist, or a leukotriene inhibitor, It will be appreciated that when the compound of the present invention is administered in combination with other therapeutic agents the same or different routes of administration may be employed.

Suitable anti-inflammatory agents include corticosteroids. Anti-inflammatory corticosteroids are well known in the art. Representative examples include fluticasone propionate, fluticasone furoate, dexamethasone or an ester thereof, and mometasone furoate.

Examples of $\beta_2$-adrenoreceptor agonists include salmeterol (e.g. as racemate or a single enantiomer such as the R-enantiomer), salbutamol, formoterol, or terbutaline and salts thereof, for example the xinafoate salt of salmeterol, the sulphate salt or free base of salbutamol or the fumatrate salt of formoterol. In one embodiment, the $\beta_2$-adrenoreceptor agonists are long-acting $B_2$-adrenoreceptor agonists, for example, those having a therapeutic effect over a 24 hour period, such as salmeterol or formoterol. A further example of a $\beta_2$-adrenoreceptor agonist is the compound 4-{(1R)-2-[(6-{2-[(2,6-dichlorophenyl)methyoxy]ethoxy}hexyl)amino]-1-hydroxyethyl}-2-(hydroxyethyl)phenol triphenylacetete.

Examples of anticholinergic compounds which may be used in combination with a compound of formula (I) or a pharmaceutically acceptable salt thereof are compounds which are antagonists of the $M_1$ or $M_3$ receptors, dual antagonists of $M_1/M_3$ or $M_2/M_3$ receptors or pan antagonists of $M_1/M_2/M_3$ receptors such as ipratropium bromide, oxitropium bromide or tiotropium bromide.

An anti-histamine usable in a combination of a compound of the invention can for example be H1 antagonists which include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine.

Other suitable combinations include, for example combinations comprising a compound of the invention together with other anti-inflammatory agents such as an anti-flammatory corticosteroid; or a non-steroidal anti-inflammatory drug (NSAID) such as leukotriene antagonist (e.g. montelukast), an iNOS inhibitor, a tryptase inhibitor, IKK2 inhibitors, a p38 inhibitor, Syk inhibitors, an elastase inhibitor, a beta-2 integrin antagonist, an adenosine a2a agonist, a chemokine antagonist such as a CCR3 antagonist, a mediator release inhibitor such as sodium chromoglycate, a 5-lipoxygenase inhibitor, a DP1 antagonist, a DP2 antagonist, a pI3K delta inhibitor, an ITK inhibitor, a LP (lysophosphatidic) inhibitor and a FLAP (five lipoxygenase activating protein) inhibitor.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

In one aspect, the present invention also provides for so-called "triple combination" therapy, comprising a compound of the invention together with $\beta_2$-adrenoreceptor agonist and an anti-inflammatory corticosteroid. This combination may be suitable for treatment and/or prophylaxis of asthma, COPD or allergic rhinitis.

Rheumatoid arthritis (RA) is a further inflammatory disease where combination therapy may be contemplated. Thus in a further aspect, the present invention provides a compound of the invention in combination with a further therapeutic agent useful in the treatment of rheumatoid arthritis, said combination being useful for the treatment of rheumatoid arthritis.

The compound and pharmaceutical compositions according to the invention may be used in combination with or include one or more other therapeutic agents, for example selected from NSAIDS, corticosteroids, COX-2 inhibitors, cytokine inhibitors, anti-TNF agents, inhibitors of oncostatin M.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Indications

Some compounds of the present invention are useful in modulating CRTH2-mediated activity. Some compounds of the present invention may be useful as anti-inflammatory agents for the treatment, amelioration or prevention of inflammatory diseases and of complications arising therefrom.

Inflammation of tissues and organs occurs in a wide range of disorders and diseases and in certain variations results from activation of the cytokine family of receptors. Example inflammatory disorders associated with activation of CRTH2 include, skin disorders, respiratory disorders, and other disorders with an allergic component. Some such disorders can be treated or prevented by modulation of CRTH2 activity, for example, by administration of a compound according to the present invention.

Example skin disorders that may be treated with compounds of the present invention include dermatitis, cutaneous eosinophilias, Lichen planus, urticaria, psoriasis, pruritus, angiodermas, chronic skin ulcers, conjunctivitis, vasculitides, or erythemas. Examples of respiratory disorders that may be treated with compounds of the present invention include asthma, rhinitis, chronic obstructive pulmonary disease, bronchitis, nasal polyposis, nasal congestion, farmer's lung, fibroid lung and cough. More examples of diseases that may be treated with compounds of the present invention include osteoarthritis, rheumatoid arthritis, corneal ulcers, uveitis, pain and inflammatory bowel disease.

According to the present invention, compounds provided herein, for example, CRTH2 inhibitors, may be administered prophylactically, namely, prior to onset of acute allergic reaction, or they may be administered after onset of the reaction, or at both times.

The following examples will further describe the present invention, and are used for the purposes of illustration only, and should not be considered as limiting.

EXAMPLES

The following abbreviations and terms have the indicated meaning throughout:

Ac=acetyl
Boc=tert-butoxycarbonyl
BSA=bovine serum albumin
Bu=butyl
BuOH=butanol
$CDCl_3$=Deuterated chloroform
$CD_3CN$=Deuterated acetonitrile
$CD_3OD$=Deuterated methanol
CHO=Chinese hamster ovary
$\delta$=NMR chemical shift referenced to tetramethylsilane
DCM=dichloromethane=methylene chloride=$CH_2Cl_2$
DCE=1,2-dichloroethane
DHK-$PGD_2$=13,14-dihydro-15-keto-prostaglandin D2
DIC=diisopropylcarbodiimide
DIEA=N,N-diisopropylethyl amine
DMF=N,N-dimethylformamide
DMSO=dimethyl sulfoxide
EA (EtOAc)=Ethyl Acetate
EDC=N-(3-Dimethylaminopropyl)-N')ethylcarbodiimide
EtOH=ethanol
GDP=Guanosine diphosphate
h=hours
HEPES=(4-(2-hydroxyethyl)-1-piperazineethanesulfonic acid)
m-=meta
Me=methyl
MeOH=methanol=$CH_3OH$
MS=mass spectrometry
min=minutes
n=normal
NMR=Nuclear Magnetic Resonance
$Na(OAc)_3BH$=sodium triacetoxy borohydride
o-=ortho
p-=para
PE=Petroleum ether
PGD2=prostaglandin D2
Ph=phenyl
s-=secondary
SPA=scintillation proximity assay
t-=tertiary
TFA=trifluoroacetic acid
THF=tetrahydrofuran General Procedures Examples provided herein include syntheses of certain precursors and intermediates of the invention. Compounds of formula I were synthesized by means of conventional organic synthesis executable by those skilled in the art.

Synthetic Route 1

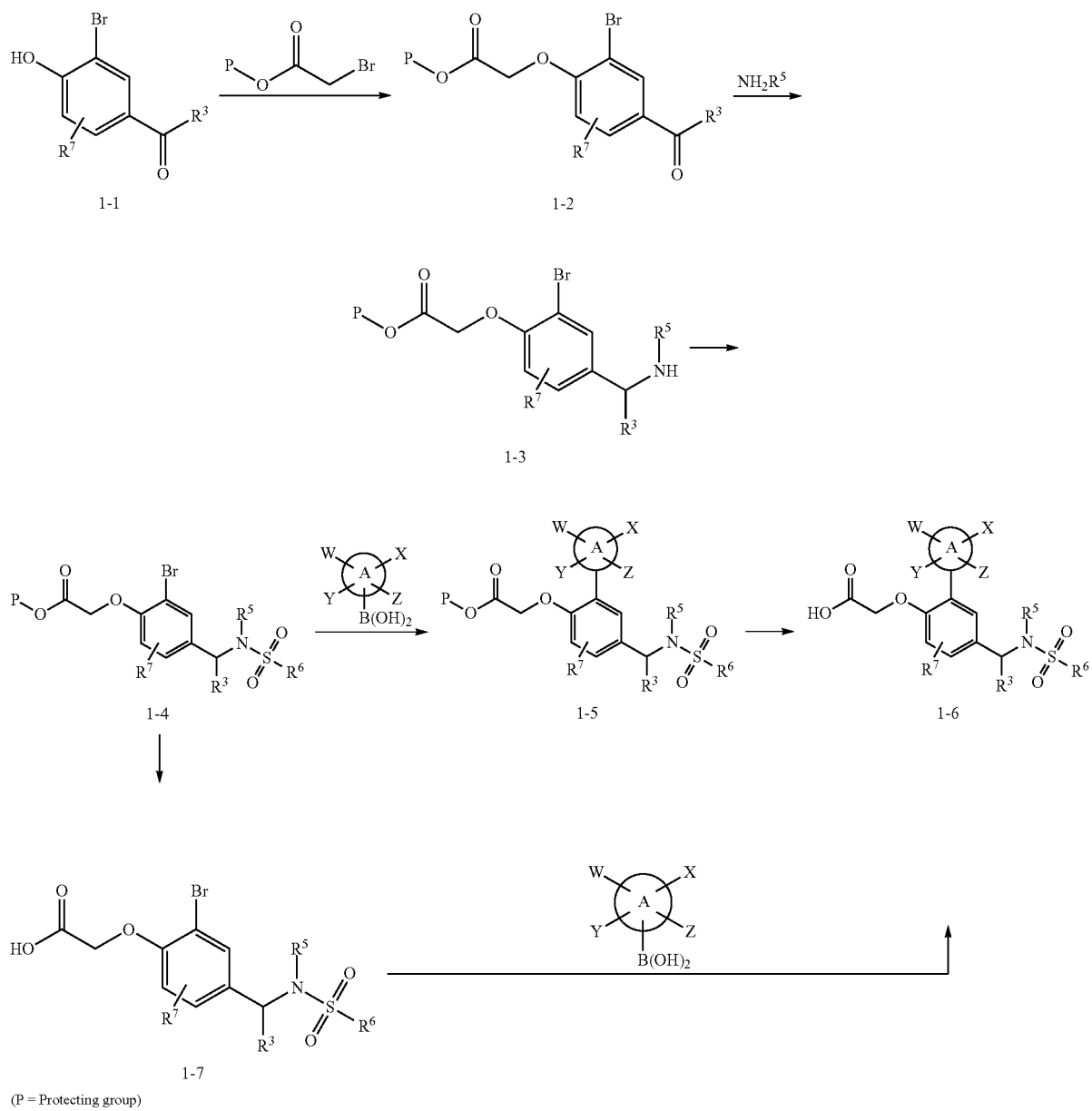

(P = Protecting group)

As shown in Synthetic Route 1, alkylation of hydroxyl derivative 1-1 with ester-protected 2-bromoacetate generates intermediate 1-2. Reductive amination with a primary amine yields amine product 1-3. In the case where $R^5$=H, the reductive amination can be carried out using ammonium acetate to generate 1-3. Amine 1-3 can be sulfonylated with an arylsulfonyl chloride to produce intermediate 1-4. Suzuki coupling with an appropriately-substituted boronic acid generates derivative 1-5 which upon deprotection of the ester yields affords carboxylic acid 1-6 of the invention. In an alternate version of Synthetic Route 1, deprotection of intermediate 1-4 may precede the Suzuki coupling reaction, generating acid intermediate 1-7. In this case, aryl coupling of 1-7 yields product 1-6 directly.

An alternative method for preparing compounds of the invention and intermediates thereof is illustrated in Synthetic Route 2.

Synthetic Route 2

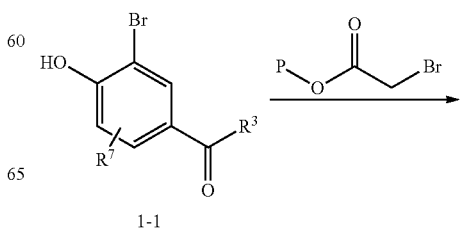

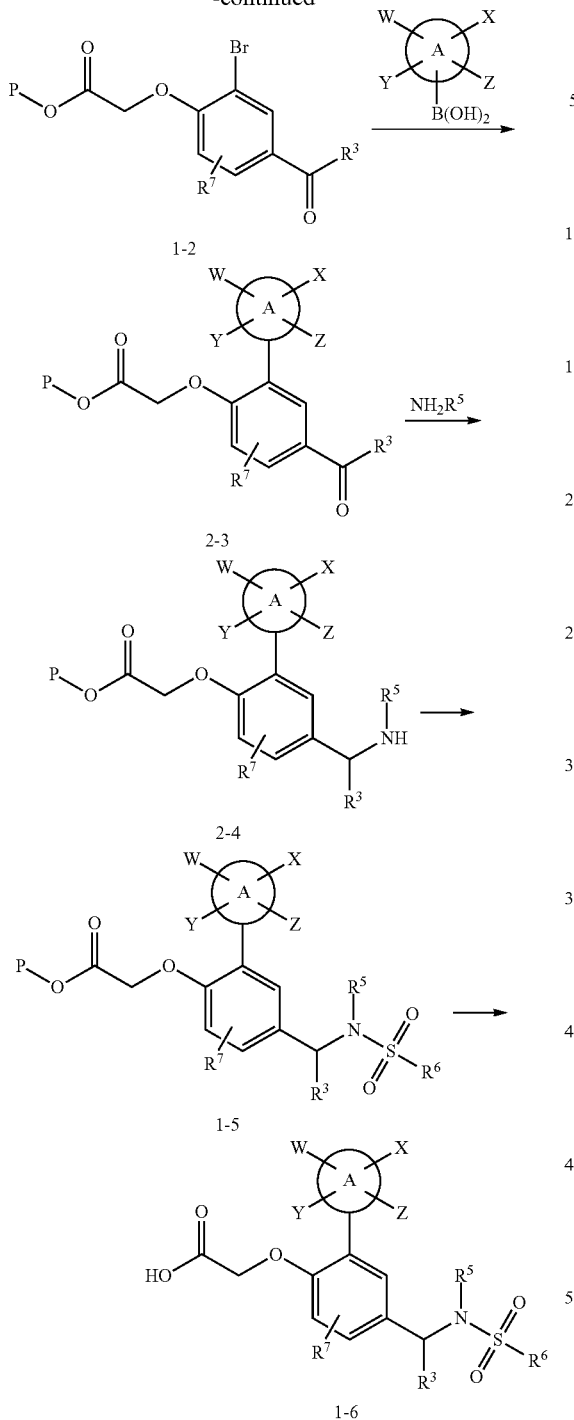

(P = Protecting Group)

Alkylation of hydroxyl derivative 1-1 with ester-protected 2-bromoacetate generates intermediate 1-2. Suzuki coupling with an appropriately-substituted boronic acid generates biaryl derivative 2-3. Reductive amination yields amine 2-4. In the case where $R^5$=H, the reductive amination can be carried out using hydroxylamine with hydrogenation over Raney nickel to generate 2-4. Sulfonylation with an arylsulfonyl chloride produces intermediate 1-5 which upon deprotection of the ester yields affords carboxylic acid 1-6 of the invention.

Alternatively, intermediate 2-3 can be synthesized as illustrated in Synthetic Route 3.

Synthetic Route 3

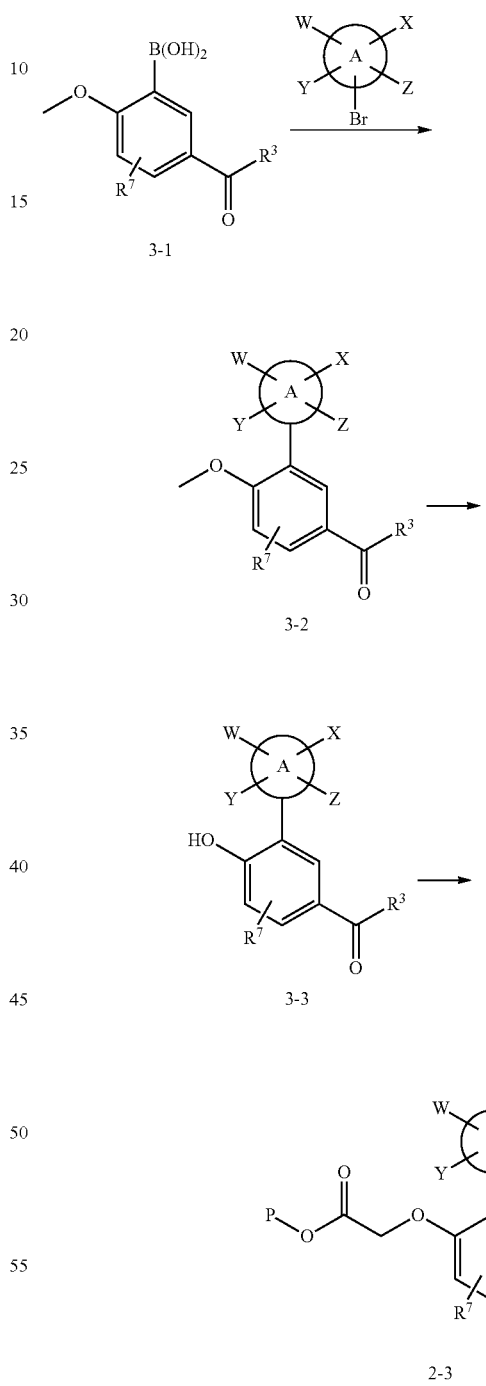

An appropriately substituted 2-methoxyphenylboronic acid derivative is coupled with an aromatic or heteroaromatic group under Suzuki conditions to generate intermediate 3-2. Deprotection of the ether, for example by boron tribromide, results in the phenol 3-3 which can be alkylated by ester-protected 2-bromoacetate to yield intermediate 2-3. Intermediate 2-3 can then be converted to a compound of the invention via the method of Synthetic Route 2.

Synthetic Route 4

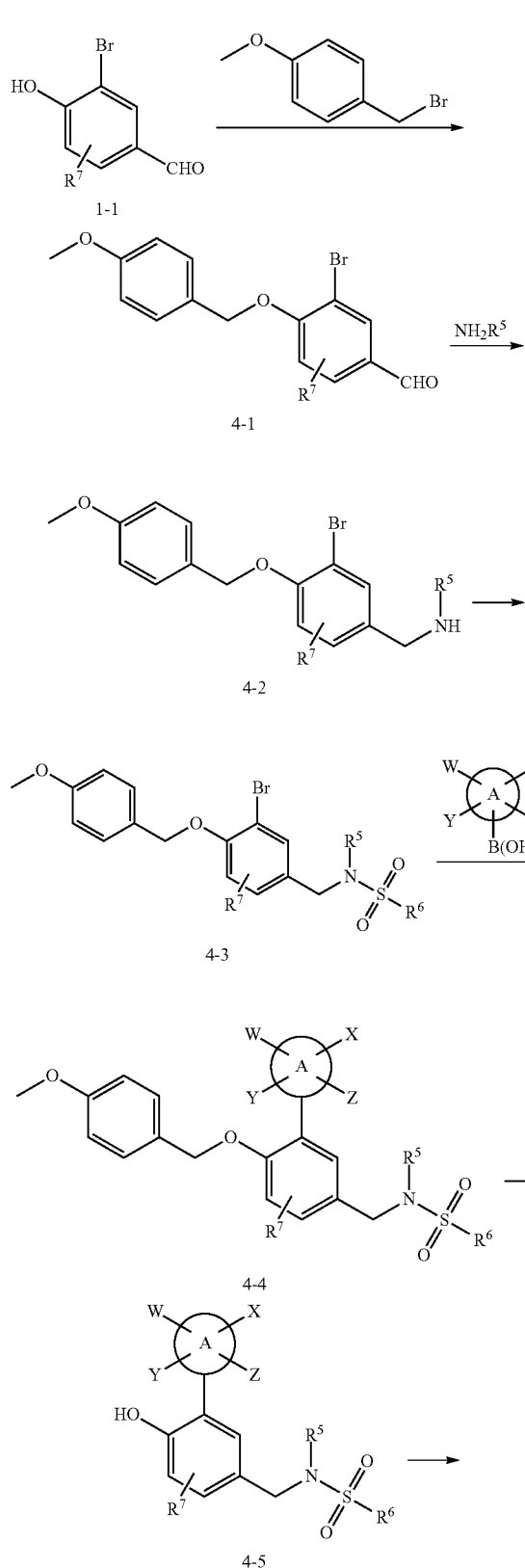

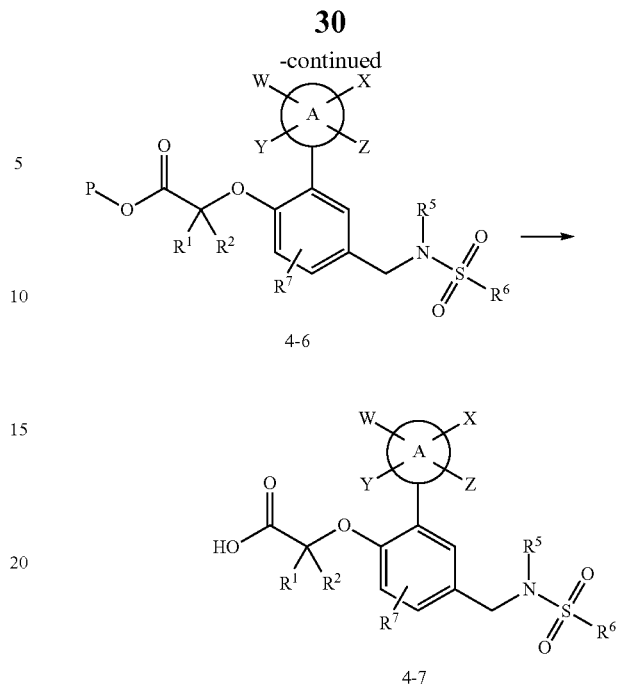

Another method for preparing compounds of the invention and intermediates thereof is illustrated in Synthetic Route 4. As shown, protection of the phenol of a substituted 3-bromo-4-hydroxybenzaldehyde derivative 1-1 produces protected ether 4-1. Reductive amination and Suzuki coupling yield intermediates 4-3 and 4-4 respectively. Ether deprotection unveils the phenol 4-5. Intermediate 4-6 can then be generated from 4-5 via either alkylation with an appropriately-protected, substituted bromoacetic acid derivative or Mitsunobu coupling with an appropriately-protected, substituted glycolic acid derivative. Final deprotection yields the acid 4-7.

Representative Examples of Synthetic Route 1

Example 5

2-(2-(3-cyanophenyl)-4-((4-fluoro-N-methylphenyl-sulfonamido)methyl)phenoxy)acetic acid

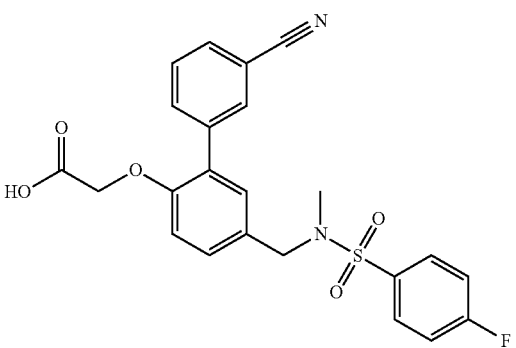

Example 5

Intermediate 1 t-butyl 2-(2-bromo-4-formylphenoxy)acetate (1)

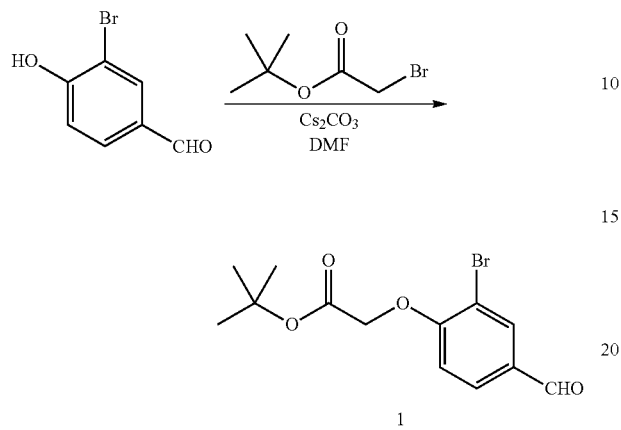

To a solution of 3-bromo-4-hydroxybenzaldehyde (5 g, 25 mmol, 1 eq, Aldrich, Milwaukee, Wis., USA) in DMF (200 mL) was added solid cesium carbonate (16.25 g, 50 mmol, 2 eq) followed by dropwise addition of t-butyl 2-bromoacetate (4.4 mL, 30 mmol, 1.2 eq, Aldrich, Milwaukee, Wis., USA). After stirring at room temperature for 18 h, the DMF was removed in vacuo and the resultant residue was extracted between EtOAc (50 mL) and brine (50 mL). The separated organic layer was dried ($Na_2SO_4$), and concentrated in vacuo to give 7.74 g (98.4%) of t-butyl 2-(2-bromo-4-formylphenoxy)acetate (1). $^1$HNMR ($CDCl_3$, 300 MHz): δ 9.83 (s, 1H), 8.08 (d, 1H), 7.76 (dd, 1H), 6.83 (d, 1H), 4.67 (s, 1H).1.44 (s, 9H).

The cesium carbonate can be replaced with other bases, for example potassium carbonate. A representative synthesis using potassium carbonate is shown below:

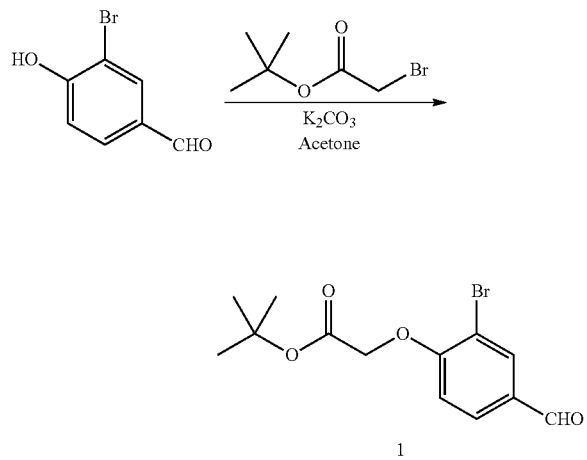

To a solution of 3-bromo-4-hydroxybenzaldehyde (100 g, 50 mol, 1 eq) in acetone (500 mL) was added potassium carbonate (135 g, 100 mmol, 2 eq) followed by t-butyl 2-bromoacetate (100 g, 50 mmol, 1 eq). After stirring at room temperature for 2 h, the acetone was removed in vacuo and the resultant residue was washed with water to give 150 g (89%) of t-butyl 2-(2-bromo-4-formylphenoxy)acetate (1).

Intermediate 2 t-butyl 2-(2-bromo-4-((methylamino)methyl)phenoxy)acetate (2)

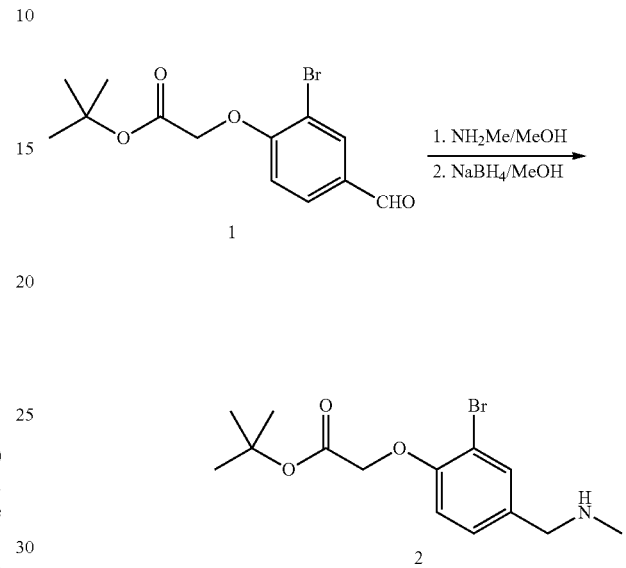

t-Butyl 2-(2-bromo-4-formylphenoxy)acetate (1) (10.11 g, 32.1 mmol, 1 eq) was dissolved in a 2 M solution of methylamine in methanol (30 mL, 60 mmol, 1.9 eq) and stirred at room temperature for 4 h. The solvent and excess methylamine were removed in vacuo and the resultant imine was dissolved in anhydrous methanol (200 mL). Sodium Borohydride (2.4 g) was added slowly under argon and the mixture was stirred for 2 h. Saturated $NaHCO_3$ (100 mL) was added and allowed to stir for 15 minutes at which point the methanol was removed in vacuo. The resultant aqueous mixture was extracted with DCM (2×50 mL) and the combined organic layers were washed with brine (100 mL), dried ($Na_2SO_4$) and concentrated in vacuo to yield 6.2 g (58%) of t-butyl 2-(2-bromo-4-((methylamino)methyl)phenoxy)acetate (2). $^1$HNMR ($CDCl_3$, 300 MHz): δ 7.50 (d, 1H), 7.15 (m, 1H), 6.72 (d, 1H), 4.55 (s, 2H), 3.65 (s, 2H), 2.41 (s, 3H), 1.45 (s, 9H).

Intermediate 3 t-butyl 2-(2-bromo-4-((4-fluoro-N-methylphenylsulfonamido)methyl)phenoxy)acetate (3)

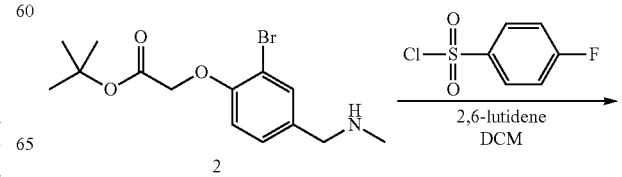

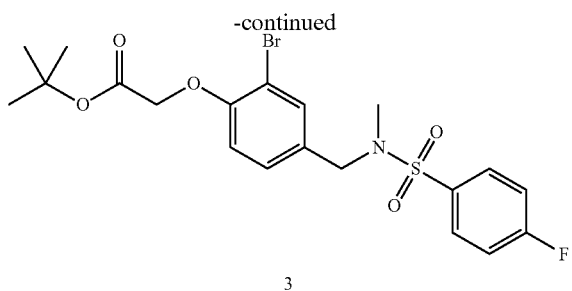

3

To a solution of t-butyl 2-(2-bromo-4-((methylamino)methyl)phenoxy)acetate (2) (4.4 g, 13.4 mmol, 1 eq) in DCM (50 mL) was added 2,6-lutidene (3.1 ml, 26.8 mmol, 2 eq) and 4-fluorobenzenesulfonyl chloride (2.9 g, 14.7 mmol. 1.1 eq, Aldrich, Milwaukee, Wis., USA). After the mixture was stirred for 18 h at room temperature, it was washed with 1 N HCl (100 mL), saturated NaHCO$_3$ (100 mL), and brine (100 mL). The washed DCM layer was dried over Na$_2$SO$_4$ and concentrated in vacuo. Silica gel purification (linear gradient of 0% EtOAc/hexanes to 100% EtOAc/hexanes) of the resultant residue yielded 2.95 g (44.8%) of t-butyl 2-(2-bromo-4-((4-fluoro-N-methylphenylsulfonamido)methyl)phenoxy)acetate (3) as a white solid. $^1$HNMR (CDCl$_3$, 300 MHz): δ 7.82 (m, 2H), 7.44 (d, 1H), 7.22 (m, 3H), 6.72 (d, 1H), 4.57 (s, 2H), 4.04 (s, 2H), 2.58 (s, 3H), 1.46 (s, 9H).

Intermediate 4 t-butyl 2-(2-(3-cyanophenyl)-4-((4-fluoro-N-methylphenylsulfonamido)methyl)phenoxy)acetate (4)

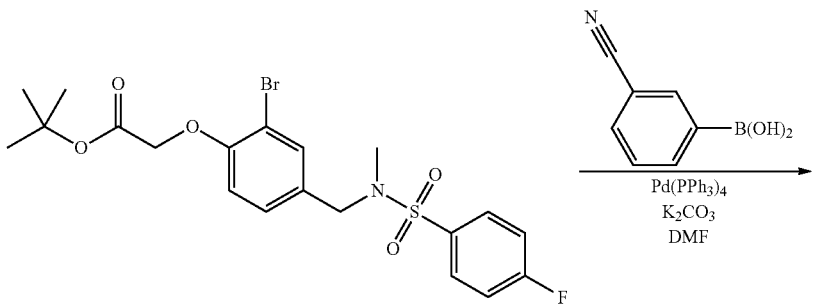

3

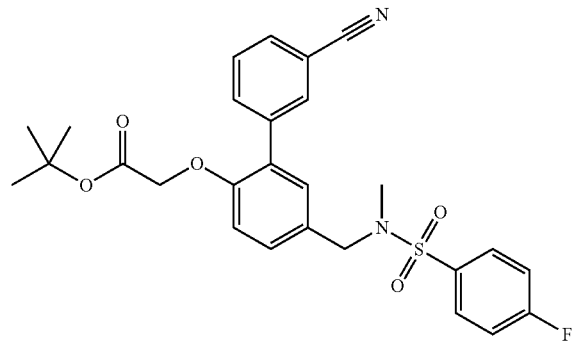

4

To a DMF (50 mL) solution of t-butyl 2-(2-bromo-4-((4-fluoro-N-methylphenylsulfonamido)methyl)phenoxy)acetate (3) (1.25 g, 2.6 mmol, 1 eq) was added 3-cyanobenzeneboronic acid (0.57 g, 3.8 mmol, 1.5 eq, Frontier Scientific, Inc., Logan, Utah, USA), potassium carbonate (1 g, 7.7 mmol, 3 eq), and tetrakis(triphenylphoshine)palladium (0.15 g, 0.13 mmol, 0.05 eq). The mixture was stirred at 90° C. for 18 h. After concentration in vacuo, the residue was extracted between EtOAc (100 ml) and brine (100 mL). The separated EtOAc layer was dried (Na$_2$SO$_4$), concentrated and purified via silica gel chromatography (linear gradient of 0% EtOAc/hexanes to 100% EtOAc/hexanes) to yield 0.78 g (59.8%) of t-butyl 2-(2-(3-cyanophenyl)-4-((4-fluoro-N-methylphenylsulfonamido)methyl)phenoxy)acetate (4). $^1$HNMR (CDCl$_3$, 300 MHz): δ 7.80 (m, 4H), 7.58 (m, 1H), 7.48 (t, 1H), 7.21 (m, 4H), 6.79 (d, 1H), 4.52 (s, 2H), 4.11 (s, 2H), 2.61 (s, 3H), 1.45 (s, 9H).

Example 5

2-(2-(3-cyanophenyl)-4-((4-fluoro-N-methylphenyl-sulfonamido)methyl)phenoxy)acetic acid

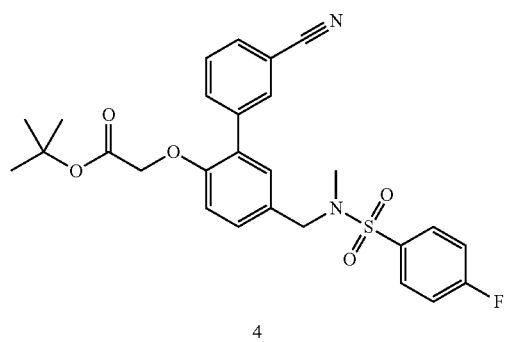

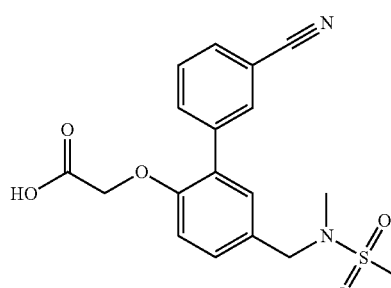

Example 5 t-butyl 2-(2-(3-cyanophenyl)-4-((4-fluoro-N-methylphenylsulfonamido)methyl)phenoxy)acetate (4) (780 mg; 1.53 mmol) was stirred in a mixture of TFA (15 mL) and DCM (30 mL) for 1 h. After concentration in vacuo, the residue was purified via reversed phase semi-preparative HPLC to yield 303 mg (43.6%) of 2-(2-(3-cyanophenyl)-4-((4-fluoro-N-methylphenylsulfonamido)methyl)phenoxy)acetic acid (Example 5) as a white solid. $^1$HNMR (CDCl$_3$, 300 MHz): δ 7.84 (m, 3H), 7.75 (m, 1H), 7.61 (m, 1H), 7.50 (t, 1H), 7.24 (m, 3H), 6.85 (d, 1H), 4.69 (s, 2H), 4.13 (s, 2H), 2.63 (s, 3H).

Example 9

2-(2-(3-cyanophenyl)-4-((4-fluorophenylsulfonamido)methyl)phenoxy)acetic acid

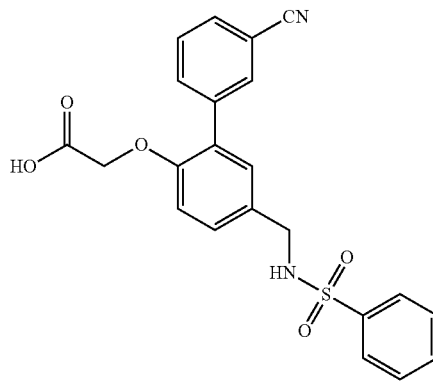

Example 9

Intermediate 6 t-butyl 2-(4-(aminomethyl)-2-bromophenoxy)acetate (6)

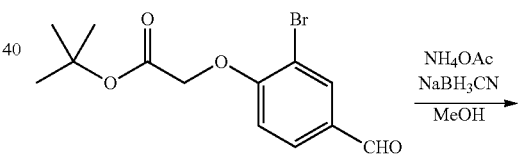

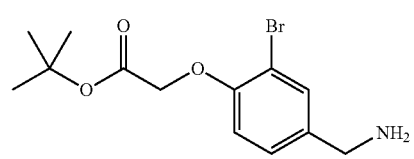

t-Butyl 2-(2-bromo-4-formylphenoxy)acetate (1) (0.5 g, 1.59 mmol, 1 eq) was dissolved in MeOH (23 mL) along with HOAc (14 mL) and NH$_4$OAc (6.23 g, 81 mmol; 51 eq). After stirring at room temperature room temperature for 4 h, sodium cyanoborohydride (146 mg; 2.27 mmol, 1.4 eq) was added and the mixture was stirred for an additional 18 h at room temperature. Water (4 mL) was added and the mixture was concentrated in vacuo. The resultant residue was purified by preparative HPLC to afford 91 mg (18.2%) of t-butyl 2-(4-(aminomethyl)-2-bromophenoxy)acetate (6).

Intermediate 7 t-butyl 2-(2-bromo-4-((4-fluorophenylsulfonamido)methyl)phenoxy)acetate (7)

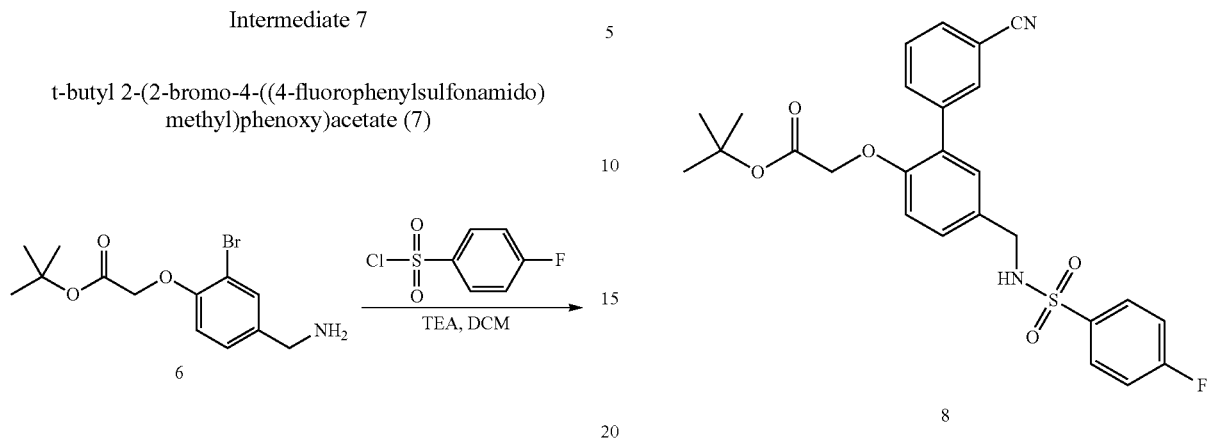

To a solution of t-butyl 2-(4-(aminomethyl)-2-bromophenoxy)acetate (6) (88 mg, 1 eq, 0.28 mmol) in DCM (15 mL) was added 4-fluoro-benzenesulfonyl chloride (65 mg, 0.33 mmol, 1.2 eq) and Et$_3$N (56 mg, 0.56 mmol, 2 eq). The mixture was stirred at room temperature for 2 h, filtered, concentrated in vacuo and purified by preparative TLC to give 64 mg (48%) of t-butyl 2-(2-bromo-4-((4-fluorophenylsulfonamido)methyl)phenoxy)acetate (7).

Intermediate 8 t-butyl 2-(2-(3-cyanophenyl)-4-((4-fluorophenylsulfonamido)methyl)phenoxy)acetate (8)

t-butyl 2-(2-bromo-4-((4-fluorophenylsulfonamido)methyl)phenoxy)acetate (7) (64 mg, 0.135 mmol, 1 eq), 3-cyanophenylboronic acid (30 mg, 0.20 mmol, 1.5 eq), K$_2$CO$_3$ (75 mg, 0.54 mmol, 4 eq), Pd(PPh$_3$)$_4$ (2.3 mg, 0.001 mmol, 0.01 eq) and 4 mL of dioxane/H$_2$O (4:1) were heated to 140° C. for 1 h in a microwave. The mixture was then cooled to room temperature, filtered, concentrated in vacuo, and purified by preparative TLC to give 51 mg (76%) of t-butyl 2-(2-(3-cyanophenyl)-4-((4-fluorophenylsulfonamido)methyl)phenoxy)acetate (8).

Example 9

2-(2-(3-cyanophenyl)-4-((4-fluorophenylsulfonamido)methyl)phenoxy)acetic acid

Example 9

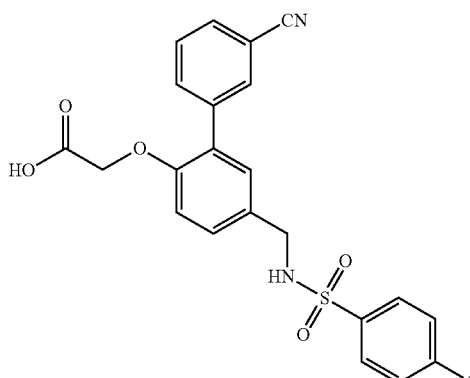

Example 9

To a solution of TFA/DCM (1:3, 6 mL) was added t-butyl 2-(2-(3-cyanophenyl)-4-((4-fluorophenylsulfonamido)methyl)phenoxy)acetate (8) (51 mg, 0.10 mmol, 1 eq) and the mixture was stirred at room temperature for 2 h. The organic solvent was removed in vacuo and the crude product was purified by reversed phase preparative HPLC to give 36 mg (82%) of 2-(2-(3-cyanophenyl)-4-((4-fluorophenylsulfonamido)methyl)phenoxy)acetic acid (Example 9).

$^1$HNMR (CD$_3$CN, 300 MHz): δ 7.92 (s, 1H), 7.80 (m, 3H), 7.70 (d, 1H), 7.59 (t, 1H), 7.20 (t, 3H), 7.10 (s, 1H), 6.88 (d, 1H), 6.14 (bm, 1H), 4.70 (s, 2H), 4.11 (d, 2H). MS (ES-API): MH$^-$=439.1. HPLC (Method A) t$_R$=2.12 min.

Example 37

2-(3-fluoro-5-methoxyphenyl)-4-((3-chloro-4-fluoro-N-methylphenylsulfonamido)methyl)phenoxyacetic acid Example 37

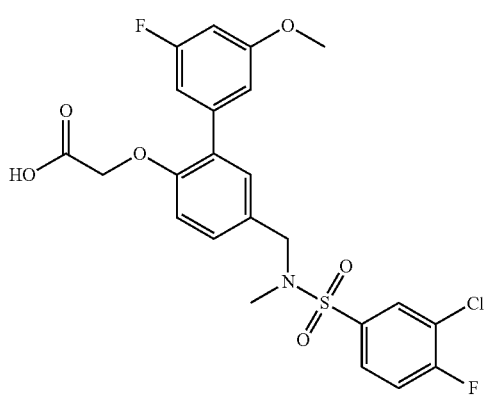

Intermediate 10 tert-butyl 2-(2-bromo-4-((3-chloro-4-fluoro-N-methylphenylsulfonamido)methyl)phenoxy)acetate (10)

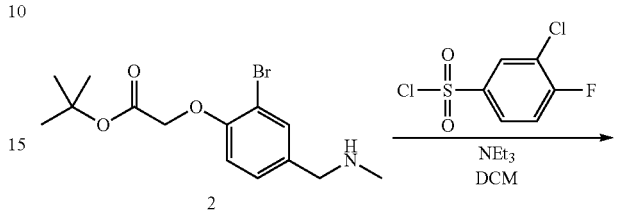

To a solution of t-butyl 2-(2-bromo-4-((methylamino)methyl)phenoxy)acetate (2) (68.8 g, 0.21 mol, 1 eq) in DCM (500 mL) was added triethylamine (42 g, 0.42 mol, 2 eq) and 3-chloro-4-fluorobenzene-1-sulfonyl chloride (47.8 g, 0.21 mol. 1 eq, Aldrich, Milwaukee, Wis., USA). After the mixture was stirred for 2 h at room temperature, DCM was evaporate. Crude product was recrystallized from ethanol to yield tert-butyl 2-(2-bromo-4-((3-chloro-4-fluoro-N-methylphenylsulfonamido)methyl)phenoxy)acetate (10) (64 g, 59%).

Intermediate 11 tert-butyl 2-(3-fluoro-5-methoxyphenyl)-4-((3-chloro-4-fluoro-N-methylphenylsulfonamido)methyl)phenoxyacetate (11)

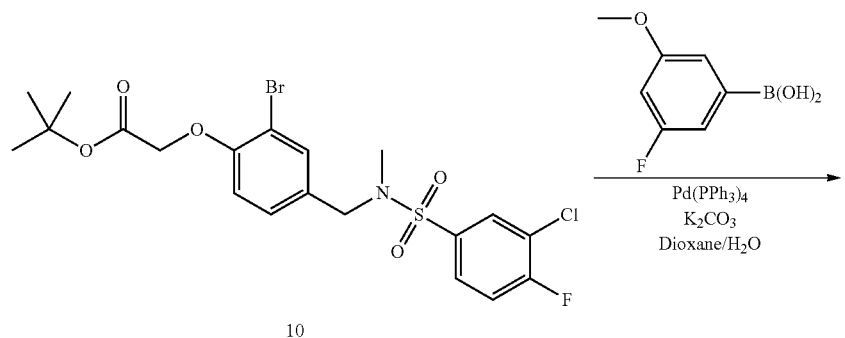

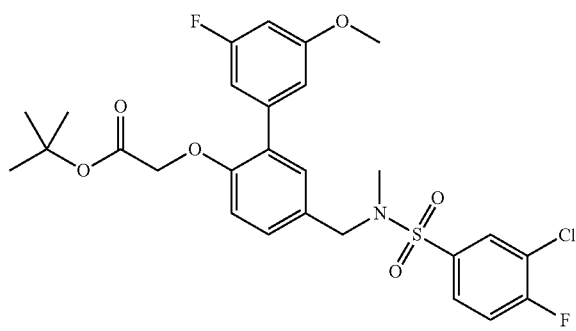

To a mixture of tert-butyl 2-(2-bromo-4-((3-chloro-4-fluoro-N-methylphenylsulfonamido)methyl)phenoxy)acetate (10) (140 g, 0.27 mol, 1 eq), 3-fluoro-5-methoxyphenylboronic acid (45.7 g, 0.27 mol, 1 eq, Combi-Blocks Inc., San Diego, Calif., USA) and potassium carbonate (111 g, 0.81 mol, 3 eq) in dioxane/water (3:1, 800 mL) was added tetrakis(triphenylphoshine)palladium (3.08 g, 2.7 mmol, 0.01 eq). The mixture was heated at 60° C. for 3 h under $N_2$. Solvent was evaporated, and the solid was dissolved in DCM and filtered. The DCM was evaporated and the crude product was recrystallized from ethanol to yield tert-butyl 2-(3-fluoro-5-methoxyphenyl)-4-((3-chloro-4-fluoro-N-methylphenylsulfonamido)methyl)phenoxyacetate (11) (70 g, 41%).

Example 37

2-(3-fluoro-5-methoxyphenyl)-4-((3-chloro-4-fluoro-N-methylphenylsulfonamido)methyl)phenoxyacetic acid

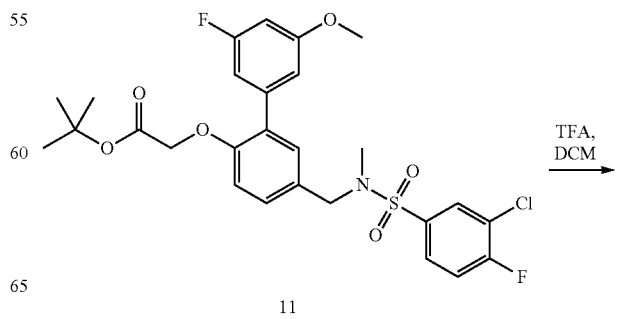

43

-continued

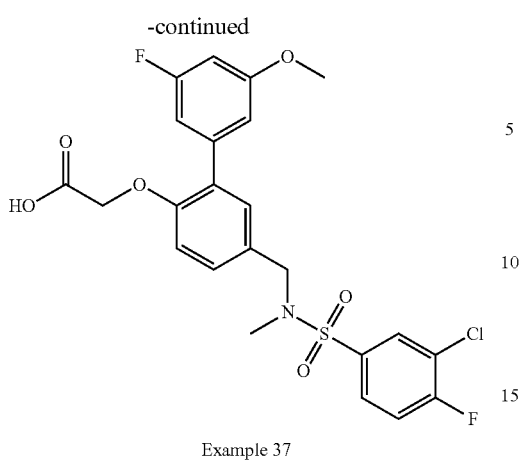

Example 37

To a solution of TFA/DCM (1:3, 80 mL) was added tert-butyl 2-(3-fluoro-5-methoxyphenyl)-4-((3-chloro-4-fluoro-N-methylphenylsulfonamido)methyl)phenoxyacetate (11) (15 g, 26 mol) and the mixture was stirred at room temperature for 2 h. The solvent was evaporated and the resulting solid was rinsed by petroleum ether/EtOAc (10:1 mixture) to yield 2-(3-fluoro-5-methoxyphenyl)-4-((3-chloro-4-fluoro-N-methylphenylsulfonamido)methyl)phenoxyacetic acid (Example 37) (9 g, 67%). $^1$HNMR (CD$_3$CN, 300 MHz): δ 7.93 (d, 1H), 7.78 (m, 1H), 7.45 (t, 1H), 7.20 (m, 2H), 6.95 (m, 3H), 6.67 (d, 1H), 4.65 (s, 2H), 4.15 (s, 2H), 3.81 (s, 3H), 2.61 (s, 3H). MS (ES-API): MH$^-$=510.0. HPLC (Method A) $t_R$=2.28 min.

Sodium Salt of Example 37. Sodium 2-(3-fluoro-5-methoxyphenyl)-4-((3-chloro-4-fluoro-N-methylphenylsulfonamido)methyl)phenoxyacetate Example 37

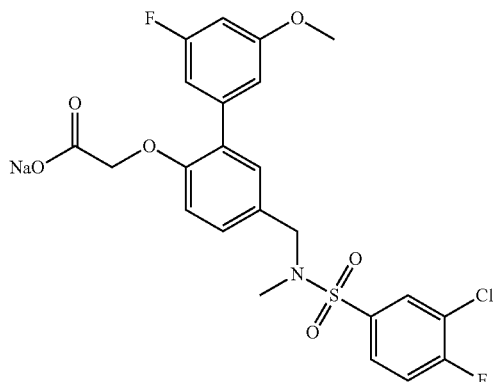

Sodium Salt

The sodium salt of Example 37 was prepared by dissolving the acid in aqueous NaOH (1 eq), following by freeze drying. Alternatively, the salt can be prepared by dissolving the acid in ethanol, following by addition of sodium ethoxide (1 eq). Evaporation of ethanol yielded sodium 2-(3-fluoro-5-methoxyphenyl)-4-((3-chloro-4-fluoro-N-methylphenylsulfonamido)methyl)phenoxyacetate).

44

$^1$HNMR (DMSO, 400 MHz): δ 8.02 (d, 1H), 7.83 (m, 1H), 7.67 (t, 1H), 7.15 (m, 2H), 7.07 (m, 2H), 6.88 (d, 1H), 6.73 (d, 1H), 4.22 (s, 2H), 4.13 (s, 2H), 3.78 (s, 3H), 2.60 (s, 3H).

Representative Examples of Synthetic Route 2

Example 16

2(3-N-methylsulfamoylphenyl)-4-((3-chloro-4-fluoro-N-methylphenylsulfonamido)methyl)phenoxyacetic acid Example 16

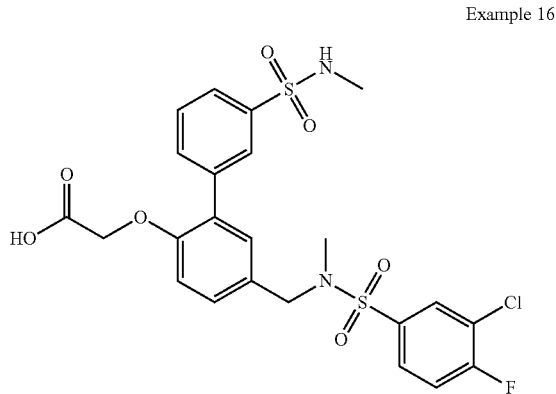 [SMILES: CNS(=O)(=O)c1cccc(-c2cc(CN(C)S(=O)(=O)c3ccc(F)c(Cl)c3)ccc2OCC(=O)O)c1]

Intermediate 12 t-butyl 2-(2-(3-N-methylsulfamoylphenyl)-4-formylphenoxy)acetate (12)

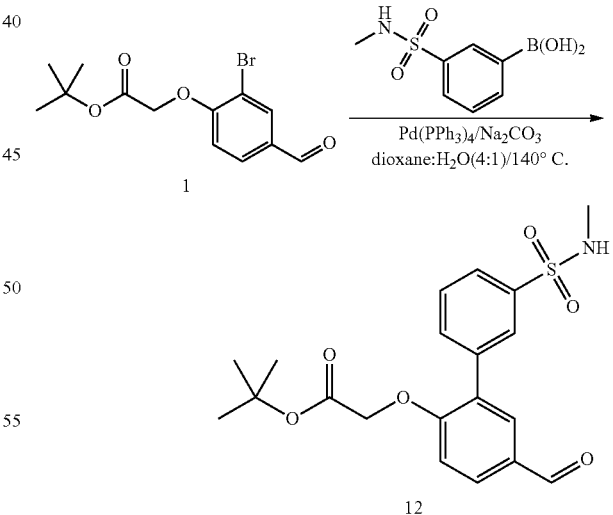

12

To a microwave tube was added t-butyl 2-(2-bromo-4-formylphenoxy)acetate (1) (300 mg, 0.96 mmol, 1 eq), 3-methylsulfamoylphenylboronic acid (413 mg, 1.92 mmol, 2 eq, Combi-Blocks Inc., San Diego, Calif., USA), K$_2$CO$_3$ (397 mg, 2.94 mmol, 3 eq), Pd(PPh$_3$)$_4$ (13.8 mg, 0.096 mmol, 0.01 eq) and a mixture of dioxane (10 mL) and water (2.5 mL). The mixture was stirred at 140° C. in a microwave for 1 h. After cooling to room temperature, the mixture was concentrated in vacuo and purified by preparative TLC to give 295 mg (76%) of t-butyl 2-(2-(3-N-methylsulfamoylphenyl)-4-formylphenoxy)acetate (12).

Intermediate 13 t-butyl 2-(2-(3-N-methylsulfamoylphenyl)-4-((methylamino)methyl)phenoxy)acetate (13)

289 mg (95%) of t-butyl 2-(2-(3-N-methylsulfamoylphenyl)-4-((methylamino)methyl)phenoxy)acetate (13) as oil.

Intermediate 14 t-butyl 2-(2-(3-N-methylsulfamoylphenyl)-4-((3-chloro-4-fluoro-N-methylphenylsulfonamido)methyl)phenoxy)acetate (14)

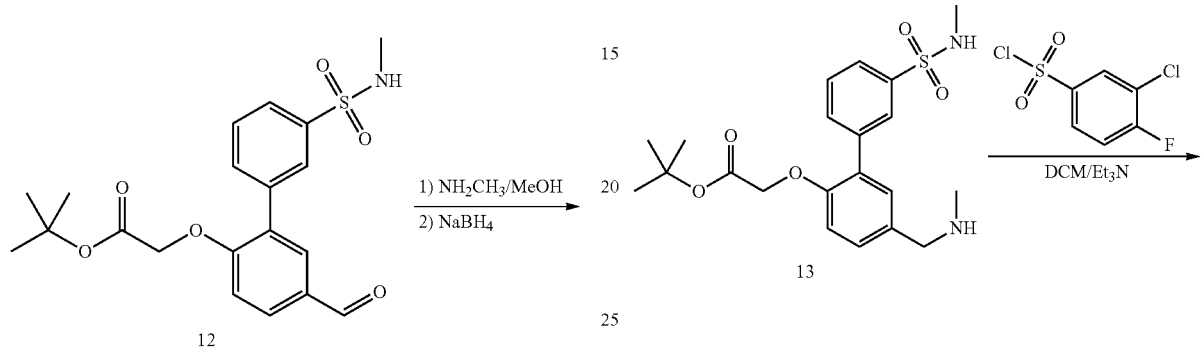

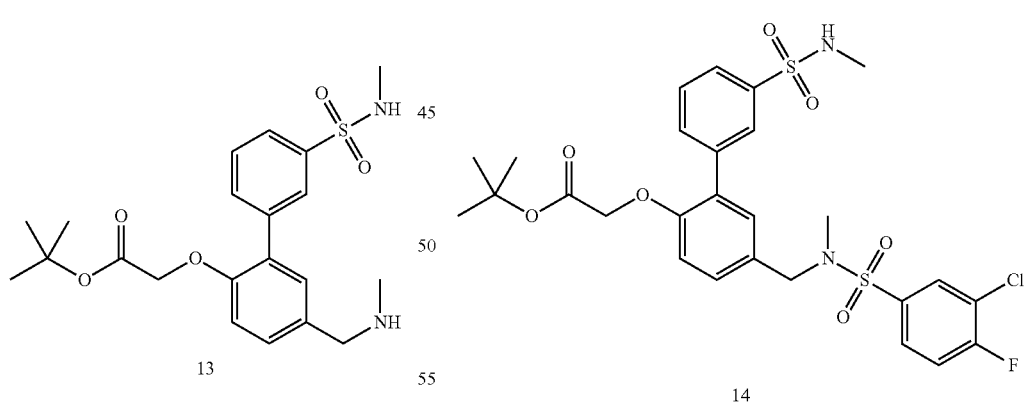

A solution of t-butyl 2-(2-(3-N-methylsulfamoylphenyl)-4-formylphenoxy)acetate (12) (291 mg, 0.72 mmol, 1 eq) and methylamine (0.53 mL of a 2M solution in THF; 1.08 mmol, 1.5 eq.) in methanol (20 mL) was stirred at room temperature for 2 h. Sodium borohydride (22 mg, 0.58 mmol, 0.5 eq.) was added, and the resulting mixture was stirred at room temperature for additional 2 h. Water (3 mL) was added and the MeOH was removed in vacuo. The resulting solution was extracted with EtOAc, and the combined organic layers were dried ($Na_2SO_4$), filtered, and concentrated in vacuo to afford To an anhydrous DCM (10 mL) solution of t-butyl 2-(2-(3-N-methylsulfamoylphenyl)-4-((methylamino)methyl)phenoxy)acetate (13) (100 mg, 0.24 mmol, 1 eq.) at 0° C., was added $Et_3N$ (73 mg, 0.72 mmol, 3 eq) followed by dropwise addition of a solution of 3-chloro-4-fluoro-benzenesulfonyl chloride (66 mg, 0.29 mmol, 1.2 eq) in DCM. After stirring at 0° C. for 20 min, the mixture was stirred at room temperature for 2 h and concentrated in vacuo to afford 140 mg of crude t-butyl 2-(2-(3-N-methylsulfamoylphenyl)-4-((3-chloro-4- fluoro-N-methylphenylsulfonamido)methyl)phenoxy)acetate (14) which was used directly without further purification.

Example 16

2-(2-(3-N-methylsulfamoylphenyl)-4-((3-chloro-4-fluoro-N-methylphenylsulfonamido)methyl)phenoxyacetic acid

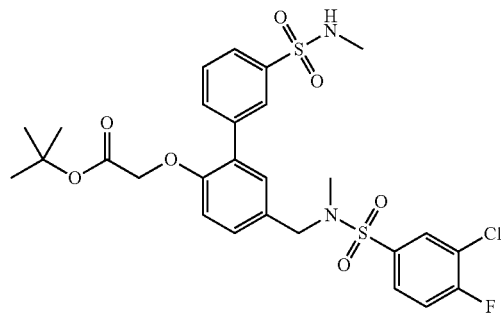

14

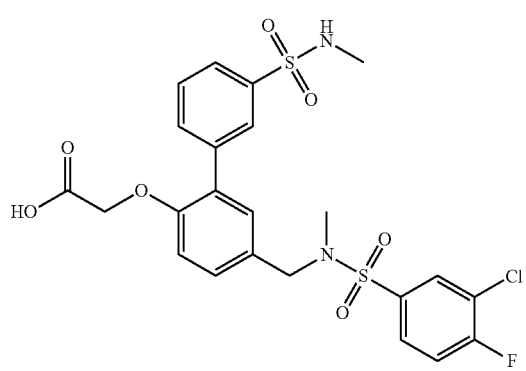

Example 16

To a solution of TFA/DCM (1:2, 30 mL) was added t-butyl 2-(2-(3-N-methylsulfamoylphenyl)-4-((3-chloro-4-fluoro-N-methylphenylsulfonamido)methyl)phenoxy)acetate (14) (250 mg, 0.41 mmol, 1 eq) and the mixture was stirred at room temperature for 8 h. The organic solvent was removed in vacuo and the crude product was purified by reversed phase semi-preparative HPLC to give 210 mg (92%) of 2-(2-(3-N-methylsulfamoylphenyl)-4-((3-chloro-4-fluoro-N-methylphenylsulfonamido)methyl)phenoxy)acetic acid (Example 16). $^1$HNMR (CD$_3$CN, 300 MHz): δ 8.08 (s, 1H), 7.96 (m, 1H), 7.79 (m, 3H), 7.67 (t, 1H), 7.47 (t, 1H), 7.29 (m, 2H), 7.01 (d, 1H), 5.55 (bm, 1H), 4.72 (s, 2H), 4.21 (s, 2H), 2.69 (s, 3H), 2.55 (d, 3H). MS (ES-API): MH$^-$=555.0. HPLC (Method A) $t_R$=2.36 min.

Example 22

2-(2-(3-trifluoromethylphenyl)-4-(1-(4-fluoro-N-methylphenylsulfonamido)ethyl)phenoxy)acetic acid

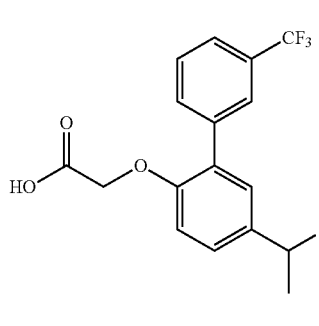

Example 22

Intermediate 15

1-(3-bromo-4-hydroxyphenyl)ethanone (15)

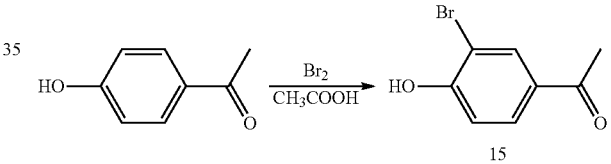

15

To a solution of 4-hydroxyacetophenone (6.8 g, 0.05 mol, 1 eq) in 60% acetic acid (50 mL), was added a solution of bromine (2.6 mL, 0.05 mol, 1 eq) in 80% acetic acid (20 mL). After stirring at room temperature for 30 min, the reaction mixture was poured into 100 mL of cold water. The solid was filtered and the filtrate was further diluted with 500 mL of cold water. The white precipitate was collected by filtration, washed with water and dried under vacuum to afford 4.2 g (39%) of 1-(3-bromo-4-hydroxyphenyl)ethanone (15) as white solid. $^1$HNMR (CDCl$_3$, 400 MHz): δ 8.15 (s, 1H), 7.86 (d, 1H), 7.18 (d, 1H), 5.96 (s, 1H), 2.56 (s, 3H). MS (ES-API): M+1=216.9. HPLC (Method B) $t_R$=2.48 min.

Intermediate 16 methyl 2-(4-acetyl-2-bromophenoxy)acetate (16)

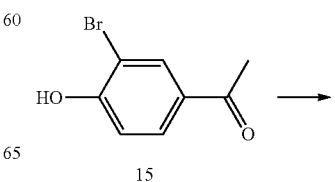

15

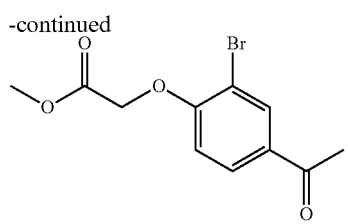

16

To a solution of 1-(3-bromo-4-hydroxyphenyl)ethanone (15) (963 mg, 4.48 mmol, 1 eq, Aldrich, Milwaukee, Wis., USA) in DMF (15 mL), was added methyl 2-bromoacetate (1.02 g, 6.72 mmol, 1.5 eq) and potassium carbonate (1.86 g, 13.5 mmol; 3 eq). The reaction mixture was stirred at room temperature for 18 h. Solvent was removed in vacuo, and the residue was dissolved in EtOAc, washed by water and brine, dried ($Na_2SO_4$), filtered, and concentrated in vacuo to give 1.05 g, (81%) of methyl 2-(4-acetyl-2-bromophenoxy)acetate (16) as a brown solid.

Intermediate 17 methyl 2-(4-acetyl-2-(3-trifluoromethylphenyl)phenoxy)acetate (17)

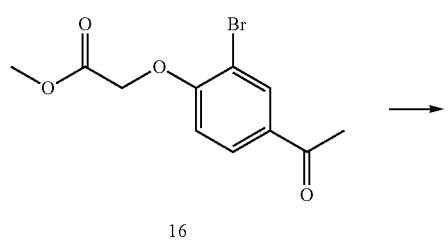

Methyl 2-(4-acetyl-2-bromophenoxy)acetate (16) (710 mg, 2.5 mmol, 1 eq), 3-(trifluoromethyl)phenylboronic acid (709 mg, 3.75 mmol, 1.5 eq, Aldrich, Milwaukee, Wis., USA) and tetrakis(triphenylphosphine) palladium (100 mg, 0.086 mmol, 0.03 eq) were dissolved in t-BuOH (1 mL) and $K_2CO_3$ (1 mL of a 4 M solution in $H_2O$) and heated in a microwave at 120° C. for 20 min. The resultant reaction mixture was diluted with EtOAc, washed with water and brine, dried ($Na_2SO_4$), filtered, and concentrated in vacuo. The obtained residue was purified via silica gel chromatography (20% EtOAc/hexane) to give 650 mg (74%) of methyl 2-(4-acetyl-2-(3-trifluoromethylphenyl)phenoxy)acetate (17) as white solid. $^1$HNMR ($CDCl_3$, 400 MHz): δ 8.43 (s, 2H), 7.90 (m, 2H), 7.60 (m, 2H), 6.89 (d, 1H), 4.72 (s, 2H), 3.79 (s, 3H), 2.59 (s, 3H). MS (ES-API): M+1=353.1. HPLC (Method B) $t_R$=3.28 min.

Intermediate 18 methyl 2-(2-(3-trifluoromethylphenyl)-4-(1-(methylamino)ethyl)phenoxy)acetate (18)

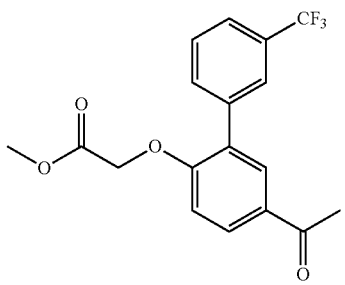

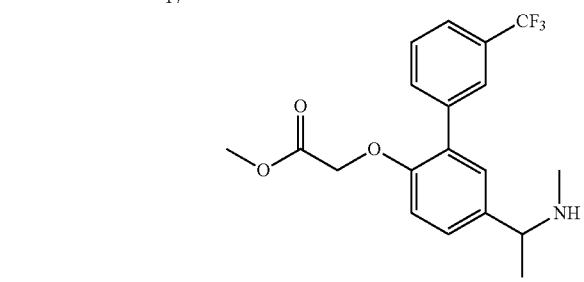

To a solution of methyl 2-(4-acetyl-2-(3-trifluoromethylphenyl)phenoxy)acetate (17) (529 mg, 1.5 mmol, 1 eq) in MeOH (5 mL) was added methylamine hydrochloride (603 mg, 9.0 mmol, 6 eq) and sodium cyanoborohydride (93 mg, 1.5 mmol, 1 eq). The reaction mixture was stirred at room temperature for 8 days, diluted with ethyl acetate, washed with water, dried ($Na_2SO_4$), and concentrated in vacuo to give crude compound methyl 2-(2-(3-trifluoromethylphenyl)-4-(1-(methylamino)ethyl)phenoxy)acetate (18) as white solid (600 mg) which was carried directly to the next step.

Intermediate 19 methyl 2-(2-(3-trifluoromethylphenyl)-4-(1-(4-fluoro-N-methylphenylsulfonamido)ethyl)phenoxy)acetate (19)

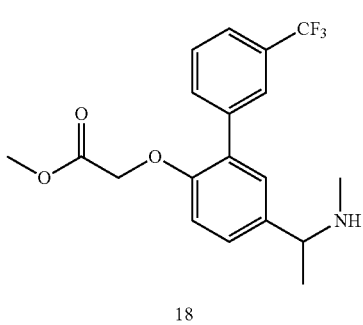

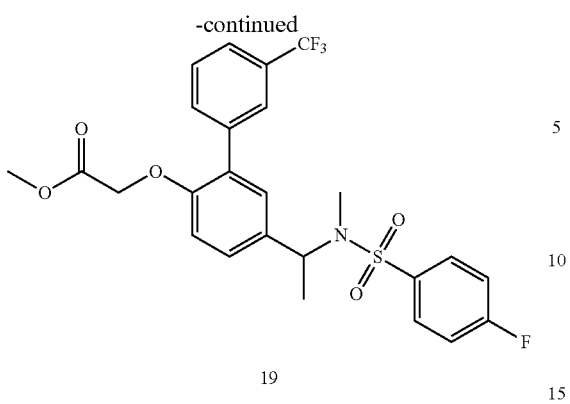

19

To a solution of crude methyl 2-(2-(3-trifluoromethylphenyl)-4-(1-(methylamino)ethyl)phenoxy)acetate (18) (100 mg) in 2 mL of THF, was added DIEA (105 mg), and 4-fluorobenzene-1-sulfonyl chloride (87 mg). The reaction mixture was stirred at room temperature for 1 hr and then purified via silica gel chromatography (25% EtOAc/hexane) to give methyl 2-(2-(3-trifluoromethylphenyl)-4-(1-(4-fluoro-N-methylphenylsulfonamido)ethyl)phenoxy)acetate (19) which was carried directly to the next step.

Example 22

2-(2-(3-trifluoromethylphenyl)-4-(1-(4-fluoro-N-methylphenylsulfonamido)ethyl)phenoxy)acetic acid

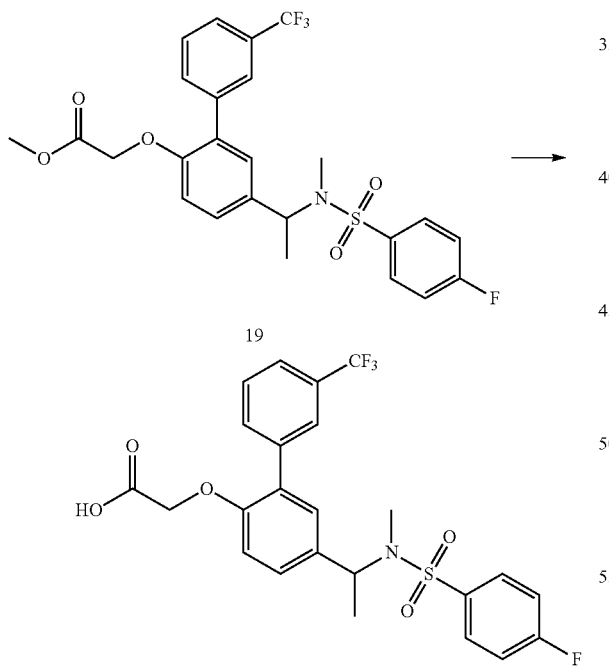

Example 22

To a solution of methyl 2-(2-(3-trifluoromethylphenyl)-4-(1-(4-fluoro-N-methylphenylsulfonamido)ethyl)phenoxy)acetate (19) in MeOH/H$_2$O (4/1) was added lithium hydroxide (2 eq) and the mixture was stirred at room temperature for 2 h. After concentrating in vacuo, the residue was purified via semi-preparative HPLC to give 21.9 mg, (15.2% from Intermediate 18) of 2-(2-(3-trifluoromethylphenyl)-4-(1-(4-fluoro-N-methylphenylsulfonamido)ethyl)phenoxy)acetic acid (Example 22) as white solid. $^1$HNMR (CDCl$_3$, 400 MHz): δ 7.61 (s, 1H), 7.53 (m, 3H), 7.31 (m, 1H), 7.25 (m, 1H), 7.22 (m, 1H), 7.03 (m, 2H), 6.72 (d, 1H), 5.01 (m, 1H), 4.14 (s, 2H), 2.38 (s, 3H), 1.06 (d, 3H). MS (ES-API): M=323.1 (main fragment). HPLC (Method B) t$_R$=3.43 min.

Example 64

2-(3-cyano-5-fluorophenyl)-4-((4-fluoro-N-methylphenylsulfonamido)methyl)phenoxyacetic acid Example 64

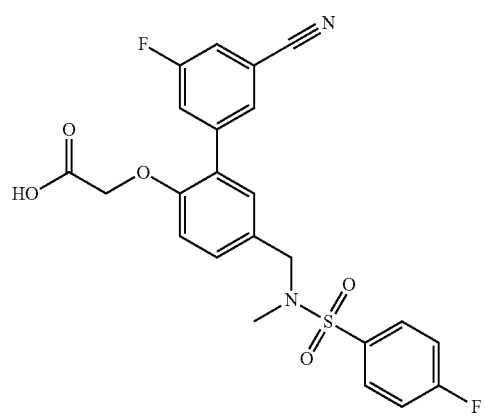

Intermediate 20

3-fluoro-5-(4,4,5,5-tetramethyl-1,3,2-dioxaborolan-2-yl)benzonitrile

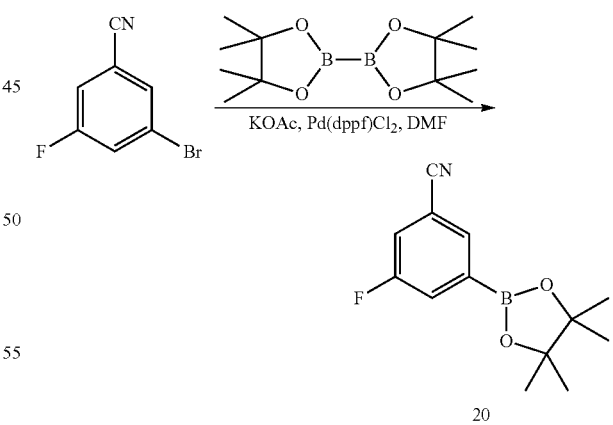

20

To a mixture of 3-bromo-5-fluorobenzonitrile (100 g, 0.5 mol, Oakwood Products, Inc., West Columbia, S.C., USA), 4,4,5,5-tetramethyl-2-(4,4,5,5-tetramethyl-1,3,2-dioxaborolan-2-yl)-1,3,2-dioxaborolane (280 g, 1.4 mol), potassium acetate (135 g, 1.1 mol) in DMF (1200 mL) was added Pd(dppf)Cl$_2$ (21 g, 28 mmol). The mixture was heated at 100-110° C. for 6 h. DMF was evaporated and the residue was suspended in water and extracted with EtOAc (3×). The combined EtOAc layers were dried over Na$_2$SO$_4$ and evaporated. The residue was purified by column chromatography (PE:EA=10:1 v/v) to give 3-fluoro-5-(4,4,5,5-tetramethyl-1,3,2-dioxaborolan-2-yl)benzonitrile (20) (190 g in 60% purity).

$^1$HNMR (CDCl$_3$, 400 MHz): δ 7.84 (s, 1H), 7.68 (d, 1H), 7.38 (m, 1H), 1.32 (s, 12H).

Intermediate 21 t-butyl 2-(2-(3-cyano-5-fluorophenyl)-4-formylphenoxy)acetate (21)

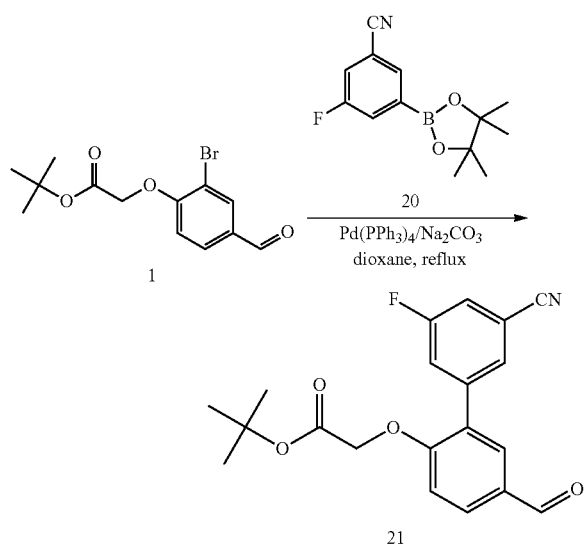

To solution of tert-butyl 2-(2-bromo-4-formylphenoxy)acetate (1) (120 g, 0.38 mol) in dioxane/H$_2$O (4:1, 700 mL) was added 3-fluoro-5-(4,4,5,5-tetramethyl-1,3,2-dioxaborolan-2-yl)benzonitrile (20) (158 g in 60% purity, 0.38 mol), Na$_2$CO$_3$ (81 g, 0.76 mol) and Pd(PPh$_3$)$_4$ (22 g, 19 mmol) under N$_2$. The mixture was stirred at 80° C. for 3 h. After cooling to room temperature, the mixture was concentrated in vacuo and purified by column chromatography (PE:EA=10:1 v/v) to give 90 g of t-butyl 2-(2-(3-cyano-5-fluorophenyl)-4-formylphenoxy)acetate (21) (90 g, 67%).

Intermediate 22 t-butyl 2-(2-(3-cyano-5-fluorophenyl)-4-((methylamino)methyl)phenoxy)acetate (22)

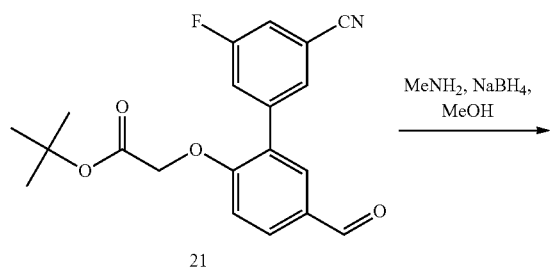

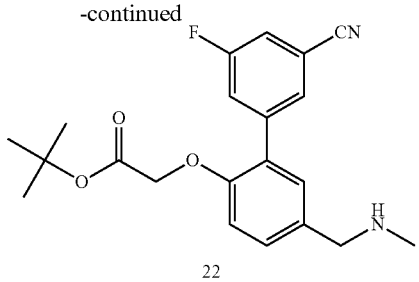

A solution of t-butyl 2-(2-(3-cyano-5-fluorophenyl)-4-formylphenoxy)acetate (21) (120 g, 338 mmol) and MeNH$_2$ (203 mL of a 2M solution in THF, 405 mmol) in methanol (300 mL) was stirred at room temperature for 2 h. Sodium borohydride (12 g, 316 mmol) was added, and the resulting mixture was stirred at room temperature for additional 2 h. Water (30 mL) was added and the MeOH was removed in vacuo. The resulting solution was extracted with EA (3×), and the combined organic layers were dried over Na$_2$SO$_4$, filtered, and concentrated. The crude product t-butyl 2-(2-(3-cyano-5-fluorophenyl)-4-((methylamino)methyl)phenoxy)acetate (22) was used in the next reaction without further purification.

Intermediate 23 t-butyl 2-(2-(3-cyano-5-fluorophenyl)-4-((4-fluoro-N-methylphenylsulfonamido)methyl)phenoxy)acetate (23)

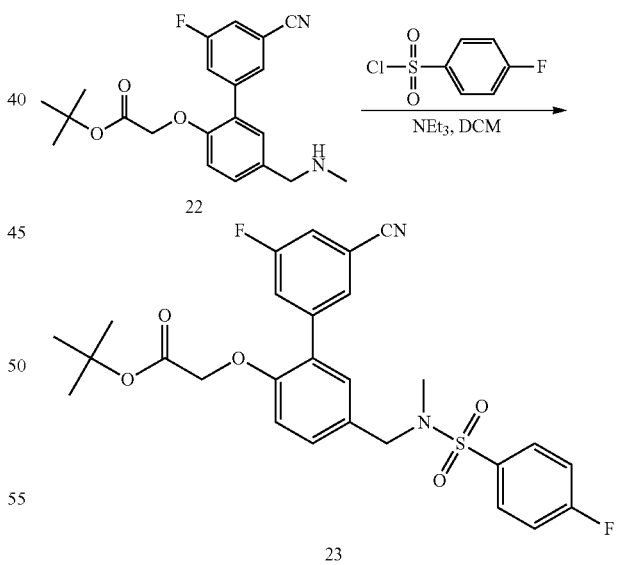

To an anhydrous DCM (50 mL) solution of t-butyl 2-(2-(3-cyano-5-fluorophenyl)-4-((methylamino)methyl)phenoxy)acetate (22) (28 g, 72 mmol), was added Et$_3$N (8.6 g, 85 mmol) followed by portionwise addition of 4-fluoro-benzenesulfonyl chloride (16.6 g, 85 mmol). The mixture was stirred at room temperature for 20 min and water (20 mL) was added. The organic layer was separated, dried and concentrated in vacuo. The crude was purified by column chromatography to give t-butyl 2-(2-(3-cyano-5-fluorophenyl)-4-((4-fluoro-N-methylphenylsulfonamido)methyl)phenoxy) acetate (23) (24 g, 63%).

Example 64

2-(3-cyano-5-fluorophenyl)-4-((4-fluoro-N-methylphenylsulfonamido)methyl)phenoxyacetic acid

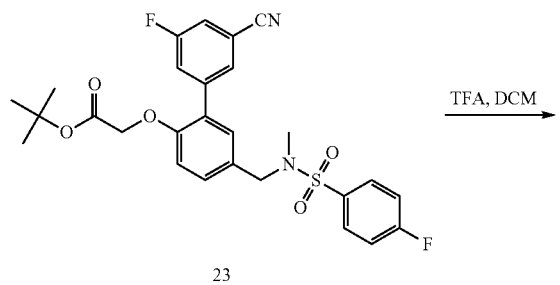

23

(d, 1H), 4.75 (s, 2H), 4.17 (s, 2H), 2.65 (s, 3H). MS (ES-API): MH⁻=471.1. HPLC (Method A) $t_R$=1.67 min.

Sodium Salt of Example 64. Sodium 2-(3-cyano-5-fluorophenyl)-4-((4-fluoro-N-methylphenylsulfonamido)methyl)phenoxyacetate

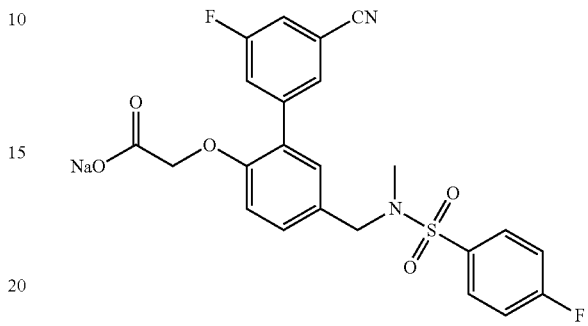

Sodium salt of Example 64

The sodium salt of Example 64 can be prepared by dissolving the acid in aqueous NaOH (1 eq). Freeze drying of the solution yielded the sodium salt.

¹HNMR (DMSO, 400 MHz): δ 8.12 (d, 1H), 8.02 (s, 1H), 7.89 (m, 2H), 7.74 (d, 1H), 7.48 (t, 2H), 7.19 (m, 2H), 6.93 (d, 1H), 4.22 (s, 2H), 4.09 (s, 2H), 2.56 (s, 3H).

Compounds with an R7 substitution (1-6) can be prepared by Synthetic Route 1 or Route 2 starting from a substituted hydroxybenzyaldehyde. Preparation of fluoro-substituted hydroxybenzyaldehydes were exemplified by Intermediate 24, 25 and 26. Similarly prepared were the chloro-substituted hydroxybenzyaldehydes.

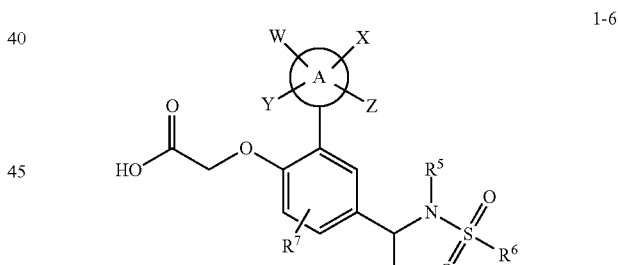

1-6

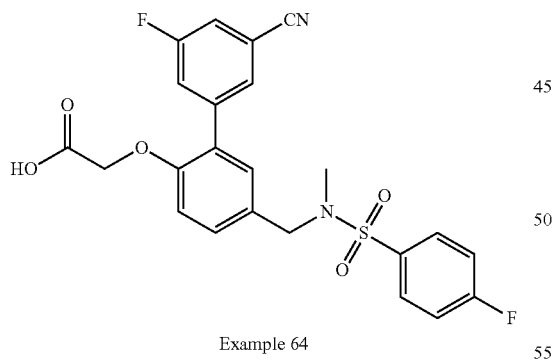

Example 64

To a solution of TFA/DCM (1:3=V/V, 30 mL) was added give t-butyl 2-(2-(3-cyano-5-fluorophenyl)-4-((4-fluoro-N-methylphenylsulfonamido)methyl)phenoxy)acetate (23) (25 g, 47.3 mmol) and the mixture was stirred at room temperature for 4 h. The organic solvent was removed in vacuo to afford of 2-(3-cyano-5-fluorophenyl)-4-((4-fluoro-N-methylphenylsulfonamido)methyl)phenoxyacetic acid (Example 64) (23 g, quantitative).

¹HNMR (CD₃CN, 300 MHz): δ 7.89 (m, 2H), 7.84 (s, 1H), 7.71 (m, 1H), 7.52 (m, 1H), 7.33 (m, 3H), 7.28 (s, 1H), 7.03

Intermediate 24

5-bromo-2-fluoro-4-hydroxybenzaldehyde (24)

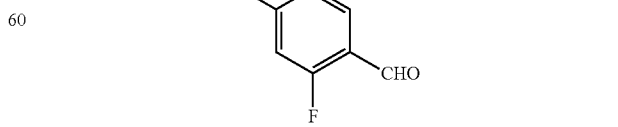

24

To the solution of 2-fluoro-4-methoxybenzaldehyde (3 g, 19.5 mmol, 1 eq., Aldrich, Milwaukee, Wis., USA) in DCM (80 mL) was added dropwise BBr₃ (14.5 g, 58.7 mmol, 3 eq.) at 0° C. The mixture was stirred for 15 min, then warmed to room temperature and continued to stir for additional 3 h. The reaction was quenched by careful addition of water (50 mL), the organic layer was separated, and remaining the aqueous layer was extracted with DCM (2×50 mL). The combined organic layers were concentrated in vacuo and purified by silica gel chromatography (DCM:MeOH=25:1 to 10:1) to afford 2.2 g (80.6%) of 2-fluoro-4-hydroxybenzaldehyde (24).

Intermediate 25

5-bromo-2-fluoro-4-hydroxybenzaldehyde (25)

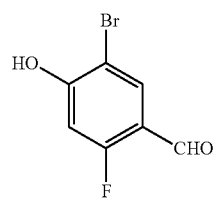

To a solution of 2-fluoro-4-hydroxybenzaldehyde (2.2 g, 15.7 mmol, 1 eq) in acetic acid (70 mL) was added a solution of bromine (2.71 g, 17.0 mmol, 1.1 eq) in acetic acid (10 mL), and the mixture was stirred at 45° C. for 26 h. The reaction was concentrated in vacuo, brine (50 mL) was added, and the mixture was extracted with EtOAc (3×80 mL). The combined organic layers were dried (Na₂SO₄), concentrated in vacuo. The resultant residue was purified by silica gel chromatography (DCM:MeOH=15:1 to 5:1) to afford 1.2 g (35%) of 5-bromo-2-fluoro-4-hydroxybenzaldehyde (25).

Intermediate 26

3-bromo-5-fluoro-4-hydroxybenzaldehyde (26)

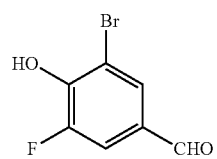

To a solution of 3-fluoro-4-hydroxybenzaldehyde (2 g, 14.3 mmol, 1 eq, Oakwood Products, Inc., West Columbia, S.C., USA) in acetic acid (60 mL), was added a solution of bromine (2.7 g, 17.0 mmol, 1.2 eq) in acetic acid (10 mL), and the mixture was stirred at 45° C. for 26 h. After concentration in vacuo, brine (50 mL) was added to the residue and the mixture was extracted with EtOAc (3×80 mL). The combined organic layers were dried (Na₂SO₄), concentrated in vacuo, and purified by reversed phase semi-preparative .HPLC to afford 1.5 g (48%) of 3-bromo-5-fluoro-4-hydroxybenzaldehyde (26).

Representative Example of Synthetic Route 3

Example 28

2-((4-fluoro-3-(methylsulfonyl)phenyl)-4-((4-fluoro-N-methylphenylsulfonamido)methyl)phenoxy)acetic acid

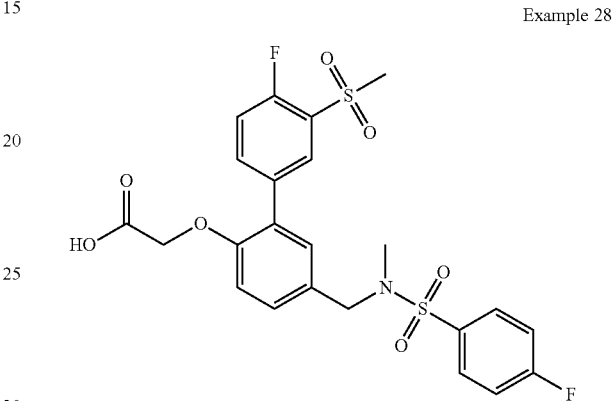

Intermediate 27

3-(4-fluoro-3-(methylsulfonyl)phenyl)-4-methoxy-benzaldehyde (27)

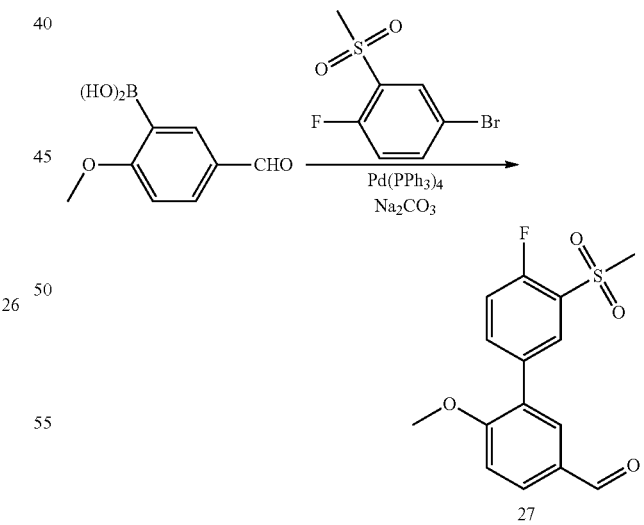

To a solution of 5-Formyl-2-methoxyphenylboronic acid (324 mg, 1.8 mmol, 1.5 eq, Frontier Scientific, Inc., Logan, Utah, USA) in dioxane:H₂O (2:1; 15 mL) was added 4-bromo-1-fluoro-2-(methylsulfonyl)benzene (300 mg, 1.2 mmol, 1.0 eq., Apollo Scientific Ltd., Stockport, Cheshire, UK), K₂CO₃ (496 mg, 3.6 mmol, 2 eq.) and Pd(PPh₃)₄ (30 mg). The mixture was stirred under nitrogen at 140° C. in a microwave for 40 min. Solvent was evaporated and the residue was dissolved in DCM and washed with water. The DCM layer was dried and evaporated. Purification via column chromatography (eluent: PE:EA=3:1) yielded 400 mg (72%) of 3-(4-fluoro-3-(methylsulfonyl)phenyl)-4-methoxybenzaldehyde (27).

Intermediate 28

3-(4-fluoro-3-(methylsulfonyl)phenyl)-4-hydroxybenzaldehyde (28)

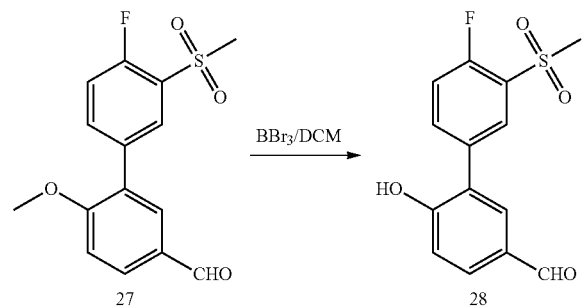

To a cooled solution (0° C.) of 3-(4-fluoro-3-(methylsulfonyl)phenyl)-4-methoxybenzaldehyde (27) (400 mg, 1.3 mmol, 1 eq.) in DCM (20 mL) was added BBr$_3$ (0.4 mL). The reaction mixture was stirred room temperature for 3 h. After cooling to 0° C., methanol was added and the mixture was concentrated under vacuum. The residue was diluted with DCM and washed with water. The DCM was dried (Na$_2$SO$_4$) and concentrated in vacuo. The residue was purified by column chromatography (eluent: PE:EA=1:1) to give 340 mg (89%) of 3-(4-fluoro-3-(methylsulfonyl)phenyl)-4-hydroxybenzaldehyde (28).

Intermediate 29 t-butyl 2-(2-(4-fluoro-3-(methylsulfonyl)phenyl)-4-formylphenoxy)acetate (29)

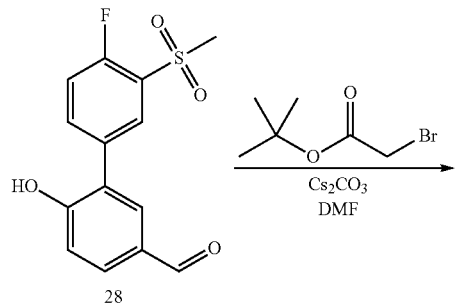

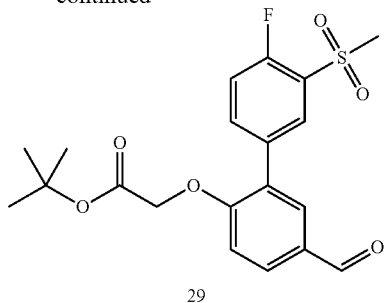

To a solution of 3-(4-fluoro-3-(methylsulfonyl)phenyl)-4-hydroxybenzaldehyde (28) (315 mg, 1.1 mmol, 1 eq.) in DMF (10 mL) was added Cs$_2$CO$_3$ (715 mg, 2.2 mmol, 2 eq.) and t-butyl 2-bromoacetate (236 mg, ~1.2 mmol, 1.2 eq.). After stirring at room temperature, for 16 h, the solvent was removed in vacuo, and the resultant residue was extracted between EtOAc and H$_2$O (3×20 mL). The organic layer was dried (Na$_2$SO$_4$), and concentrated in vacuo. The resultant residue was purified by column chromatography (eluent: PE:EA=1:1) to give 250 mg (57%) of t-butyl 2-(2-(4-fluoro-3-(methylsulfonyl)phenyl)-4-formylphenoxy)acetate (29) as oil.

Intermediate 30 t-butyl 2-(2-(4-fluoro-3-(methylsulfonyl)phenyl)-4-((methylamino)methyl)phenoxy)acetate (30)

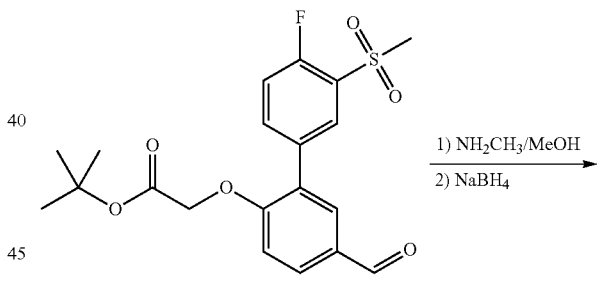

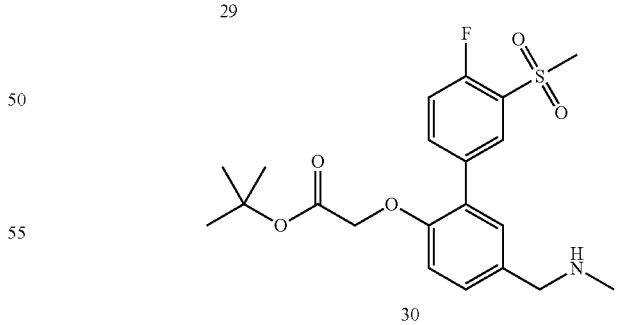

Intermediate 29 (270 mg, 0.66 mmol, 1 eq) was stirred with methylamine (1.5 mL of a 0.88 M THF solution, 1.32 mmol, 2 eq.) in MeOH for 2 h. Sodium borohydride (50 mg, 0.66 mmol, 1 eq.) was added, and the resulting mixture was stirred at room temperature for an additional 2 h. Water (3 mL) was added and the MeOH was removed in vacuo. The resulting solution was extracted with EtOAc, dried (Na$_2$SO$_4$), and concentrated in vacuo to give 260 mg (93%) of t-butyl 2-(2-(4-fluoro-3-(methylsulfonyl)phenyl)-4-((methylamino)methyl)phenoxy)acetate (30) as oil.

Intermediate 31 t-butyl 2-((4-fluoro-3-(methylsulfonyl)phenyl)-4-((4-fluoro-N-methylphenylsulfonamido)methyl)phenoxy)acetate (31)

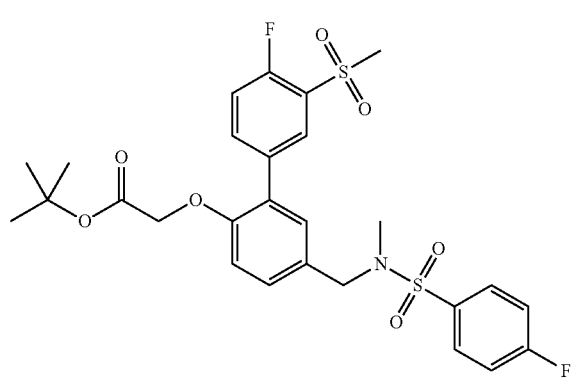

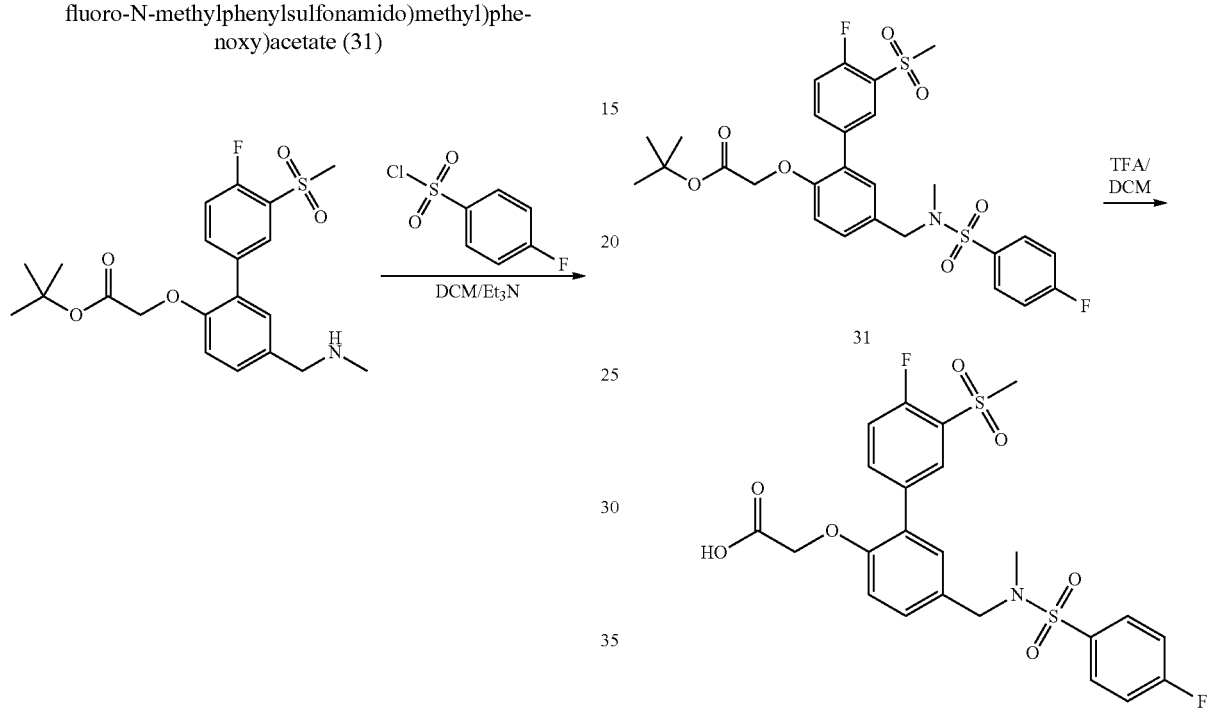

To secondary amine 30 (150 mg, 0.35 mmol, 1 eq.) in dry DCM (15 mL) at 0° C. was added Et₃N (3 mL) followed by dropwise addition of a DCM solution of 4-fluorobenzenesulfonyl chloride (90 mg, 0.42 mmol, 1.2 eq). After stirring at 0° C. for 20 min, the mixture was stirred at room temperature for 2 h. The reaction was extracted between DCM and water and the organic layer was washed with 1N HCl, saturated NaHCO₃ solution, and brine, dried (Na₂SO₄), and concentrated in vacuo to give 150 mg (72%) of t-butyl 2-((4-fluoro-3-(methylsulfonyl)phenyl)-4-((4-fluoro-N-methylphenyl-sulfonamido)methyl)phenoxy)acetate (31) as oil which was used in the next step without further purification.

Example 28

2-((4-fluoro-3-(methylsulfonyl)phenyl)-4-((4-fluoro-N-methylphenylsulfonamido)methyl)phenoxy)acetic acid To a solution of TFA/DCM (1:3, 10 mL) was added intermediate 31 (150 mg, 0.26 mmol, 1 eq) and the mixture was stirred at room temperature for 2 h. The organic solvent was removed in vacuo and the crude product was purified by reversed phase semi-preparative HPLC to afford 100 mg (73%) of 2-((4-fluoro-3-(methylsulfonyl)phenyl)-4-((4-fluoro-N-methylphenylsulfonamido)methyl)phenoxy)acetic acid (Example 28). ¹HNMR (CD₃CN, 300 MHz): δ 8.08 (m, 1H), 7.95 (m, 1H), 7.88 (m, 2H), 7.26-7.44 (m, 5H), 7.00 (d, 1H), 4.71 (s, 2H), 4.18 (s, 2H), 3.25 (s, 3H), 2.55 (d, 3H). MS (ES-API): MH⁻=524.1. HPLC (Method A) $t_R$=2.02 min.

Representative Examples of Synthetic Route 4

Intermediate 32

4-(4-methoxybenzyloxy)-3-bromobenzaldehyde (32)

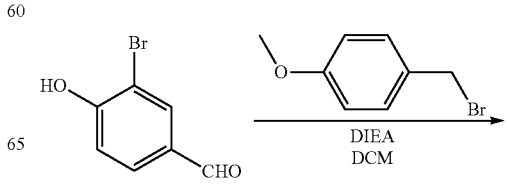

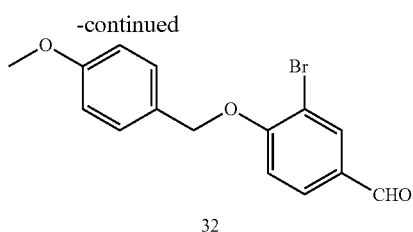

To a solution of 3-bromo-4-hydroxybenzaldehyde (5.0 g, 24.9 mmol; 1 eq) in DCM (10 mL), was added 1-(bromomethyl)-4-methoxybenzene (6.0 g, 29.88 mmol, 1.2 eq, Aldrich, Milwaukee, Wis., USA) and DIEA (8.7 mL, 49.7 mmol, 2 eq). After stirring at room temperature for 18 h, the reaction mixture was diluted with DCM and washed with saturated NaHCO$_3$ and brine. The organic layer was dried (Na$_2$SO$_4$), filtered and concentrated in vacuo to give 8.0 g of 4-(4-methoxybenzyloxy)-3-bromobenzaldehyde (32).

Intermediate 33

(4-(4-methoxybenzyloxy)-3-bromophenyl)-N-methylmethanamine (33)

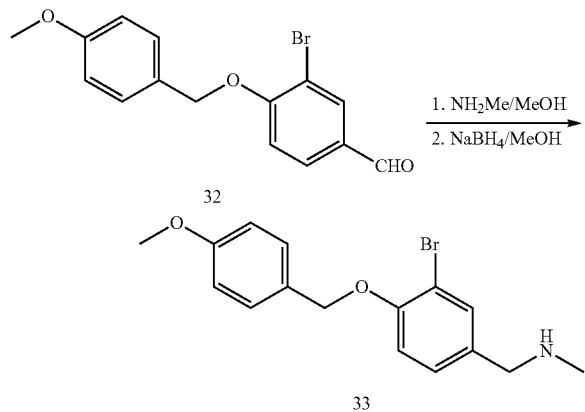

To a solution of 2M methylamine in MeOH (30 mL) was added intermediate 32 (2.91 g, 9.1 mmol, 1 eq). After stirring this mixture at room temperature for 30 min, the solvent was removed and the residue was partitioned between saturated NaHCO$_3$ and DCM (2×100 mL). The organic layer was dried (Na$_2$SO$_4$) and concentrated. The resultant residue was dissolved in MeOH (25 mL) and, after addition of sodium borohydride (1.0 g, 27.6 mmol, 3 eq), the mixture was stirred at room temperature for 1 h. Solvent was removed and the residue was partitioned between a Na$_2$CO$_3$ solution and CHCl$_3$. The resultant organic layer was dried (Na$_2$SO$_4$) and concentrated in vacuo to give 2.7 g, (88%) of (4-(4-methoxybenzyloxy)-3-bromophenyl)-N-methylmethanamine (33).

Intermediate 34

N-(4-(4-methoxybenzyloxy)-3-bromobenzyl)-4-fluoro-N-methylbenzenesulfonamide (34)

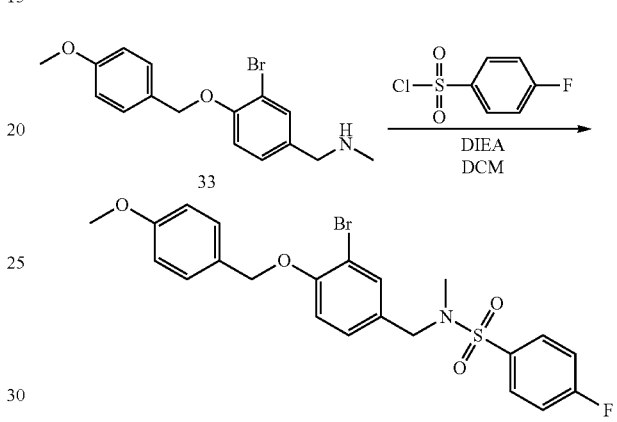

To a solution of intermediate 33 (2.7 g, 8.0 mmol, 1 eq) in DCM (10 mL) was added 4-fluorobenzene-1-sulfonyl chloride (1.9 g, 9.6 mmol, 1.2 eq) and DIEA (2.8 mL, 16.0 mmol, 2 eq). After stirring at room temperature for 1 h, the reaction was washed with saturated NaHCO$_3$ and brine, dried (Na$_2$SO$_4$), and concentrated in vacuo. The crude product was purified via silica gel chromatography (0-40% EtOAc/hexane) to give 2.48 g (63%) of N-(4-(4-methoxybenzyloxy)-3-bromobenzyl)-4-fluoro-N-methylbenzenesulfonamide (34).

Intermediate 35

N-(4-(4-methoxybenzyloxy)-3-(3-trifluoromethylphenyl)benzyl)-4-fluoro-N-methylbenzenesulfonamide (35)

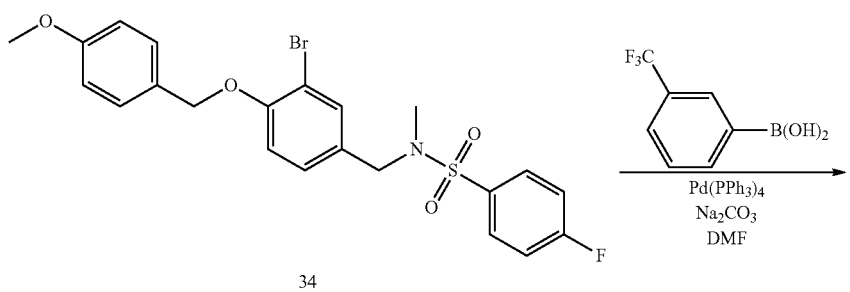

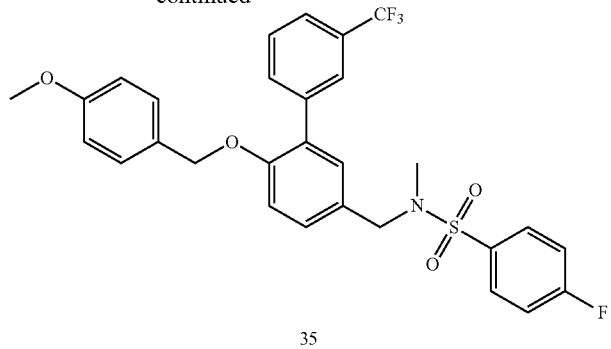

35

To a solution of bromide 34 (1.0 g, 2.02 mmol, 1 eq) and 3-(trifluoromethyl)phenyl boronic acid (575 mg, 3.03 mmol, 1.5 eq, Aldrich, Milwaukee, Wis., USA) in dimethoxyethane (70 mL), was added sodium carbonate solution (9 mL of a 2 M solution) and tetrakis-triphenylphosphine palladium (233 mg, 0.1 eq). The mixture was stirred at 90° C. for 16 h, cooled to room temperature, and concentrated in vacuo. The resultant residue was partitioned between EtOAc and saturated sodium bicarbonate solution, dried (Na$_2$SO$_4$), concentrated in vacuo and purified by silica gel chromatography (0-40% EtOAc/hexane) to give 790 mg (72%) of N-(4-(4-methoxybenzyloxy)-3-(3-trifluoromethylphenyl)benzyl)-4-fluoro-N-methylbenzenesulfonamide (35). $^1$HNMR (CD$_3$OD, 400 MHz): δ 7.84 (m, 3H), 7.65 (d, 1H), 7.44-7.54 (m, 3H), 7.18-7.30 (m, 5H), 7.04 (d, 1H), 6.85 (d, 2H), 5.02 (s, 2H), 4.14 (s, 2H), 3.80 (s, 3H), 2.63 (s, 3H). MS (ESI): MH+=560.1. HPLC (Method B) t$_R$=4.57 min.

Intermediate 36

N-(3-(3-trifluoromethylphenyl)-4-hydroxybenzyl)-4-fluoro-N-methylbenzenesulfonamide (36)

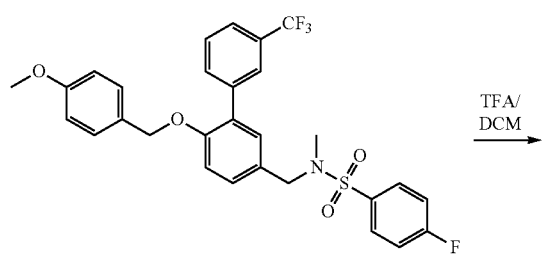

Intermediate 35 (700 mg, 1.25 mmol) was dissolved in TFA/DCM (1/1) and stirred at room temperature for 1 h. Solvent was removed in vacuo and the residue was purified via silica gel chromatography (0-40% EtOAc/hexane) to afford 350 mg (64%) of N-(3-(3-trifluoromethylphenyl)-4-hydroxybenzyl)-4-fluoro-N-methylbenzenesulfonamide (36). $^1$HNMR (CD$_3$OD, 400 MHz): δ 7.91 (m, 2H), 7.80 (s, 1H), 7.65 (m, 2H), 7.59 (d, 1H), 7.15-7.25 (m, 4H), 6.94 (d, 1H), 4.97 (s, 1H), 4.13 (s, 2H), 2.64 (s, 3H). MS (ESI): MH+=440.1. HPLC (Method B) t$_R$=3.45 min.

Example 34

2-(2-(3-trifluoromethylphenyl)-4-((4-fluoro-N-methylphenylsulfonamido)methyl)phenoxy)-2-methylpropanoic acid Example 34

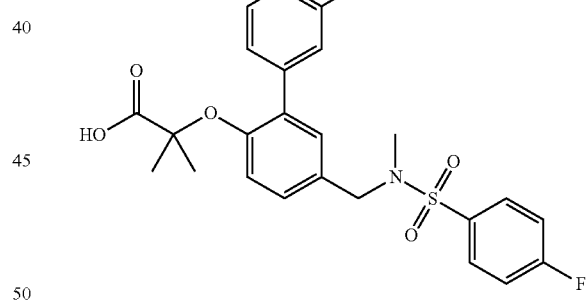

To a solution of N-(3-(3-trifluoromethylphenyl)-4-hydroxybenzyl)-4-fluoro-N-methylbenzenesulfonamide (36) (50.0 mg, 0.114 mmol, 1 eq) in DMF (3 mL) under argon, was added t-butyl-2-bromo-2-methylpropanoate (66.0 mg, 0.296 mmol, 2.6 eq) and potassium carbonate (31 mg, 0.224 mmol, 2 eq). The mixture was stirred at 80° C. for 16 h, cooled to room temperature and partitioned with saturated sodium bicarbonate and EtOAc. The organic layer was separated, dried (Na$_2$SO$_4$), and concentrated in vacuo. The crude residue was dissolved in TFA/DCM (1 mL/1 mL) and stirred at room temperature for 1 h. Solvent was removed in vacuo and the residue was purified via reversed phase semi-preparative HPLC to afford 2.8 mg of 2-(2-(3-trifluoromethylphenyl)-4-((4-fluoro-N-methylphenylsulfonamido)methyl)phenoxy)-2-methylpropanoic acid (Example 34). $^1$HNMR (CD$_3$OD, 400 MHz): δ 7.91 (m, 3H), 7.88 (m, 1H), 7.61 (m, 2H), 7.35

(t, 2H), 7.27 (d, 2H), 6.90 (d, 1H), 4.20 (s, 2H), 2.67 (s, 3H), 1.46 (s, 6H). MS (ESI): MH+=526.1. HPLC (Method B) $t_R$=2.53 min.

Example 35

(R)-2-(2-(3-trifluoromethylphenyl)-4-((4-fluoro-N-methylphenylsulfonamido)methyl)phenoxy)propanoic acid

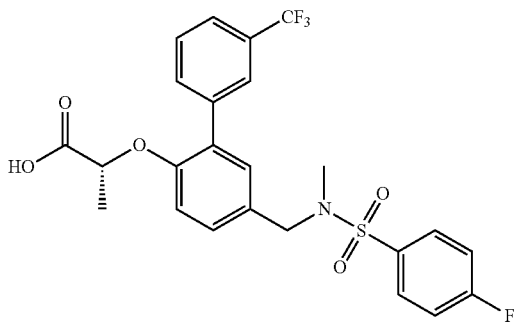

Example 35

To a solution of N-(3-(3-trifluoromethylphenyl)-4-hydroxybenzyl)-4-fluoro-N-methylbenzenesulfonamide (36) (50.0 mg, 0.114 mmol, 1 eq) and (S)-benzyl-2-hydroxypropanoate (21 μL, 0.125 mmol, 1.1 eq, Aldrich, Milwaukee, Wis., USA) in THF (2 mL) at 0° C. was added diethyl azodicarboxylate (20 μL, 0.125 mmol, 1.1 eq) and triphenylphosphine (33 mg, 0.125 mmol, 1.1 eq). After stirring at 0° C. for 4 h, the mixture was extracted between saturated sodium bicarbonate and EtOAc, dried (Na₂SO₄), concentrated in vacuo, and purified on via silica gel chromatography (linear gradient of 5-10% EtOAc/hexane). The isolated material was further purified via reversed phase semi-preparative HPLC to give 12 mg of benzyl-(R)-2-(2-(3-trifluoromethylphenyl)-4-((4-fluoro-N-methylphenylsulfonamido)methyl)phenoxy)propanate. This intermediate was stirred in the presence of 10 mg of 10% Pd/C under a hydrogen atmosphere in EtOH. (5 mL) at room temperature for 16 h. The reaction mixture was then filtered through a celite pad and the filtrate was concentrated in vacuo. The crude residue was purified via reversed phase semi-preparative HPLC to give 7.8 mg of (R)-2-(2-(3-trifluoromethylphenyl)-4-((4-fluoro-N-methylphenylsulfonamido)methyl)phenoxy)propanoic acid (Example 35). ¹HNMR (CDCl₃, 400 MHz): δ 7.78 (m, 3H), 7.64(d, 1H), 7.48 (m, 2H), 7.25 (m, 3H), 7.17 (d, 1H), 6.73 (d, 1H), 4.87 (m, 1H), 4.04 (s, 2H), 2.53 (s, 3H), 1.32 (d, 3H). MS (ESI): MH+=512.1. HPLC (Method B) $t_R$=3.48 min.

Example 36

(S)-2-(2-(3-trifluoromethylphenyl)-4-((4-fluoro-N-methylphenylsulfonamido)methyl)phenoxy)propanoic acid

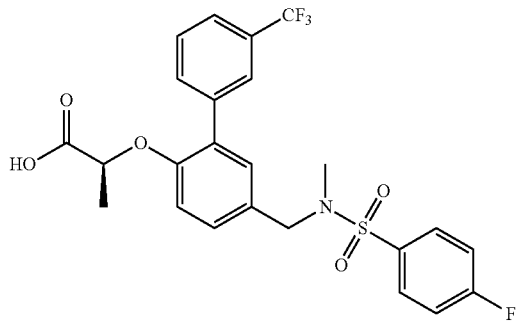

Example 36

A solution of N-(3-(3-trifluoromethylphenyl)-4-hydroxybenzyl)-4-fluoro-N-methylbenzenesulfonamide (36) (50.0 mg, 0.114 mmol) and (R)-t-butyl-2-hydroxypropanoate (18.3 mg, 0.125 mmol, 1.1 eq, Chem-Impex International, Inc., Wood Dale, Ill., USA) in THF (2 mL) at 0° C. was added diethyl azodicarboxylate (20 μL, 0.125 mmol, 1.1 eq) and triphenylphosphine (33 mg 0.125 mmol, 1.1 eq). After stirring at 0° C. for 4 h the mixture was extracted between saturated sodium bicarbonate and ethyl acetate, dried (Na₂SO₄) and concentrated in vacuo. This crude product was purified on reversed phase semi-preparative HPLC to give 9 mg of t-butyl-(S)-2-(2-(3-trifluoromethylphenyl)-4-((4-fluoro-N-methylphenylsulfonamido)methyl)phenoxy)propanate. This intermediate was then dissolved in TFA/DCM (1 mL/1 mL) and stirred at room temperature for 30 min. Solvent was removed in vacuo and the residue was purified via reversed phase semi-preparative HPLC to afford 4.9 mg of (S)-2-(2-(3-trifluoromethylphenyl)-4-((4-fluoro-N-methylphenylsulfonamido)methyl)phenoxy)propanoic acid (Example 36). ¹HNMR (CDCl₃, 400 MHz): δ 7.84 (m, 3H), 7.70 (d, 1H), 7.56 (m, 2H), 7.26 (m, 3H), 7.20 (d, 1H), 6.88 (d, 1H), 4.80 (m, 1H), 4.15 (s, 2H), 2.64 (s, 3H), 1.57 (d, 3H). MS (ESI): MH+=512.1. HPLC (Method B) $t_R$=2.78 min.

Analytical HPLC Analysis:

Method A: Agilent 1200 LC/6110 MSD analytical system employing an Agilent Zorbax SB-Aq, 3.5 um, 2.1×50 mm analytical column. The aqueous acetonitrile based solvent gradient involves: 0-0.4 min—Isocratic 10% of (0.05% TFA/acetonitrile); 0.4 min-3.4 min—Linear gradient of 10-100% of (0.05% TFA/acetonitrile); 3.4 min-3.9 min—Isocratic 100% of (0.05% TFA/acetonitrile); 3.9 min-3.95 min—Linear gradient of 100-10% of (0.05% TFA/acetonitrile), 3.95 min-4.5 min—Isocratic 10% of (0.05% TFA/acetonitrile). Flow rate=0.8 ml/min.

Method B: Waters Millenium Micromass ZQ/2996PDA separations system employing a Phenomenex Luna, 3μ C18, 50×2.00 mm analytical column. The aqueous acetonitrile based solvent gradient involves: 0-0.25 min—Isocratic 10% of (0.05% TFA/acetonitrile); 0.25 min-2.75 min—Linear gradient of 10-90% of (0.05% TFA/acetonitrile): 2.75 min-3.75 min—Isocratic 90% of (0.05% TFA/acetonitrile); 3.75 min—

4.00 min—Linear gradient of 90-10% of (0.05% TFA/acetonitrile); 4.00 min-5.00 min—Isocratic 10% of (0.05% TFA/acetonitrile). Flow rate=0.5 mL/min.

Method C: Waters Millenium 2695/996PDA separations system employing a Phenomenex Columbus 5μ C18 110A column 100×2.0 mm analytical column. The aqueous acetonitrile based solvent gradient involves: 0-0.5 min—Isocratic 10% of (0.05% TFA/acetonitrile); 0.5 min-5.5 min—Linear gradient of 10-90% of (0.05% TFA/acetonitrile): 5.5 min-7.5 min—Isocratic 90% of (0.05% TFA/acetonitrile); 7.5 min-8 min—Linear gradient of 90-10% of (0.05% TFA/acetonitrile); 8 min-10 min—Isocratic 10% of (0.05% TFA/acetonitrile). Flow rate=0.4 mL/min.

Semi-preparative HPLC Purification

Semi-preparative HPLC purification was conducted on a Waters 600 Semi-preparative liquid chromatograph equipped with a 996 diode array detector employing a Sunfire™ Prep C18 OBD 5 μm 19×100 mm column. The aqueous acetonitrile based solvent gradient involves: 0 min-9 min—Linear gradient of 10-90% of (0.05% TFA/acetonitrile): 9 min-10 min—Isocratic 90% of (0.05% TFA/acetonitrile); 10 min-10.5 min—Linear gradient of 90-10% of (0.05% TFA/acetonitrile).

Mass Spectroscopy

Mass Spectroscopy was conducted using an Applied Biosciences PE Sciex API150ex. Liquid Chromatography Mass Spectroscopy was conducted using a Waters Millenium 2695/996PDA linked Thermo-electron LCQ classic or a Waters Micromass ZQ utilizing a Waters 1525 HPLC pump.

NMR Spectroscopy $^1$H NMR spectroscopy was conducted using a Varian 300 MHz Gemini 2000 FTNMR.

Chemical Structure Naming

Names for each aryl fragment in the biaryl structure were generated using "Convert Structure to Name" function in ChemDraw version 8.8.0 (ChembridgeSoft Corporation, MA, USA). The final biaryl compounds were named based on IUPAC convention.

[$^{35}$S]GTPγS Binding Assay

SPA [$^{35}$S]G-TPγS binding was performed on membranes from CHO-K1 cells stably expressing human CRTH2. To a white, clear-bottomed 384-well plate, 4 μg membrane protein was incubated in the binding buffer (20 mM HEPES, pH 7.4, 10 mM MgCl$_2$, 300 mM NaCl, 0.2% BSA) with 60 nM DHK-PGD$_2$, 500 pM [$^{35}$S]GTPγS, 10 μM GDP, and 100 μg wheat germ agglutinin-coupled SPA beads (GE Healthcare) with and without increasing concentrations of compounds. The final assay volume was 40 μL and contained 1% DMSO. Samples were incubated for 2 h at ambient temperature. Plates were centrifuged 5 min at 1500 rpm. Plates were read after an additional 4 h using the Trilux 1450 Microbeta (PerkinElmer) with a 30 sec/well reading time. The IC$_{50}$ data for certain Examples are shown in Table 1.

TABLE 1

| Example No. | CRTH2 hGTPγS IC$_{50}$ (nM) |
| --- | --- |
| Example 37 | 0.6 |
| Example 38 | 0.7 |
| Example 42 | 1.5 |
| Example 44 | 1.8 |
| Example 45 | 2.0 |
| Example 46 | 2.1 |
| Example 48 | 2.9 |
| Example 51 | 3.4 |
| Example 64 | 12 |
| Example 67 | 13 |
| Example 97 | 43 |
| Example 110 | 169 |
| Example 187 | 19 |
| Example 192 | 0.2 |
| Example 194 | 15 |
| Example 196 | 0.7 |
| Example 197 | 0.6 |

Compounds that are active in the GTPγS assay have the potential to trigger an in vivo response (Mathiesen et al., 2006, Mol. Pharmacology. 69: 1441-1453; Uller et al., 2007, Respiratory Research 8:16, incorporated by reference in their entireties).

Exemplified compounds are shown below in Table 2. Compounds exhibited IC$_{50}$ values for CRTH2<10 μM. Potency of compound is further divided into two groups: +++, IC$_{50}$<100 nM; ++, IC$_{50}$>100 nM to <1 μM; +, IC$_{50}$>1 μM to <10 μM.

TABLE 2

| Example No. | Structure | Chemical Name | CRTH2 hGTPγS IC$_{50}$ (nM) | Route |
| --- | --- | --- | --- | --- |
| 41 | 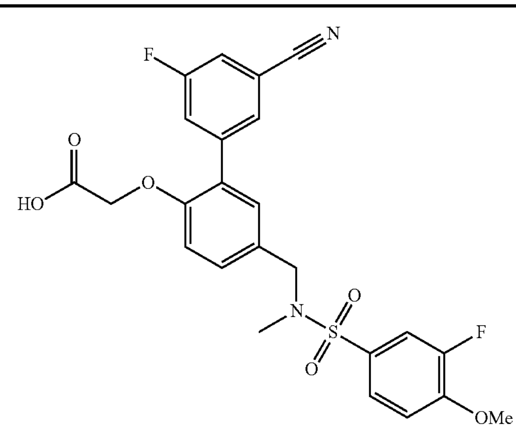 | 2-(3-cyano-5-fluorophenyl)-4-((3-fluoro-4-methoxy-N-methylphenylsulfonamido)methyl)phenoxyacetic acid | +++ | 3 |

TABLE 2-continued

| Example No. | Structure | Chemical Name | CRTH2 hGTPγS IC$_{50}$ (nM) | Route |
|---|---|---|---|---|
| 96 | 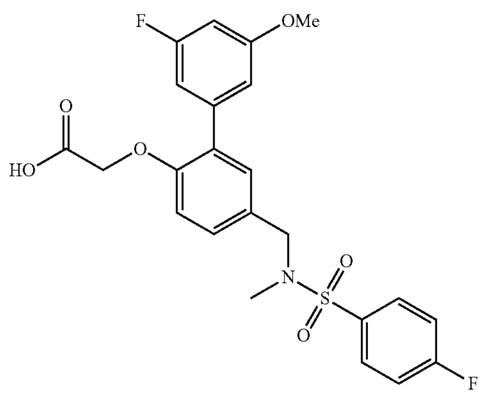 [SMILES: COc1cc(F)cc(-c2cc(CN(C)S(=O)(=O)c3ccc(F)cc3)ccc2OCC(=O)O)c1] | 2-(3-methoxy-5-fluorophenyl)-4-((4-fluoro-N-methylphenyl-sulfonamido)methyl)phenoxyacetic acid | +++ | 1 |
| 44 | 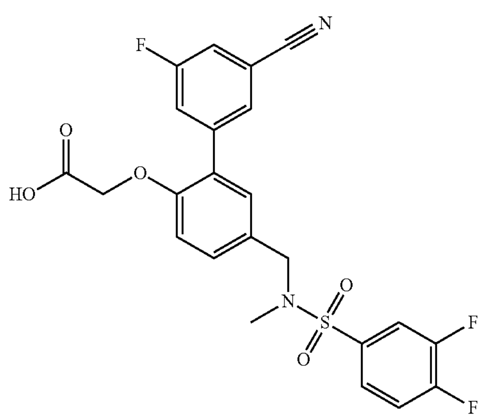 [SMILES: CN(Cc1ccc(OCC(=O)O)c(-c2cc(F)cc(C#N)c2)c1)S(=O)(=O)c1ccc(F)c(F)c1] | 2-(3-cyano-5-fluorophenyl)-4-((3,4-difluoro-N-methylphenyl-sulfonamido)methyl)phenoxyacetic acid | +++ | 3 |
| 37 | 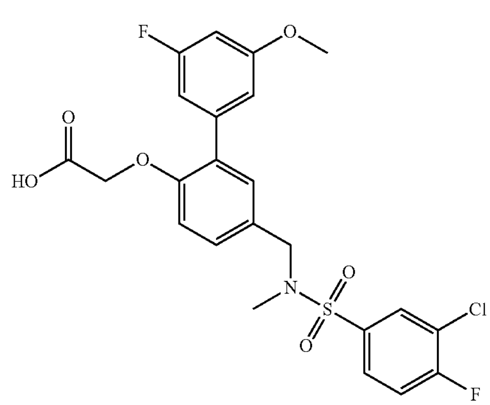 [SMILES: COc1cc(F)cc(-c2cc(CN(C)S(=O)(=O)c3ccc(F)c(Cl)c3)ccc2OCC(=O)O)c1] | 2-(3-fluoro-5-methoxyphenyl)-4-((3-chloro-4-fluoro-N-methylphenyl-sulfonamido)methyl)phenoxyacetic acid | +++ | 1 |

TABLE 2-continued

| Example No. | Structure | Chemical Name | CRTH2 hGTPγS IC$_{50}$ (nM) | Route |
|---|---|---|---|---|
| 16 | 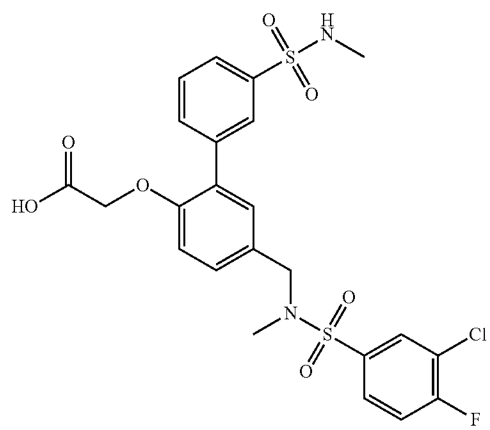 [SMILES: CNS(=O)(=O)c1cccc(-c2cc(CN(C)S(=O)(=O)c3ccc(F)c(Cl)c3)ccc2OCC(=O)O)c1] | 2 (3-N-methylsulfamoyl phenyl)-4-((3-chloro-4-fluoro-N-methylphenyl-sulfonamido)methyl) phenoxyacetic acid | +++ | 2 |
| 39 | 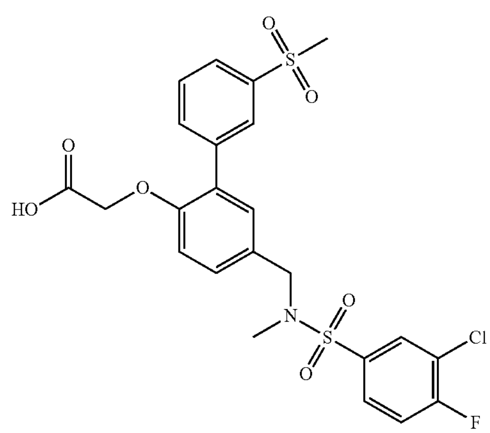 [SMILES: CN(Cc1ccc(OCC(=O)O)c(-c2cccc(S(C)(=O)=O)c2)c1)S(=O)(=O)c1ccc(F)c(Cl)c1] | 2-(3-methylsulfonyl-phenyl)-4-((3-chloro-4-fluoro-N-methylphenyl-sulfonamido)methyl) phenoxyacetic acid | +++ | 2 |
| 194 | 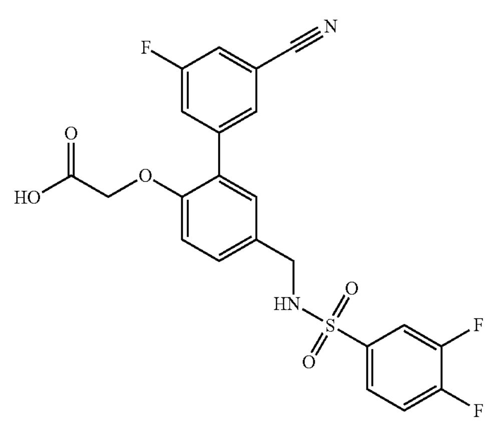 [SMILES: N#Cc1cc(F)cc(-c2cc(CNS(=O)(=O)c3ccc(F)c(F)c3)ccc2OCC(=O)O)c1] | 2-(3-cyano-5-fluorophenyl)-4-((3,4-difluoro-phenylsulfonamido) methyl)phenoxy-acetic acid | +++ | 3 |

TABLE 2-continued

| Example No. | Structure | Chemical Name | CRTH2 hGTPγS IC$_{50}$ (nM) | Route |
|---|---|---|---|---|
| 74 | 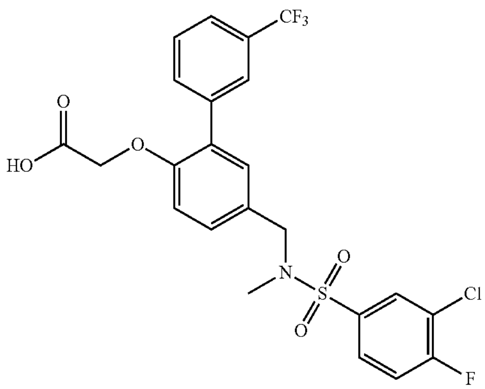 [SMILES: CN(Cc1ccc(OCC(=O)O)c(-c2cccc(C(F)(F)F)c2)c1)S(=O)(=O)c1ccc(F)c(Cl)c1] | 2-(3-trifluoromethyl-phenyl)-4-((3-chloro-4-fluoro-N-methylphenyl-sulfonamido)methyl)phenoxyacetic acid | +++ | 2 |
| 45 | 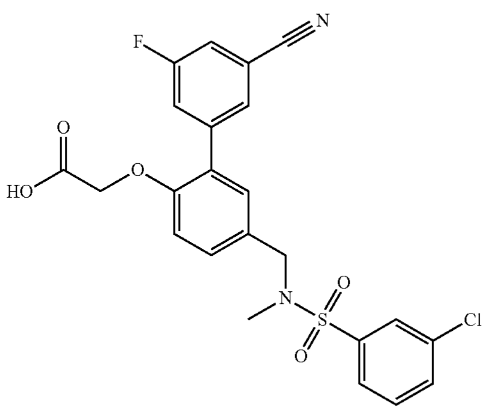 [SMILES: CN(Cc1ccc(OCC(=O)O)c(-c2cc(F)cc(C#N)c2)c1)S(=O)(=O)c1cccc(Cl)c1] | 2-(3-cyano-5-fluorophenyl)-4-((3-chloro-N-methylphenyl-sulfonamido)methyl)phenoxyacetic acid | +++ | 3 |
| 54 | 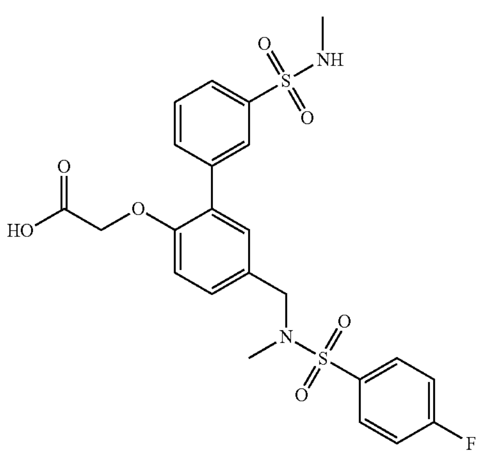 [SMILES: CNS(=O)(=O)c1cccc(-c2cc(CN(C)S(=O)(=O)c3ccc(F)cc3)ccc2OCC(=O)O)c1] | 2-(3-N-methylsulfamoyl phenyl)-4-((4-fluoro-N-methylphenyl-sulfonamido)methyl)phenoxyacetic acid | +++ | 1 |

TABLE 2-continued

| Example No. | Structure | Chemical Name | CRTH2 hGTPγS IC$_{50}$ (nM) | Route |
|---|---|---|---|---|
| 46 | 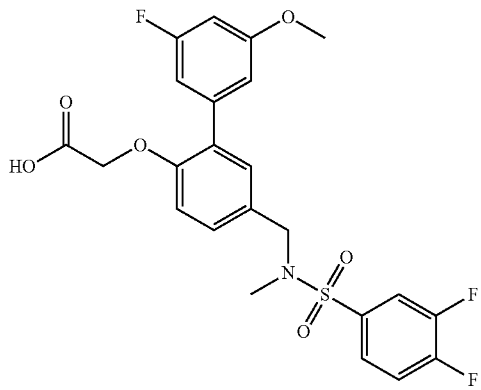 [SMILES: COc1cc(F)cc(-c2cc(CN(C)S(=O)(=O)c3ccc(F)c(F)c3)ccc2OCC(=O)O)c1] | 2-(3-fluoro-5-methoxyphenyl)-4-((3,4-difluoro-N-methylphenyl-sulfonamido)methyl)phenoxyacetic acid | +++ | 2 |
| 99 | 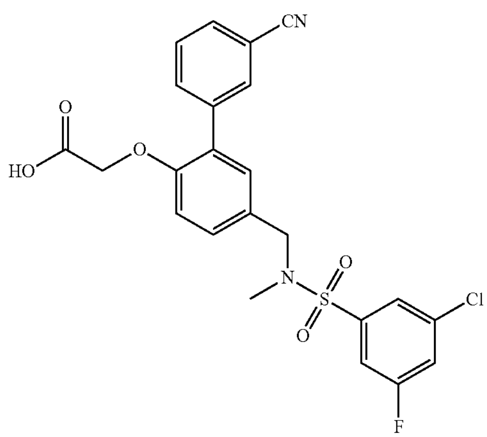 [SMILES: CN(Cc1ccc(OCC(=O)O)c(-c2cccc(C#N)c2)c1)S(=O)(=O)c1cc(F)cc(Cl)c1] | 2-(3-cyanophenyl)-4-((3-chloro-5-fluoro-N-methylphenyl-sulfonamido)methyl)phenoxyacetic acid | +++ | 2 |
| 48 | 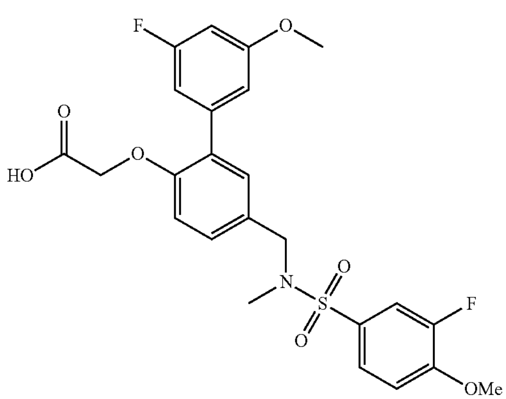 [SMILES: COc1cc(F)cc(-c2cc(CN(C)S(=O)(=O)c3ccc(OC)c(F)c3)ccc2OCC(=O)O)c1] | 2-(3-fluoro-5-methoxyphenyl)-4-((3-fluoro-4-methoxy-N-methylphenyl-sulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 49 | 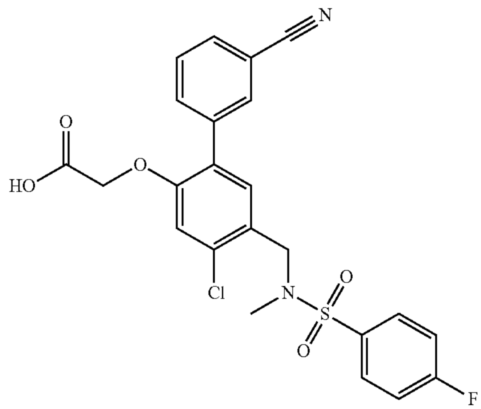 [SMILES: CN(Cc1cc(-c2cccc(C#N)c2)c(OCC(=O)O)cc1Cl)S(=O)(=O)c1ccc(F)cc1] | 2-(3-cyanophenyl)-4-((4-fluoro-N-methylphenyl-sulfonamido)methyl)-5-chlorophenoxyacetic acid | +++ | 2 |
| 50 | 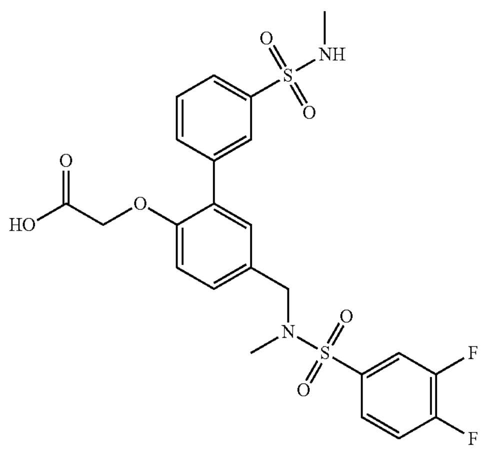 [SMILES: CNS(=O)(=O)c1cccc(-c2cc(CN(C)S(=O)(=O)c3ccc(F)c(F)c3)ccc2OCC(=O)O)c1] | 2-(3-N-methylsulfamoyl phenyl)-4-((3,4-difluoro-N-methylphenyl-sulfonamido)methyl)phenoxyacetic acid | +++ | 2 |
| 97 | 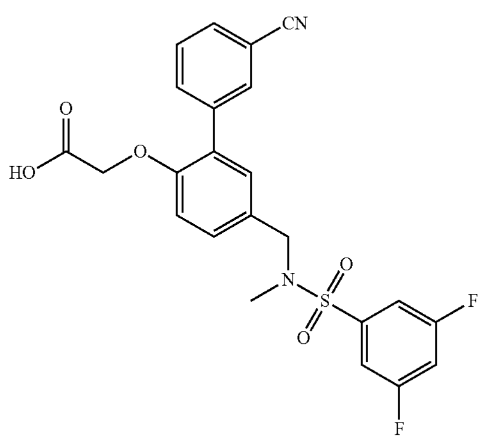 [SMILES: CN(Cc1ccc(OCC(=O)O)c(-c2cccc(C#N)c2)c1)S(=O)(=O)c1cc(F)cc(F)c1] | 2-(3-cyanophenyl)-4-((3,5-difluoro-N-methylphenyl-sulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 51 | 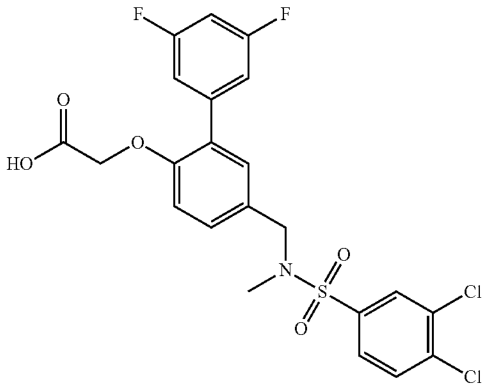 | 2-(3,5-difluorophenyl)-4-((3,4-dichloro-N-methylphenyl-sulfonamido)methyl)phenoxyacetic acid | +++ | 2 |
| 192 | 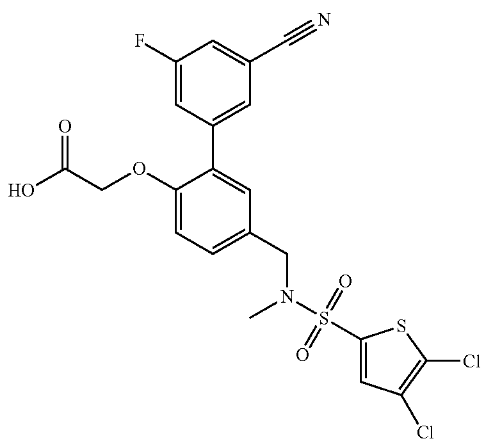 [SMILES: CN(Cc1ccc(OCC(=O)O)c(-c2cc(F)cc(C#N)c2)c1)S(=O)(=O)c1cc(Cl)c(Cl)s1] | 2-(3-cyano-5-fluorophenyl)-4-((2,3-dichloro-N-methylthiophene-5-sulfonamido)methyl)phenoxyacetic acid | +++ | 3 |
| 53 | 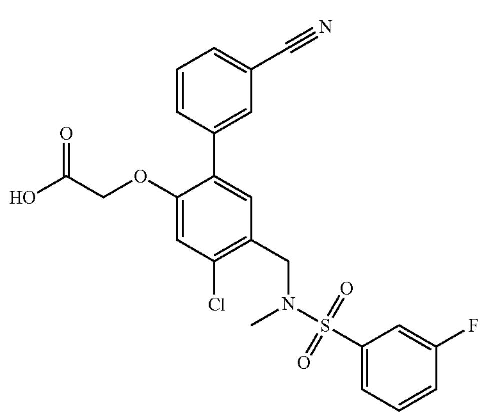 [SMILES: CN(Cc1cc(-c2cccc(C#N)c2)c(OCC(=O)O)cc1Cl)S(=O)(=O)c1cccc(F)c1] | 2-(3-cyanophenyl)-4-((3-fluoro-N-methylphenyl-sulfonamido)methyl)-5-chlorophenoxy-acetic acid | +++ | 2 |

TABLE 2-continued

| Example No. | Structure | Chemical Name | CRTH2 hGTPγS IC$_{50}$ (nM) | Route |
|---|---|---|---|---|
| 28 | 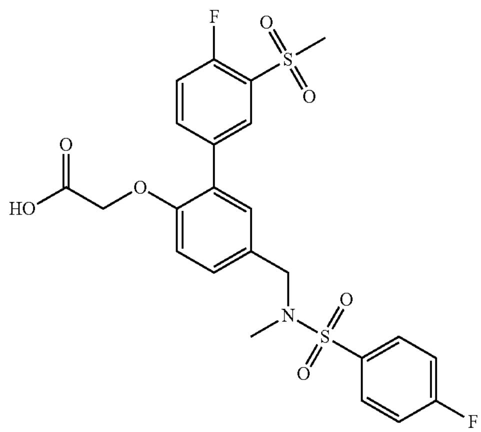 [SMILES: CN(Cc1ccc(OCC(=O)O)c(-c2ccc(F)c(S(C)(=O)=O)c2)c1)S(=O)(=O)c1ccc(F)cc1] | 2-(4-fluoro-3-(methylsulfonyl)phenyl)-4-((4-fluoro-N-methylphenyl-sulfonamido)methyl)phenoxyacetic acid | +++ | 3 |
| 55 | 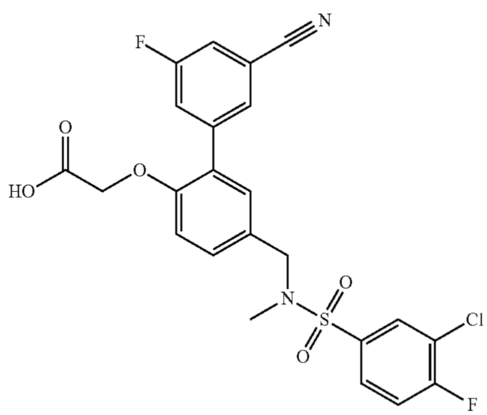 [SMILES: CN(Cc1ccc(OCC(=O)O)c(-c2cc(F)cc(C#N)c2)c1)S(=O)(=O)c1ccc(F)c(Cl)c1] | 2-(3-cyano-5-fluorophenyl)-4-((3-chloro-4-fluoro-N-methylphenyl-sulfonamido)methyl)phenoxyacetic acid | +++ | 3 |
| 65 | 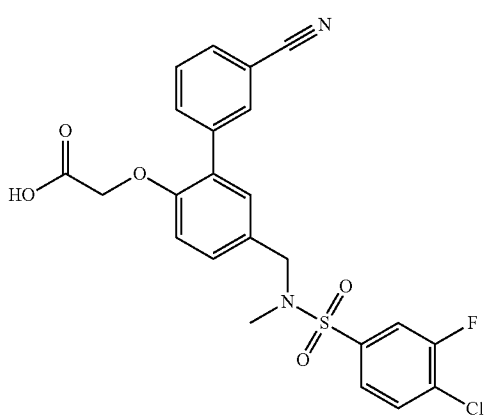 [SMILES: CN(Cc1ccc(OCC(=O)O)c(-c2cccc(C#N)c2)c1)S(=O)(=O)c1ccc(Cl)c(F)c1] | 2-(3-cyanophenyl)-4-((3-fluoro-4-chloro-N-methylphenyl-sulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 57 | 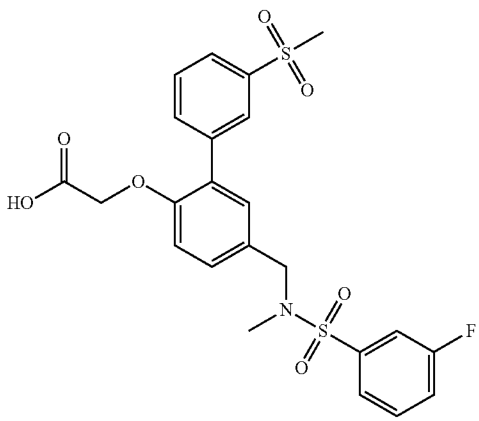 [SMILES: CN(Cc1ccc(OCC(=O)O)c(-c2cccc(S(C)(=O)=O)c2)c1)S(=O)(=O)c1cccc(F)c1] | 2-(3-methylsulfonylphenyl)-4-((3-fluoro-N-methylphenylsulfonamido)methyl)phenoxyacetic acid | +++ | 2 |
| 47 | 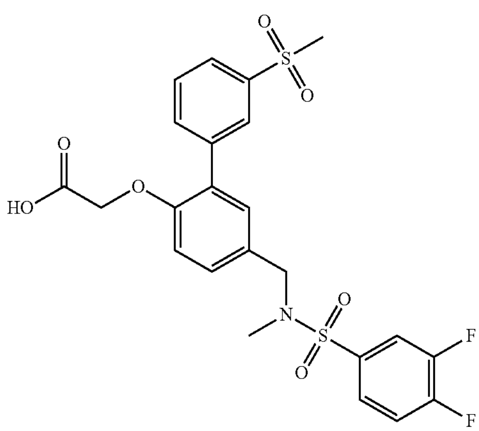 [SMILES: CN(Cc1ccc(OCC(=O)O)c(-c2cccc(S(C)(=O)=O)c2)c1)S(=O)(=O)c1ccc(F)c(F)c1] | 2-(3-methylsulfonylphenyl)-4-((3,4-difluoro-N-methylphenylsulfonamido)methyl)phenoxyacetic acid | +++ | 2 |
| 58 | 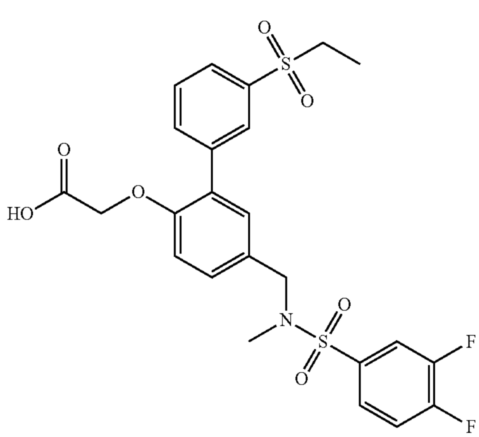 [SMILES: CCS(=O)(=O)c1cccc(-c2cc(CN(C)S(=O)(=O)c3ccc(F)c(F)c3)ccc2OCC(=O)O)c1] | 2-(3-ethylsulfonylphenyl)-4-((3,4-difluoro-N-methylphenylsulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 189 | 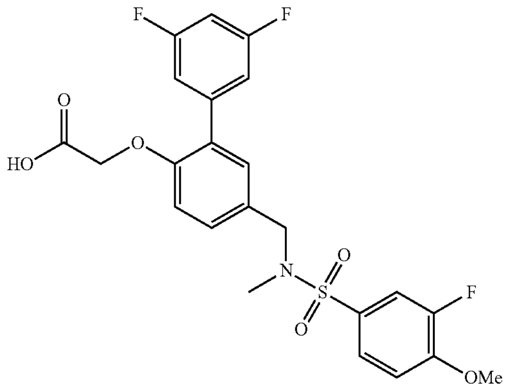 [SMILES: COc1ccc(S(=O)(=O)N(C)Cc2ccc(OCC(=O)O)c(-c3cc(F)cc(F)c3)c2)cc1F] | 2-(3,5-difluorophenyl)-4-((3-fluoro-4-methoxy-N-methylphenyl-sulfonamido)methyl)phenoxyacetic acid | +++ | 1 |
| 59 | 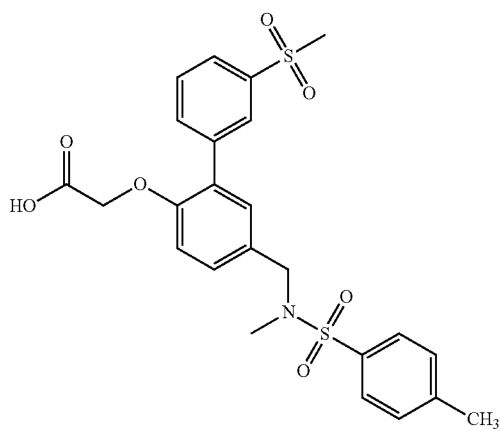 [SMILES: Cc1ccc(S(=O)(=O)N(C)Cc2ccc(OCC(=O)O)c(-c3cccc(S(C)(=O)=O)c3)c2)cc1] | 2-(3-methylsulfonyl-phenyl)-4-((4-methyl-N-methylphenyl-sulfonamido)methyl)phenoxyacetic acid | +++ | 2 |
| 187 | 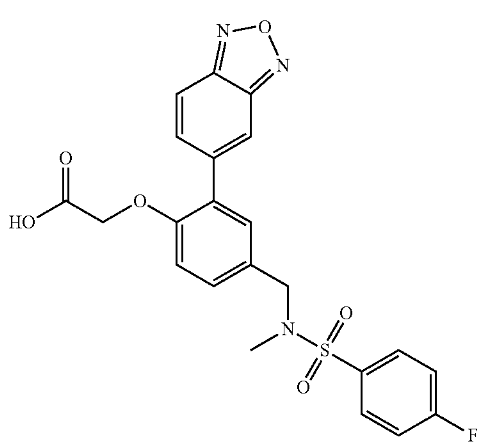 [SMILES: CN(Cc1ccc(OCC(=O)O)c(-c2ccc3nonc3c2)c1)S(=O)(=O)c1ccc(F)cc1] | 2-(5-benzo[c][1,2,5]oxadiazolyl)-4-((4-fluoro-N-methylphenyl-sulfonamido)methyl)phenoxyacetic acid | +++ | 1 |

TABLE 2-continued

| Example No. | Structure | Chemical Name | CRTH2 hGTPγS IC$_{50}$ (nM) | Route |
|---|---|---|---|---|
| 191 | 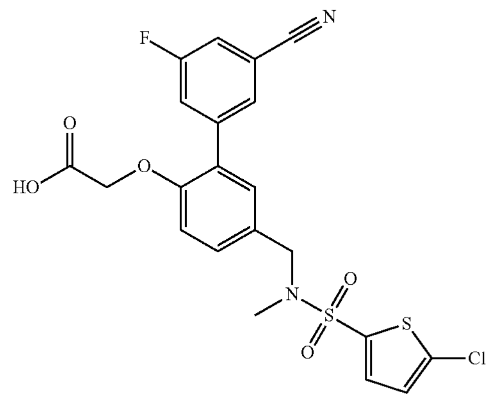 [SMILES: CN(Cc1ccc(OCC(=O)O)c(-c2cc(F)cc(C#N)c2)c1)S(=O)(=O)c1ccc(Cl)s1] | 2-(3-cyano-5-fluorophenyl)-4-((2-chloro-N-methylthiophene-5-sulfonamido)methyl)phenoxyacetic acid | +++ | 3 |
| 61 | 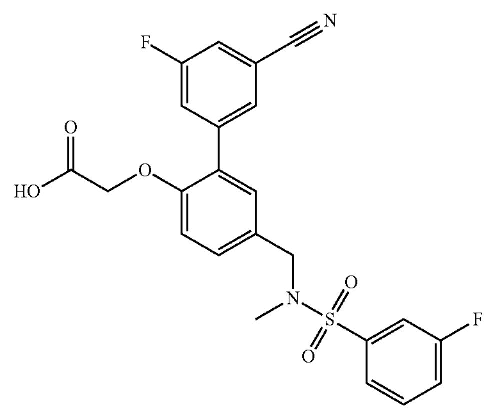 [SMILES: CN(Cc1ccc(OCC(=O)O)c(-c2cc(F)cc(C#N)c2)c1)S(=O)(=O)c1cccc(F)c1] | 2-(3-cyano-5-fluorophenyl)-4-((3-fluoro-N-methylphenyl-sulfonamido)methyl)phenoxyacetic acid | +++ | 3 |
| 92 | 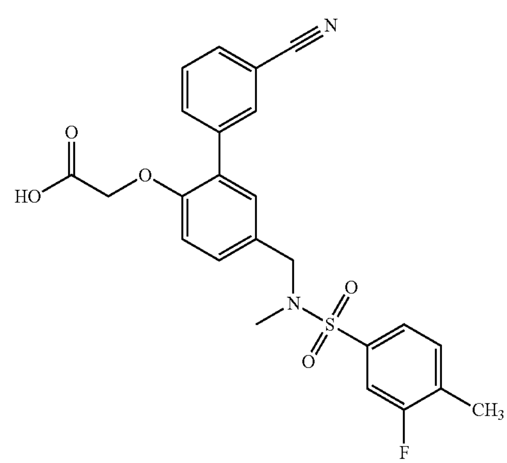 [SMILES: Cc1ccc(S(=O)(=O)N(C)Cc2ccc(OCC(=O)O)c(-c3cccc(C#N)c3)c2)cc1F] | 2-(3-cyanophenyl)-4-((3-fluoro-4-methyl-N-methylphenyl-sulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 63 | 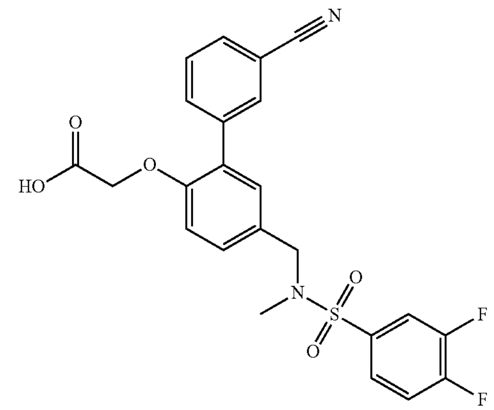 [SMILES: CN(Cc1ccc(OCC(=O)O)c(-c2cccc(C#N)c2)c1)S(=O)(=O)c1ccc(F)c(F)c1] | 2-(3-cyanophenyl)-4-((3,4-difluoro-N-methylphenyl-sulfonamido)methyl) phenoxyacetic acid | +++ | 2 |
| 64 | 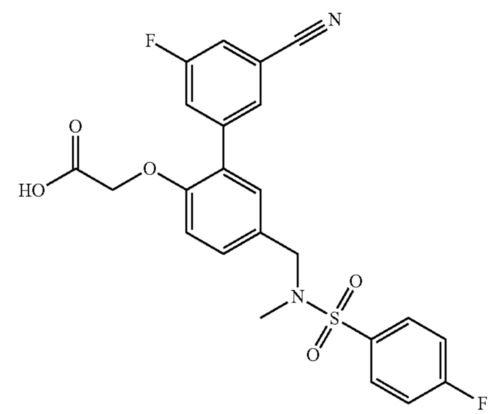 [SMILES: CN(Cc1ccc(OCC(=O)O)c(-c2cc(F)cc(C#N)c2)c1)S(=O)(=O)c1ccc(F)cc1] | 2-(3-cyano-5-fluorophenyl)-4-((4-fluoro-N-methylphenyl-sulfonamido)methyl) phenoxyacetic acid | +++ | 2 |
| 66 | 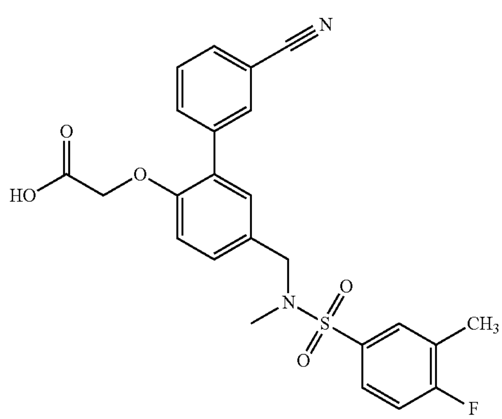 [SMILES: Cc1cc(S(=O)(=O)N(C)Cc2ccc(OCC(=O)O)c(-c3cccc(C#N)c3)c2)ccc1F] | 2-(3-cyanophenyl)-4-((3-methyl-4-fluoro-N-methylphenyl-sulfonamido)methyl) phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 67 | 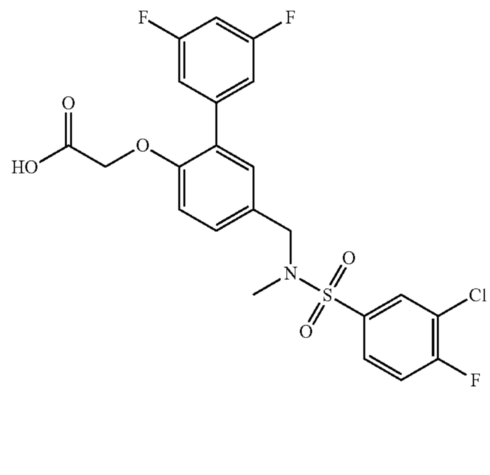 [SMILES: CN(Cc1ccc(OCC(=O)O)c(-c2cc(F)cc(F)c2)c1)S(=O)(=O)c1ccc(F)c(Cl)c1] | 2-(3,5-difluorophenyl)-4-((3-chloro4-fluoro-N-methylphenyl-sulfonamido)methyl) phenoxyacetic acid | +++ | 2 |
| 75 | 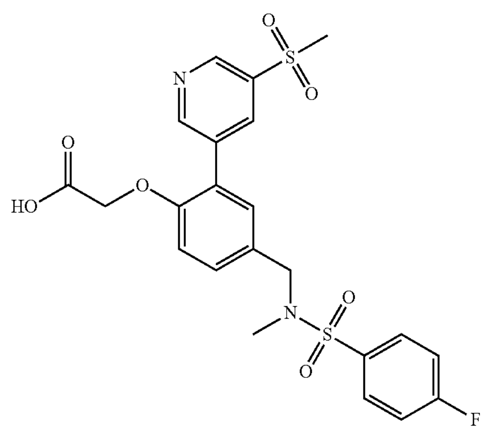 [SMILES: CN(Cc1ccc(OCC(=O)O)c(-c2cncc(S(C)(=O)=O)c2)c1)S(=O)(=O)c1ccc(F)cc1] | 2-(3-methylsulfonyl-5-pyridinyl)-4-((4-fluoro-N-methylphenyl-sulfonamido)methyl) phenoxyacetic acid | +++ | 1 |
| 68 | 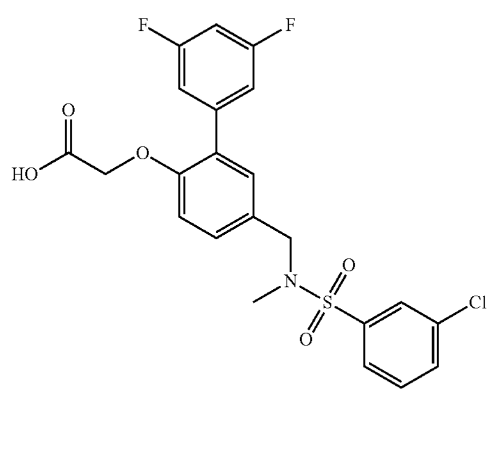 [SMILES: CN(Cc1ccc(OCC(=O)O)c(-c2cc(F)cc(F)c2)c1)S(=O)(=O)c1cccc(Cl)c1] | 2-(3,5-difluorophenyl)-4-((3-chloro-N-methylphenyl-sulfonamido)methyl) phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 190 | 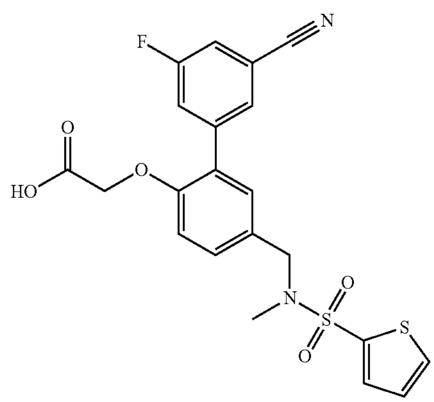 [SMILES: CN(Cc1ccc(OCC(=O)O)c(-c2cc(F)cc(C#N)c2)c1)S(=O)(=O)c1cccs1] | 2-(3-cyano-5-fluorophenyl)-4-((N-methylthiophene-2-sulfonamido)methyl)phenoxyacetic acid | +++ | 3 |
| 43 | 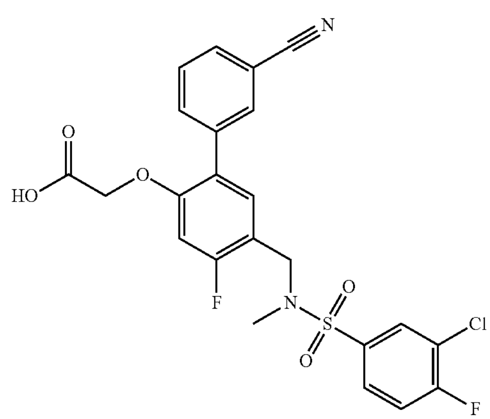 [SMILES: CN(Cc1cc(-c2cccc(C#N)c2)c(OCC(=O)O)cc1F)S(=O)(=O)c1ccc(F)c(Cl)c1] | 2-(3-cyanophenyl)-4-((3-chloro-4-fluoro-N-methylphenyl-sulfonamido)methyl)-5-fluorophenoxy-acetic acid | +++ | 2 |
| 69 | 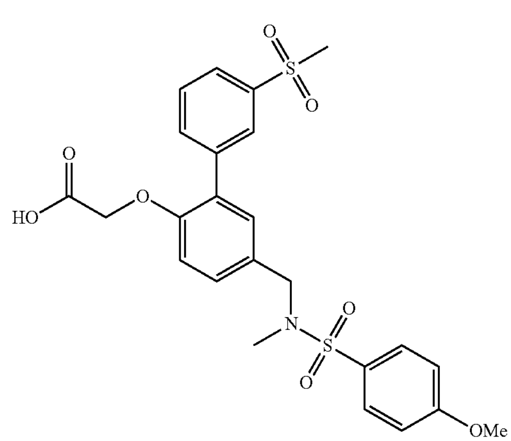 [SMILES: COc1ccc(S(=O)(=O)N(C)Cc2ccc(OCC(=O)O)c(-c3cccc(S(C)(=O)=O)c3)c2)cc1] | 2-(3-methylsulfonyl-phenyl)-4-((4-methoxy-N-methylphenyl-sulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 52 | 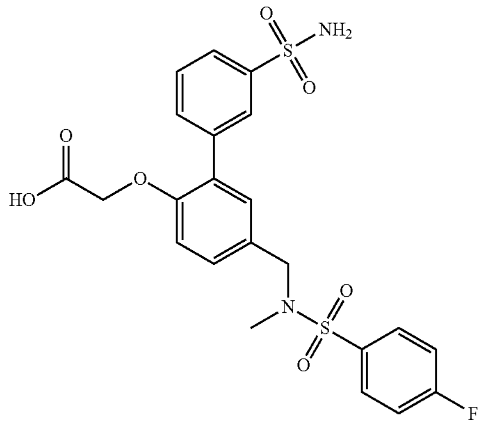 [SMILES: CN(Cc1ccc(OCC(=O)O)c(-c2cccc(S(N)(=O)=O)c2)c1)S(=O)(=O)c1ccc(F)cc1] | 2-(3-aminosulfonyl-phenyl)-4-((4-fluoro-N-methylphenyl-sulfonamido)methyl) phenoxyacetic acid | +++ | 1 |
| 70 | 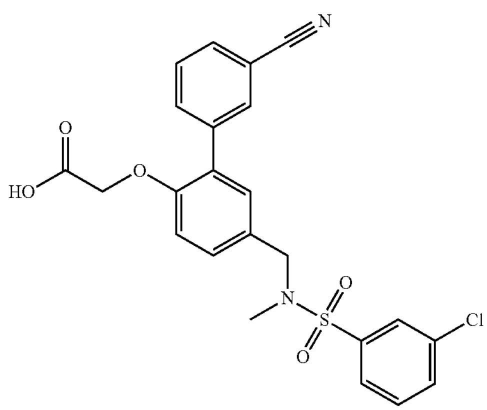 [SMILES: CN(Cc1ccc(OCC(=O)O)c(-c2cccc(C#N)c2)c1)S(=O)(=O)c1cccc(Cl)c1] | 2-(3-cyanophenyl)-4-((3-chloro-N-methylphenyl-sulfonamido)methyl) phenoxyacetic acid | +++ | 2 |
| 56 | 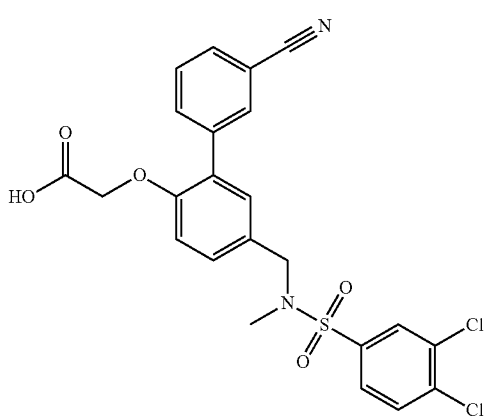 [SMILES: CN(Cc1ccc(OCC(=O)O)c(-c2cccc(C#N)c2)c1)S(=O)(=O)c1ccc(Cl)c(Cl)c1] | 2-(3-cyanophenyl)-4-((3,4-dichloro-N-methylphenyl-sulfonamido)methyl) phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 71 | 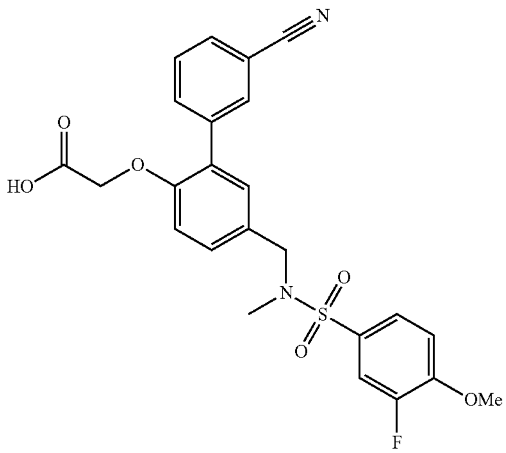 [SMILES: COc1ccc(S(=O)(=O)N(C)Cc2ccc(OCC(=O)O)c(-c3cccc(C#N)c3)c2)cc1F] | 2-(3-cyanophenyl)-4-((3-fluoro-4-methoxy-N-methylphenyl-sulfonamido)methyl)phenoxyacetic acid | +++ | 2 |
| 60 | 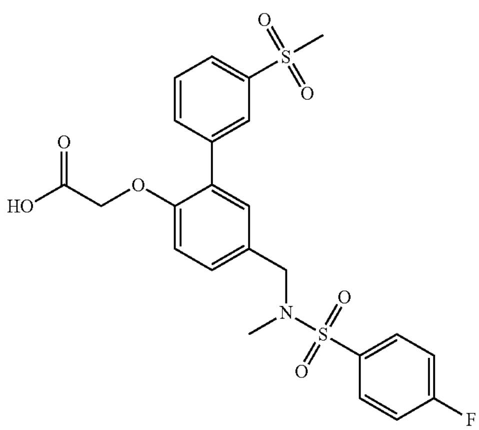 [SMILES: CN(Cc1ccc(OCC(=O)O)c(-c2cccc(S(C)(=O)=O)c2)c1)S(=O)(=O)c1ccc(F)cc1] | 2-(3-methylsulfonyl-phenyl)-4-((4-fluoro-N-methylphenyl-sulfonamido)methyl)phenoxyacetic acid | +++ | 1 |
| 72 | 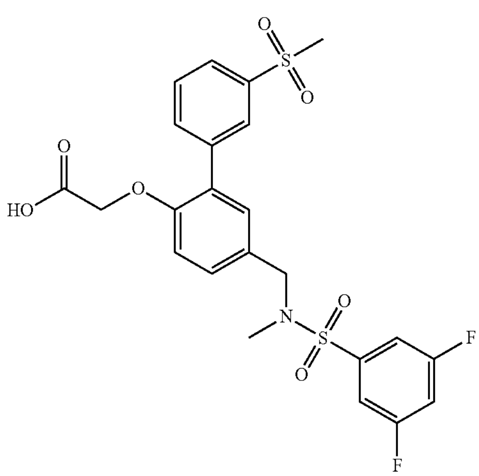 [SMILES: CN(Cc1ccc(OCC(=O)O)c(-c2cccc(S(C)(=O)=O)c2)c1)S(=O)(=O)c1cc(F)cc(F)c1] | 2-(3-methylsulfonyl-phenyl)-4-((3,5-difluoro-N-methylphenyl-sulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 73 | 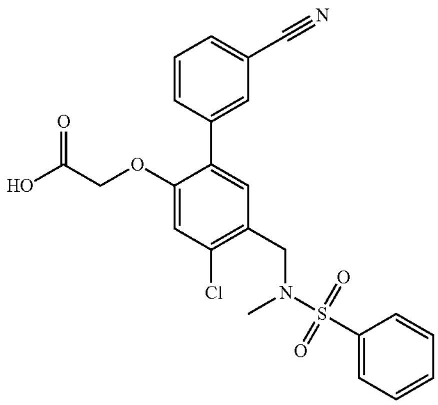 [SMILES: CN(Cc1cc(-c2cccc(C#N)c2)c(OCC(=O)O)cc1Cl)S(=O)(=O)c1ccccc1] | 2-(3-cyanophenyl)-4-((N-methylphenyl-sulfonamido)methyl)-5-chlorophenoxy-acetic acid | +++ | 2 |
| 195 | 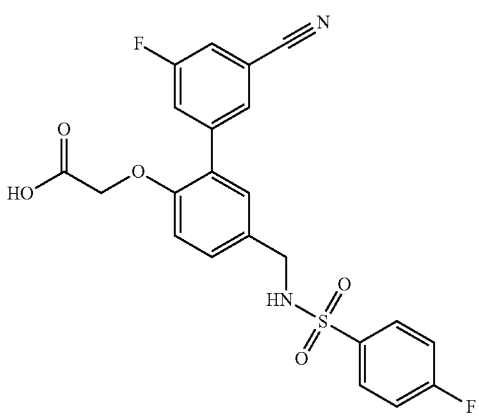 [SMILES: N#Cc1cc(F)cc(-c2cc(CNS(=O)(=O)c3ccc(F)cc3)ccc2OCC(=O)O)c1] | 2-(3-cyano-5-fluorophenyl)-4-((4-fluoro-phenylsulfonamido)methyl)phenoxy-acetic acid | +++ | 3 |
| 62 | 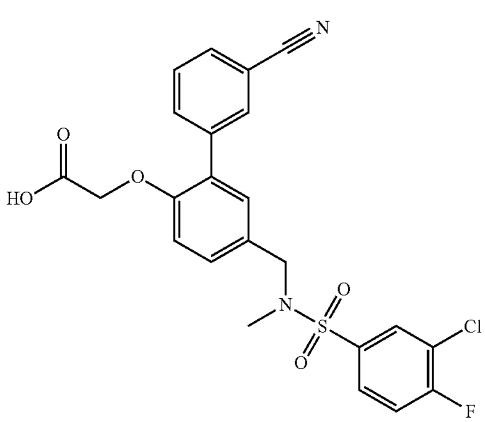 [SMILES: CN(Cc1ccc(OCC(=O)O)c(-c2cccc(C#N)c2)c1)S(=O)(=O)c1ccc(F)c(Cl)c1] | 2-(3-cyanophenyl)-4-((3-chloro-4-fluoro-N-methylphenyl-sulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 77 | 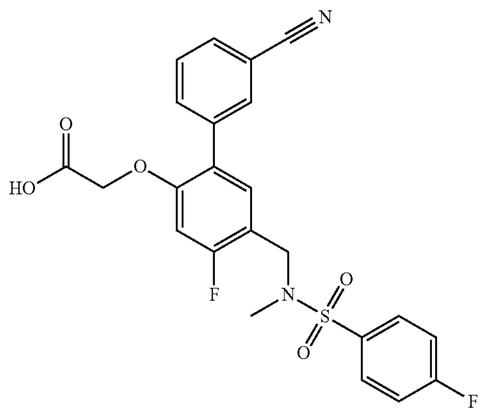 [SMILES: CN(Cc1cc(-c2cccc(C#N)c2)c(OCC(=O)O)cc1F)S(=O)(=O)c1ccc(F)cc1] | 2-(3-cyanophenyl)-4-((4-fluoro-N-methylphenyl-sulfonamido)methyl)-5-fluorophenoxy-acetic acid | +++ | 2 |
| 85 | 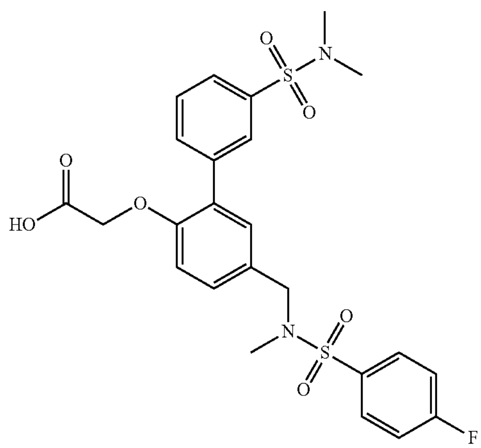 [SMILES: CN(C)S(=O)(=O)c1cccc(-c2cc(CN(C)S(=O)(=O)c3ccc(F)cc3)ccc2OCC(=O)O)c1] | 2-(3-N,N-dimethylsulfamoyl-phenyl)-4-((4-fluoro-N-methylphenyl-sulfonamido)methyl)phenoxyacetic acid | +++ | 1 |
| 78 | 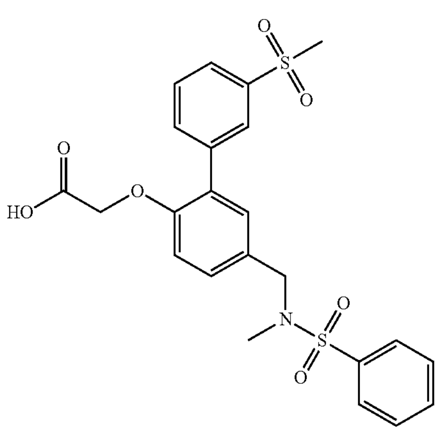 [SMILES: CN(Cc1ccc(OCC(=O)O)c(-c2cccc(S(C)(=O)=O)c2)c1)S(=O)(=O)c1ccccc1] | 2-(3-methylsulfonyl-phenyl)-4-((N-methylphenyl-sulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 81 | 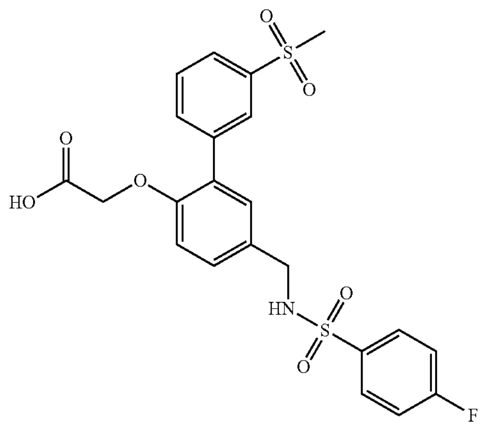 [SMILES: CS(=O)(=O)c1cccc(-c2cc(CNS(=O)(=O)c3ccc(F)cc3)ccc2OCC(=O)O)c1] | 2-(3-methylsulfonyl-phenyl)-4-((4-fluorophenyl-sulfonamido)methyl)phenoxyacetic acid | +++ | 2 |
| 193 | 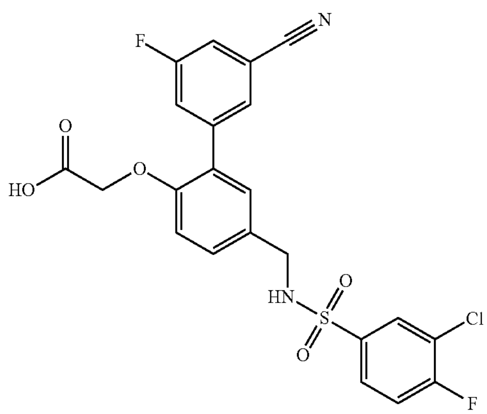 [SMILES: N#Cc1cc(F)cc(-c2cc(CNS(=O)(=O)c3ccc(F)c(Cl)c3)ccc2OCC(=O)O)c1] | 2-(3-cyano-5-fluorophenyl)-4-((3-chloro-4-fluoro-phenylsulfonamido)methyl)phenoxy-acetic acid | +++ | 3 |
| 83 | 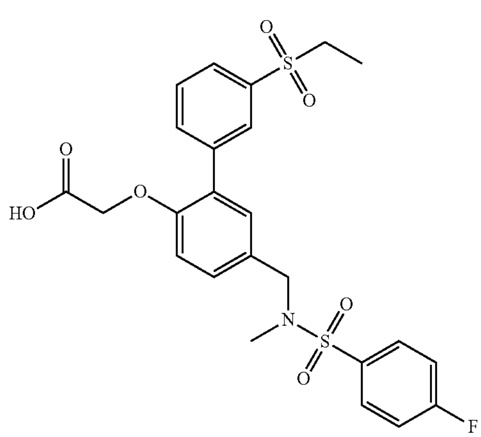 [SMILES: CCS(=O)(=O)c1cccc(-c2cc(CN(C)S(=O)(=O)c3ccc(F)cc3)ccc2OCC(=O)O)c1] | 2-(3-ethylsulfonyl-phenyl)-4-((4-fluoro-N-methylphenyl-sulfonamido)methyl)phenoxyacetic acid | +++ | 2 |

TABLE 2-continued
| Example No. | Structure | Chemical Name | CRTH2 hGTPγS IC$_{50}$ (nM) | Route |
|---|---|---|---|---|
| 9 | 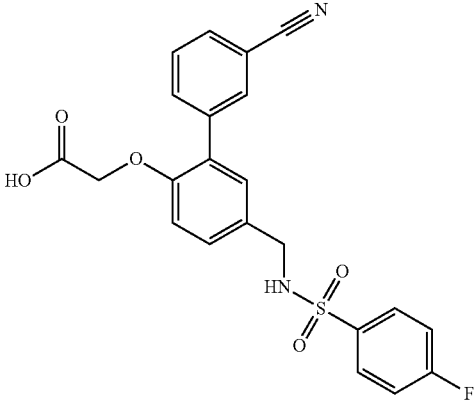 [SMILES: N#Cc1cccc(-c2cc(CNS(=O)(=O)c3ccc(F)cc3)ccc2OCC(=O)O)c1] | 2-(3-cyanophenyl)-4-((4-fluorophenyl-sulfonamido)methyl)phenoxyacetic acid | +++ | 1 |
| 84 | 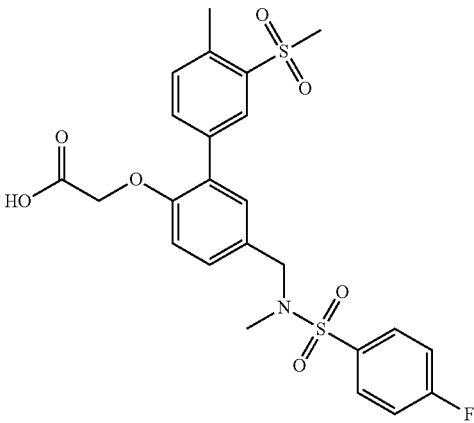 [SMILES: Cc1ccc(-c2cc(CN(C)S(=O)(=O)c3ccc(F)cc3)ccc2OCC(=O)O)cc1S(C)(=O)=O] | 2-(3-methylsulfonyl-4-methyl-phenyl)-4-((4-fluoro-N-methylphenyl-sulfonamido)methyl)phenoxyacetic acid | +++ | 3 |
| 5 | 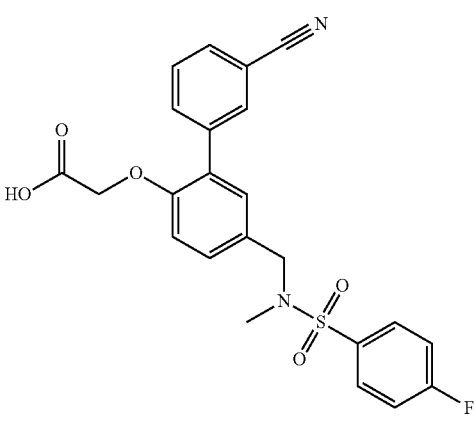 [SMILES: CN(Cc1ccc(OCC(=O)O)c(-c2cccc(C#N)c2)c1)S(=O)(=O)c1ccc(F)cc1] | 2-(3-cyanophenyl)-4-((4-fluoro-N-methylphenyl-sulfonamido)methyl)phenoxyacetic acid | +++ | 1 |

TABLE 2-continued

| Example No. | Structure | Chemical Name | CRTH2 hGTPγS IC$_{50}$ (nM) | Route |
|---|---|---|---|---|
| 86 | 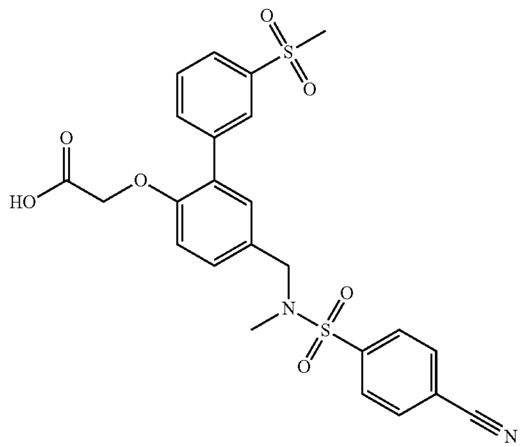 [SMILES: CN(Cc1ccc(OCC(=O)O)c(-c2cccc(S(C)(=O)=O)c2)c1)S(=O)(=O)c1ccc(C#N)cc1] | 2-(3-methylsulfonyl-phenyl)-4-((4-cyano-N-methylphenyl-sulfonamido)methyl) phenoxyacetic acid | +++ | 2 |
| 78 | 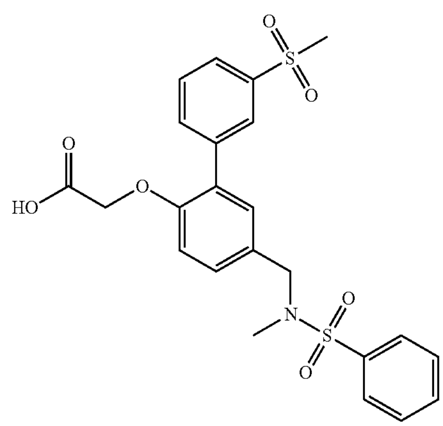 [SMILES: CN(Cc1ccc(OCC(=O)O)c(-c2cccc(S(C)(=O)=O)c2)c1)S(=O)(=O)c1ccccc1] | 2-(3-methylsulfonyl-phenyl)-4-((N-methylphenyl-sulfonamido)methyl) phenoxyacetic acid | +++ | 2 |
| 87 | 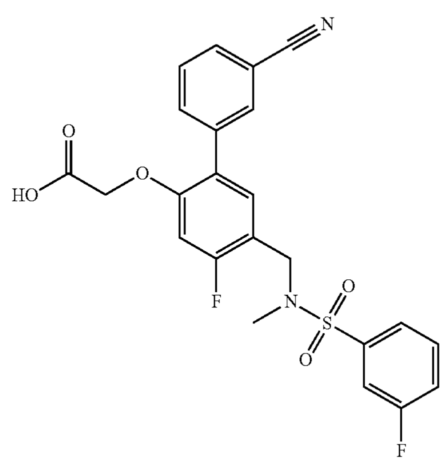 [SMILES: CN(Cc1cc(-c2cccc(C#N)c2)c(OCC(=O)O)cc1F)S(=O)(=O)c1cccc(F)c1] | 2-(3-cyanophenyl)-4-((3-fluoro-N-methylphenyl-sulfonamido) methyl)-5-fluorophenoxy-acetic acid | +++ | 2 |

TABLE 2-continued

| Example No. | Structure | Chemical Name | CRTH2 hGTPγS IC$_{50}$ (nM) | Route |
|---|---|---|---|---|
| 38 | 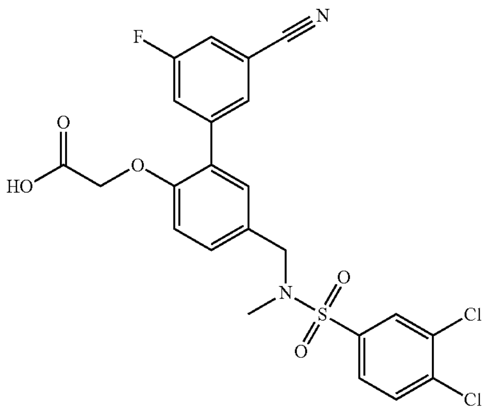 [SMILES: CN(Cc1ccc(OCC(=O)O)c(-c2cc(F)cc(C#N)c2)c1)S(=O)(=O)c1ccc(Cl)c(Cl)c1] | 2-(3-cyano-5-fluorophenyl)-4-((3,4-dichloro-N-methylphenyl-sulfonamido)methyl)phenoxyacetic acid | +++ | 3 |
| 79 | 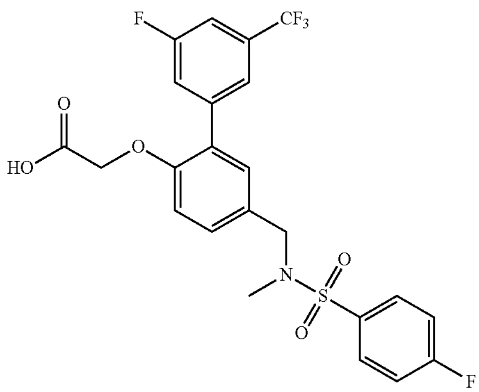 [SMILES: CN(Cc1ccc(OCC(=O)O)c(-c2cc(F)cc(C(F)(F)F)c2)c1)S(=O)(=O)c1ccc(F)cc1] | 2-(3-trifluoromethyl-5-fluorophenyl)-4-((4-fluoro-N-methylphenyl-sulfonamido)methyl)phenoxyacetic acid | +++ | 1 |
| 88 | 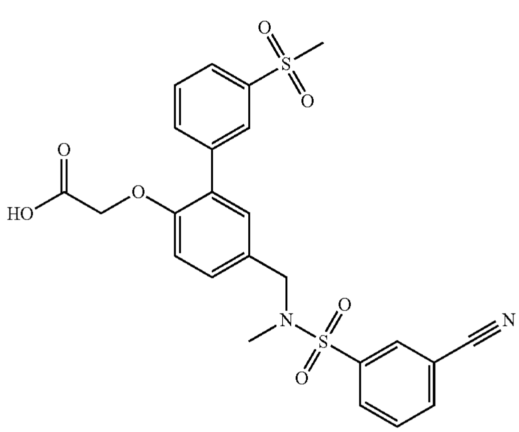 [SMILES: CN(Cc1ccc(OCC(=O)O)c(-c2cccc(S(C)(=O)=O)c2)c1)S(=O)(=O)c1cccc(C#N)c1] | 2-(3-methylsulfonyl-phenyl)-4-((3-cyano-N-methylphenyl-sulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 101 | 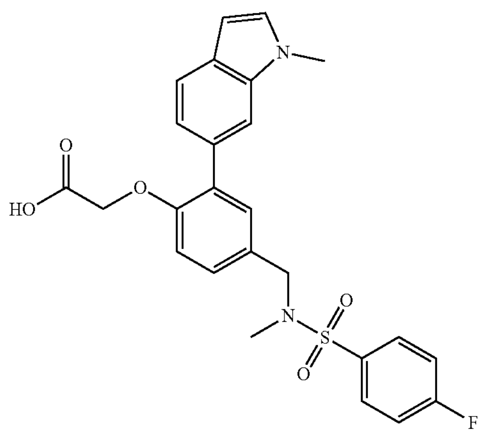 | 2-(1-methyl-indol-6-yl)-4-((4-fluoro-N-methylphenyl-sulfonamido)methyl)phenoxyacetic acid | +++ | 1 |
| 188 | 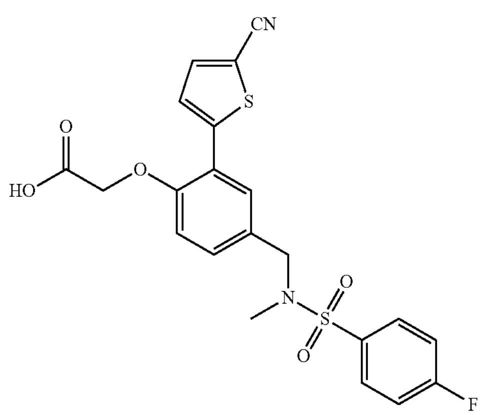 [SMILES: CN(Cc1ccc(OCC(=O)O)c(-c2ccc(C#N)s2)c1)S(=O)(=O)c1ccc(F)cc1] | 2-(2-cyanothiophen-5-yl)-4-((4-fluoro-N-methylphenyl-sulfonamido)methyl)phenoxyacetic acid | +++ | 1 |
| 89 | 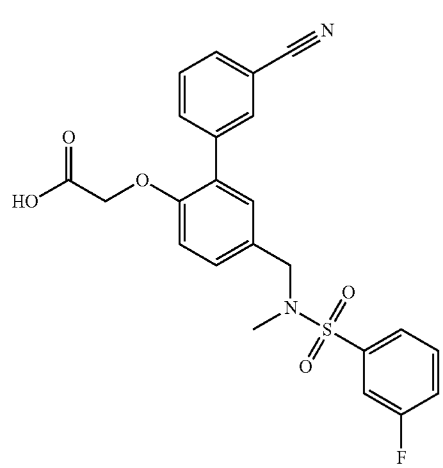 [SMILES: CN(Cc1ccc(OCC(=O)O)c(-c2cccc(C#N)c2)c1)S(=O)(=O)c1cccc(F)c1] | 2-(3-cyanophenyl)-4-((3-fluoro-N-methylphenyl-sulfonamido)methyl)phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 82 | 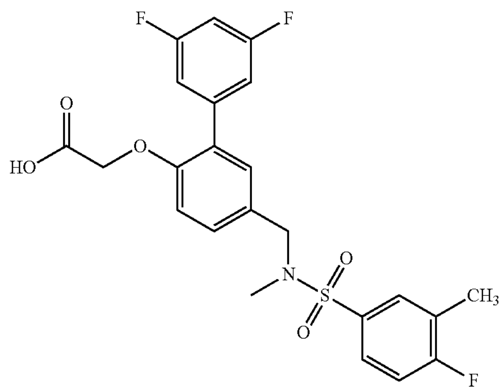 [SMILES: Cc1cc(S(=O)(=O)N(C)Cc2ccc(OCC(=O)O)c(-c3cc(F)cc(F)c3)c2)ccc1F] | 2-(3,5-difluorophenyl)-4-((3-methyl-4-fluoro-N-methylphenyl-sulfonamido)methyl) phenoxyacetic acid | +++ | 2 |
| 90 | 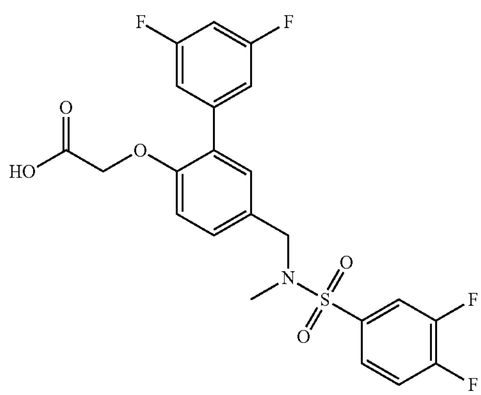 [SMILES: CN(Cc1ccc(OCC(=O)O)c(-c2cc(F)cc(F)c2)c1)S(=O)(=O)c1ccc(F)c(F)c1] | 2-(3,5-difluorophenyl)-4-((3,4-difluoro-N-methylphenyl-sulfonamido)methyl) phenoxyacetic acid | +++ | 2 |
| 91 | 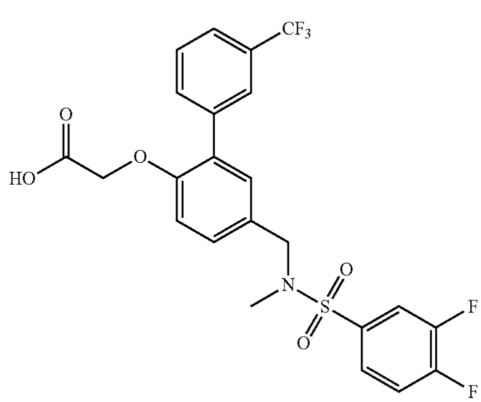 [SMILES: CN(Cc1ccc(OCC(=O)O)c(-c2cccc(C(F)(F)F)c2)c1)S(=O)(=O)c1ccc(F)c(F)c1] | 2-(3-trifluoromethyl-phenyl)-4-((3,4-difluoro-N-methylphenyl-sulfonamido)methyl) phenoxyacetic acid | +++ | 1 |

TABLE 2-continued

| Example No. | Structure | Chemical Name | CRTH2 hGTPγS IC$_{50}$ (nM) | Route |
|---|---|---|---|---|
| 76 | 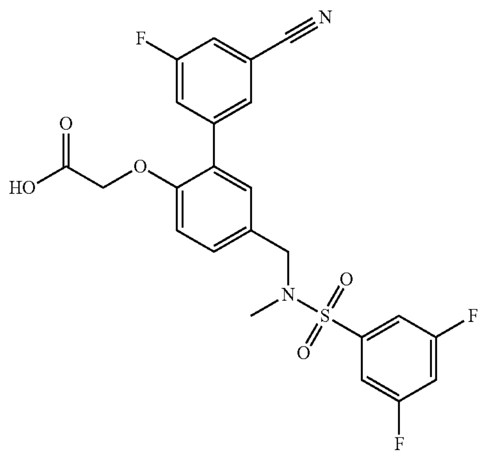 [SMILES: CN(Cc1ccc(OCC(=O)O)c(-c2cc(F)cc(C#N)c2)c1)S(=O)(=O)c1cc(F)cc(F)c1] | 2-(3-cyano-5-fluorophenyl)-4-((3,5-difluoro-N-methylphenyl-sulfonamido)methyl) phenoxyacetic acid | +++ | 3 |
| 93 | 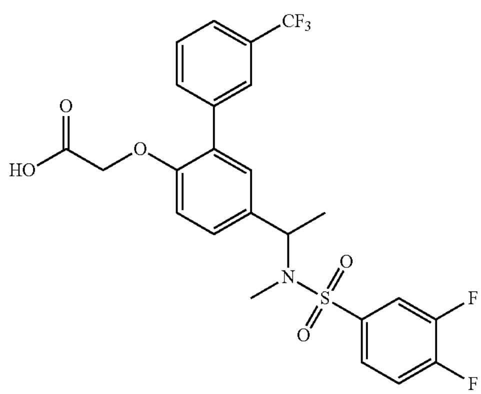 [SMILES: CC(c1ccc(OCC(=O)O)c(-c2cccc(C(F)(F)F)c2)c1)N(C)S(=O)(=O)c1ccc(F)c(F)c1] | 2-(3-trifluoromethyl-phenyl)-4-(1-(3,4-difluoro-N-methylphenyl-sulfonamido)ethyl) phenoxyacetic acid | +++ | 2 |
| 94 | 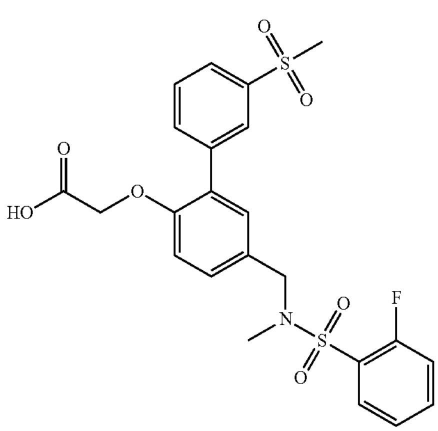 [SMILES: CN(Cc1ccc(OCC(=O)O)c(-c2cccc(S(C)(=O)=O)c2)c1)S(=O)(=O)c1ccccc1F] | 2-(3-methylsulfonyl-phenyl)-4-((2-fluoro-N-methylphenyl-sulfonamido)methyl) phenoxyacetic acid | +++ | 2 |

TABLE 2-continued

| Example No. | Structure | Chemical Name | CRTH2 hGTPγS IC$_{50}$ (nM) | Route |
|---|---|---|---|---|
| 80 | 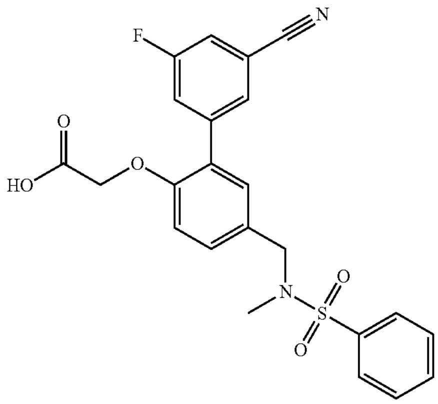 [SMILES: CN(Cc1ccc(OCC(=O)O)c(-c2cc(F)cc(C#N)c2)c1)S(=O)(=O)c1ccccc1] | 2-(3-cyano-5-fluorophenyl)-4-((N-methylphenyl-sulfonamido)methyl)phenoxyacetic acid | +++ | 3 |
| 98 | 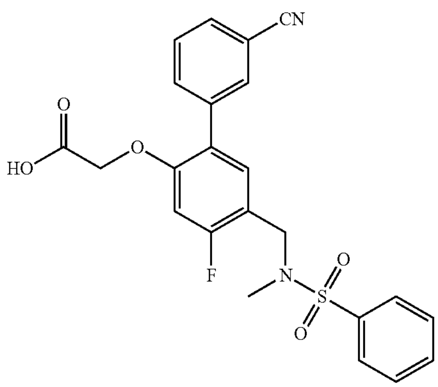 [SMILES: CN(Cc1cc(-c2cccc(C#N)c2)c(OCC(=O)O)cc1F)S(=O)(=O)c1ccccc1] | 2-(3-cyanophenyl)-4-((N-methylphenyl-sulfonamido)methyl)-5-fluorophenoxyacetic acid | +++ | 2 |
| 42 | 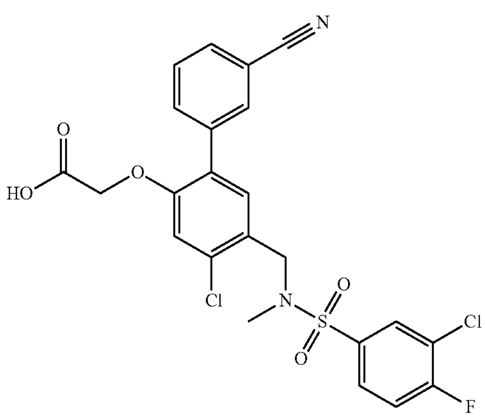 [SMILES: CN(Cc1cc(-c2cccc(C#N)c2)c(OCC(=O)O)cc1Cl)S(=O)(=O)c1ccc(F)c(Cl)c1] | 2-(3-cyanophenyl)-4-((3-chloro-4-fluoro-N-methylphenyl-sulfonamido)methyl)-5-chlorophenoxy-acetic acid | +++ | 2 |
| 100 | 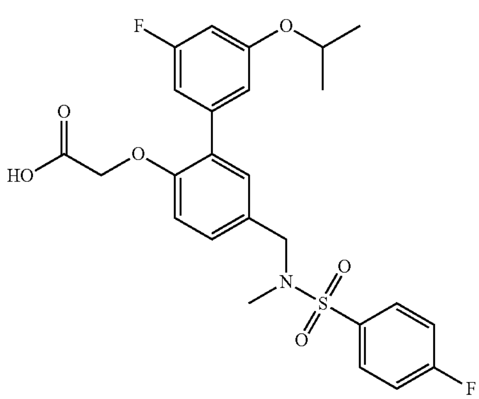 [SMILES: CC(C)Oc1cc(F)cc(-c2cc(CN(C)S(=O)(=O)c3ccc(F)cc3)ccc2OCC(=O)O)c1] | 2-(3-isopropoxy-5-fluorophenyl)-4-((4-fluoro-N-methylphenyl-sulfonamido)methyl)phenoxyacetic acid | +++ | 1 |

TABLE 2-continued

| Example No. | Structure | Chemical Name | CRTH2 hGTPγS IC$_{50}$ (nM) | Route |
|---|---|---|---|---|
| 95 | 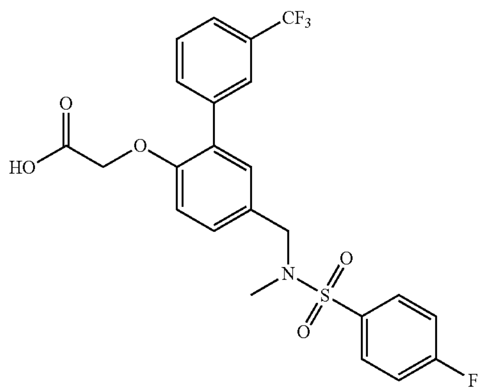 [SMILES: CN(Cc1ccc(OCC(=O)O)c(-c2cccc(C(F)(F)F)c2)c1)S(=O)(=O)c1ccc(F)cc1] | 2-(3-trifluoromethyl-phenyl)-4-((4-fluoro-N-methylphenyl-sulfonamido)methyl) phenoxyacetic acid | +++ | 2 |
| 196 | 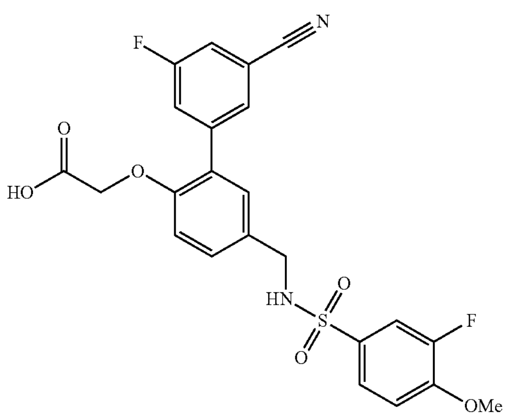 [SMILES: COc1ccc(S(=O)(=O)NCc2ccc(OCC(=O)O)c(-c3cc(F)cc(C#N)c3)c2)cc1F] | 2-(3-cyano-5-fluorophenyl)-4-((3-fluoro-4-methoxyphenyl-sulfonamido)methyl) phenoxyacetic acid | +++ | 3 |
| 197 | 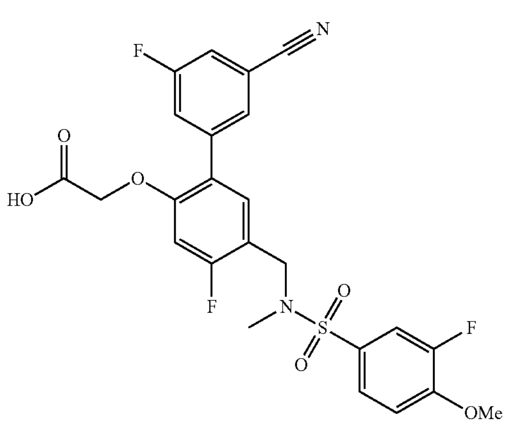 [SMILES: COc1ccc(S(=O)(=O)N(C)Cc2cc(-c3cc(F)cc(C#N)c3)c(OCC(=O)O)cc2F)cc1F] | 2-(3-cyano-5-fluorophenyl)-(5-fluoro-4-((3-fluoro-4-methoxy-N-methylphenyl-sulfonamido)methyl) phenoxy)acetic acid | +++ | 2 |

TABLE 2-continued

| Example No. | Structure | Chemical Name | CRTH2 hGTPγS IC$_{50}$ (nM) | Route |
|---|---|---|---|---|
| 36 | 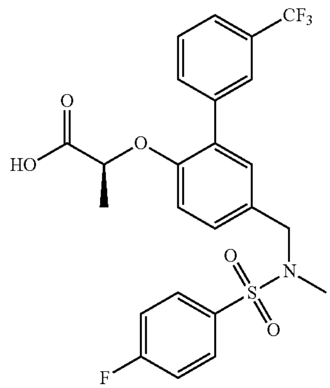 [SMILES: C[C@H](Oc1ccc(CN(C)S(=O)(=O)c2ccc(F)cc2)cc1-c1cccc(C(F)(F)F)c1)C(=O)O] | (S)-2-(2-(3-trifluoromethyl-phenyl)-4-((4-fluoro-N-methylphenyl-sulfonamido)methyl)phenoxy)propanoic acid | ++ | 4 |
| 103 | 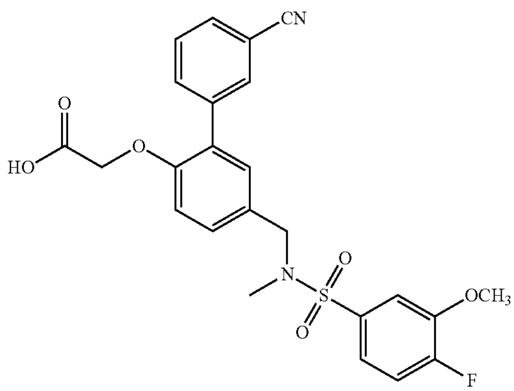 [SMILES: COc1cc(S(=O)(=O)N(C)Cc2ccc(OCC(=O)O)c(-c3cccc(C#N)c3)c2)ccc1F] | 2-(3-cyanophenyl)-4-((3-methoxy-4-fluoro-N-methylphenyl-sulfonamido)methyl)phenoxyacetic acid | ++ | 2 |
| 114 | 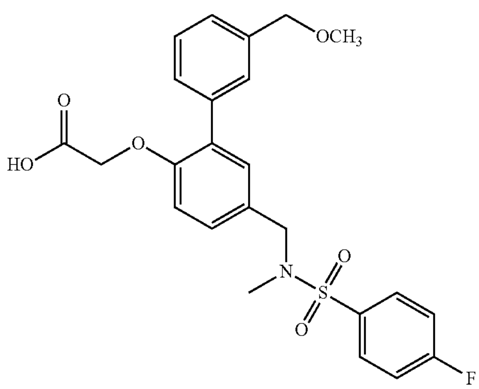 [SMILES: COCc1cccc(-c2cc(CN(C)S(=O)(=O)c3ccc(F)cc3)ccc2OCC(=O)O)c1] | 2-(3-methoxymethyl-phenyl)-4-((4-fluoro-N-methylphenyl-sulfonamido)methyl)phenoxyacetic acid | ++ | 1 |
| 104 | 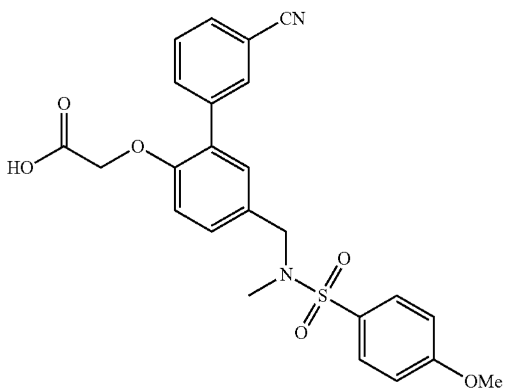 [SMILES: COc1ccc(S(=O)(=O)N(C)Cc2ccc(OCC(=O)O)c(-c3cccc(C#N)c3)c2)cc1] | 2-(3-cyanophenyl)-4-((4-methoxy-N-methylphenyl-sulfonamido)methyl)phenoxyacetic acid | ++ | 2 |

| Example No. | Structure | Chemical Name | CRTH2 hGTPγS IC$_{50}$ (nM) | Route |
|---|---|---|---|---|
| 105 | 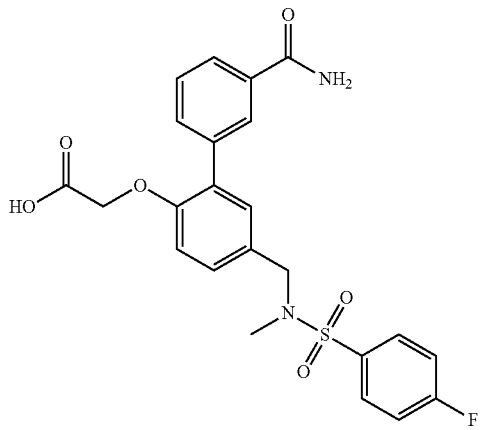 [SMILES: CN(Cc1ccc(OCC(=O)O)c(-c2cccc(C(N)=O)c2)c1)S(=O)(=O)c1ccc(F)cc1] | 2-(3-aminocarbonyl-phenyl)-4-((4-fluoro-N-methylphenyl-sulfonamido)methyl)phenoxyacetic acid | ++ | 1 |
| 110 | 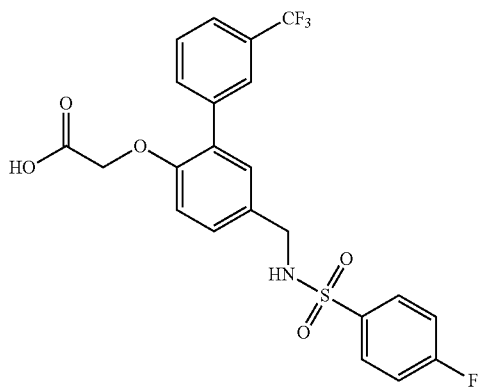 [SMILES: O=C(O)COc1ccc(CNS(=O)(=O)c2ccc(F)cc2)cc1-c1cccc(C(F)(F)F)c1] | 2-(3-trifluoromethyl-phenyl)-4-((4-fluoro-N-methylphenyl-sulfonamido)methyl)phenoxyacetic acid | ++ | 2 |
| 107 | 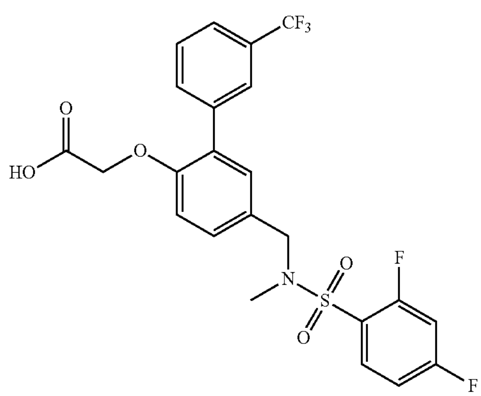 [SMILES: CN(Cc1ccc(OCC(=O)O)c(-c2cccc(C(F)(F)F)c2)c1)S(=O)(=O)c1ccc(F)cc1F] | 2-(3-trifluoromethyl-phenyl)-4-((2,4-difluoro-N-methylphenyl-sulfonamido)methyl)phenoxyacetic acid | ++ | 2 |

TABLE 2-continued

| Example No. | Structure | Chemical Name | CRTH2 hGTPγS IC$_{50}$ (nM) | Route |
|---|---|---|---|---|
| 102 | 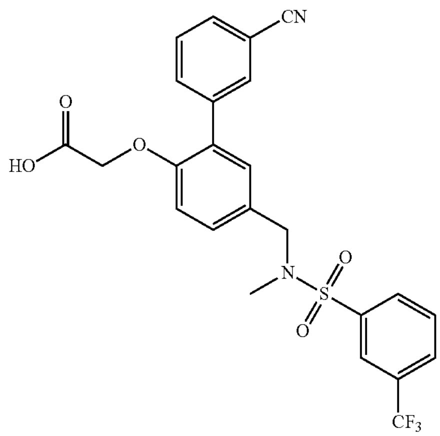 [SMILES: CN(Cc1ccc(OCC(=O)O)c(-c2cccc(C#N)c2)c1)S(=O)(=O)c1cccc(C(F)(F)F)c1] | 2-(3-cyanophenyl)-4-((3-trifluoromethyl-N-methylphenyl-sulfonamido)methyl) phenoxyacetic acid | ++ | 2 |
| 125 | 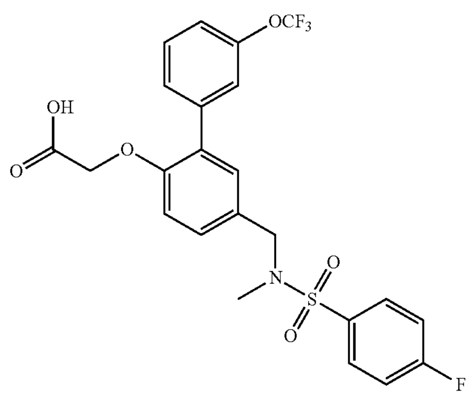 [SMILES: CN(Cc1ccc(OCC(=O)O)c(-c2cccc(OC(F)(F)F)c2)c1)S(=O)(=O)c1ccc(F)cc1] | 2-(3-trifluoromethoxy phenyl)-4-((4-fluoro-N-methylphenyl-sulfonamido)methyl) phenoxyacetic acid | ++ | 1 |
| 108 | 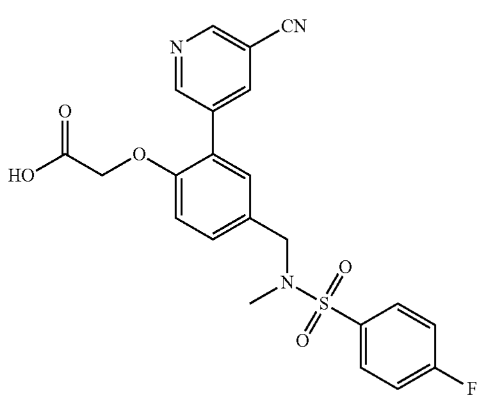 [SMILES: CN(Cc1ccc(OCC(=O)O)c(-c2cncc(C#N)c2)c1)S(=O)(=O)c1ccc(F)cc1] | 2-(3-cyano-5-pyridinyl)-4-((4-fluoro-N-methylphenyl-sulfonamido)methyl) phenoxyacetic acid | ++ | 1 |

TABLE 2-continued

| Example No. | Structure | Chemical Name | CRTH2 hGTPγS IC$_{50}$ (nM) | Route |
|---|---|---|---|---|
| 118 | 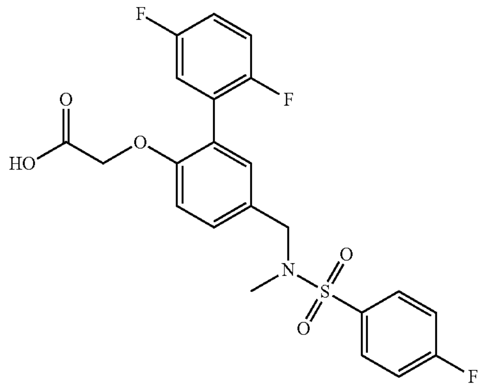 [SMILES: CN(Cc1ccc(OCC(=O)O)c(-c2cc(F)ccc2F)c1)S(=O)(=O)c1ccc(F)cc1] | 2-(2,5-difluorophenyl)-4-((4-fluoro-N-methylphenyl-sulfonamido)methyl)phenoxyacetic acid | ++ | 1 |
| 116 | 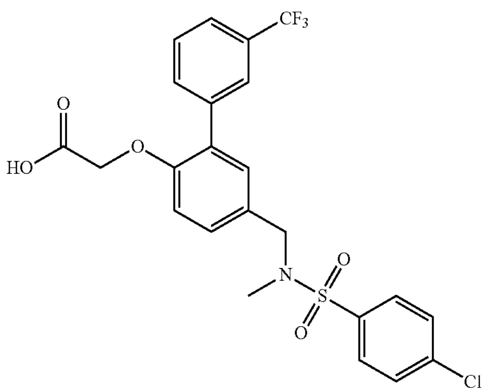 [SMILES: CN(Cc1ccc(OCC(=O)O)c(-c2cccc(C(F)(F)F)c2)c1)S(=O)(=O)c1ccc(Cl)cc1] | 2-(3-trifluoromethyl-phenyl)-4-((4-chloro-N-methylphenyl-sulfonamido)methyl)phenoxyacetic acid | ++ | 2 |
| 111 | 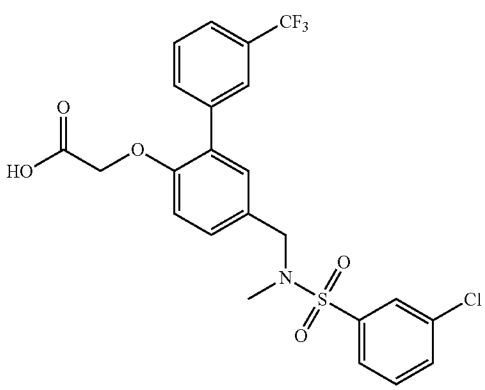 [SMILES: CN(Cc1ccc(OCC(=O)O)c(-c2cccc(C(F)(F)F)c2)c1)S(=O)(=O)c1cccc(Cl)c1] | 2-(3-trifluoromethyl-phenyl)-4-((3-chloro-N-methylphenyl-sulfonamido)methyl)phenoxyacetic acid | ++ | 2 |
| 106 | 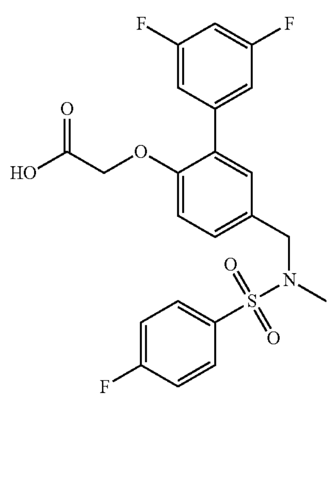 [SMILES: CN(Cc1ccc(OCC(=O)O)c(-c2cc(F)cc(F)c2)c1)S(=O)(=O)c1ccc(F)cc1] | 2-(3,5-difluorophenyl)-4-((4-fluoro-N-methylphenyl-sulfonamido)methyl)phenoxyacetic acid | ++ | 1 |

TABLE 2-continued

| Example No. | Structure | Chemical Name | CRTH2 hGTPγS IC$_{50}$ (nM) | Route |
|---|---|---|---|---|
| 112 | 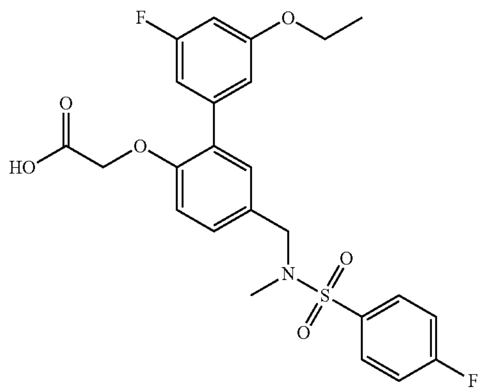 [SMILES: CCOc1cc(F)cc(-c2cc(CN(C)S(=O)(=O)c3ccc(F)cc3)ccc2OCC(=O)O)c1] | 2-(3-ethoxy-5-fluorophenyl)-4-((4-fluoro-N-methylphenyl-sulfonamido)methyl) phenoxyacetic acid | ++ | 1 |
| 113 | 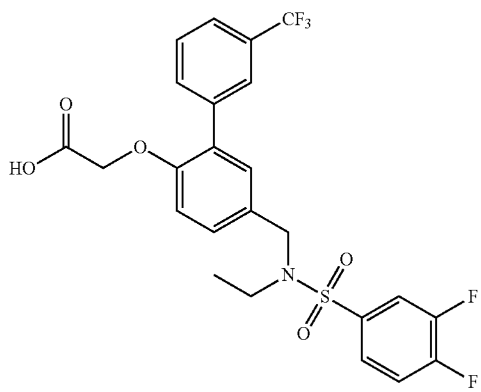 [SMILES: CCN(Cc1ccc(OCC(=O)O)c(-c2cccc(C(F)(F)F)c2)c1)S(=O)(=O)c1ccc(F)c(F)c1] | 2-(3-trifluoromethyl-phenyl)-4-((3,4-difluoro-N-ethylphenyl-sulfonamido)methyl) phenoxyacetic acid | ++ | 2 |
| 150 | 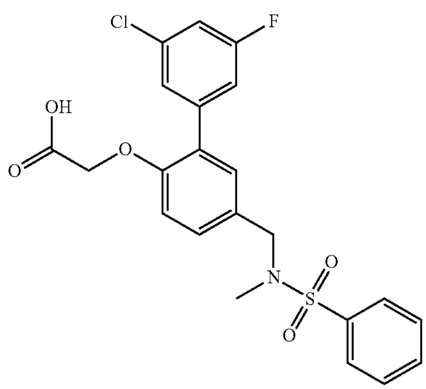 [SMILES: CN(Cc1ccc(OCC(=O)O)c(-c2cc(F)cc(Cl)c2)c1)S(=O)(=O)c1ccccc1] | 2-(3-chloro-5-fluorophenyl)-4-((-N-methylphenyl-sulfonamido)methyl) phenoxyacetic acid | ++ | 1 |
| 115 | 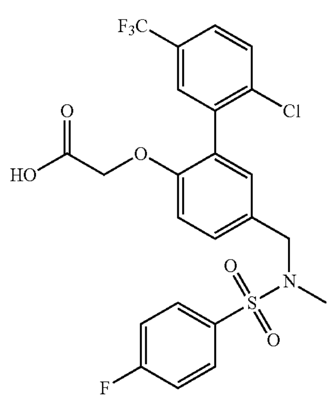 [SMILES: CN(Cc1ccc(OCC(=O)O)c(-c2cc(C(F)(F)F)ccc2Cl)c1)S(=O)(=O)c1ccc(F)cc1] | 2-(2-chloro-5-trifluoromethyl-phenyl)-4-((4-fluoro-N-methylphenyl-sulfonamido)methyl) phenoxyacetic acid | ++ | 1 |

TABLE 2-continued

| Example No. | Structure | Chemical Name | CRTH2 hGTPγS IC$_{50}$ (nM) | Route |
|---|---|---|---|---|
| 117 | 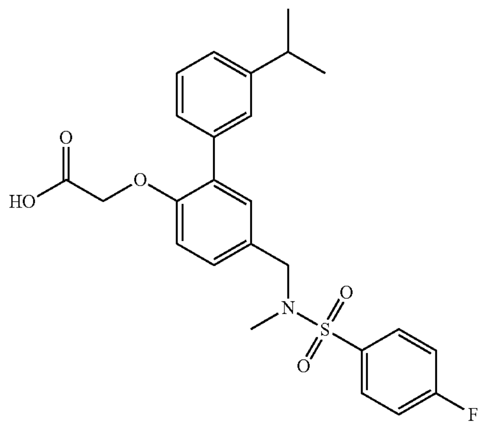 [SMILES: CC(C)c1cccc(-c2cc(CN(C)S(=O)(=O)c3ccc(F)cc3)ccc2OCC(=O)O)c1] | 2-(3-isopropylphenyl)-4-((4-fluoro-N-methylphenyl-sulfonamido)methyl) phenoxyacetic acid | ++ | 1 |
| 120 | 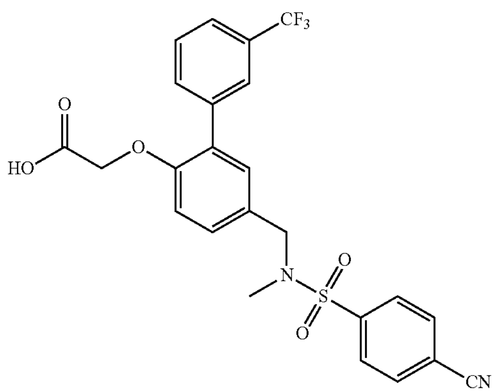 [SMILES: CN(Cc1ccc(OCC(=O)O)c(-c2cccc(C(F)(F)F)c2)c1)S(=O)(=O)c1ccc(C#N)cc1] | 2-(3-trifluoromethyl-phenyl)-4-((4-cyano-N-methylphenyl-sulfonamido)methyl) phenoxyacetic acid | ++ | 2 |
| 136 | 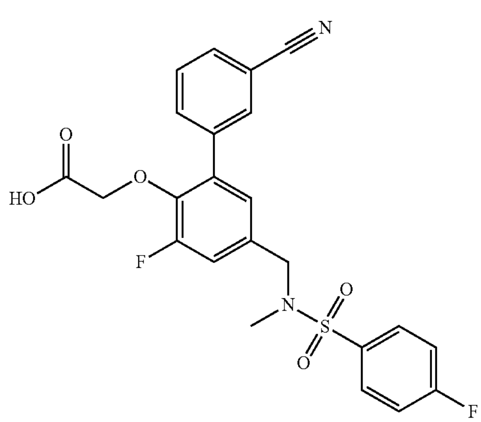 [SMILES: CN(Cc1cc(F)c(OCC(=O)O)c(-c2cccc(C#N)c2)c1)S(=O)(=O)c1ccc(F)cc1] | 2-(3-cyanophenyl)-4-((4-fluoro-N-methylphenyl-sulfonamido) methyl)-6-fluorophenoxy-acetic acid | ++ | 1 |

TABLE 2-continued

| Example No. | Structure | Chemical Name | CRTH2 hGTPγS IC$_{50}$ (nM) | Route |
|---|---|---|---|---|
| 121 | 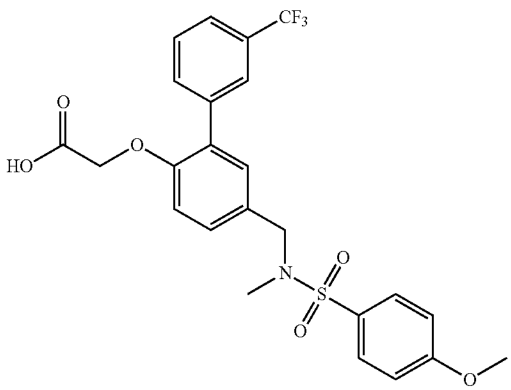 [SMILES: COc1ccc(S(=O)(=O)N(C)Cc2ccc(OCC(=O)O)c(-c3cccc(C(F)(F)F)c3)c2)cc1] | 2-(3-trifluoromethylphenyl)-4-((4-methoxy-N-methylphenylsulfonamido)methyl)phenoxyacetic acid | ++ | 2 |
| 122 | 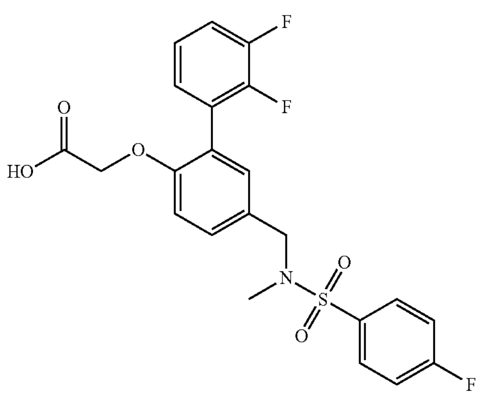 [SMILES: CN(Cc1ccc(OCC(=O)O)c(-c2cccc(F)c2F)c1)S(=O)(=O)c1ccc(F)cc1] | 2-(2,3-difluorophenyl)-4-((4-fluoro-N-methylphenylsulfonamido)methyl)phenoxyacetic acid | ++ | 1 |
| 22 | 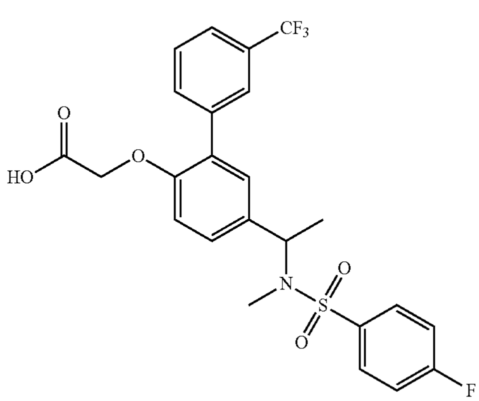 [SMILES: CC(c1ccc(OCC(=O)O)c(-c2cccc(C(F)(F)F)c2)c1)N(C)S(=O)(=O)c1ccc(F)cc1] | 2-(3-trifluoromethylphenyl)-4-(1-(4-fluoro-N-methylphenylsulfonamido)ethyl)phenoxyacetic acid | ++ | 2 |

TABLE 2-continued

| Example No. | Structure | Chemical Name | CRTH2 hGTPγS IC$_{50}$ (nM) | Route |
|---|---|---|---|---|
| 124 | 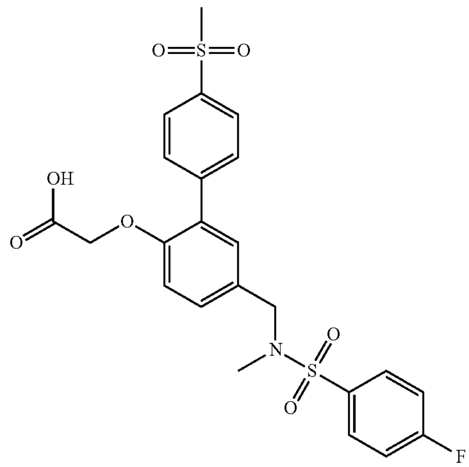 [SMILES: CN(Cc1ccc(OCC(=O)O)c(-c2ccc(S(C)(=O)=O)cc2)c1)S(=O)(=O)c1ccc(F)cc1] | 2-(4-methylsulfonylphenyl)-4-((4-fluoro-N-methylphenylsulfonamido)methyl)phenoxyacetic acid | ++ | 1 |
| 127 | 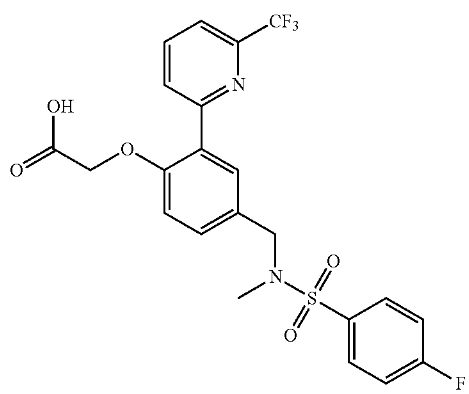 [SMILES: CN(Cc1ccc(OCC(=O)O)c(-c2cccc(C(F)(F)F)n2)c1)S(=O)(=O)c1ccc(F)cc1] | 2-(6-trifluoromethyl-2-pyridinyl)-4-((4-fluoro-N-methylphenylsulfonamido)methyl)phenoxyacetic acid | ++ | 1 |
| 128 | 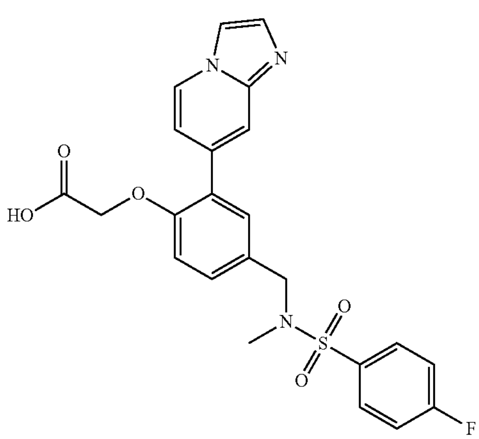 [SMILES: CN(Cc1ccc(OCC(=O)O)c(-c2ccn3ccnc3c2)c1)S(=O)(=O)c1ccc(F)cc1] | 2-(imidazo[1,2-a]pyridin-7-yl)-4-((4-fluoro-N-methylphenylsulfonamido)methyl)phenoxyacetic acid | ++ | 3 |

TABLE 2-continued

| Example No. | Structure | Chemical Name | CRTH2 hGTPγS IC$_{50}$ (nM) | Route |
|---|---|---|---|---|
| 129 | 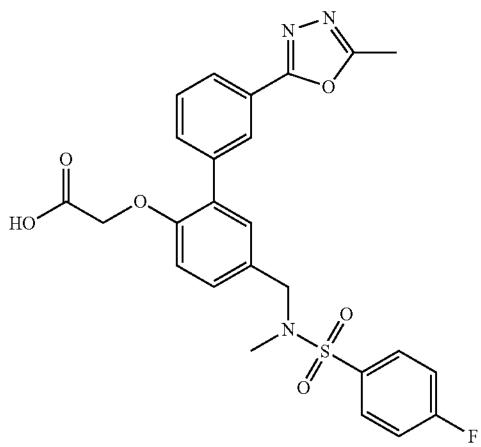 [SMILES: Cc1nnc(-c2cccc(-c3cc(CN(C)S(=O)(=O)c4ccc(F)cc4)ccc3OCC(=O)O)c2)o1] | 2-(3-(5-methyl-1,3,4-oxadiazol-2-yl)phenyl)-4-((4-fluoro-N-methylphenyl-sulfonamido)methyl)phenoxyacetic acid | ++ | 1 |
| 130 | 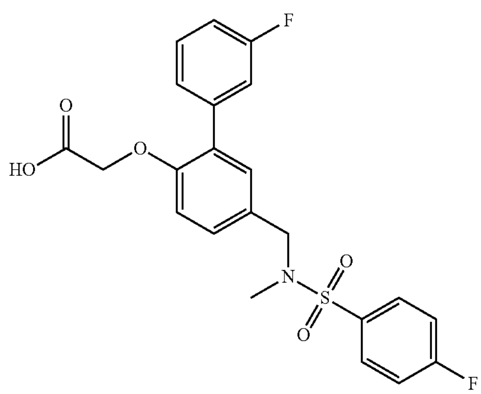 [SMILES: CN(Cc1ccc(OCC(=O)O)c(-c2cccc(F)c2)c1)S(=O)(=O)c1ccc(F)cc1] | 2-(3-fluorophenyl)-4-((4-fluoro-N-methylphenyl-sulfonamido)methyl)phenoxyacetic acid | ++ | 1 |
| 131 | 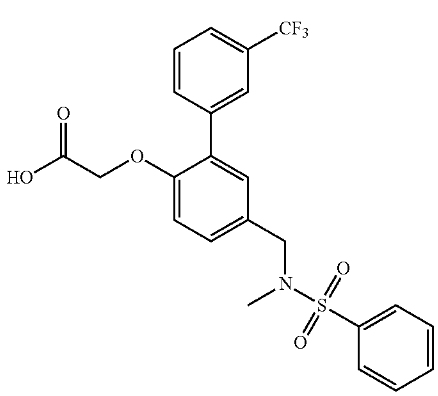 [SMILES: CN(Cc1ccc(OCC(=O)O)c(-c2cccc(C(F)(F)F)c2)c1)S(=O)(=O)c1ccccc1] | 2-(3-trifluoromethyl-phenyl)-4-((N-methylphenyl-sulfonamido)methyl)phenoxyacetic acid | ++ | 2 |

TABLE 2-continued

| Example No. | Structure | Chemical Name | CRTH2 hGTPγS IC$_{50}$ (nM) | Route |
|---|---|---|---|---|
| 132 | 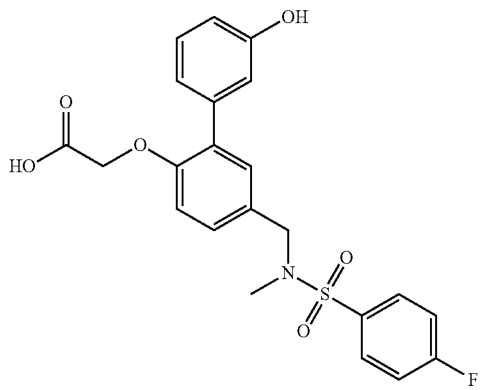 [SMILES: CN(Cc1ccc(OCC(=O)O)c(-c2cccc(O)c2)c1)S(=O)(=O)c1ccc(F)cc1] | 2-(3-hydroxyphenyl)-4-((4-fluoro-N-methylphenyl-sulfonamido)methyl) phenoxyacetic acid | ++ | 1 |
| 119 | 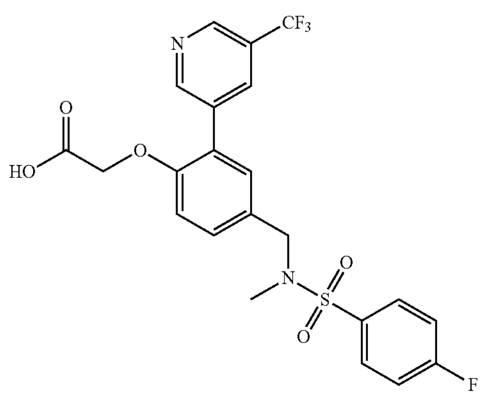 | 2-(3-trifluoromethyl-5-pyridinyl)-4-((4-fluoro-N-methylphenyl-sulfonamido)methyl) phenoxyacetic acid | ++ | 1 |
| 133 | 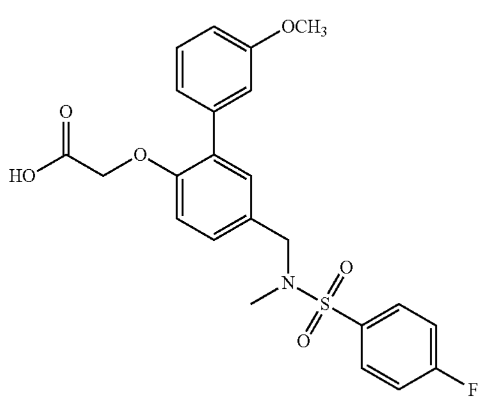 [SMILES: COc1cccc(-c2cc(CN(C)S(=O)(=O)c3ccc(F)cc3)ccc2OCC(=O)O)c1] | 2-(3-methoxyphenyl)-4-((4-fluoro-N-methylphenyl-sulfonamido)methyl) phenoxyacetic acid | ++ | 1 |

TABLE 2-continued

| Example No. | Structure | Chemical Name | CRTH2 hGTPγS IC$_{50}$ (nM) | Route |
|---|---|---|---|---|
| 134 | 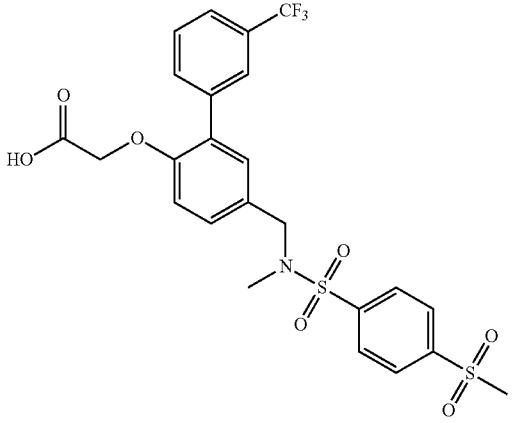 [SMILES: CN(Cc1ccc(OCC(=O)O)c(-c2cccc(C(F)(F)F)c2)c1)S(=O)(=O)c1ccc(S(C)(=O)=O)cc1] | 2-(3-trifluoromethyl-phenyl)-4-((4-methylsulfonyl-N-methylphenyl-sulfonamido)methyl) phenoxyacetic acid | ++ | 2 |
| 149 | 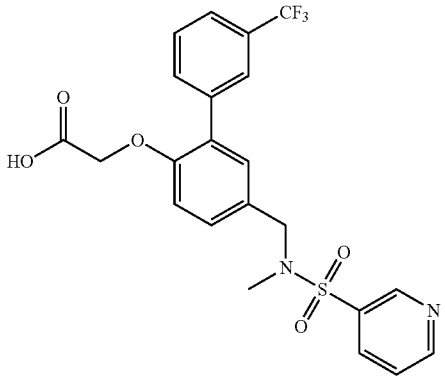 [SMILES: CN(Cc1ccc(OCC(=O)O)c(-c2cccc(C(F)(F)F)c2)c1)S(=O)(=O)c1cccnc1] | 2-(3-trifluoromethyl-phenyl)-4-((N-methylpyridine-3-sulfonamido) methyl)phenoxy-acetic acid | ++ | 2 |
| 135 | 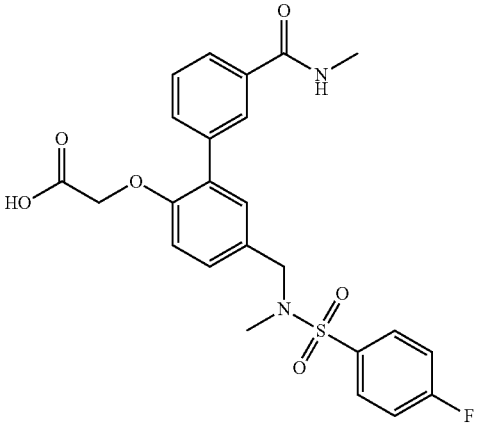 [SMILES: CNC(=O)c1cccc(-c2cc(CN(C)S(=O)(=O)c3ccc(F)cc3)ccc2OCC(=O)O)c1] | 2-(3-N-methylamino-carbonylphenyl)-4-((4-fluoro-N-methylphenyl-sulfonamido)methyl) phenoxyacetic acid | ++ | 1 |

TABLE 2-continued

| Example No. | Structure | Chemical Name | CRTH2 hGTPγS IC$_{50}$ (nM) | Route |
|---|---|---|---|---|
| 137 | 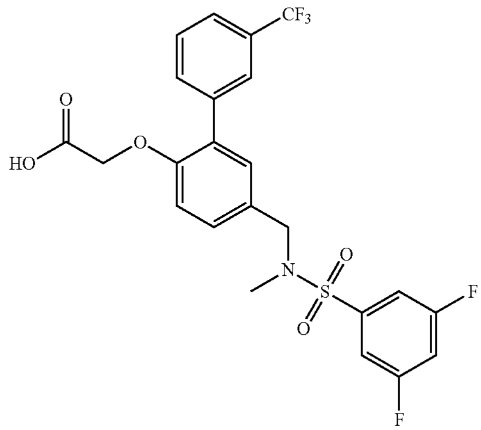 [SMILES: CN(Cc1ccc(OCC(=O)O)c(-c2cccc(C(F)(F)F)c2)c1)S(=O)(=O)c1cc(F)cc(F)c1] | 2-(3-trifluoromethyl-phenyl)-4-((3,5-difluoro-N-methylphenyl-sulfonamido)methyl) phenoxyacetic acid | ++ | 2 |
| 139 | 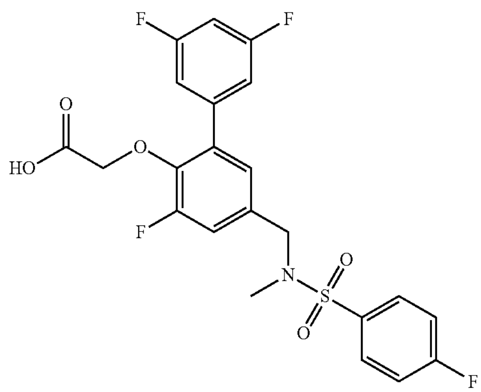 [SMILES: CN(Cc1cc(F)c(OCC(=O)O)c(-c2cc(F)cc(F)c2)c1)S(=O)(=O)c1ccc(F)cc1] | 2-(3,5-difluorophenyl)-4-((4-fluoro-N-methylphenyl-sulfonamido) methyl)-6-fluoro-phenoxyacetic acid | ++ | 1 |
| 140 | 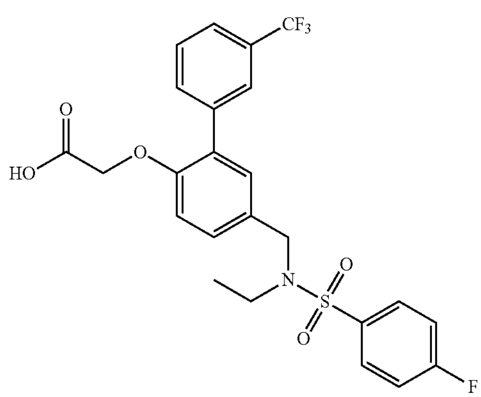 [SMILES: CCN(Cc1ccc(OCC(=O)O)c(-c2cccc(C(F)(F)F)c2)c1)S(=O)(=O)c1ccc(F)cc1] | 2-(3-trifluoromethyl-phenyl)-4-((4-fluoro-N-ethylphenyl-sulfonamido)methyl) phenoxyacetic acid | ++ | 2 |

TABLE 2-continued

| Example No. | Structure | Chemical Name | CRTH2 hGTPγS IC$_{50}$ (nM) | Route |
|---|---|---|---|---|
| 141 | 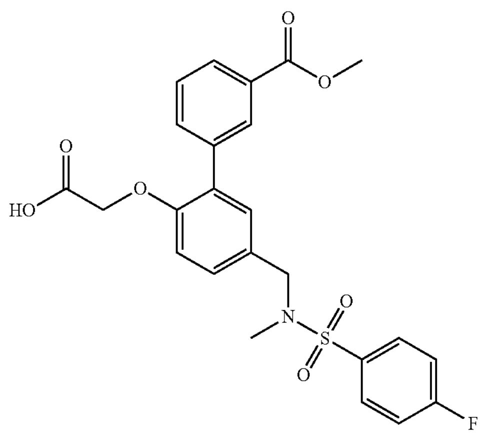 [SMILES: COC(=O)c1cccc(-c2cc(CN(C)S(=O)(=O)c3ccc(F)cc3)ccc2OCC(=O)O)c1] | 2-(3-methoxycarbonylphenyl)-4-((4-fluoro-N-methylphenyl-sulfonamido)methyl)phenoxyacetic acid | ++ | 1 |
| 142 | 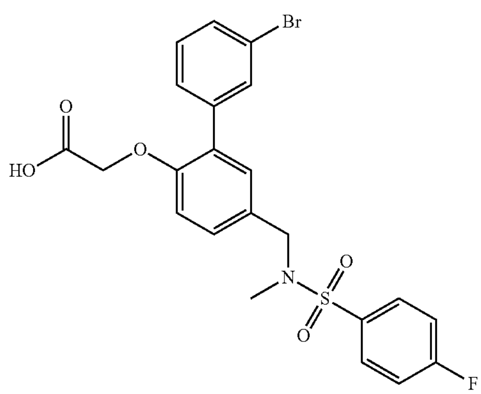 [SMILES: CN(Cc1ccc(OCC(=O)O)c(-c2cccc(Br)c2)c1)S(=O)(=O)c1ccc(F)cc1] | 2-(3-bromophenyl)-4-((4-fluoro-N-methylphenyl-sulfonamido)methyl)phenoxyacetic acid | ++ | 3 |
| 126 | 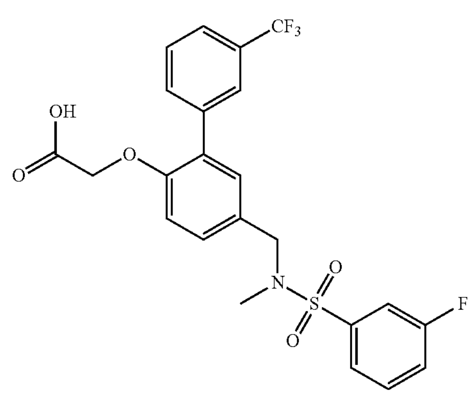 [SMILES: CN(Cc1ccc(OCC(=O)O)c(-c2cccc(C(F)(F)F)c2)c1)S(=O)(=O)c1cccc(F)c1] | 2-(3-trifluoromethyl-phenyl)-4-((3-fluoro-N-methylphenyl-sulfonamido)methyl)phenoxyacetic acid | ++ | 2 |

TABLE 2-continued

| Example No. | Structure | Chemical Name | CRTH2 hGTPγS IC$_{50}$ (nM) | Route |
|---|---|---|---|---|
| 143 | 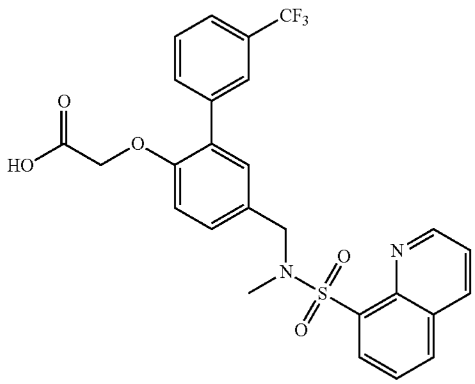 [SMILES: CN(Cc1ccc(OCC(=O)O)c(-c2cccc(C(F)(F)F)c2)c1)S(=O)(=O)c1cccc2cccnc12] | 2-(3-trifluoromethyl-phenyl)-4-((N-methylquinoline-8-sulfonamido)methyl) phenoxyacetic acid | ++ | 2 |
| 144 | 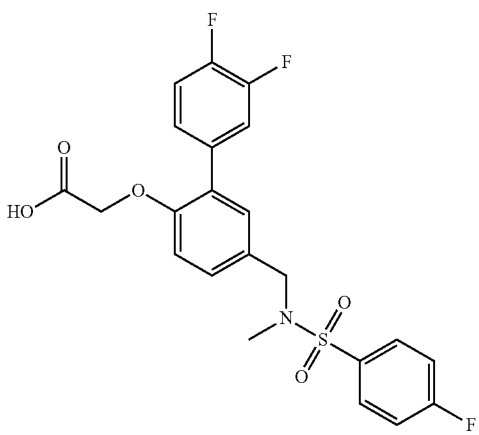 [SMILES: CN(Cc1ccc(OCC(=O)O)c(-c2ccc(F)c(F)c2)c1)S(=O)(=O)c1ccc(F)cc1] | 2-(3,4-difluorophenyl)-4-((4-fluoro-N-methylphenyl-sulfonamido)methyl) phenoxyacetic acid | ++ | 1 |
| 146 | 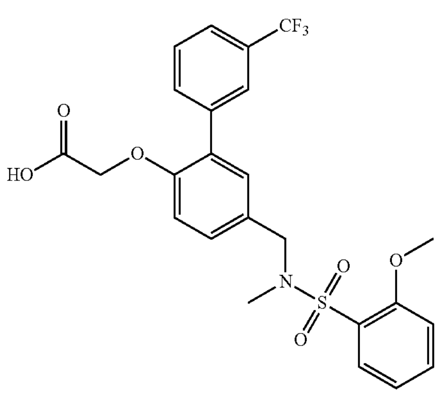 [SMILES: COc1ccccc1S(=O)(=O)N(C)Cc1ccc(OCC(=O)O)c(-c2cccc(C(F)(F)F)c2)c1] | 2-(3-trifluoromethyl-phenyl)-4-((2-methoxy-N-methylphenyl-sulfonamido)methyl) phenoxyacetic acid | ++ | 2 |

TABLE 2-continued

| Example No. | Structure | Chemical Name | CRTH2 hGTPγS IC$_{50}$ (nM) | Route |
|---|---|---|---|---|
| 109 | 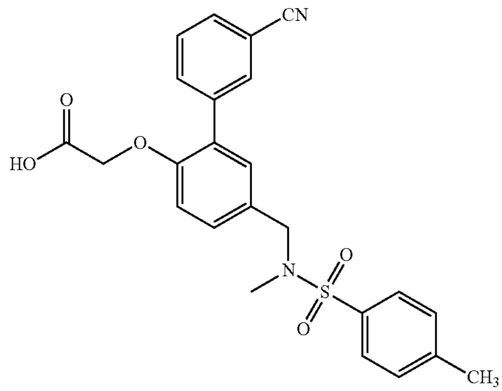 [SMILES: Cc1ccc(S(=O)(=O)N(C)Cc2ccc(OCC(=O)O)c(-c3cccc(C#N)c3)c2)cc1] | 2-(3-cyanophenyl)-4-((4-methyl-N-methylphenyl-sulfonamido)methyl)phenoxyacetic acid | ++ | 2 |
| 147 | 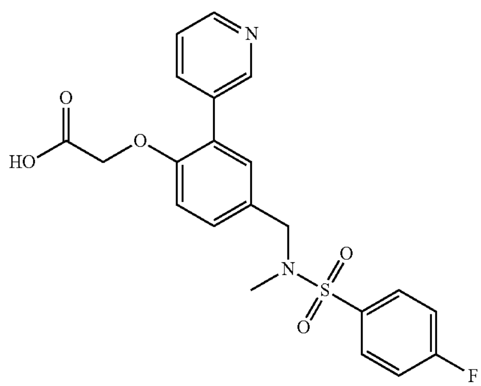 [SMILES: CN(Cc1ccc(OCC(=O)O)c(-c2cccnc2)c1)S(=O)(=O)c1ccc(F)cc1] | 2-(3-pyridinyl)-4-((4-fluoro-N-methylphenyl-sulfonamido)methyl)phenoxyacetic acid | ++ | 1 |
| 138 | 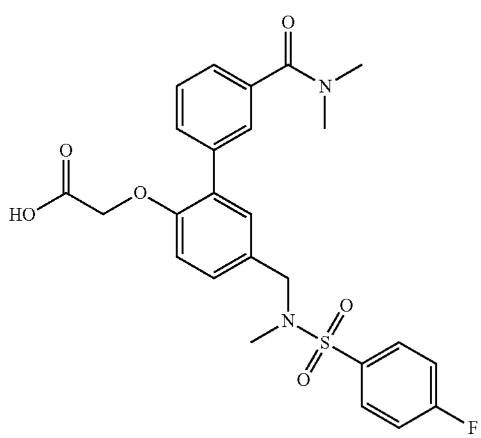 [SMILES: CN(C)C(=O)c1cccc(-c2cc(CN(C)S(=O)(=O)c3ccc(F)cc3)ccc2OCC(=O)O)c1] | 2-(3-dimethylamino-carbonylphenyl)-4-((4-fluoro-N-methylphenyl-sulfonamido)methyl)phenoxyacetic acid | ++ | 3 |

TABLE 2-continued

| Example No. | Structure | Chemical Name | CRTH2 hGTPγS IC$_{50}$ (nM) | Route |
|---|---|---|---|---|
| 145 | 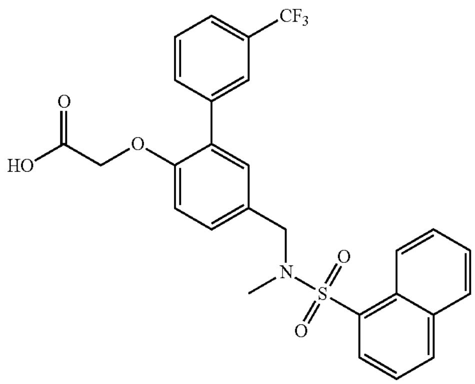 [SMILES: CN(Cc1ccc(OCC(=O)O)c(-c2cccc(C(F)(F)F)c2)c1)S(=O)(=O)c1cccc2ccccc12] | 2-(3-trifluoromethyl-phenyl)-4-((N-methylnaphthalene-1-sulfonamido)methyl)phenoxyacetic acid | ++ | 2 |
| 148 | 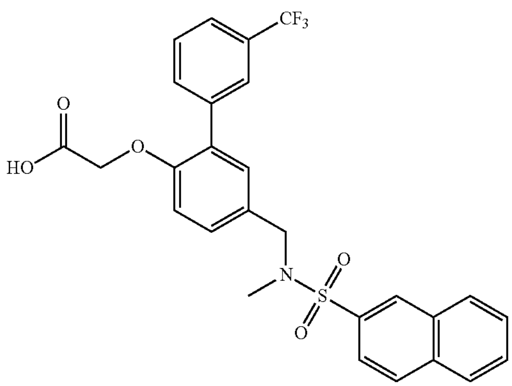 [SMILES: CN(Cc1ccc(OCC(=O)O)c(-c2cccc(C(F)(F)F)c2)c1)S(=O)(=O)c1ccc2ccccc2c1] | 2-(3-trifluoromethyl-phenyl)-4-((N-methylnaphthalene-2-sulfonamido)methyl)phenoxyacetic acid | ++ | 2 |
| 162 | 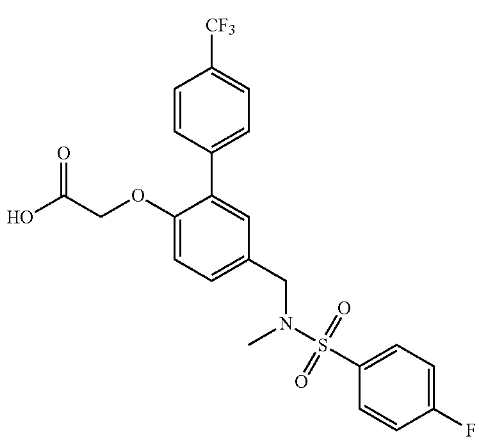 [SMILES: CN(Cc1ccc(OCC(=O)O)c(-c2ccc(C(F)(F)F)cc2)c1)S(=O)(=O)c1ccc(F)cc1] | 2-(4-trifluoromethyl-phenyl)-4-((4-fluoro-N-methylphenyl-sulfonamido)methyl)phenoxyacetic acid | + | 1 |

TABLE 2-continued

| Example No. | Structure | Chemical Name | CRTH2 hGTPγS IC$_{50}$ (nM) | Route |
|---|---|---|---|---|
| 156 | 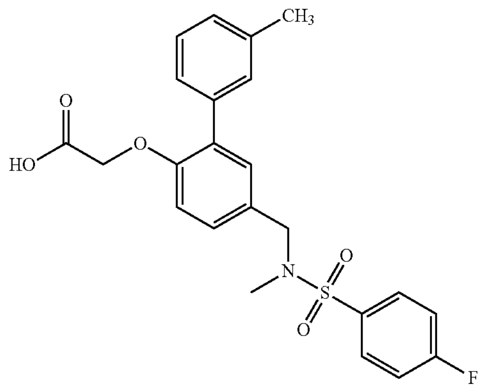 [SMILES: Cc1cccc(-c2cc(CN(C)S(=O)(=O)c3ccc(F)cc3)ccc2OCC(=O)O)c1] | 2-(3-methylphenyl)-4-((4-fluoro-N-methylphenyl-sulfonamido)methyl)phenoxyacetic acid | + | 1 |
| 152 | 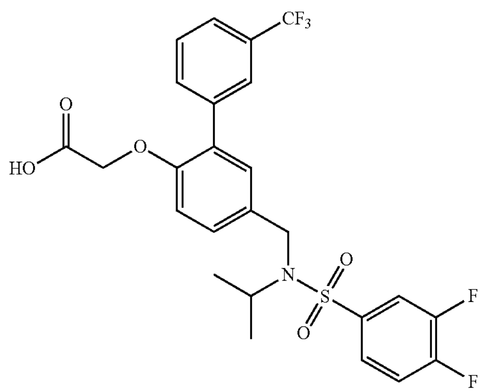 [SMILES: CC(C)N(Cc1ccc(OCC(=O)O)c(-c2cccc(C(F)(F)F)c2)c1)S(=O)(=O)c1ccc(F)c(F)c1] | 2-(3-trifluoromethyl-phenyl)-4-((3,4-difluoro-N-isopropylphenyl-sulfonamido)methyl)phenoxyacetic acid | + | 2 |
| 153 | 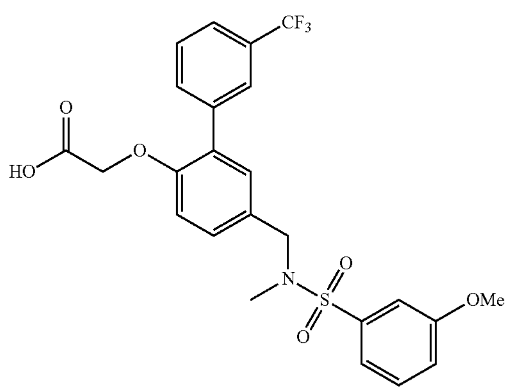 [SMILES: COc1cccc(S(=O)(=O)N(C)Cc2ccc(OCC(=O)O)c(-c3cccc(C(F)(F)F)c3)c2)c1] | 2-(3-trifluoromethyl-phenyl)-4-((3-methoxy-N-methylphenyl-sulfonamido)methyl)phenoxyacetic acid | + | 2 |
| 35 | 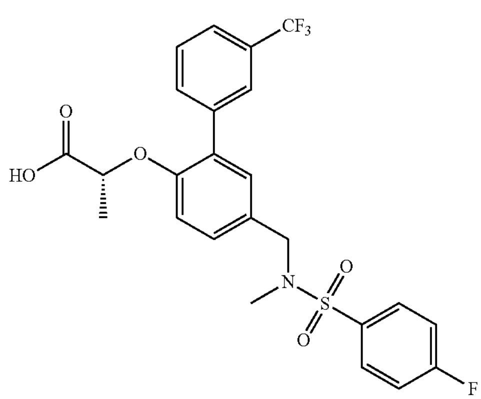 [SMILES: C[C@@H](Oc1ccc(CN(C)S(=O)(=O)c2ccc(F)cc2)cc1-c1cccc(C(F)(F)F)c1)C(=O)O] | (R)-2-(2-(3-trifluoromethyl-phenyl)-4-((4-fluoro-N-methylphenyl-sulfonamido)methyl)phenoxy)propanoic acid | + | 4 |

TABLE 2-continued

| Example No. | Structure | Chemical Name | CRTH2 hGTPγS IC$_{50}$ (nM) | Route |
|---|---|---|---|---|
| 154 | 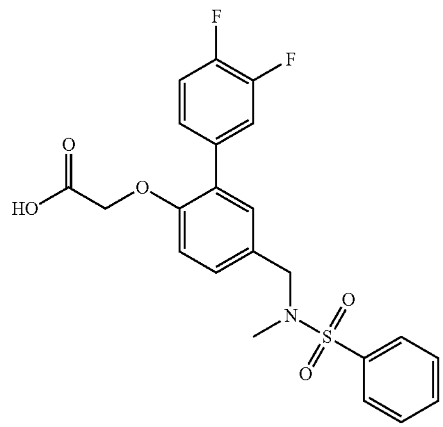 [SMILES: CN(Cc1ccc(OCC(=O)O)c(-c2ccc(F)c(F)c2)c1)S(=O)(=O)c1ccccc1] | 2-(3,4-difluorophenyl)-4-((N-methylphenyl-sulfonamido)methyl)phenoxyacetic acid | + | 1 |
| 157 | 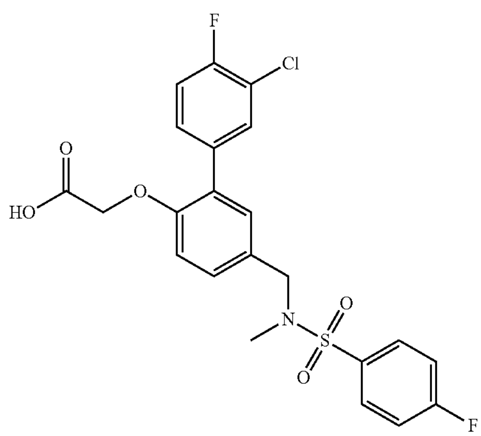 [SMILES: CN(Cc1ccc(OCC(=O)O)c(-c2ccc(F)c(Cl)c2)c1)S(=O)(=O)c1ccc(F)cc1] | 2-(3-chloro-4-fluorophenyl)-4-((4-fluoro-N-methylphenyl-sulfonamido)methyl)phenoxyacetic acid | + | 1 |
| 158 | 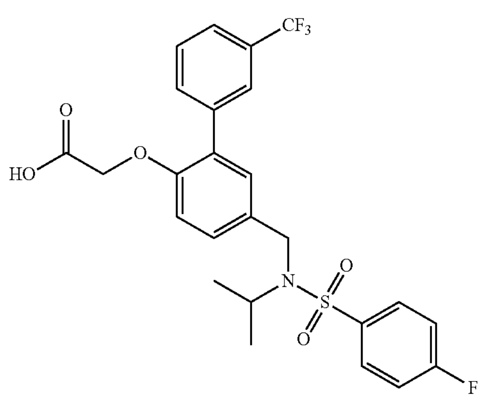 [SMILES: CC(C)N(Cc1ccc(OCC(=O)O)c(-c2cccc(C(F)(F)F)c2)c1)S(=O)(=O)c1ccc(F)cc1] | 2-(3-trifluoromethyl-phenyl)-4-((4-fluoro-N-isopropylphenyl-sulfonamido)methyl)phenoxyacetic acid | + | 2 |

TABLE 2-continued

| Example No. | Structure | Chemical Name | CRTH2 hGTPγS IC$_{50}$ (nM) | Route |
|---|---|---|---|---|
| 168 | 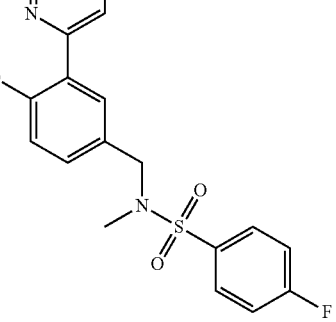 | 2-(4-trifluoromethyl-pyridinyl)-4-((4-fluoro-N-methylphenyl-sulfonamido)methyl) phenoxyacetic acid | + | 3 |
| 159 | 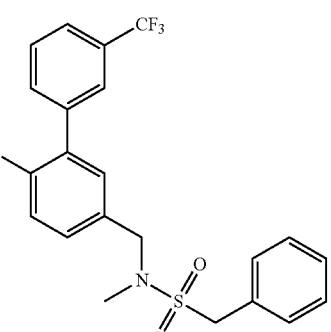 | 2-(3-trifluoromethyl-phenyl)-4-((N-methylbenzyl-sulfonamido)methyl) phenoxyacetic acid | + | 2 |
| 185 | 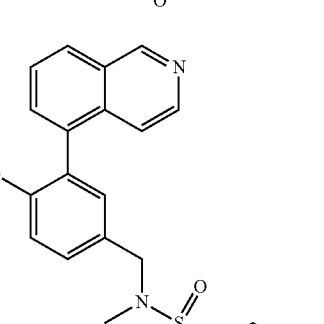 | 2-(isoquinolin-5-yl)-4-((4-fluoro-N-methylphenyl-sulfonamido)methyl) phenoxyacetic acid | + | 1 |
| 160 | 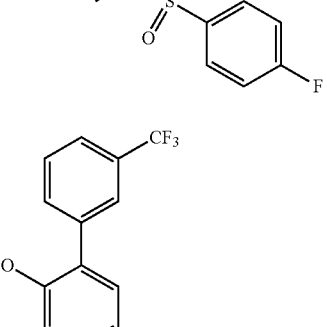 | 2-(3-trifluoromethyl-phenyl)-4-((N,3,5-trimethylisoxazole-4-sulfonamido) methyl)phenoxy-acetic acid | + | 2 |

TABLE 2-continued

| Example No. | Structure | Chemical Name | CRTH2 hGTPγS IC$_{50}$ (nM) | Route |
|---|---|---|---|---|
| 161 | 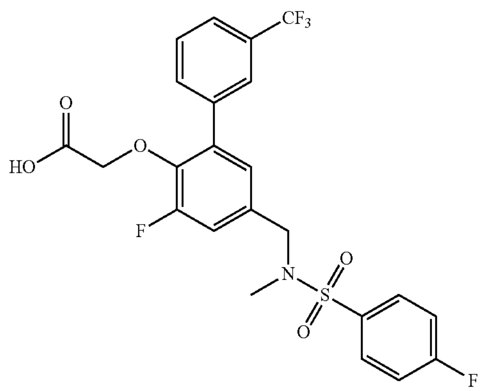 [SMILES: CN(Cc1cc(F)c(OCC(=O)O)c(-c2cccc(C(F)(F)F)c2)c1)S(=O)(=O)c1ccc(F)cc1] | 2-(3-trifluoromethyl-phenyl)-4-((4-fluoro-N-methylphenyl-sulfonamido)methyl)-6-fluorophenoxy-acetic acid | + | 1 |
| 163 | 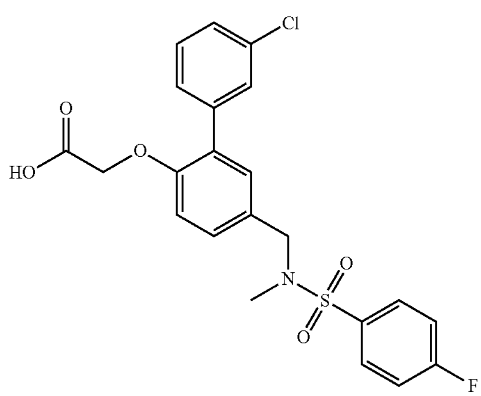 [SMILES: CN(Cc1ccc(OCC(=O)O)c(-c2cccc(Cl)c2)c1)S(=O)(=O)c1ccc(F)cc1] | 2-(3-chlorophenyl)-4-((4-fluoro-N-methylphenyl-sulfonamido)methyl)phenoxyacetic acid | + | 1 |
| 155 | 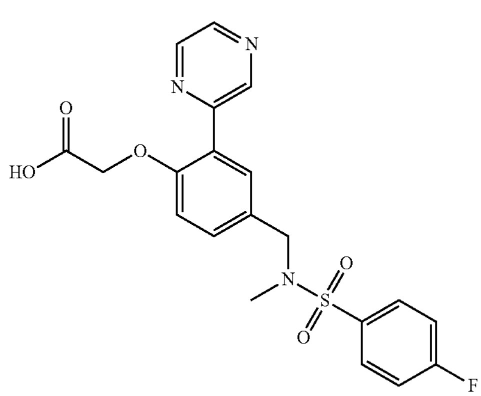 | 2-(pyrazinyl)-4-((4-fluoro-N-methylphenyl-sulfonamido)methyl)phenoxyacetic acid | + | 3 |

TABLE 2-continued
| Example No. | Structure | Chemical Name | CRTH2 hGTPγS IC$_{50}$ (nM) | Route |
|---|---|---|---|---|
| 164 | 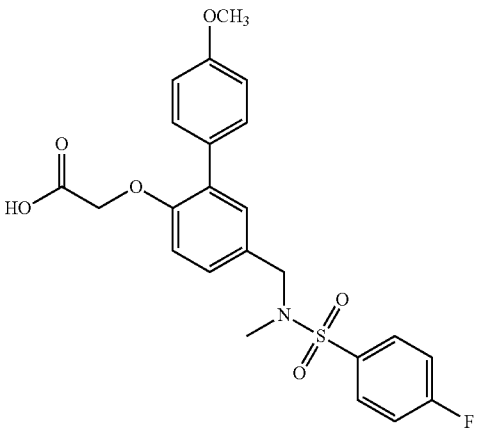 [SMILES: COc1ccc(-c2cc(CN(C)S(=O)(=O)c3ccc(F)cc3)ccc2OCC(=O)O)cc1] | 2-(4-methoxyphenyl)-4-((4-fluoro-N-methylphenyl-sulfonamido)methyl)phenoxyacetic acid | + | 1 |
| 166 | 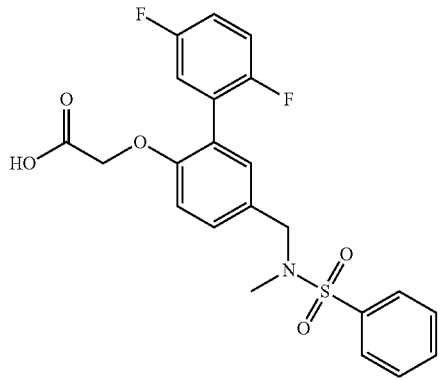 [SMILES: CN(Cc1ccc(OCC(=O)O)c(-c2cc(F)ccc2F)c1)S(=O)(=O)c1ccccc1] | 2-(2,5-difluorophenyl)-4-((N-methylphenyl-sulfonamido)methyl)phenoxyacetic acid | + | 1 |
| 167 | 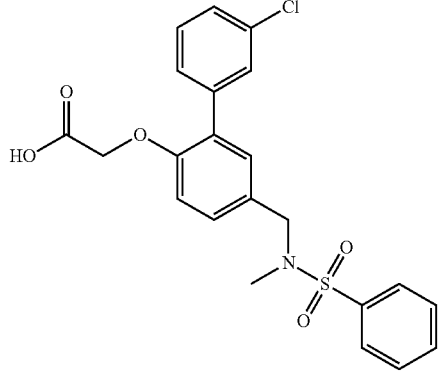 [SMILES: CN(Cc1ccc(OCC(=O)O)c(-c2cccc(Cl)c2)c1)S(=O)(=O)c1ccccc1] | 2-(3-chlorophenyl)-4-((N-methylphenyl-sulfonamido)methyl)phenoxyacetic acid | + | 1 |

TABLE 2-continued

| Example No. | Structure | Chemical Name | CRTH2 hGTPγS IC$_{50}$ (nM) | Route |
|---|---|---|---|---|
| 176 | 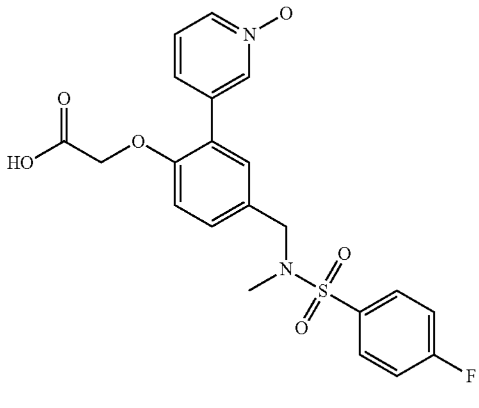 | 2-(N-oxy-pyridine-3-yl)-4-((4-fluoro-N-methylphenyl-sulfonamido)methyl)phenoxyacetic acid | + | 1 |
| 169 | 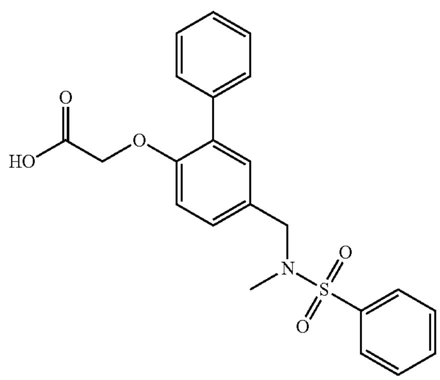 [SMILES: CN(Cc1ccc(OCC(=O)O)c(-c2ccccc2)c1)S(=O)(=O)c1ccccc1] | 2-phenyl-4-((N-methylphenyl-sulfonamido)methyl)phenoxyacetic acid | + | 1 |
| 170 | 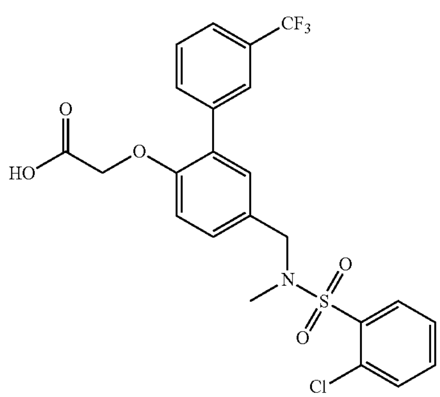 [SMILES: CN(Cc1ccc(OCC(=O)O)c(-c2cccc(C(F)(F)F)c2)c1)S(=O)(=O)c1ccccc1Cl] | 2-(3-trifluoromethyl-phenyl)-4-((2-chloro-N-methylphenyl-sulfonamido)methyl)phenoxyacetic acid | + | 2 |
| 171 | 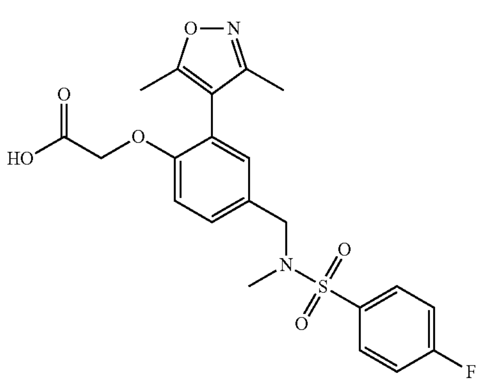 [SMILES: Cc1noc(C)c1-c1cc(CN(C)S(=O)(=O)c2ccc(F)cc2)ccc1OCC(=O)O] | 2-(3,5-dimethylisoxazol-4-yl)-4-((4-fluoro-N-methylphenyl-sulfonamido)methyl)phenoxyacetic acid | + | 1 |

TABLE 2-continued

| Example No. | Structure | Chemical Name | CRTH2 hGTPγS IC$_{50}$ (nM) | Route |
|---|---|---|---|---|
| 172 | 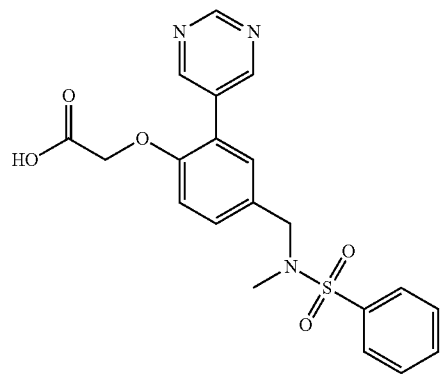 [SMILES: CN(Cc1ccc(OCC(=O)O)c(-c2cncnc2)c1)S(=O)(=O)c1ccccc1] | 2-(pyrimidin-5-yl)-4-((N-methylphenyl-sulfonamido)methyl) phenoxyacetic acid | + | 1 |
| 173 | 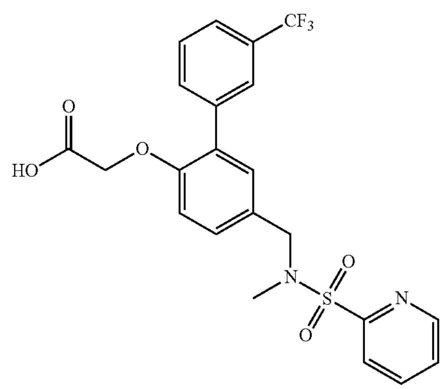 [SMILES: CN(Cc1ccc(OCC(=O)O)c(-c2cccc(C(F)(F)F)c2)c1)S(=O)(=O)c1ccccn1] | 2-(3-trifluoromethyl-phenyl)-4-((N-methylpyridine-2-sulfonamido) methyl)phenoxy-acetic acid | + | 2 |
| 34 | 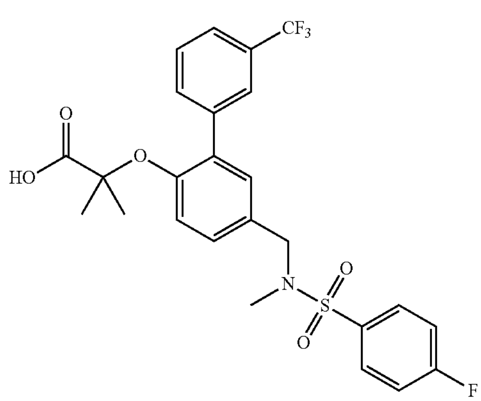 [SMILES: CN(Cc1ccc(OC(C)(C)C(=O)O)c(-c2cccc(C(F)(F)F)c2)c1)S(=O)(=O)c1ccc(F)cc1] | 2-((3-trifluoromethyl-phenyl)-4-((4-fluoro-N-methylphenyl-sulfonamido)methyl) phenoxy)-2-methylpropanoic acid | + | 4 |

TABLE 2-continued

| Example No. | Structure | Chemical Name | CRTH2 hGTPγS IC$_{50}$ (nM) | Route |
|---|---|---|---|---|
| 174 | 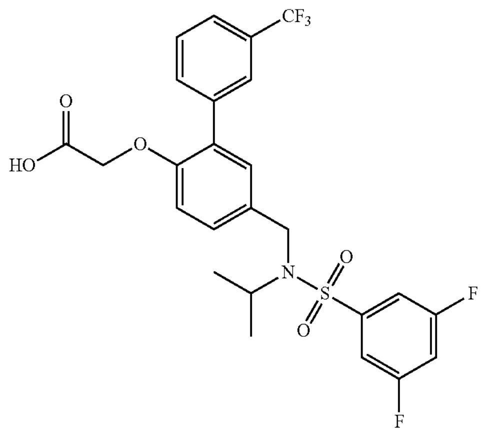 [SMILES: CC(C)N(Cc1ccc(OCC(=O)O)c(-c2cccc(C(F)(F)F)c2)c1)S(=O)(=O)c1cc(F)cc(F)c1] | 2-(3-trifluoromethyl-phenyl)-4-((3,5-difluoro-N-isopropylphenyl-sulfonamido)methyl) phenoxyacetic acid | + | 2 |
| 184 | 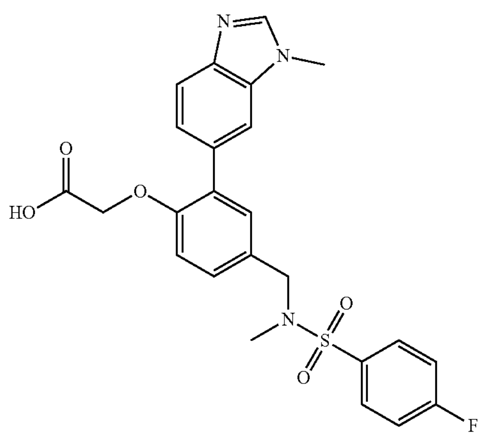 [SMILES: CN(Cc1ccc(OCC(=O)O)c(-c2ccc3ncn(C)c3c2)c1)S(=O)(=O)c1ccc(F)cc1] | 2-(3-methyl-3H-benzo[d]imidazol-5-yl)-4-((4-fluoro-N-methylphenyl-sulfonamido)methyl) phenoxyacetic acid | + | 1 |
| 175 | 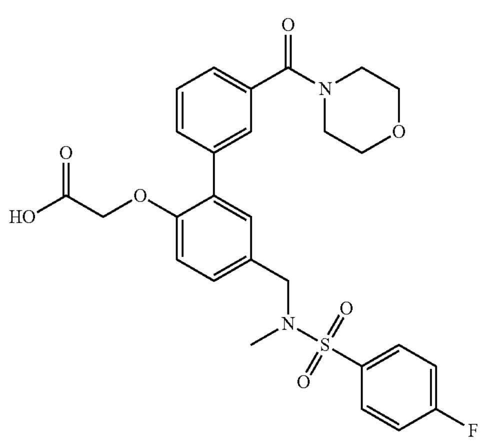 [SMILES: CN(Cc1ccc(OCC(=O)O)c(-c2cccc(C(=O)N3CCOCC3)c2)c1)S(=O)(=O)c1ccc(F)cc1] | 2-(3-morpholino-carbonylphenyl)-4-((4-fluoro-N-methylphenyl-sulfonamido)methyl) phenoxyacetic acid | + | 1 |

TABLE 2-continued

| Example No. | Structure | Chemical Name | CRTH2 hGTPγS IC$_{50}$ (nM) | Route |
|---|---|---|---|---|
| 165 | 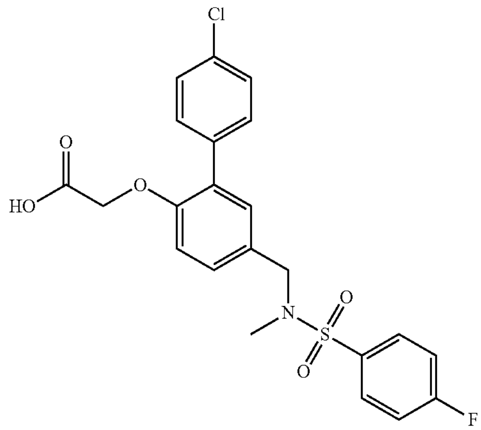 [SMILES: CN(Cc1ccc(OCC(=O)O)c(-c2ccc(Cl)cc2)c1)S(=O)(=O)c1ccc(F)cc1] | 2-(4-chlorophenyl)-4-((4-fluoro-N-methylphenyl-sulfonamido)methyl) phenoxyacetic acid | + | 1 |
| 177 | 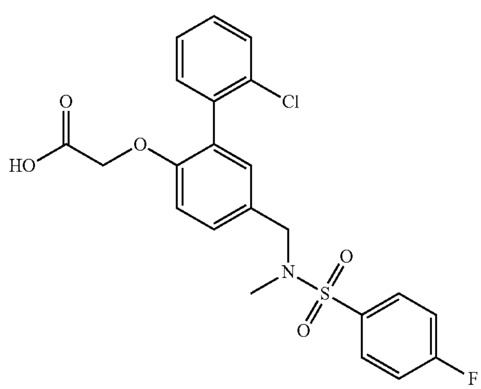 [SMILES: CN(Cc1ccc(OCC(=O)O)c(-c2ccccc2Cl)c1)S(=O)(=O)c1ccc(F)cc1] | 2-(2-chlorophenyl)-4-((4-fluoro-N-methylphenyl-sulfonamido)methyl) phenoxyacetic acid | + | 1 |
| 179 | 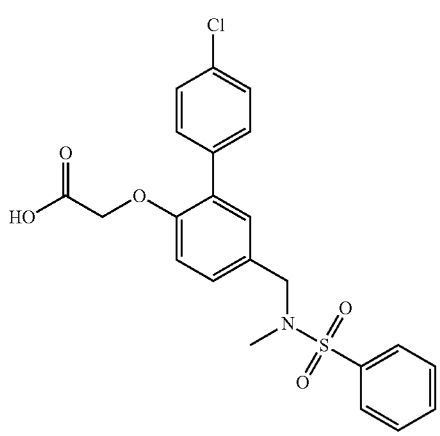 [SMILES: CN(Cc1ccc(OCC(=O)O)c(-c2ccc(Cl)cc2)c1)S(=O)(=O)c1ccccc1] | 2-(4-chlorophenyl)-4-((N-methylphenyl-sulfonamido)methyl) phenoxyacetic acid | + | 1 |

TABLE 2-continued

| Example No. | Structure | Chemical Name | CRTH2 hGTPγS IC$_{50}$ (nM) | Route |
|---|---|---|---|---|
| 180 | 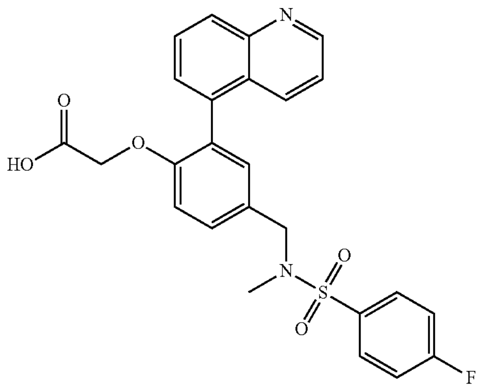 [SMILES: CN(Cc1ccc(OCC(=O)O)c(-c2cccc3ncccc23)c1)S(=O)(=O)c1ccc(F)cc1] | 2-(quinolin-5-yl)-4-((4-fluoro-N-methylphenyl-sulfonamido)methyl)phenoxyacetic acid | + | 1 |
| 181 | 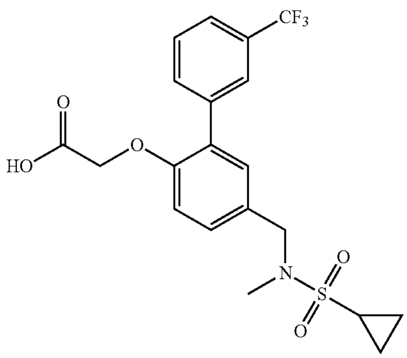 [SMILES: CN(Cc1ccc(OCC(=O)O)c(-c2cccc(C(F)(F)F)c2)c1)S(=O)(=O)C1CC1] | 2-(3-trifluoromethyl-phenyl)-4-((N-methylcyclo-propane-sulfonamido)methyl)phenoxyacetic acid | + | 2 |
| 182 | 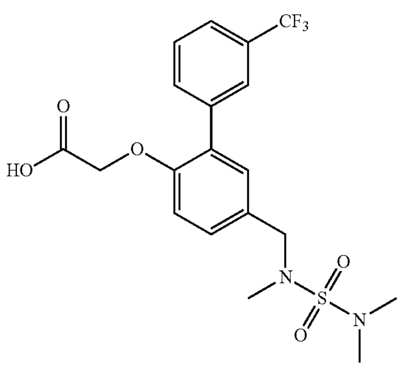 [SMILES: CN(C)S(=O)(=O)N(C)Cc1ccc(OCC(=O)O)c(-c2cccc(C(F)(F)F)c2)c1] | 2-(3-trifluoromethyl-phenyl)-4-((N-methyldimethyl-aminosulfonamido)methyl)phenoxy acetic acid | + | 2 |
| 178 | 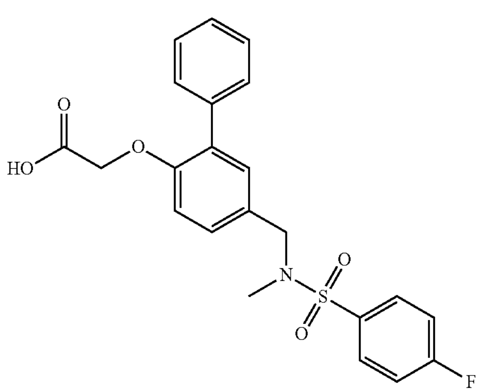 [SMILES: CN(Cc1ccc(OCC(=O)O)c(-c2ccccc2)c1)S(=O)(=O)c1ccc(F)cc1] | 2-phenyl-4-((4-fluoro-N-methylphenyl-sulfonamido)methyl)phenoxyacetic acid | + | 1 |

TABLE 2-continued

| Example No. | Structure | Chemical Name | CRTH2 hGTPγS IC$_{50}$ (nM) | Route |
|---|---|---|---|---|
| 183 | 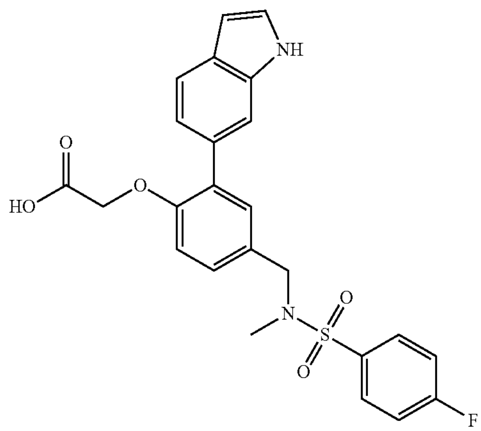 [SMILES: CN(Cc1ccc(OCC(=O)O)c(-c2ccc3cc[nH]c3c2)c1)S(=O)(=O)c1ccc(F)cc1] | 2-(1H-indol-6-yl)-4-((4-fluoro-N-methylphenyl-sulfonamido)methyl)phenoxyacetic acid | + | 1 |
| 151 | 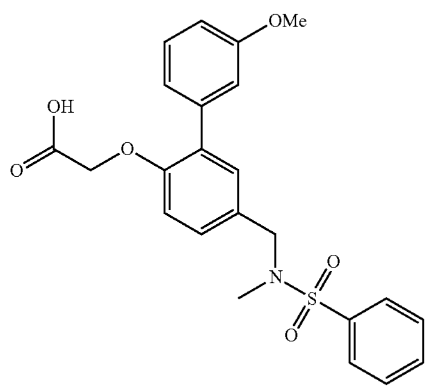 [SMILES: COc1cccc(-c2cc(CN(C)S(=O)(=O)c3ccccc3)ccc2OCC(=O)O)c1] | 2-(3-methoxyphenyl)-4-((-N-methylphenyl-sulfonamido)methyl)phenoxyacetic acid | + | 1 |
| 186 | 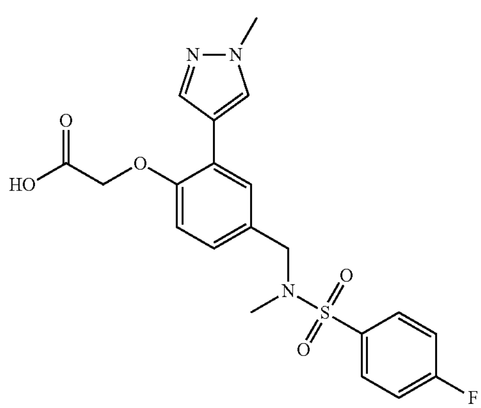 [SMILES: CN(Cc1ccc(OCC(=O)O)c(-c2cnn(C)c2)c1)S(=O)(=O)c1ccc(F)cc1] | 2-(1-methyl-1H-pyrazol-4-yl)-4-((4-fluoro-N-methylphenyl-sulfonamido)methyl)phenoxyacetic acid | + | 1 |

TABLE 2-continued

| Example No. | Structure | Chemical Name | CRTH2 hGTPγS IC$_{50}$ (nM) | Route |
|---|---|---|---|---|
| 207 | 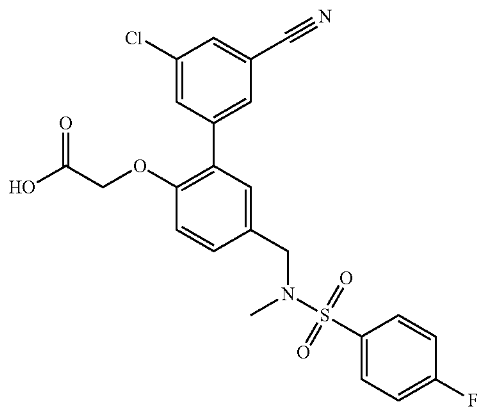 [SMILES: CN(Cc1ccc(OCC(=O)O)c(-c2cc(Cl)cc(C#N)c2)c1)S(=O)(=O)c1ccc(F)cc1] | 2-(3-cyano-5-chloro-phenyl)-4-((4-fluoro-N-methylphenyl-sulfonamido)methyl) phenoxyacetic acid | +++ | 3 |
| 208 | 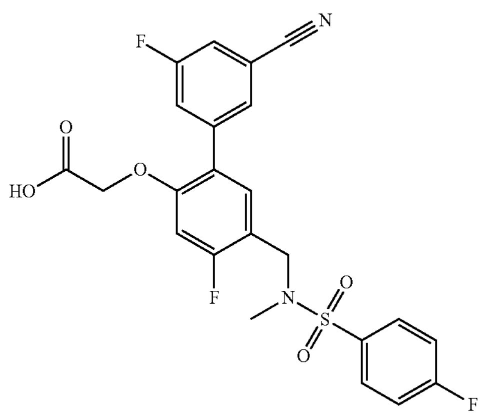 | 2-(3-cyano-5-fluoro-phenyl)-4-((4-fluoro-N-methylphenyl-sulfonamido) methyl)-5-fluorophenoxy-acetic acid | +++ | 2 |
| 209 | 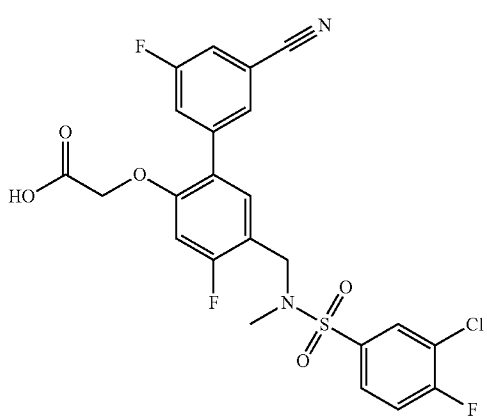 | 2-(3-cyano-5-fluoro-phenyl)-4-((3-chloro-4-fluoro-N-methylphenyl-sulfonamido) methyl)-5-fluorophenoxy-acetic acid | +++ | 2 |

TABLE 2-continued

| Example No. | Structure | Chemical Name | CRTH2 hGTPγS IC$_{50}$ (nM) | Route |
|---|---|---|---|---|
| 210 | 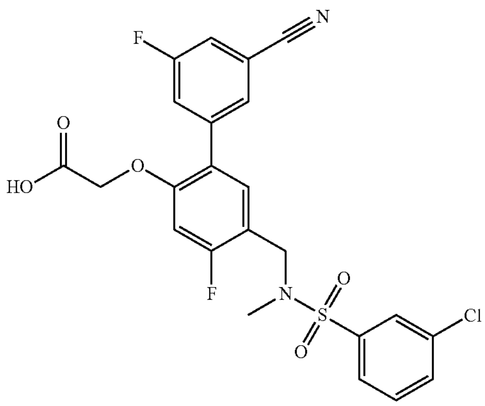 [SMILES: CN(Cc1cc(-c2cc(F)cc(C#N)c2)c(OCC(=O)O)cc1F)S(=O)(=O)c1cccc(Cl)c1] | 2-(3-cyano-5-fluoro-phenyl)-4-((3-chloro-N-methylphenyl-sulfonamido)methyl)-5-fluorophenoxy-acetic acid | +++ | 2 |
| 211 | 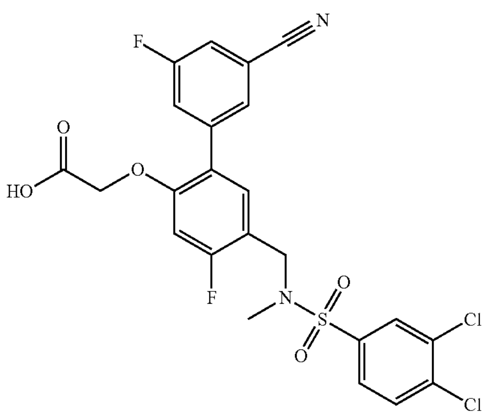 [SMILES: CN(Cc1cc(-c2cc(F)cc(C#N)c2)c(OCC(=O)O)cc1F)S(=O)(=O)c1ccc(Cl)c(Cl)c1] | 2-(3-cyano-5-fluoro-phenyl)-4-((3,4-dichloro-N-methylphenyl-sulfonamido)methyl)-5-fluorophenoxy-acetic acid | +++ | 2 |
| 212 | 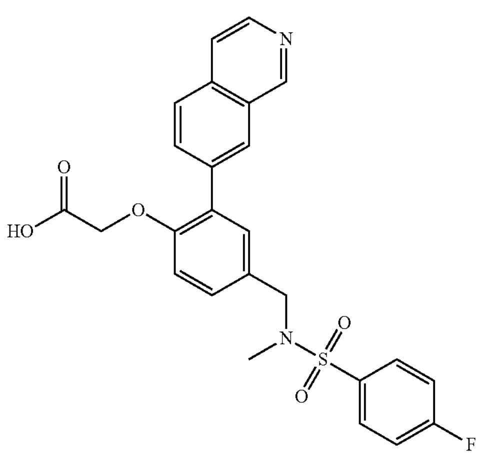 [SMILES: CN(Cc1ccc(OCC(=O)O)c(-c2ccc3ccncc3c2)c1)S(=O)(=O)c1ccc(F)cc1] | 2-(isoquinolin-7-yl)-4-((4-fluoro-N-methylphenyl-sulfonamido)methyl)phenoxyacetic acid | ++ | 3 |

TABLE 2-continued

| Example No. | Structure | Chemical Name | CRTH2 hGTPγS IC$_{50}$ (nM) | Route |
|---|---|---|---|---|
| 213 | 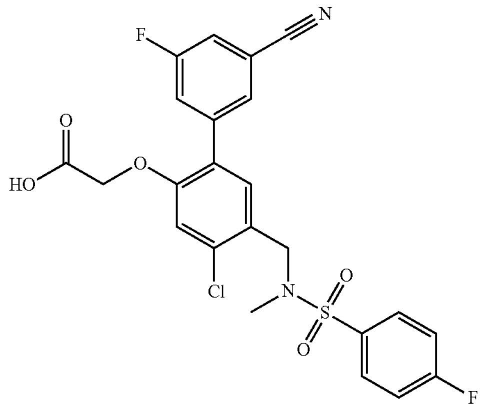 [SMILES: CN(Cc1cc(-c2cc(F)cc(C#N)c2)c(OCC(=O)O)cc1Cl)S(=O)(=O)c1ccc(F)cc1] | 2-(3-cyano-5-fluoro-phenyl)-4-((4-fluoro-N-methylphenyl-sulfonamido)methyl)-5-chlorophenoxy-acetic acid | +++ | 2 |
| 214 | 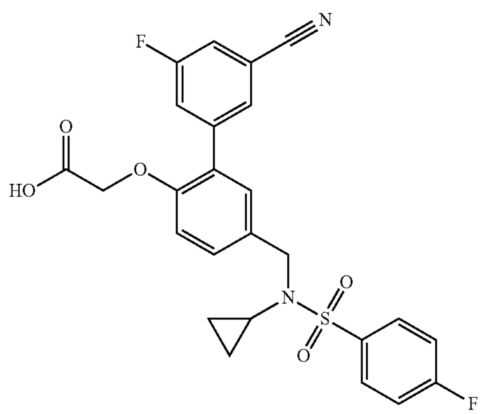 [SMILES: N#Cc1cc(F)cc(-c2cc(CN(C3CC3)S(=O)(=O)c3ccc(F)cc3)ccc2OCC(=O)O)c1] | 2-(3-cyano-5-fluoro-phenyl)-4-((4-fluoro-N-cyclopropyl-phenylsulfonamido)methyl)-phenoxy-acetic acid | | |

$^1$H NMR data and LCMS data for certain compounds from Table 2 is given below:

Example 37

$^1$HNMR (CD$_3$CN, 300 MHz): δ 7.93 (d, 1H), 7.78 (m, 1H), 7.45 (t, 1H), 7.20 (m, 2H), 6.95 (m, 3H), 6.67 (d, 1H), 4.65 (s, 2H), 4.15 (s, 2H), 3.81 (s, 3H), 2.61 (s, 3H). MS (ES-API): MH$^-$=510.0. HPLC (Method A) t$_R$=2.28 min.

Sodium Salt of Example 37

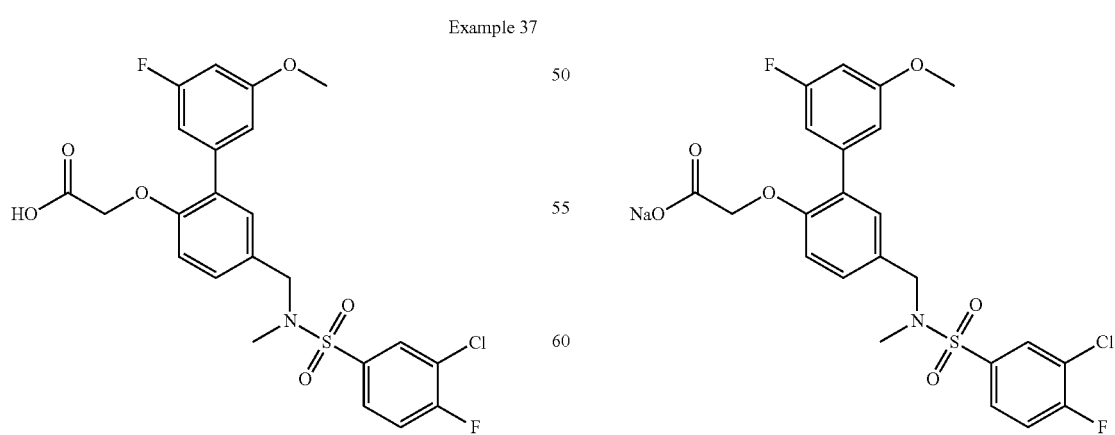

Example 37-Sodium Salt

¹HNMR (DMSO, 400 MHz): δ 8.02 (d, 1H), 7.83 (m, 1H), 7.67 (t, 1H), 7.15 (m, 2H), 7.07 (m, 2H), 6.88 (d, 1H), 6.73 (d, 1H), 4.22 (s, 2H), 4.13 (s, 2H), 3.78 (s, 3H), 2.60 (s, 3H).

Example 16

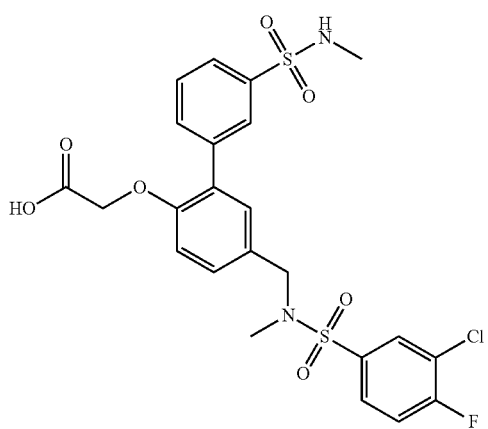

Example 16

¹HNMR (CD₃CN, 300 MHz): δ 8.08 (s, 1H), 7.96 (m, 1H), 7.79 (m, 3H), 7.67 (t, 1H), 7.47 (t, 1H), 7.29 (m, 2H), 7.01 (d, 1H), 5.55 (bm, 1H), 4.72 (s, 2H), 4.21 (s, 2H), 2.69 (s, 3H), 2.55 (d, 3H). MS (ES-API): MH⁻=555.0. HPLC (Method A) t_R=2.36 min.

Example 38

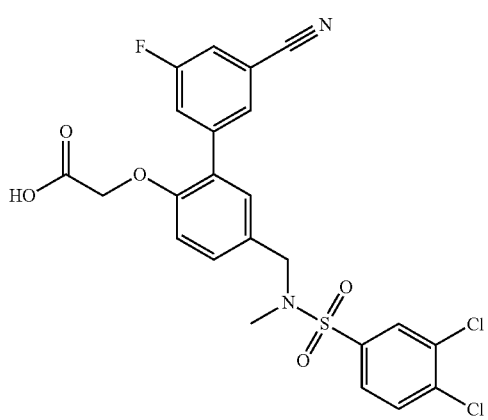

Example 38

¹HNMR (CD₃CN, 300 MHz): δ 7.95 (s, 1H), 7.83 (s, 1H), 7.71 (m, 3H), 7.50 (d, 1H), 7.35 (d, 1H), 7.25 (s, 1H), 7.01 (d,

1H), 4.75 (s, 2H), 4.22 (s, 2H), 2.71 (s, 3H). MS (ES-API): MH⁻=520.9. HPLC (Method A) t_R=2.31 min.

Example 39

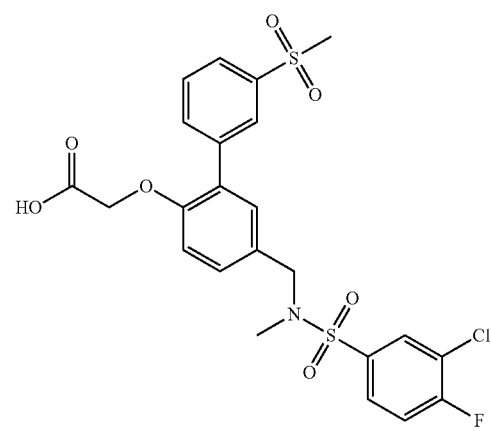

Example 39

¹HNMR (CDCl₃, 400 MHz): δ 8.08 (s, 1H), 7.90 (m, 2H), 7.86 (m, 1H), 7.80 (m, 1H), 7.63 (t, 1H), 7.33 (m, 3H), 6.90 (d, 1H), 4.69 (s, 2H), 4.18 (s, 2H), 3.11 (s, 3H), 2.67 (s, 3H). MS (ESI): MH⁺=542.1. HPLC (Method B) t_R=2.37 min.

Example 41

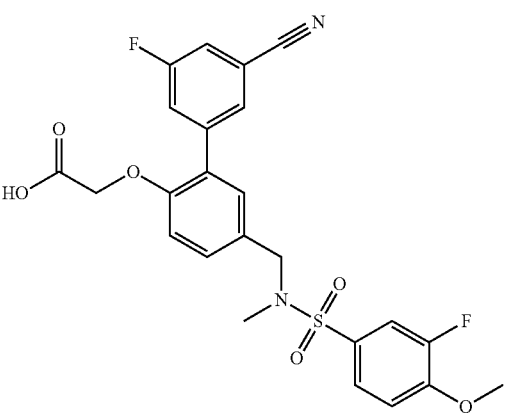

Example 41

¹HNMR (CD₃CN, 400 MHz): δ 7.82 (s, 1H), 7.71 (d, 1H), 7.60 (m, 2H), 7.50 (d, 1H), 7.25 (m, 2H), 7.00 (s, 1H), 4.71 (s,

2H), 4.15 (s, 2H), 3.95 (s, 3H), 2.64 (s, 3H). MS (ES-API): MH⁻=501.1. HPLC (Method A) $t_R$=1.70 min.

Example 42

Example 42

¹HNMR (CD₃CN, 300 MHz): δ 7.98 (d, 2H), 7.82 (m, 2H), 7.72 (d, 1H), 7.60 (t, 1H), 7.45 (t, 1H), 7.31 (s, 1H), 7.10 (s, 1H), 4.73 (s, 2H), 4.32 (s, 2H), 2.72 (s, 3H). MS (ES-API): MH⁻=522.8. HPLC (Method A) $t_R$=2.28 min.

Example 43

Example 43

¹HNMR (CD₃CN, 300 MHz): δ 7.82 (m, 2H), 7.71 (m, 2H), 7.63 (d, 1H), 7.49 (t, 1H), 7.34 (t, 1H), 7.17 (d, 1H), 6.73

(d, 1H), 4.61 (s, 2H), 4.17 (s, 2H), 2.63 (s, 3H). MS (ES-API): MH⁻=505.1. HPLC (Method A) $t_R$=2.20 min.

Example 44

Example 44

¹HNMR (CD₃CN, 400 MHz): δ 7.85 (s, 1H), 7.75 (m, 2H), 7.68 (m, 1H), 7.50 (m, 2H), 7.32 (d, 1H), 7.25 (s, 1H), 7.00 (d, 1H), 4.71 (s, 2H), 4.19 (s, 2H), 2.66 (s, 3H). MS (ES-API): MH⁻=489.1. HPLC (Method A) $t_R$=1.72 min.

Example 45

Example 45

¹HNMR (CD₃CN, 300 MHz): δ 7.84 (m, 2H), 7.75 (m, 2H), 7.70 (d, 1H), 7.61 (d, 1H), 7.50 (d, 1H), 7.35 (d, 1H), 7.25 (s, 1H), 7.00 (d, 1H), 4.75 (s, 2H), 4.21 (s, 2H), 2.70 (s, 3H). MS (ES-API): MH⁻=487.0. HPLC (Method A) $t_R$=2.20 min.

Example 46

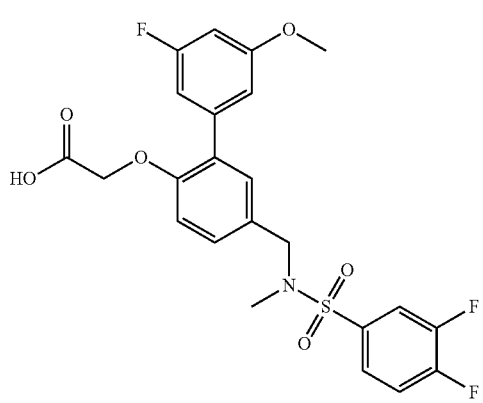

Example 46

¹HNMR (CD₃CN, 300 MHz): δ 7.65 (t, 1H), 7.55 (m, 1H), 7.39 (m, 1H), 7.06 (m, 2H), 6.89 (s, 1H), 6.79 (d, 2H), 6.55 (d, 1H), 4.50 (s, 2H), 4.00 (s, 2H), 3.67 (s, 3H), 2.50 (s, 3H). MS (ES-API): MH⁻=494.0. HPLC (Method A) $t_R$=2.25 min.

Example 47

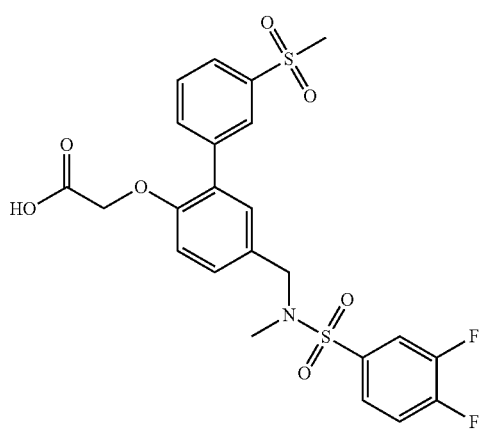

Example 47

¹HNMR (CDCl₃, 400 MHz): δ 8.25 (s, 1H), 7.92 (m, 1H), 7.80 (m, 1H), 7.63 (m, 3H), 7.32 (m, 3H), 6.90 (d, 1H), 4.70

(s, 2H), 4.18 (s, 2H), 3.11 (s, 3H), 2.67 (s, 3H). MS (ESI): MH⁺=526.1. HPLC (Method B) $t_R$=2.38 min.

Example 48

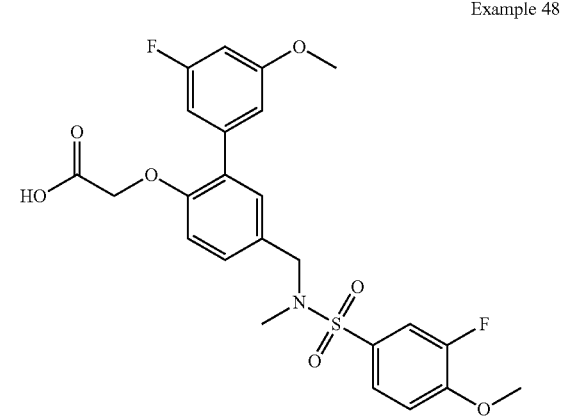 [SMILES: COc1cc(F)cc(-c2cc(CN(C)S(=O)(=O)c3ccc(OC)c(F)c3)ccc2OCC(=O)O)c1]

Example 48

¹HNMR (CD₃CN, 300 MHz): δ 7.61 (m, 2H), 7.25 (m, 3H), 6.96 (m, 3H), 6.70 (d, 1H), 4.70 (s, 2H), 4.15 (s, 2H), 3.95 (s, 3H), 3.84 (s, 3H), 2.60 (s, 3H). MS (ES-API): MH⁻=506.0. HPLC (Method A) $t_R$=2.20 min.

Example 49

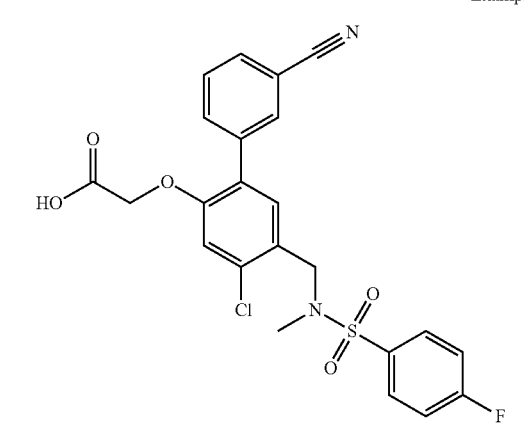

Example 49

¹HNMR (CD₃CN, 300 MHz): δ 7.99 (s, 1H), 7.82-7.92 (m, 3H), 7.73 (d, 1H), 7.61 (t, 1H), 7.35 (m, 3H), 7.10 (s, 1H), 4.75

Example 50

Example 50

¹HNMR (CD₃CN, 300 MHz): δ 8.10 (s, 1H), 7.81 (m, 3H), 7.68 (m, 2H), 7.53 (m, 1H), 7.32 (d, 2H), 7.01 (d, 1H), 5.60 (bm, 1H), 4.71 (s, 2H), 4.20 (s, 2H), 2.66 (s, 3H), 2.55 (d, 3H). MS (ES-API): MH⁻=539.0. HPLC (Method A) $t_R$=2.30 min.

Example 51

Example 51

¹HNMR (CD₃Cl₃, 300 MHz): δ 7.88 (s, 1H), 7.63 (m, 2H), 7.25 (m, 2H), 7.06 (d, 2H), 6.80 (m, 2H), 4.69 (s, 2H), 4.16 (s, 2H), 4.30 (s, 2H), 2.70 (s, 3H). MS (ES-API): M+23=511.0. HPLC (Method A) $t_R$=2.52 min.

Example 52

Example 52

2H), 2.66 (s, 3H). MS (ES-API): main fragment=277.1. HPLC (Method B) $t_R$=2.82 min.

¹HNMR (CD₃CN, 400 MHz): δ 8.16 (s, 1H), 7.90 (m, 3H), 7.79 (d, 1H), 7.61 (t, 1H), 7.34 (m, 4H), 7.00 (d, 1H), 5.72 (s, 2H), 4.72 (s, 2H), 4.19 (s, 2H), 2.65 (s, 3H). MS (ES-API): MH⁻=506.8. HPLC (Method A) $t_R$=1.98 min.

Example 53

Example 53

¹HNMR (CD₃CN, 300 MHz): δ 7.99 (s, 1H), 7.85 (d, 1H), 7.58-7.77 (m, 5H), 7.45 (t, 1H), 7.32 (s, 1H), 7.10 (s, 1H), 4.75 (s, 2H), 4.33 (s, 2H), 2.71 (s, 3H). MS (ES-API): M+18=505.9. HPLC (Method A) $t_R$=2.53 min.

Example 28

5.08 (bm, 1H), 4.72 (s, 2H), 4.18 (s, 2H), 2.64 (s, 3H), 2.55 (d, 3H). MS (ES-API): MH⁻=521.0. HPLC (Method A) $t_R$=2.06 min.

Example 56

Example 28

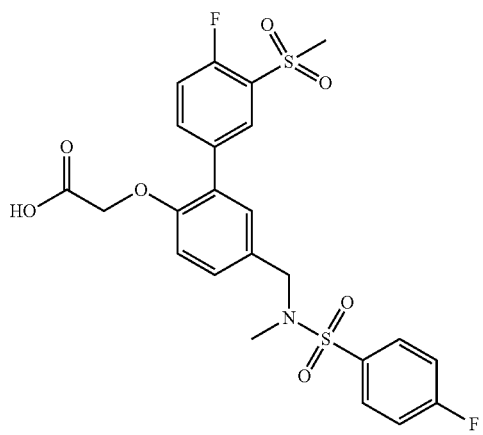

Example 56

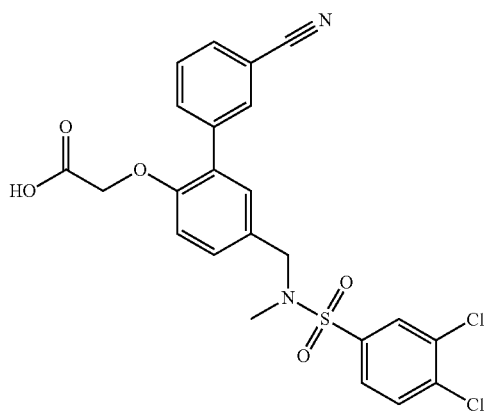

¹HNMR (CD₃CN, 300 MHz): δ 8.08 (m, 1H), 7.95 (m, 1H), 7.88 (m, 2H), 7.26-7.44 (m, 5H), 7.00 (d, 1H), 4.71 (s, 2H), 4.18 (s, 2H), 3.25 (s, 3H), 2.55 (d, 3H). MS (ES-API): MH⁻=524.1. HPLC (Method A) $t_R$=2.02 min.

¹HNMR (CD₃CN, 300 MHz): δ 7.95 (d, 2H), 7.85 (m, 1H), 7.71 (m, 3H), 7.60 (t, 1H), 7.32 (d, 1H), 7.21 (s, 1H), 7.10 (d, 1H), 4.71 (s, 2H), 4.22 (s, 2H), 2.70 (s, 3H). MS (ES-API): MH⁻=504.1. HPLC (Method A) $t_R$=2.22 min.

Example 54

Example 57

Example 54

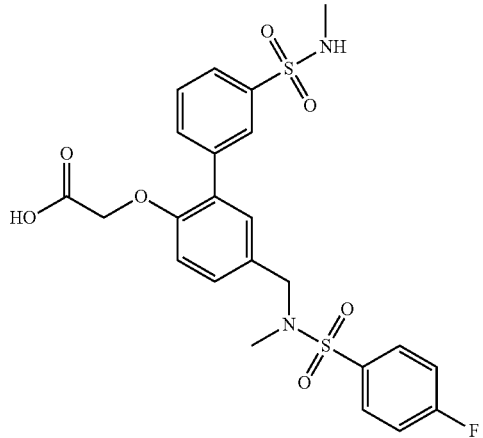

Example 57

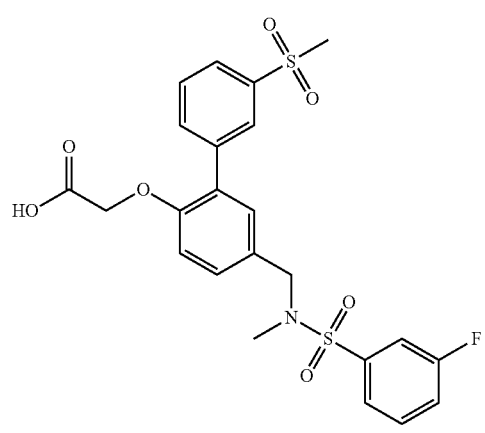

¹HNMR (CD₃CN, 400 MHz): δ 8.10 (s, 1H), 7.90 (m, 2H), 7.80 (m, 2H), 7.62 (t, 1H), 7.28-7.38 (m, 4H), 7.00 (d, 1H),

¹HNMR (CDCl₃, 400 MHz): δ 8.20 (s, 1H), 7.92 (m, 1H), 7.81 (m, 1H), 7.63 (m, 2H), 7.55 (m, 2H), 7.33 (m, 3H), 6.90

(d, 1H), 4.69 (s, 2H), 4.18 (s, 2H), 3.12 (s, 3H), 2.67 (s, 3H). MS (ESI): MH$^+$=508.2. HPLC (Method B) $t_R$=2.28 min.

Example 58

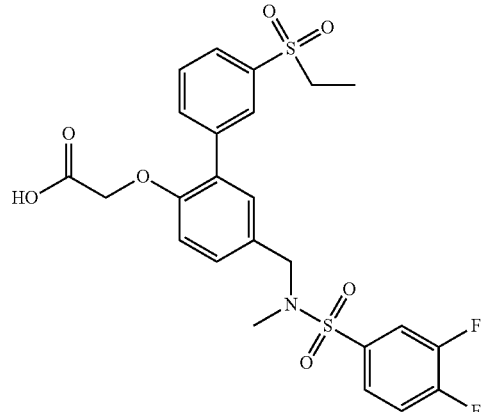

Example 58

$^1$HNMR (CD$_3$Cl$_3$, 300 MHz): δ 8.14 (s, 1H), 7.81 (m, 2H), 7.61 (m, 3H), 7.30 (m, 3H), 7.86 (d, 1H), 7.12 (m, 1H), 6.94 (d, 1H), 4.65 (s, 2H), 4.14 (s, 2H), 3.14 (q, 2H), 2.63 (s, 3H), 1.26 (t, 3H). MS (ES-API): main fragment=333.1. HPLC (Method B) $t_R$=2.45 min.

Example 59

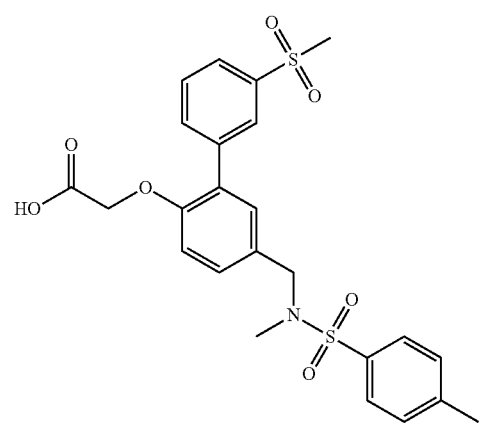

Example 59

$^1$HNMR (CDCl$_3$, 400 MHz): δ 8.22 (s, 1H), 7.91 (d, 1H), 7.81 (d, 1H), 7.72 (d, 2H), 7.62 (t, 1H), 7.35 (m, 4H), 6.89 (d,

1H), 4.69 (s, 2H), 4.13 (s, 2H), 3.11 (s, 3H), 2.61 (s, 3H), 2.45 (s, 3H). MS (ESI): MH$^+$=504.1. HPLC (Method B) $t_R$=2.38 min.

Example 60

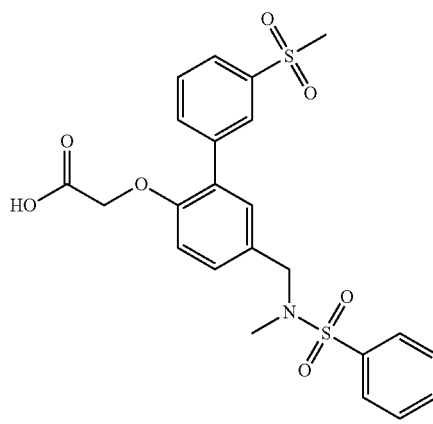

Example 60

$^1$HNMR (CD$_3$CN, 300 MHz): δ 8.08 (s, 1H), 7.79 (m, 4H), 7.58 (t, 1H), 7.22 (m, 4H), 6.90 (d, 1H), 4.62 (s, 2H), 4.18 (s, 2H), 3.04 (s, 3H), 2.54 (d, 3H). MS (ES-API): MH$^-$=506.1. HPLC (Method A) $t_R$=1.94 min.

Example 62

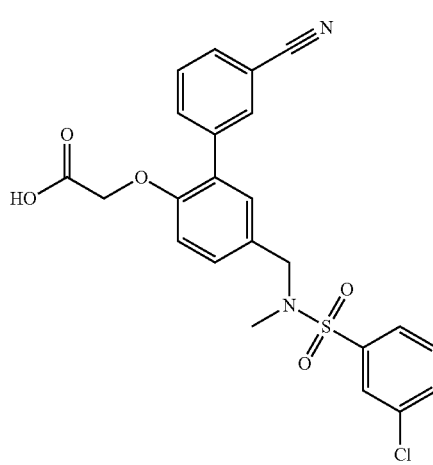

Example 62

$^1$HNMR (CDCl$_3$, 400 MHz): δ 8.07 (s, 1H), 7.99 (d, 1H), 7.85 (m, 2H), 7.72 (d, 1H), 7.61 (m, 1H), 7.32-7.45 (m, 3H), 6.97 (d, 1H), 4.74 (s, 2H), 4.26 (s, 2H), 2.76 (s, 3H). MS (ES-API): M=266.1 (main fragment). HPLC (Method B) $t_R$=3.22 min.

Example 63

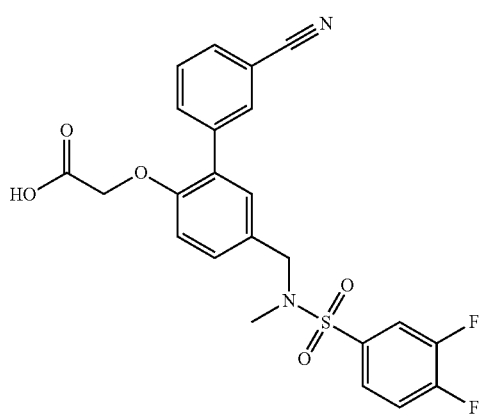

Example 63

$^1$HNMR (CDCl$_3$, 400 MHz): δ 7.91 (s, 1H), 7.77 (d, 1H), 7.59-7.70 (m, 3H), 7.51 (m, 1H), 7.36 (m, 1H), 7.25 (m, 2H), 6.87 (d, 1H), 4.69 (s, 2H), 4.17 (s, 2H), 2.67 (s, 3H). MS (ES-API): M=266.1 (main fragment). HPLC (Method B) $t_R$=3.20 min.

Example 64

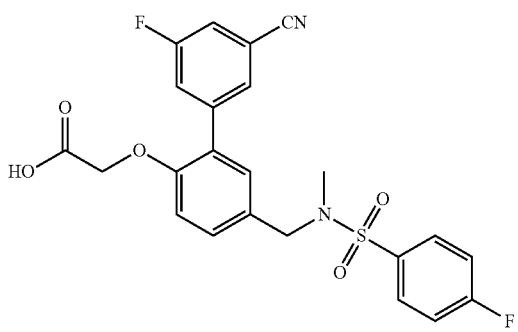

Example 64

$^1$HNMR (CD$_3$CN, 300 MHz): δ 7.89 (m, 2H), 7.84 (s, 1H), 7.71 (m, 1H), 7.52 (m, 1H), 7.33 (m, 3H), 7.28 (s, 1H), 7.03 (d, 1H), 4.75 (s, 2H), 4.17 (s, 2H), 2.65 (s, 3H). MS (ES-API): MH$^-$=471.1. HPLC (Method A) $t_R$=1.67 min.

Sodium Salt of Example 64

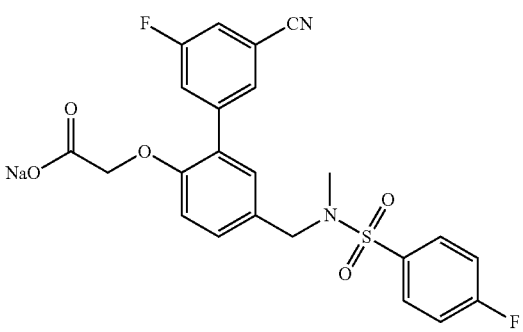

Sodium Salt of Example 64

$^1$HNMR (DMSO, 400 MHz): δ 8.12 (d, 1H), 8.02 (s, 1H), 7.89 (m, 2H), 7.74 (d, 1H), 7.48 (t, 2H), 7.19 (m, 2H), 6.93 (d, 1H), 4.22 (s, 2H), 4.09 (s, 2H), 2.56 (s, 3H).

Example 65

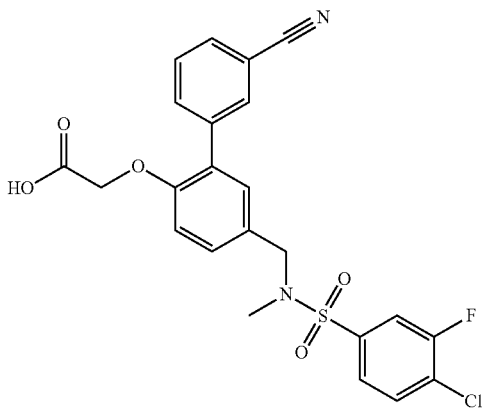

Example 65

$^1$HNMR (CD$_3$CN, 300 MHz): δ 8.00 (s, 1H), 7.87 (d, 1H), 7.58-7.78 (m, 5H), 7.34 (d, 1H), 7.24 (s, 1H), 7.00 (d, 1H), 4.73 (s, 2H), 4.22 (s, 2H), 2.70 (s, 3H). MS (ES-API): MH⁻=487.0. HPLC (Method A) $t_R$=2.37 min.

Example 66

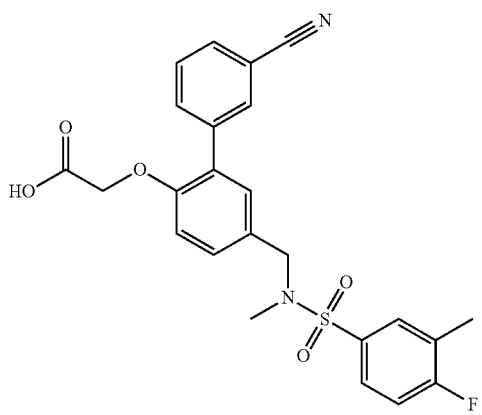

Example 66

¹HNMR (CD₃CN, 300 MHz): δ 8.00 (s, 1H), 7.85 (d, 1H), 7.71 (m, 3H), 7.59 (t, 1H), 7.21-7.38 (m, 3H), 7.00 (d, 1H), 4.73 (s, 2H), 4.19 (s, 2H), 2.66 (s, 3H), 2.34 (s, 3H). MS (ES-API): MH⁻=467.1. HPLC (Method A) $t_R$=2.16 min.

Example 67

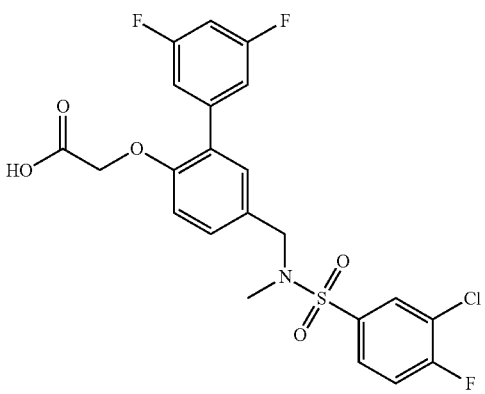

Example 67

¹HNMR (CD₃CN, 300 MHz): δ 7.95 (d, 1H), 7.80 (m, 1H), 7.47 (t, 1H), 7.20-7.35 (m, 4H), 6.98 (m, 2H), 4.75 (s, 2H), 4.22 (s, 2H), 2.70 (s, 3H). MS (ES-API): MH⁻=498.0. HPLC (Method A) $t_R$=2.49 min.

Example 69

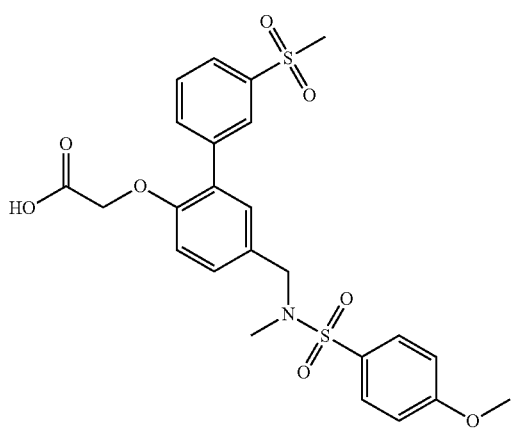

Example 69

¹HNMR (CDCl₃, 400 MHz): δ 8.22 (s, 1H), 7.81 (d, 1H), 7.77 (m, 3H), 7.63 (t, 1H), 7.30 (m, 2H), 7.03 (d, 2H), 6.89 (d, 1H), 4.69 (s, 2H), 4.13 (s, 2H), 3.89 (s, 3H), 3.11 (s, 3H), 2.61 (s, 3H). MS (ESI): MH⁺=520.2. HPLC (Method B) $t_R$=2.32 min.

Example 70

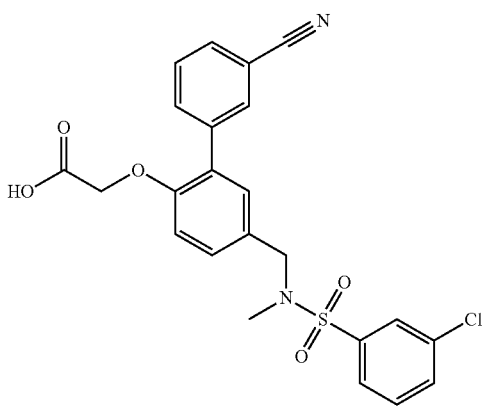

Example 70

¹HNMR (CD₃CN, 400 MHz): δ 7.95 (s, 1H), 7.83 (m, 2H), 7.75 (d, 1H), 7.66 (m, 2H), 7.59 (bs, 2H), 7.29 (d, 1H), 7.21 (s,

1H), 6.96 (d, 1H), 4.71 (s, 2H), 4.19 (s, 2H), 2.65 (s, 3H). MS (ES-API): MH⁻=469.0. HPLC (Method A) $t_R$=2.19 min.

Example 71

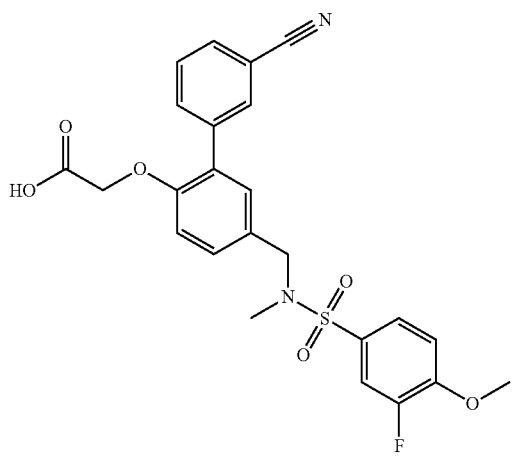

Example 71

¹HNMR (CD₃CN, 300 MHz): δ 8.00 (s, 1H), 7.86 (d, 1H), 7.72 (d, 1H), 7.58-7.68 (m, 3H), 7.23-7.36 (m, 3H), 7.00 (d, 1H), 4.73 (s, 2H), 4.18 (s, 2H), 3.95 (s, 3H), 2.68 (s, 3H). MS (ES-API): MH⁻=483.1. HPLC (Method A) $t_R$=2.21 min.

Example 72

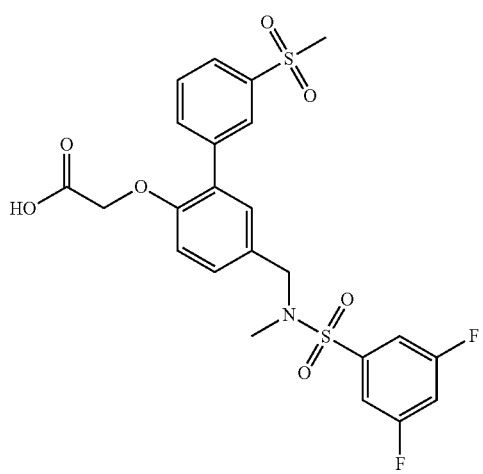

Example 72

¹HNMR (CDCl₃, 400 MHz): δ 8.22 (s, 1H), 7.82 (d, 1H), 7.64 (d, 1H), 7.37 (t, 1H), 7.32 (m, 4H), 7.26 (m, 1H), 6.90 (d,

1H), 4.70 (s, 2H), 4.20 (s, 2H), 3.11 (s, 3H), 2.69 (s, 3H). MS (ESI): MH⁺=526.1. HPLC (Method B) $t_R$=2.33 min.

Example 75

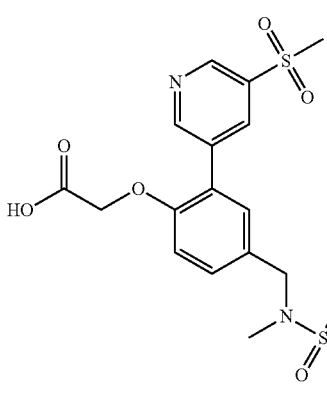

Example 75

¹HNMR (d-DMSO, 300 MHz): δ 9.16 (s, 1H), 9.00 (s, 1H), 8.62 (s, 1H), 7.94 (m, 2H), 7.50 (t, 2H), 7.35 (d, 2H), 7.05 (d, 1H), 4.45 (s, 2H), 4.15 (s, 2H), 3.39 (s, 3H), 2.59 (s, 3H). MS (ES-API): MH⁻=507.0. HPLC (Method A) $t_R$=2.04 min.

Example 77

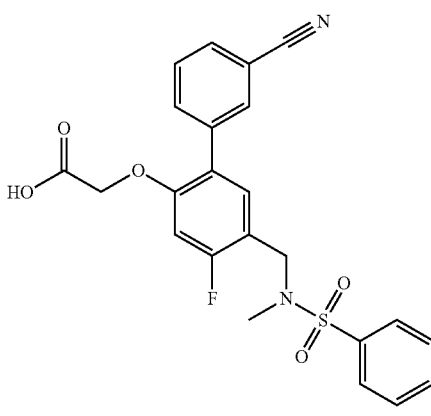

Example 77

¹HNMR (CD₃CN, 300 MHz): δ 7.95 (s, 1H), 7.87 (m, 3H), 7.71 (d, 1H), 7.59 (t, 1H), 7.30 (m, 3H), 6.82 (d, 1H), 4.70 (s,

2H), 4.22 (s, 2H), 2.68 (s, 3H). MS (ES-API): MH⁻=471.1. HPLC (Method A) t_R=2.08 min.

Example 78

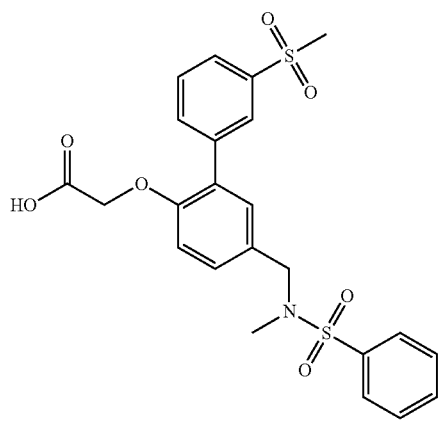

Example 78

¹HNMR (CDCl₃, 400 MHz): δ 8.24 (s, 1H), 7.81 (d, 1H), 7.62 (m, 3H), 7.58 (m, 4H), 7.31 (m, 2H), 6.89 (d, 1H), 4.68 (s, 2H), 4.16 (s, 2H), 3.10 (s, 3H), 2.64 (s, 3H). MS (ESI): MH⁺=490.1. HPLC (Method B) t_R=2.30 min.

Example 83

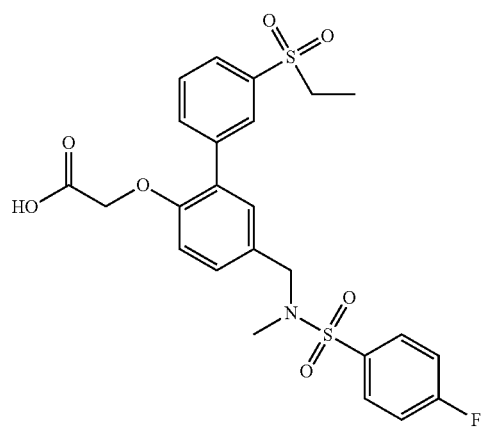

Example 83

¹HNMR (CD₃Cl₃, 300 MHz): δ 8.13 (m, 1H), 7.81 (m, 4H), 7.57 (t, 1H), 7.24 (m, 4H), 6.85 (d, 1H), 4.65 (s, 2H), 4.11

(d, 2H), 3.15 (q, 2H), 2.60 (s, 3H), 1.26 (t, 3H). MS (ES-API): main fragment=333.1. HPLC (Method B) t_R=2.97 min.

Example 9

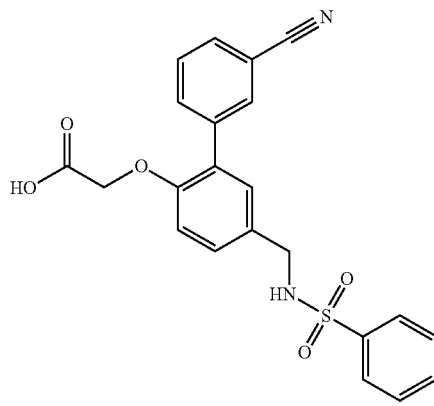

Example 9

¹HNMR (CD₃CN, 300 MHz): δ 7.92 (s, 1H), 7.80 (m, 3H), 7.70 (d, 1H), 7.59 (t, 1H), 7.20 (t, 3H), 7.10 (s, 1H), 6.88 (d, 1H), 6.14 (bm, 1H), 4.70 (s, 2H), 4.11 (d, 2H). MS (ES-API): MH⁻=439.1. HPLC (Method A) t_R=2.12 min.

Example 5

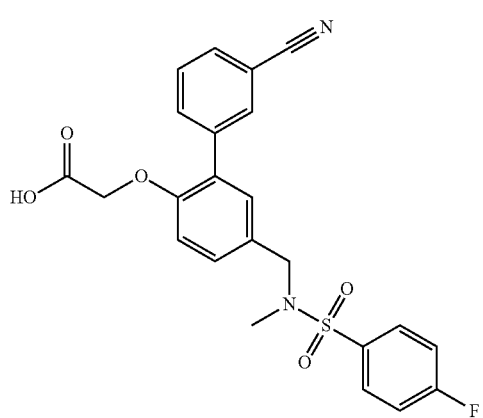

Example 5

¹HNMR (CD₃CN, 300 MHz): δ 7.90 (s, 1H), 7.80 (m, 3H), 7.61 (m, 1H), 7.50 (m, 1H), 7.25 (m, 3H), 7.15 (s, 1H), 6.91

(d, 1H), 4.62 (s, 2H), 4.09 (s, 2H), 2.62 (s, 3H). MS (ES-API): MH⁻=453.0. HPLC (Method A) t_R=2.10 min.

Example 85

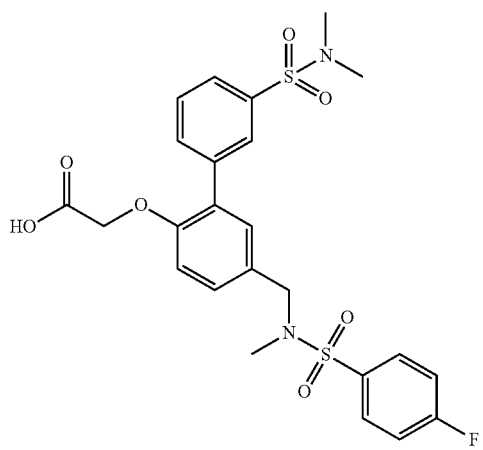

Example 85

¹HNMR (CD₃CN, 400 MHz): δ 8.01 (s, 1H), 7.89 (m, 3H), 7.78 (d, 1H), 7.69 (t, 1H), 7.28-7.39 (m, 4H), 7.01 (d, 1H), 4.72 (s, 2H), 4.19 (s, 2H), 2.72 (s, 6H), 2.54 (s, 3H). MS (ES-API): MH⁻=535.0. HPLC (Method A) t_R=2.16 min.

Example 86

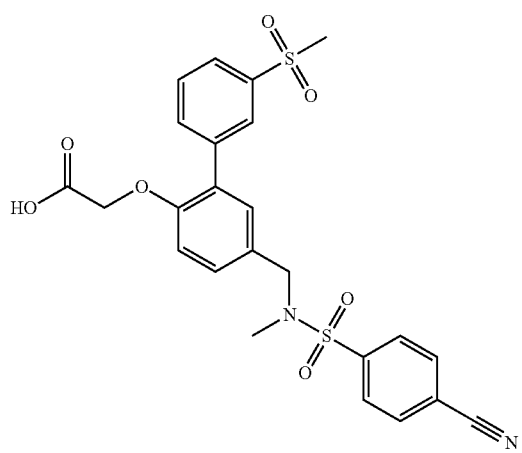

Example 86

¹HNMR (CDCl₃, 400 MHz): δ 8.22 (s, 1H), 7.85 (m, 3H), 7.81 (m, 3H), 7.62 (t, 1H), 7.27 (m, 2H), 6.89 (d, 1H), 4.70 (s,

2H), 4.20 (s, 2H), 3.11 (s, 3H), 2.70 (s, 3H). MS (ESI): MH⁺=515.2. HPLC (Method B) t_R=2.23 min.

Example 88

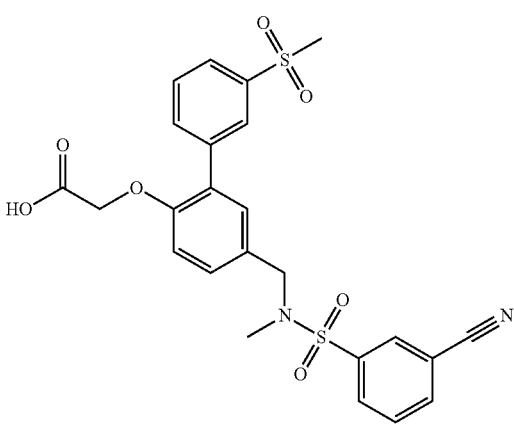

Example 88

¹HNMR (CDCl₃, 400 MHz): δ 8.22 (s, 1H), 7.87 (m, 2H), 7.80 (m, 4H), 7.65 (t, 1H), 7.63 (t, 1H), 7.26 (d, 1H), 6.90 (d, 1H), 4.71 (s, 2H), 4.22 (s, 2H), 3.12 (s, 3H), 2.71 (s, 3H). MS (ESI): MH⁺=515.2. HPLC (Method B) t_R=2.20 min.

Example 89

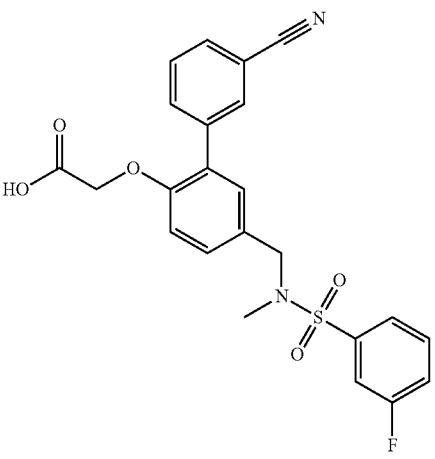

Example 89

¹HNMR (CDCl₃, 400 MHz): δ 7.91 (s, 1H), 7.77 (d, 1H), 7.63 (m, 2H), 7.49-7.66 (m, 3H), 7.31 (m, 2H), 7.25 (m, 1H), 6.87 (d, 1H), 4.72 (s, 2H), 4.18 (s, 2H), 2.68 (s, 3H). MS (ES-API): M=266.1 (main fragment). HPLC (Method B) $t_R$=3.03 min.

Example 90

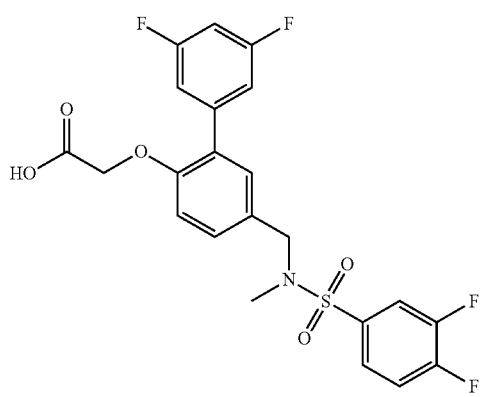

Example 90

$^1$HNMR (CD$_3$CN, 300 MHz): δ 7.80 (t, 1H), 7.68 (m, 1H), 7.51 (q, 1H), 7.20-7.35 (m, 4H), 6.98 (m, 2H), 4.75 (s, 2H), 4.20 (s, 2H), 2.69 (s, 3H). MS (ES-API): MH$^-$=482.0. HPLC (Method A) $t_R$=2.44 min.

Example 91

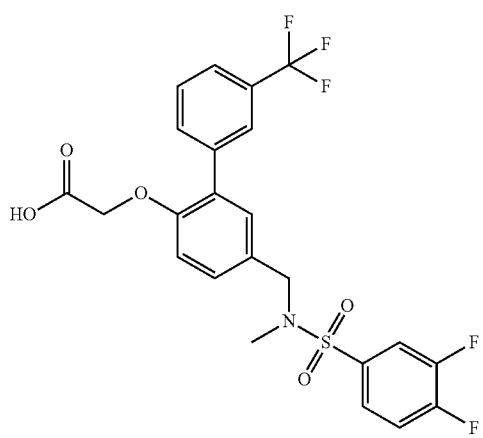

Example 91

$^1$HNMR (CDCl$_3$, 300 MHz): δ 7.80 (s, 1H), 7.61 (m, 3H), 7.30-7.50 (m, 3H), 7.18 (m, 2H), 6.78 (d, 1H), 4.35 (s, 2H), 4.10 (s, 2H), 2.60 (s, 3H). MS (ES-API): MH$^-$=513.8. HPLC (Method A) $t_R$=1.79 min.

Example 92

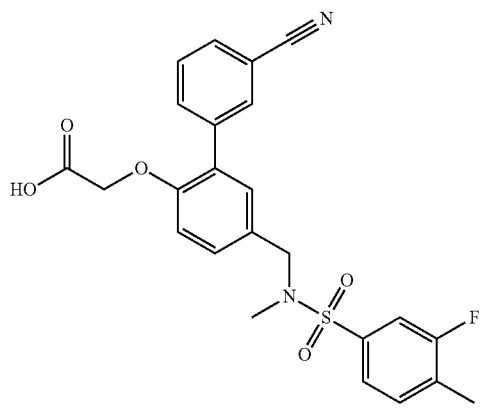

Example 92

$^1$HNMR (CD$_3$CN, 300 MHz): δ 8.00 (s, 1H), 7.86 (d, 1H), 7.72 (d, 1H), 7.48-7.64 (m, 4H), 7.32 (d, 1H), 7.22 (d, 1H), 7.00 (d, 1H), 4.72 (s, 2H), 4.19 (s, 2H), 2.66 (s, 3H), 2.35 (s, 3H). MS (ES-API): MH$^-$=467.1. HPLC (Method A) $t_R$=2.26 min.

Example 93

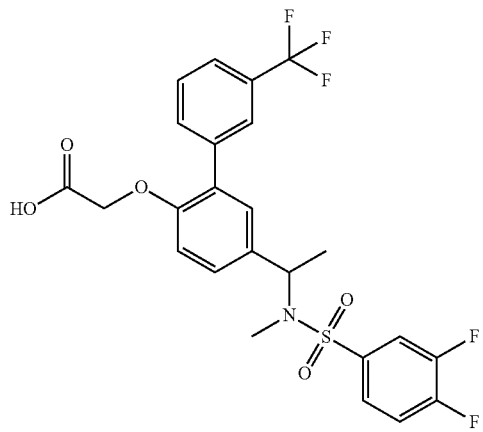

Example 93

$^1$HNMR (CDCl$_3$, 400 MHz): δ 7.61 (s, 1H), 7.53 (m, 3H), 7.31 (m, 1H), 7.25 (m, 1H), 7.22 (m, 1H), 7.03 (m, 2H), 6.72

(d, 1H), 5.01 (m, 1H), 4.14 (s, 2H), 2.38 (s, 3H), 1.06 (d, 3H). MS (ES-API): M=323.1 (main fragment). HPLC (Method B) $t_R$=3.43 min.

Example 94

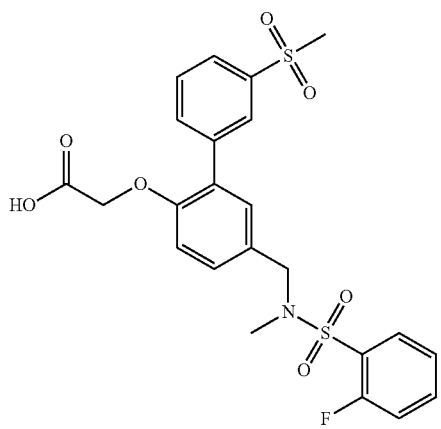

Example 94

$^1$HNMR (CDCl$_3$, 400 MHz): δ 8.22 (s, 1H), 7.85 (m, 2H), 7.78 (d, 1H), 7.60 (m, 3H), 7.26 (m, 3H), 6.90 (d, 1H), 4.71 (s, 2H), 4.22 (s, 2H), 3.11 (s, 3H), 2.70 (s, 3H). MS (ESI): MH$^+$=508.2. HPLC (Method B) $t_R$=2.25 min.

Example 95

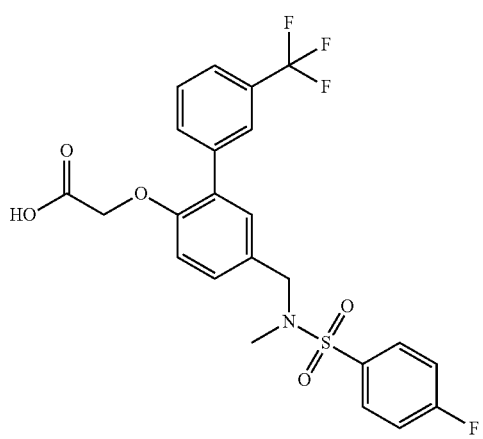

Example 95

$^1$HNMR (d-DMSO, 300 MHz): δ 13.1 (s, 1H), 7.95 (m, 3H), 7.84 (d, 1H), 7.69 (m, 2H), 7.50 (t, 2H), 7.31 (d, 1H), 7.25 (s, 1H), 7.06 (d, 1H), 4.76 (s, 2H), 4.15 (s, 2H), 2.60 (s, 3H). MS (ES-API): M+23=520.0. HPLC (Method A) $t_R$=2.70 min.

Example 96

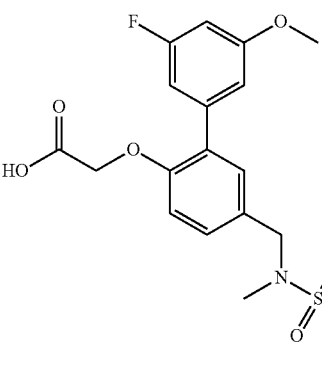

Example 96

$^1$HNMR (CD$_3$CN, 300 MHz): δ 7.90 (m, 2H), 7.22-7.39 (m, 4H), 6.96 (m, 3H), 6.72 (d, 1H), 4.72 (s, 2H), 4.18 (s, 2H), 3.85 (s, 3H), 2.65 (s, 3H). MS (ES-API): MH$^-$=476.0. HPLC (Method A) $t_R$=2.20 min.

Example 97

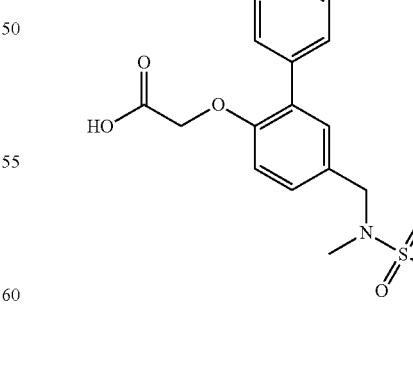

Example 97

$^1$HNMR (CDCl$_3$, 400 MHz): δ 7.91 (s, 1H), 7.77 (d, 1H), 7.63 (d, 1H), 7.53 (t, 1H), 7.28-7.38 (m, 4H), 7.07 (m, 1H), 6.88 (d, 1H), 4.71 (s, 2H), 4.20 (s, 2H), 2.70 (s, 3H). MS (ES-API): M=266.1 (main fragment). HPLC (Method B) $t_R$=3.13 min.

Example 98

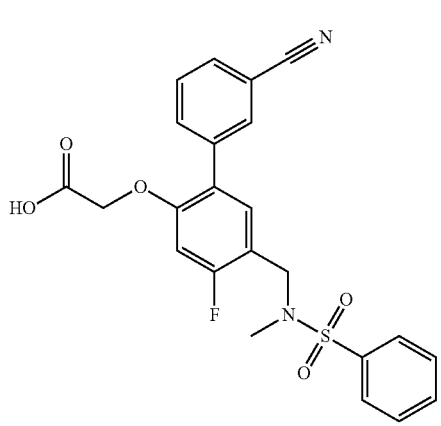

Example 98

$^1$HNMR (CD$_3$CN, 400 MHz): δ 7.95 (s, 1H), 7.85 (m, 3H), 7.71 (m, 2H), 7.63 (m, 3H), 7.29 (d, 1H), 6.84 (d, 1H), 4.73 (s, 2H), 4.23 (s, 2H), 2.70 (s, 3H). MS (ES-API): MH$^-$=453.1. HPLC (Method A) $t_R$=2.06 min.

Example 99

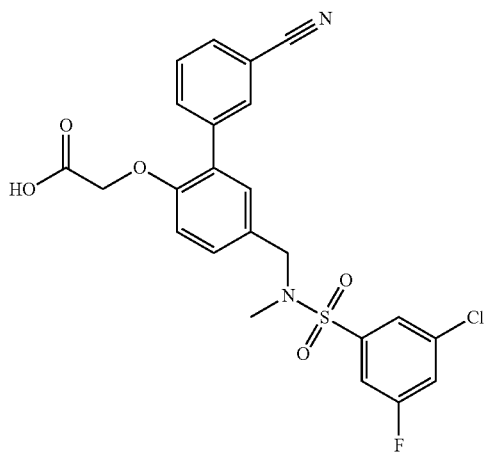

Example 99

$^1$HNMR (CD$_3$CN, 300 MHz): δ 8.00 (s, 1H), 7.88 (d, 1H), 7.70 (t, 2H), 7.50-7.62 (m, 3H), 7.33 (d, 1H), 7.24 (s, 1H), 7.00 (d, 1H), 4.72 (s, 2H), 4.24 (s, 2H), 2.71 (s, 3H). MS (ES-API): MH$^-$=487.1. HPLC (Method A) $t_R$=2.20 min.

Example 100

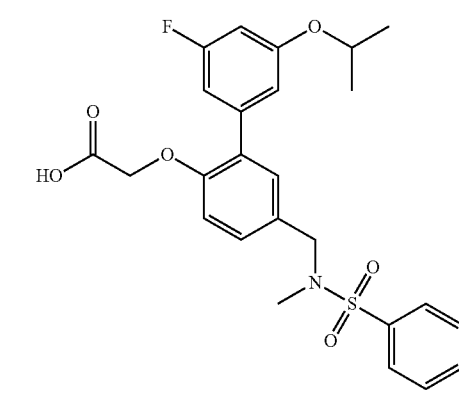

Example 100

$^1$HNMR (CD$_3$CN, 300 MHz): δ 7.89 (m, 2H), 7.22-7.38 (m, 4H), 6.95 (m, 3H), 6.65 (d, 1H), 4.71 (s, 2H), 4.65 (m, 1H), 4.16 (s, 2H), 2.68 (s, 3H), 1.36 (d, 6H). MS (ES-API): MH$^-$=504.1. HPLC (Method A) $t_R$=1.86 min.

Example 101

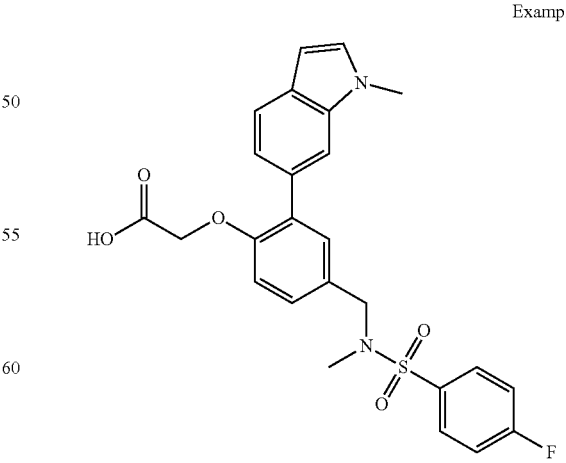

Example 101

$^1$HNMR (CD$_3$CN, 300 MHz): δ 7.89 (m, 2H), 7.67 (s, 1H), 7.58 (d, 1H), 7.34 (m, 3H), 7.21 (m, 3H), 6.95 (bm, 1H), 6.45

(d, 1H), 4.61 (s, 2H), 4.15 (s, 2H), 3.80 (s, 3H), 2.62 (s, 3H). MS (ES-API): MH⁻=481.1. HPLC (Method A) $t_R$=1.68 min.

Example 36

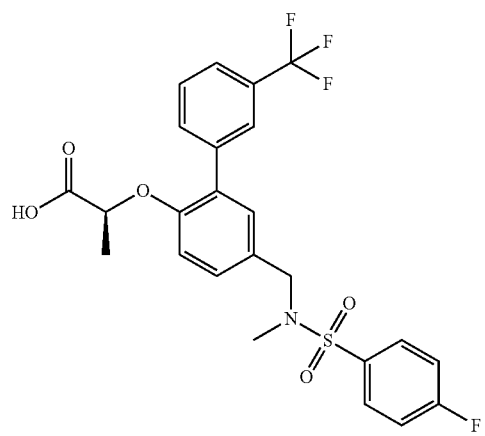

Example 36

¹HNMR (CDCl₃, 400 MHz): δ 7.84 (m, 3H), 7.70(d, 1H), 7.56 (m, 2H), 7.26 (m, 3H), 7.20 (d, 1H), 6.88 (d, 1H), 4.80 (m, 1H), 4.15 (s, 2H), 2.64 (s, 3H), 1.57 (d, 3H). MS (ESI): MH⁺=512.1. HPLC (Method B) $t_R$=2.78 min.

Example 102

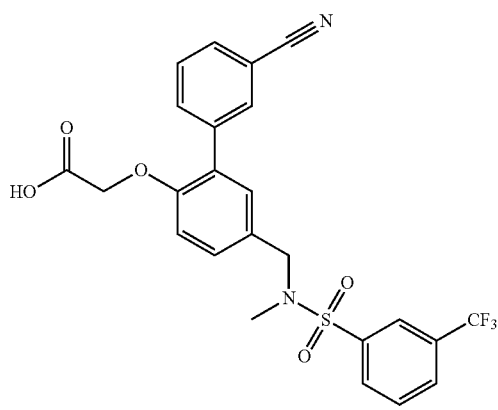

Example 102

¹HNMR (CDCl₃, 400 MHz): δ 8.10 (s, 1H), 8.04 (d, 1H), 7.90 (d, 2H), 7.75 (m, 2H), 7.63 (d, 1H), 7.52 (t, 1H), 7.28 (m, 2H), 6.89 (d, 1H), 4.72 (s, 2H), 4.20 (s, 2H), 2.70 (s, 3H). MS (ES-API): M=266.1 (main fragment). HPLC (Method B) $t_R$=3.20 min.

Example 103

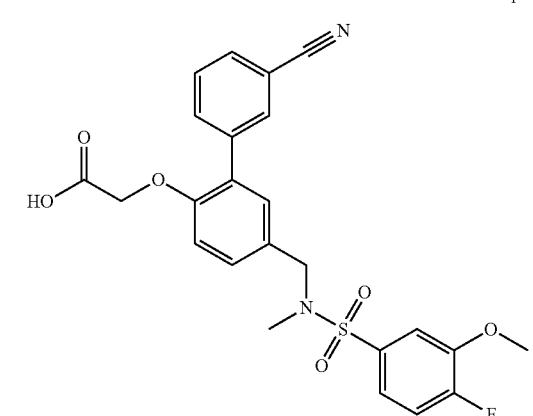

Example 103

¹HNMR (CD₃CN, 300 MHz): δ 8.00 (s, 1H), 7.88 (d, 1H), 7.71 (d, 1H), 7.60 (t, 1H), 7.45 (m, 2H), 7.33 (m, 2H), 7.24 (s, 1H), 7.00 (d, 1H), 4.72 (s, 2H), 4.21 (s, 2H), 3.94 (s, 3H), 2.68 (s, 3H). MS (ES-API): MH⁻=483.2. HPLC (Method A) $t_R$=2.15 min.

Example 104

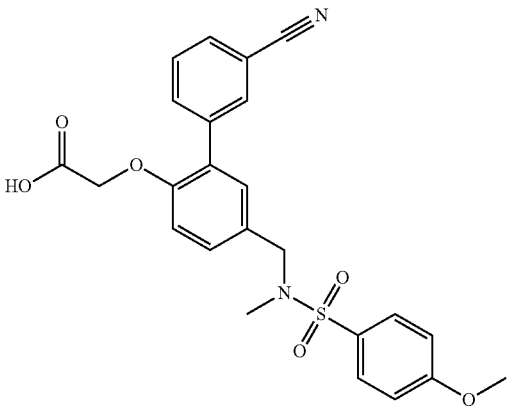

Example 104

¹HNMR (CDCl₃, 400 MHz): δ 7.99 (s, 1H), 7.78 (m, 3H), 7.61 (d, 1H), 7.50 (t, 1H), 7.25 (m, 2H), 7.04 (m, 2H), 6.88 (d,

1H), 4.63 (s, 2H), 4.12 (s, 2H), 3.89 (s, 3H), 2.61 (s, 3H). MS (ES-API): M=266.1 (main fragment). HPLC (Method B) $t_R$=2.98 min.

Example 105

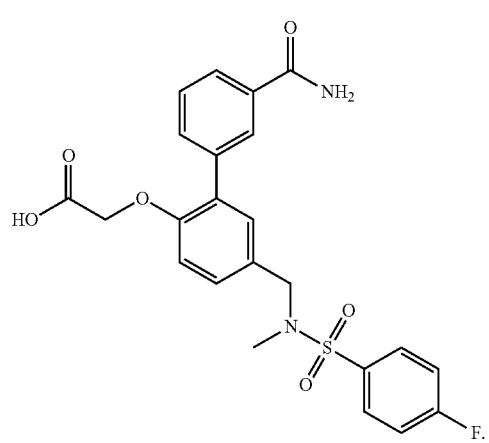

Example 105

$^1$HNMR (d-DMSO, 400 MHz): δ 8.35 (d, 2H), 7.90 (t, 2H), 7.76 (d, 1H), 7.68 (d, 1H), 7.46 (m, 3H), 7.22 (m, 3H), 6.94 (d, 1H), 4.39 (s, 2H), 4.11 (s, 2H), 2.56 (s, 3H). MS (ES-API): MH$^-$=471.0. HPLC (Method A) $t_R$=2.10 min.

Example 106

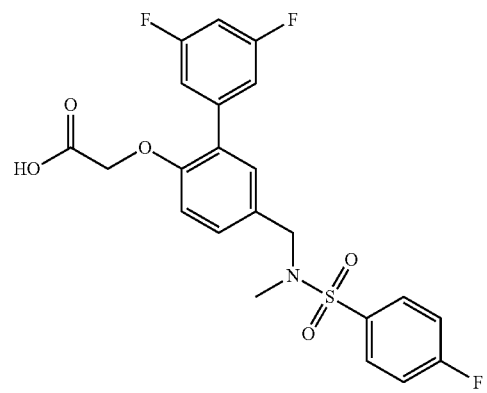

Example 106

$^1$HNMR (CD$_3$CN, 300 MHz): δ 7.79 (m, 2H), 7.10-7.29 (m, 6H), 6.85 (m, 2H), 4.62 (s, 2H), 4.05 (s, 2H), 2.55 (s, 3H). MS (ES-API): MH$^-$=464.1. HPLC (Method A) $t_R$=2.27 min.

Example 107

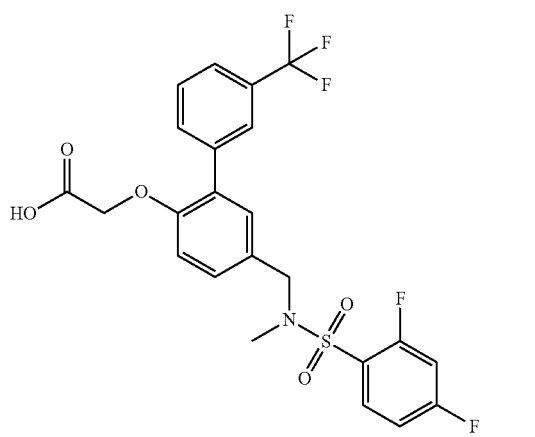

Example 107

$^1$HNMR (CDCl$_3$, 400 MHz): δ 7.98 (m, 1H), 7.88 (s, 1H), 7.75 (d, 1H), 7.65 (d, 1H), 7.59 (m, 1H), 7.36 (d, 1H), 7.29 (s, 1H), 7.03 (m, 2H), 6.91 (d, 1H), 4.71 (s, 2H), 4.36 (s, 2H), 2.79 (s, 3H). MS (ES-API): MH$^-$=514.0. HPLC (Method A) $t_R$=2.31 min.

Example 109

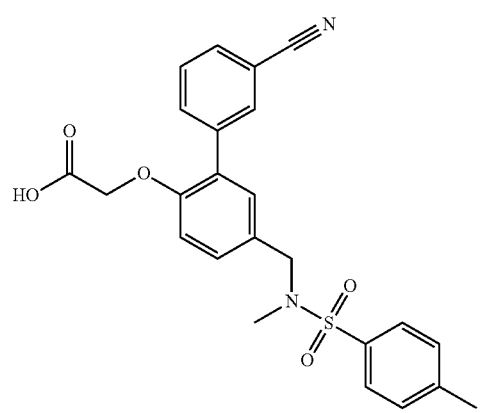

Example 109

$^1$HNMR (CDCl$_3$, 400 MHz): δ 7.96 (s, 1H), 7.80 (d, 1H), 7.72 (d, 2H), 7.61 (d, 1H), 7.51 (t, 1H), 7.36 (d, 2H), 7.25 (m,

2H), 6.87 (d, 1H), 4.63 (s, 2H), 4.11 (s, 2H), 2.61 (s, 3H), 2.46 (s, 3H). MS (ES-API): M=266.1 (main fragment). HPLC (Method B) $t_R$=3.08 min.

Example 110

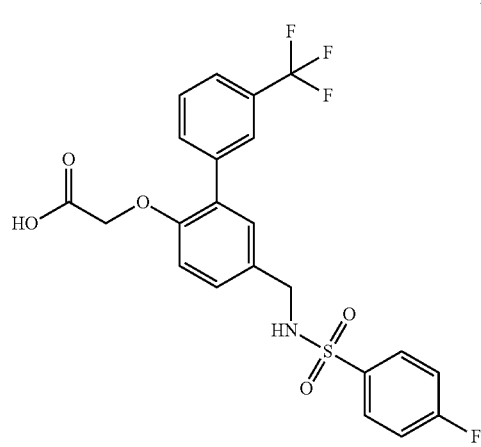

Example 110

$^1$HNMR (CD$_3$CN, 300 MHz): δ 7.74-7.79 (m, 4H), 7.64 (m, 2H), 7.10-7.25 (m, 4H), 6.91 (d, 1H), 6.10 (bm, 1H), 4.70 (s, 2H), 4.12 (d, 2H). MS (ES-API): MH$^-$=482.1. HPLC (Method A) $t_R$=2.13 min.

Example 111

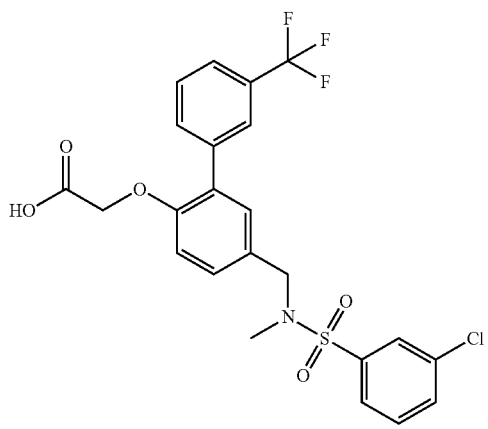

Example 111

$^1$HNMR (CDCl$_3$, 300 MHz): δ 7.71 (s, 2H), 7.64 (d, 2H), 7.40-7.55 (m, 5H), 7.14 (s, 1H), 6.80 (m, 1H), 4.50 (s, 2H), 4.18 (s, 2H), 2.56 (s, 3H). MS (ES-API): MH$^-$=512.0. HPLC (Method A) $t_R$=2.34 min.

Example 114

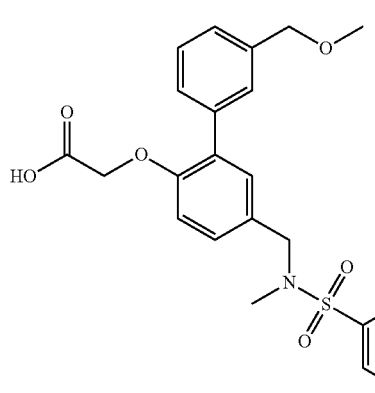

Example 114

$^1$HNMR (CD$_3$Cl$_3$, 300 MHz): δ 7.83 (m, 2H), 7.48 (m, 1H), 7.41 (m, 2H), 7.29 (m, 1H), 7.22 (m, 4H), 6.85 (d, 1H), 4.59 (s, 2H), 4.49 (d, 2H), 4.12 (s, 2H), 3.40 (s, 3H), 2.61 (s, 3H). MS (ES-API): main fragment=285.1. HPLC (Method B) $t_R$=3.13 min.

Example 115

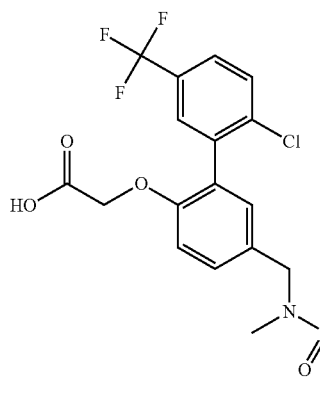

Example 115

¹HNMR (CD₃CN, 300 MHz): δ 7.79 (m, 2H), 7.60 (m, 3H), 7.25 (m, 3H), 7.04 (s, 1H), 6.90 (d, 1H), 4.56 (s, 2H), 4.08 (s, 2H), 2.56 (s, 3H). MS (ES-API): MH⁻=530.0. HPLC (Method A) $t_R$=2.31 min.

Example 116

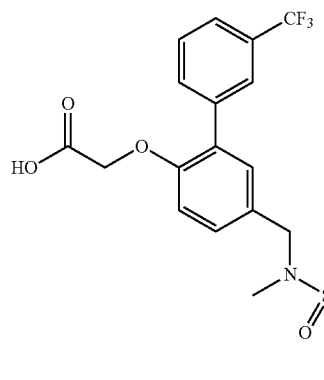

Example 116

¹HNMR (CDCl₃, 400 MHz): δ 7.89 (s, 1H), 7.80 (d, 2H), 7.75 (d, 1H), 7.63 (d, 1H), 7.56 (m, 3H), 7.30 (m, 2H), 6.91 (d, 1H), 4.70 (s, 2H), 4.20 (s, 2H), 2.68 (s, 3H). MS (ES-API): M+18=531.1. HPLC (Method A) $t_R$=2.17 min.

Example 117

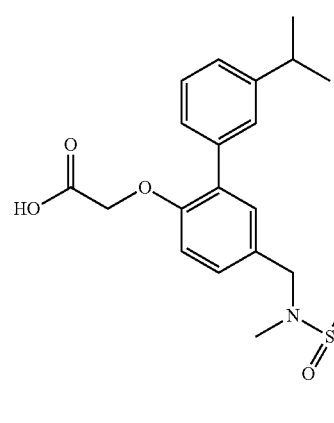

Example 117

¹HNMR (CD₃CN, 300 MHz): δ 7.78 (m, 2H), 7.37 (s, 1H), 7.23 (m, 4H), 7.13 (m, 3H), 6.85 (d, 1H), 4.58 (s, 2H), 4.04 (s, 2H), 2.85 (m, 1H), 2.54 (s, 3H), 1.18 (d, 6H). MS (ES-API): MH⁻=470.1. HPLC (Method A) $t_R$=1.80 min.

Example 119

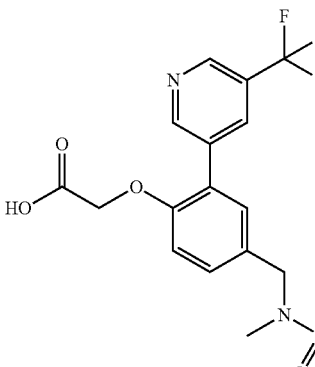

Example 119

¹HNMR (CD₃CN, 400 MHz): δ 9.01 (s, 1H), 8.88 (s, 1H), 8.34 (s, 1H), 7.89 (m, 2H), 7.35 (m, 4H), 7.04 (d, 1H), 4.74 (s, 2H), 4.18 (s, 2H), 2.64 (s, 3H). MS (ES-API): MH⁺=499.0. HPLC (Method A) $t_R$=2.96 min.

Example 120

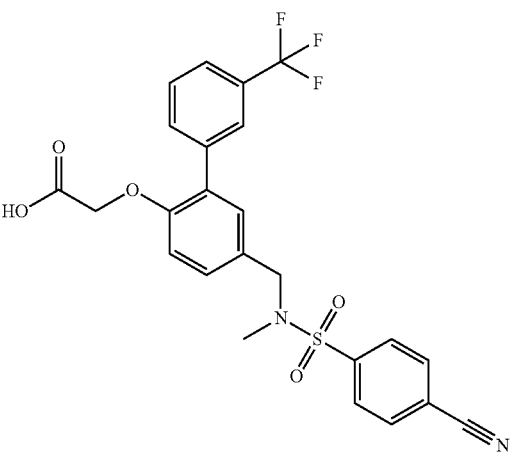

Example 120

¹HNMR (CD₃CN, 400 MHz): δ 7.94 (s, 4H), 7.90 (s, 1H), 7.81 (d, 1H), 7.59 (m, 2H), 7.19 (m, 2H), 6.91 (d, 1H), 4.49 (s,

2H), 4.14 (s, 2H), 2.62 (s, 3H). MS (ES-API): MH⁻=503.0. HPLC (Method A) t$_R$=2.30 min.

Example 121

Example 121

¹HNMR (CDCl$_3$, 400 MHz): δ 7.78 (s, 1H), 7.72 (d, 2H), 7.64 (d, 1H), 7.43 (m, 1H), 7.37 (m, 1H), 7.16 (m, 2H), 7.00 (d, 2H), 6.75 (d, 1H), 4.30 (s, 2H), 4.00 (s, 2H), 3.88 (s, 3H), 2.51 (s, 3H). MS (ES-API): M+23=532.0. HPLC (Method A) t$_R$=2.71 min.

Example 22

Example 22

¹HNMR (CDCl$_3$, 400 MHz): δ 7.82 (m, 2H), 7.68 (s, 1H), 7.62 (d, 1H), 7.48 (d, 1H), 7.43 (d, 1H), 7.10-7.20 (m, 4H), 6.81 (d, 1H), 5.22 (m, 1H), 4.52 (s, 2H), 2.59 (s, 3H), 1.26 (d, 3H). MS (ES-API): M=323.1 (main fragment). HPLC (Method B) t$_R$=3.40 min.

Example 125

Example 125

¹HNMR (CD$_3$CN, 300 MHz): δ 7.79 (m, 2H), 7.45 (m, 3H), 7.16-7.28 (m, 4H), 7.12 (s, 1H), 6.89 (d, 1H), 4.62 (s, 2H), 4.08 (s, 2H), 2.55 (s, 3H). MS (ES-API): MH⁻=512.0. HPLC (Method A) t$_R$=2.32 min.

Example 126

Example 126

¹HNMR (CD$_3$CN, 300 MHz): δ 7.95 (s, 1H), 7.83 (d, 1H), 7.59-7.71 (m, 5H), 7.62 (m, 1H), 7.31 (d, 1H), 7.26 (s, 1H), 7.00 (d, 1H), 4.72 (s, 2H), 4.21 (s, 2H), 2.70 (s, 3H). MS (ES-API): MH⁻=496.0. HPLC (Method A) $t_R$=2.37 min.
Example 127
1H), 7.36 (m, 3H), 7.08 (d, 1H), 4.78 (s, 2H), 4.18 (s, 2H), 2.64 (s, 3H). MS (ES-API): MH⁻=468.2. HPLC (Method A) $t_R$=1.99 min.
Example 130
Example 127
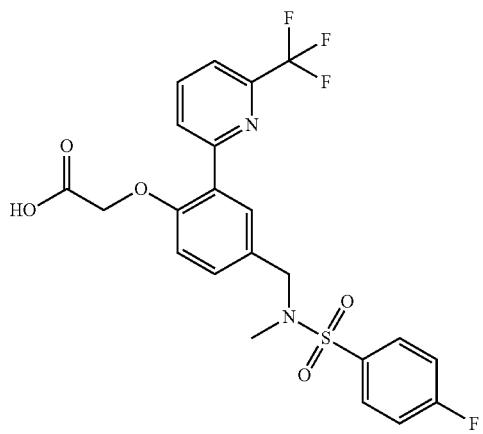
Example 130
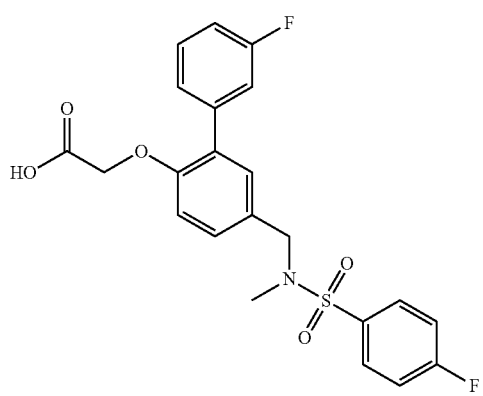
¹HNMR (CD₃CN, 400 MHz): δ 8.29 (d, 1H), 8.04 (t, 1H), 7.90 (m, 2H), 7.74 (m, 2H), 7.36 (m, 3H), 7.06 (d, 1H), 4.79 (s, 2H), 4.18 (s, 2H), 2.63 (s, 3H). MS (ES-API): MH⁺=499.0. HPLC (Method A) $t_R$=2.71 min.
Example 128
¹HNMR (CD₃CN, 400 MHz): δ 7.89 (m, 2H), 7.25-7.47 (m, 6H), 7.22 (s, 1H), 7.10 (t, 1H), 6.95 (d, 2H), 4.71 (s, 2H), 4.14 (s, 2H), 2.62 (s, 3H). MS (ES-API): MH⁻=446.1. HPLC (Method A) $t_R$=1.69 min.
Example 131
Example 128
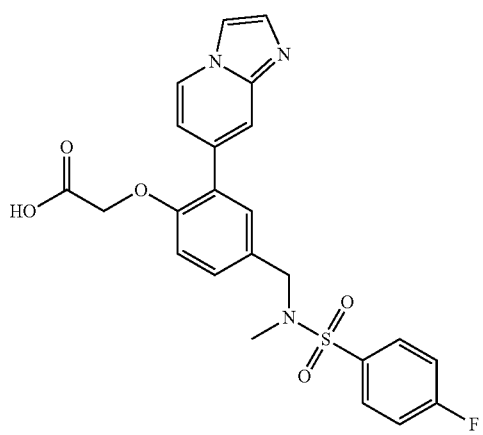
Example 131
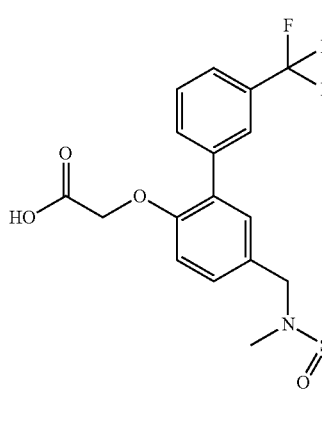
¹HNMR (CD₃CN, 300 MHz): δ 8.58 (d, 1H), 8.43 (s, 1H), 7.99 (s, 1H), 7.90 (m, 2H), 7.84 (s, 1H), 7.71 (d, 1H), 7.44 (s, ¹HNMR (CDCl₃, 300 MHz): δ 7.83 (d, 3H), 7.40-7.70 (m, 6H), 7.21 (m, 2H), 6.82 (d, 1H), 4.44 (s, 2H), 4.10 (s, 2H), 2.61 (s, 3H). MS (ES-API): M+18=497.0. HPLC (Method A) t_R=2.96 min.

Example 132

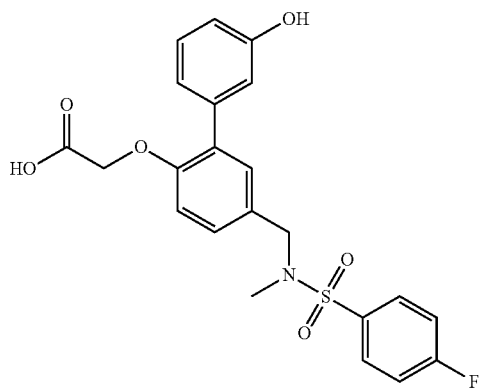

Example 132

¹HNMR (CD₃CN, 300 MHz): δ 7.76 (m, 2H), 7.23 (t, 2H), 7.11 (m, 3H), 6.92 (m, 2H), 6.82 (d, 1H), 6.69 (d, 1H), 4.59 (s, 2H), 4.02 (s, 2H), 2.50 (s, 3H). MS (ES-API): MH⁻=444.1. HPLC (Method A) t_R=2.09 min.

Example 133

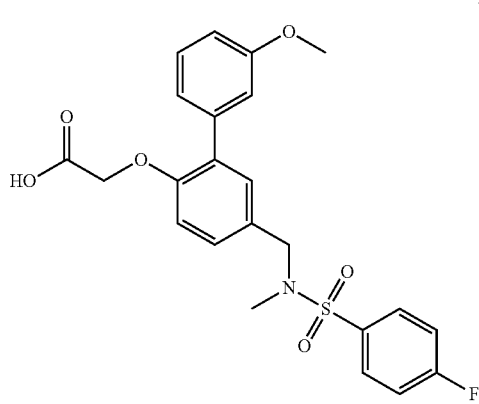

Example 133

¹HNMR (CD₃CN, 300 MHz): δ 7.90 (m, 2H), 7.35 (t, 3H), 7.23 (m, 3H), 7.10 (d, 1H), 6.95 (m, 2H), 4.70 (s, 2H), 4.16 (s, 2H), 3.82 (s, 3H), 2.63 (s, 3H). MS (ES-API): MH⁻=458.0. HPLC (Method A) t_R=2.14 min.

Example 134

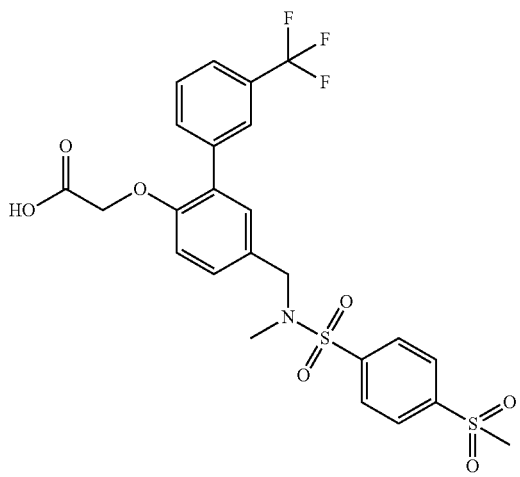

Example 134

¹HNMR (CD₃CN, 400 MHz): δ 8.14 (d, 2H), 8.05 (d, 2H), 7.95 (s, 1H), 7.81 (d, 1H), 7.65 (m, 2H), 7.30 (m, 2H), 7.00 (d, 1H), 4.71 (s, 2H), 4.22 (s, 2H), 3.12 (s, 3H), 2.70 (s, 3H). MS (ES-API): MH⁻=556.2. HPLC (Method A) t_R=2.10 min.

Example 136

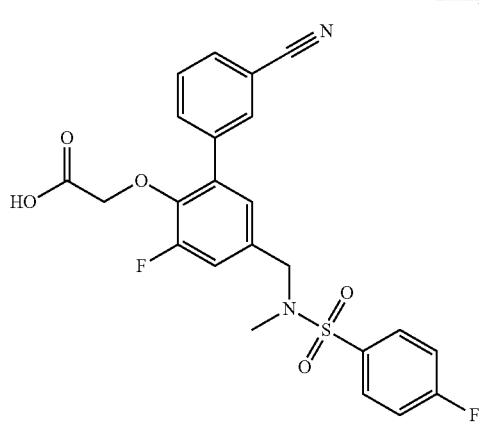

Example 136

¹HNMR (CD₃CN, 300 MHz): δ 7.92 (m, 3H), 7.82 (d, 1H), 7.75 (d, 1H), 7.62 (t, 1H), 7.35 (t, 2H), 7.20 (d, 1H), 7.09 (d,

1H), 4.60 (s, 2H), 4.19 (s, 2H), 2.69 (s, 3H). MS (ES-API): M+18=490.1. HPLC (Method A) $t_R$=2.67 min.

Example 137

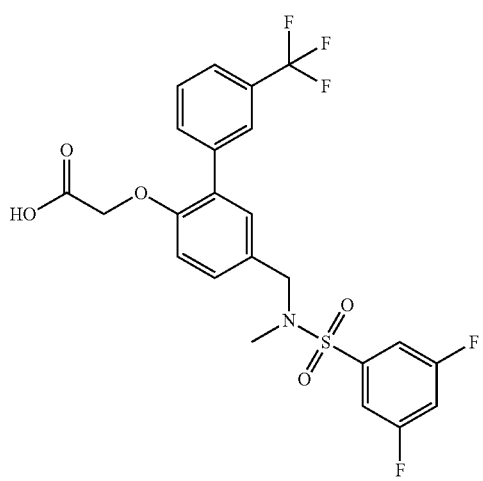

Example 137

¹HNMR (CD₃CN, 400 MHz): δ 7.94 (s, 1H), 7.80 (d, 1H), 7.64 (m, 2H), 7.45 (m, 2H), 7.26 (m, 3H), 6.99 (d, 1H), 4.71 (s, 2H), 4.14 (s, 2H), 2.62 (s, 3H). MS (ES-API): MH⁻=514.0. HPLC (Method A) $t_R$=2.44 min.

Example 141

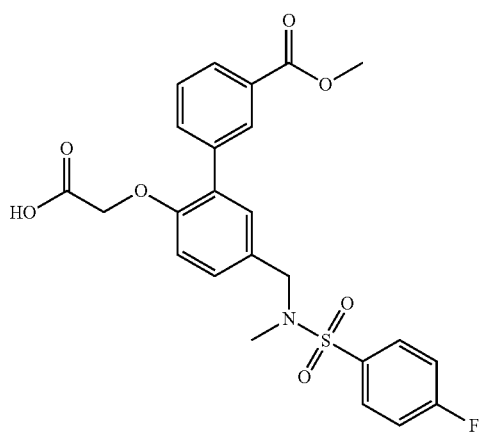

Example 141

¹HNMR (CD₃CN, 300 MHz): δ 8.16 (s, 1H), 8.00 (d, 1H), 7.89 (m, 2H), 7.82 (d, 1H), 7.55 (t, 1H), 7.34 (m, 3H), 7.22 (s, 1H), 6.99 (d, 1H), 4.71 (s, 2H), 4.19 (s, 2H), 3.91 (s, 3H), 2.66 (s, 3H). MS (ES-API): M+18=505.0. HPLC (Method A) $t_R$=2.51 min.

Example 142

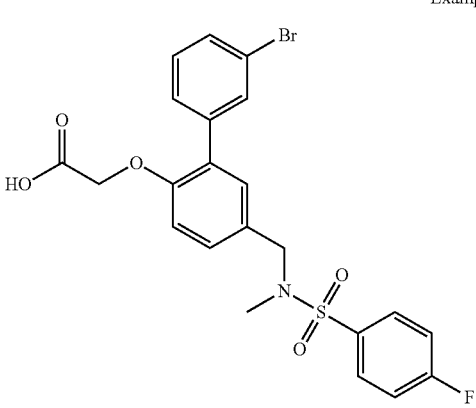

Example 142

¹HNMR (CD₃CN, 300 MHz): δ 7.90 (m, 2H), 7.79 (s, 1H), 7.54 (d, 2H), 7.35 (m, 4H), 7.21 (s, 1H), 6.97 (d, 1H), 4.71 (s, 2H), 4.18 (s, 2H), 2.65 (s, 3H). MS (ES-API): MH⁻=508.1. HPLC (Method A) $t_R$=2.16 min.

Example 143

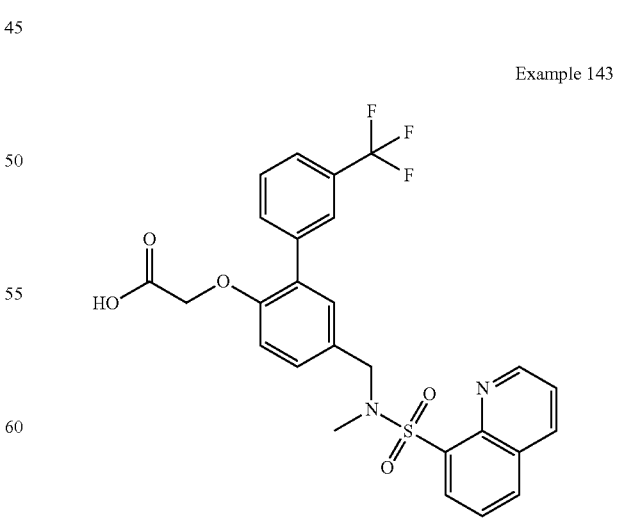

Example 143

¹HNMR (CD₃CN, 300 MHz): δ 9.01 (s, 1H), 8.44 (d, 1H), 8.32 (d, 1H), 8.12 (d, 1H), 7.85 (s, 1H), 7.68 (m, 3H), 7.55 (m,

2H), 7.23 (d, 1H), 7.09 (s, 1H), 6.89 (d, 1H), 4.51 (d, 4H), 2.83 (s, 3H). MS (ESI): MH⁺=531.1. HPLC (Method A) $t_R$=2.81 min.

Example 145

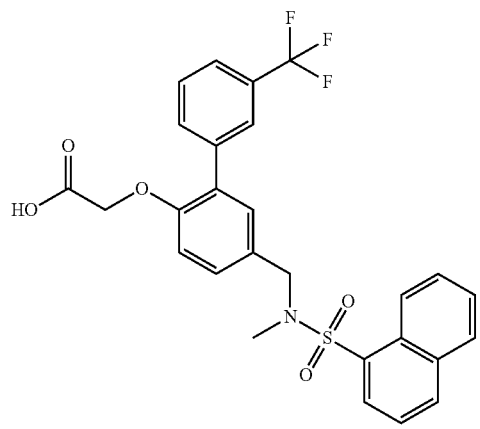

Example 145

¹HNMR (CD₃CN, 400 MHz): δ 8.69 (d, 1H), 8.19 (d, 1H), 8.15 (d, 1H), 7.99 (d, 1H), 7.84 (s, 1H), 7.50-7.70 (m, 6H), 7.16 (d, 1H), 6.97 (s, 1H), 6.86 (d, 1H), 4.49 (s, 2H), 4.29 (s, 2H), 2.70 (s, 3H). MS (ES-API): M+23=552.0. HPLC (Method A) $t_R$=2.32 min.

Example 146

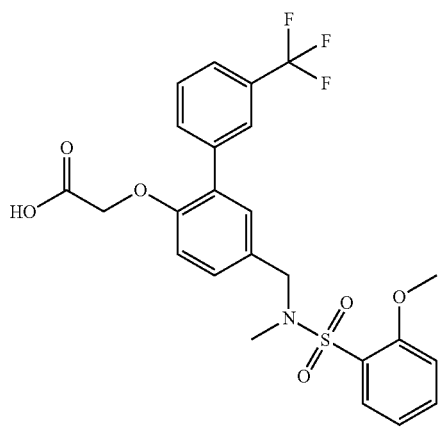

Example 146

¹HNMR (CDCl₃, 300 MHz): δ 7.90 (d, 1H), 7.74 (s, 1H), 7.65 (d, 1H), 7.45 (m, 3H), 7.25 (d, 1H), 7.15 (s, 1H), 6.95 (m, 2H), 6.80 (d, 1H), 4.60 (s, 2H), 4.29 (s, 2H), 3.83 (s, 3H), 2.69 (s, 3H). MS (ES-API): MH⁻=508.1. HPLC (Method A) $t_R$=2.27 min.

Example 147

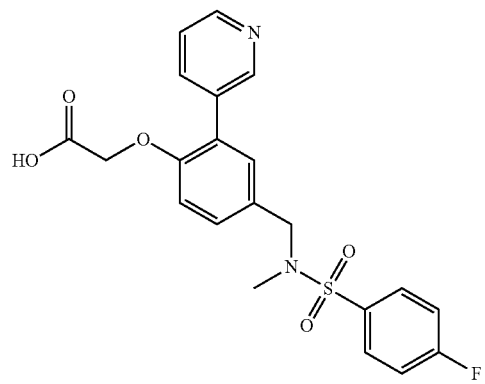

Example 147

¹HNMR (CD₃CN, 400 MHz): δ 9.11 (d, 1H), 8.71 (d, 1H), 8.62 (d, 1H), 7.96 (m, 1H), 7.89 (m, 2H), 7.39 (m, 4H), 7.09 (d, 1H), 4.79 (s, 2H), 4.20 (s, 2H), 2.65 (s, 3H). MS (ES-API): MH⁻=429.1. HPLC (Method A) $t_R$=1.90 min.

Example 148

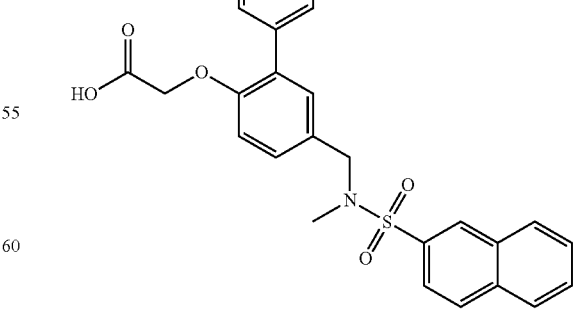

Example 148

¹HNMR (CD₃CN, 400 MHz): δ 8.45 (s, 1H), 8.09 (d, 2H), 8.02 (d, 1H), 7.91 (s, 1H), 7.83 (d, 1H), 7.60-7.78 (m, 4H), 7.58 (m, 1H), 7.31 (d, 1H), 7.22 (s, 1H), 6.95 (d, 1H), 4.70 (s,

2H), 4.22 (s, 2H), 2.70 (s, 3H). MS (ES-API): MH⁻=528.1. HPLC (Method A) $t_R$=2.07 min.
Example 149
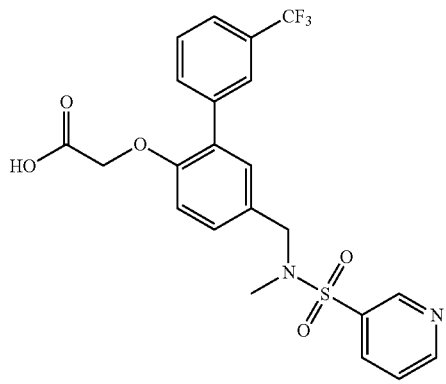
Example 149
¹HNMR (CD₃CN, 400 MHz): δ 8.95 (s, 1H), 8.79 (m, 1H), 8.11 (d, 1H), 7.88 (s, 1H), 7.80 (d, 1H), 7.54 (m, 3H), 7.16 (m, 2H), 6.90 (d, 1H), 4.45 (s, 2H), 4.11 (s, 2H), 2.62 (s, 3H). MS (ES-API): MH⁺=481.0. HPLC (Method A) $t_R$=2.91 min.
Example 151
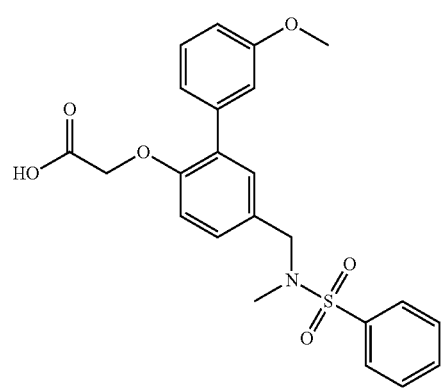
Example 151
¹HNMR (d-DMSO, 400 MHz): δ 7.85 (d, 2H), 7.71 (m, 1H), 7.64 (m, 2H), 7.31 (t, 1H), 7.20 (m, 2H), 7.15 (s, 1H), 7.05 (d, 1H), 6.99 (d, 1H), 6.89 (d, 1H), 4.70 (s, 2H), 4.12 (s,
2H), 3.76 (s, 3H), 2.58 (s, 3H). MS (ES-API): M+18=459.1. HPLC (Method A) $t_R$=2.01 min.
Example 35
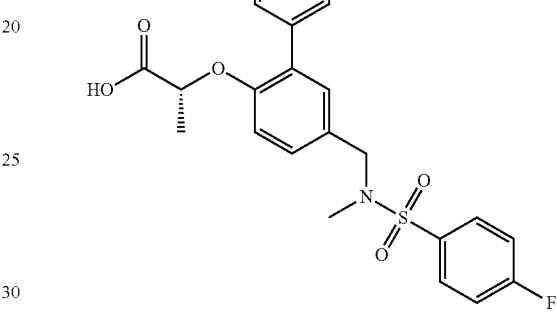
Example 35
¹HNMR (CDCl₃, 400 MHz): δ 7.78 (m, 3H), 7.64 (d, 1H), 7.48 (m, 2H), 7.25 (m, 3H), 7.17 (d, 1H), 6.73 (d, 1H), 4.87 (m, 1H), 4.04 (s, 2H), 2.53 (s, 3H), 1.32 (d, 3H). MS (ESI): MH⁺=512.1. HPLC (Method B) $t_R$=3.48 min.
Example 154
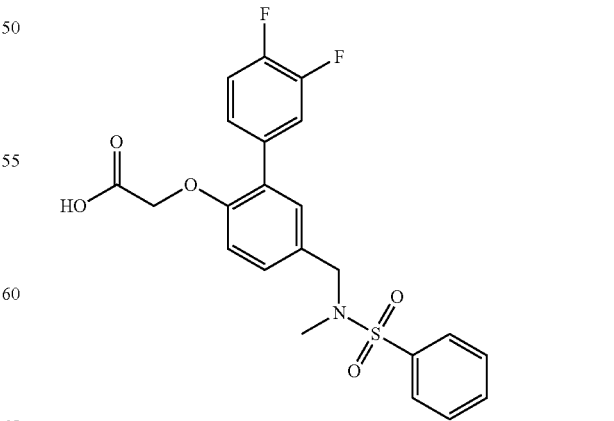
Example 154

¹HNMR (CDCl₃, 400 MHz): δ 7.83 (d, 2H), 7.60 (m, 3H), 7.44 (m, 1H), 7.25 (m, 4H), 6.85 (d, 1H), 4.68 (s, 2H), 4.14 (s, 2H), 2.63 (s, 3H). MS (ESI): MH⁺=448.1. HPLC (Method B) $t_R$=3.17 min.

Example 156

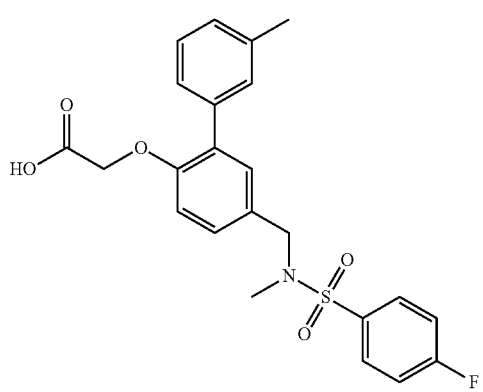

Example 156

¹HNMR (CD₃CN, 400 MHz): δ 7.88 (m, 2H), 7.33 (m, 5H), 7.20 (m, 3H), 6.94 (d, 1H), 4.68 (s, 2H), 4.15 (s, 2H), 2.64 (s, 3H), 2.39 (s, 3H). MS (ES-API): MH⁻=442.1. HPLC (Method A) $t_R$=1.74 min.

Example 157

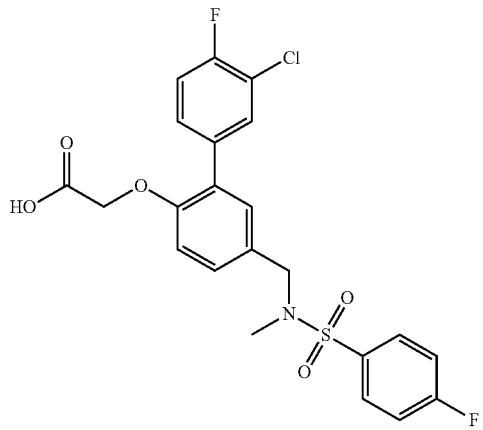

Example 157

¹HNMR (CD₃CN, 300 MHz): δ 7.79 (m, 2H), 7.64 (d, 1H), 7.41 (m, 1H), 7.13-7.29 (m, 4H), 7.10 (s, 1H), 6.86 (d, 1H), 4.61 (s, 2H), 4.15 (s, 2H), 2.55 (s, 3H). MS (ES-API): MH⁻=480.0. HPLC (Method A) $t_R$=2.25 min.

Example 159

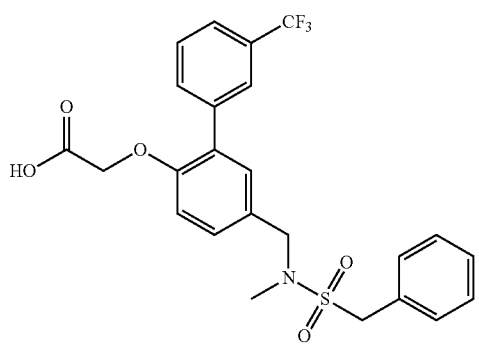

Example 159

¹HNMR (CDCl₃, 400 MHz): δ 7.84 (s, 1H), 7.74 (d, 1H), 7.62 (d, 1H), 7.57 (m, 1H), 7.41 (s, 5H), 7.29 (s, 1H), 7.22 (s, 1H), 6.89 (d, 1H), 4.69 (s, 2H), 4.34 (s, 2H), 4.07 (s, 2H), 2.66 (s, 3H). MS (ES-API): MH⁻=492.0. HPLC (Method A) $t_R$=2.26 min.

Example 160

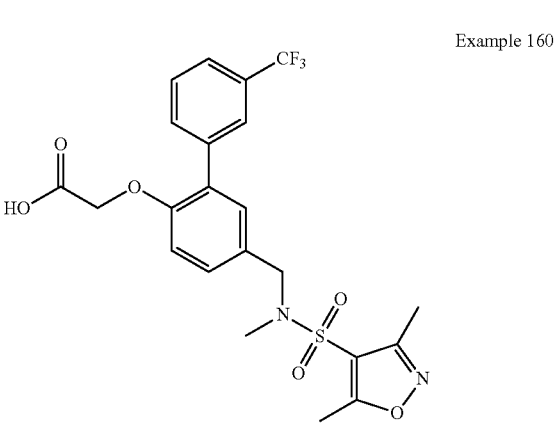 [SMILES: Cc1noc(C)c1S(=O)(=O)N(C)Cc1ccc(OCC(=O)O)c(-c2cccc(C(F)(F)F)c2)c1]

Example 160

¹HNMR (CDCl₃, 300 MHz): δ 7.82 (s, 1H), 7.64 (d, 1H), 7.45 (m, 2H), 7.21 (s, 1H), 7.18 (d, 1H), 6.79 (d, 1H), 4.33 (s,

2H), 4.19 (s, 2H), 2.64 (s, 6H), 2.40 (s, 3H). MS (ES-API): MH⁻=496.9. HPLC (Method A) t_R=1.65 min.
Example 162
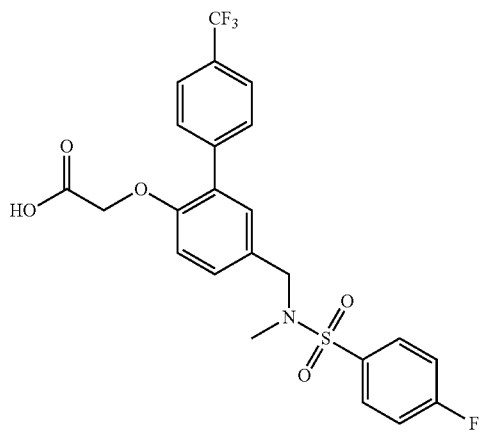
Example 162
¹HNMR (CD₃CN, 300 MHz): δ 7.90 (m, 2H), 7.75 (m, 4H), 7.34 (m, 3H), 7.24 (s, 1H), 7.00 (d, 1H), 4.71 (s, 2H), 4.16 (s, 2H), 2.64 (s, 3H). MS (ES-API): MH⁻=496.0. HPLC (Method A) t_R=2.31 min.
Example 163
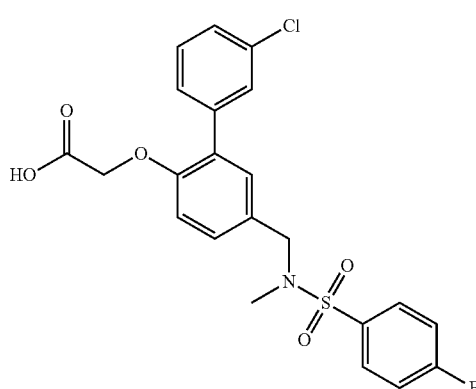
Example 163
¹HNMR (CD₃CN, 300 MHz): δ 7.90 (m, 2H), 7.63 (s, 1H), 7.20-7.50 (m, 7H), 6.98 (d, 1H), 4.70 (s, 2H), 4.16 (s, 2H), 2.62 (s, 3H). MS (ES-API): MH⁻=462.0. HPLC (Method A) t_R=2.22 min.
Example 165
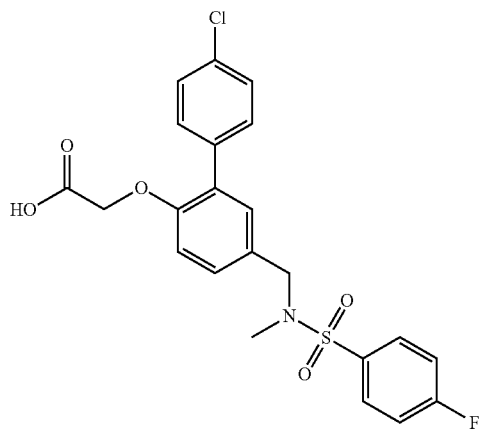
Example 165
¹HNMR (CD₃CN, 300 MHz): δ 7.79 (m, 2H), 7.48 (d, 2H), 7.33 (d, 2H), 7.25 (t, 2H), 7.15 (d, 1H), 7.10 (s, 1H), 6.86 (d, 1H), 4.59 (s, 2H), 4.15 (s, 2H), 2.55 (s, 3H). MS (ES-API): MH⁻=462.0. HPLC (Method A) t_R=2.37 min.
Example 166
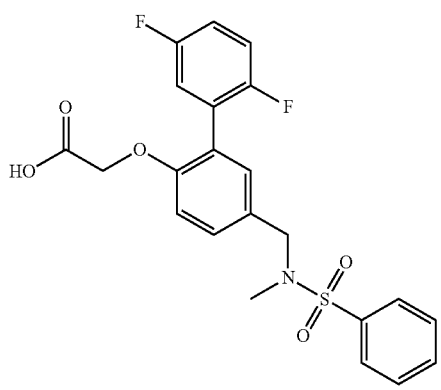
Example 166

¹HNMR (CDCl₃, 400 MHz): δ 7.83 (d, 2H), 7.57 (m, 3H), 7.33 (d, 1H), 7.21 (s, 1H), 7.08 (m, 3H), 6.89 (d, 1H), 4.66 (s, 2H), 4.15 (s, 2H), 2.64 (s, 3H). MS (ESI): MH⁺=448.1. HPLC (Method B) $t_R$=3.08 min.

Example 167

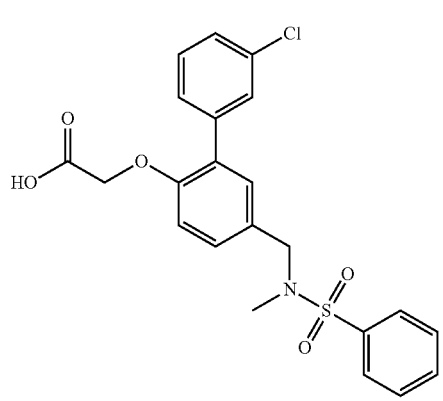

Example 167

¹HNMR (d-DMSO, 400 MHz): δ 7.82 (d, 2H), 7.71 (m, 1H), 7.62 (m, 3H), 7.42 (m, 3H), 7.27 (d, 1H), 7.20 (s, 1H), 7.00 (d, 1H), 4.75 (s, 2H), 4.12 (s, 2H), 2.58 (s, 3H). MS (ES-API): M+23=467.9. HPLC (Method A) $t_R$=2.65 min.

Example 168

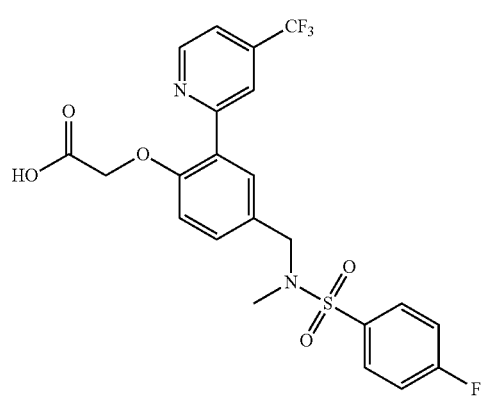

Example 168

¹HNMR (CD₃CN, 400 MHz): δ 8.89 (d, 1H), 8.27 (s, 1H), 7.90 (m, 2H), 7.71 (s, 1H), 7.67 (d, 1H), 7.42 (d, 1H), 7.34 (t, 2H), 7.16 (d, 1H), 4.85 (s, 2H), 4.20 (s, 2H), 2.64 (s, 3H). MS (ES-API): MH⁻=497.0. HPLC (Method A) $t_R$=2.17 min.

Example 169

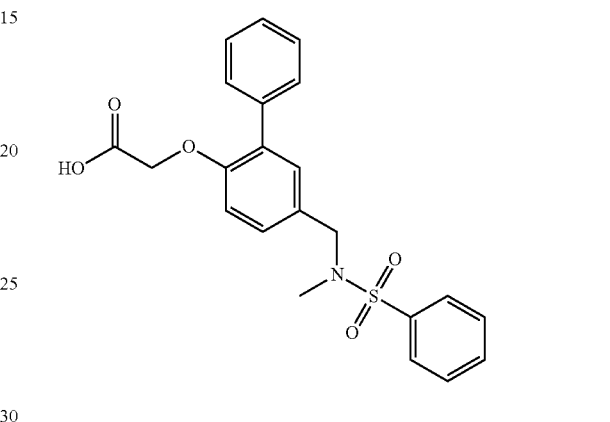

Example 169

¹HNMR (d-DMSO, 400 MHz): δ 13.1 (s, 1H), 7.84 (d, 2H), 7.71 (m, 1H), 7.65 (m, 2H), 7.52 (m, 2H), 7.39 (m, 2H), 7.31 (m, 1H), 7.20 (m, 2H), 6.98 (d, 1H), 4.70 (s, 2H), 4.12 (s, 2H), 2.58 (s, 3H). MS (ES-API): M+23=434.0. HPLC (Method A) $t_R$=2.56 min.

Example 170

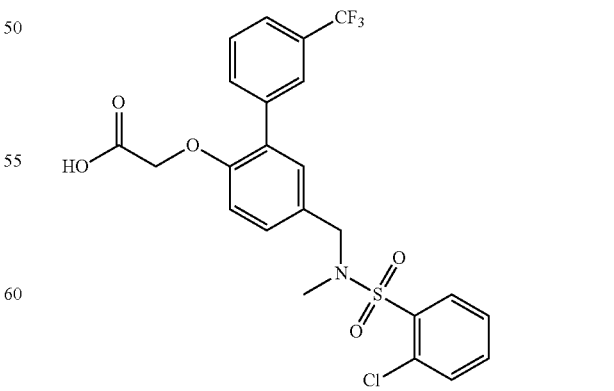

Example 170

¹HNMR (CDCl₃, 300 MHz): δ 8.02 (d, 1H), 7.74 (s, 1H), 7.64 (d, 1H), 7.44 (m, 4H), 7.32 (m, 1H), 7.20 (m, 1H), 7.12

(s, 1H), 6.77 (d, 1H), 4.45 (s, 2H), 4.31 (s, 2H), 2.70 (s, 3H). MS (ES-API): MH⁻=512.0. HPLC (Method A) $t_R$=2.28 min.

Example 172

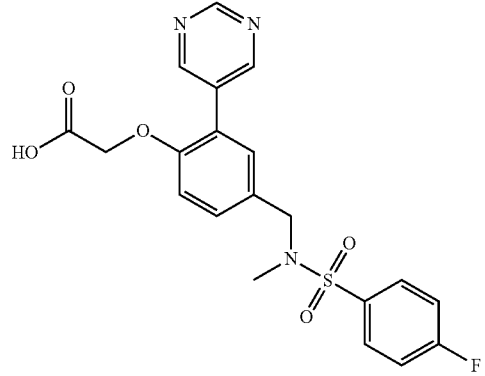

Example 172

$^1$HNMR (d-DMSO, 400 MHz): δ 13.11 (s, 1H), 9.14 (s, 1H), 9.00 (s, 2H), 7.84 (d, 2H), 7.70 (m, 1H), 7.64 (m, 2H), 7.31 (m, 2H), 7.11 (d, 1H), 4.79 (s, 2H), 4.14 (s, 2H), 2.59 (s, 3H). MS (ES-API): MH⁺=414.0. HPLC (Method A) $t_R$=2.57 min.

Example 173

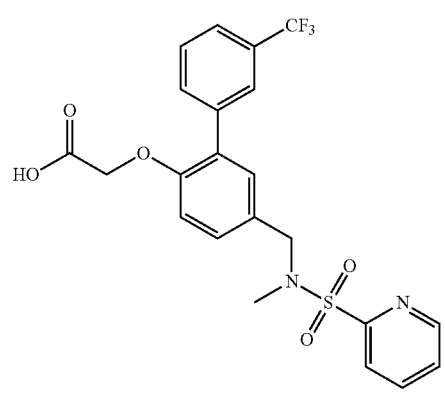

Example 173

$^1$HNMR (CD₃CN, 300 MHz): δ 8.68 (d, 1H), 7.92 (m, 3H), 7.83 (d, 1H), 7.55 (m, 3H), 7.20 (m, 2H), 6.90 (d, 1H), 4.45 (s,

2H), 4.30 (s, 2H), 2.63 (s, 3H). MS (ES-API): MH⁻=479.0. HPLC (Method A) $t_R$=2.26 min.

Example 34

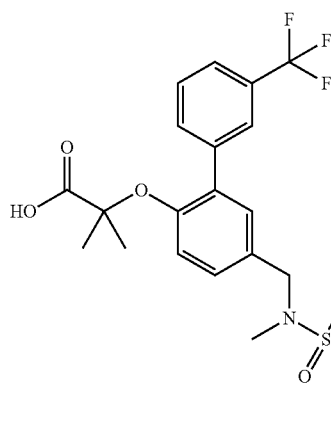

Example 34

$^1$HNMR (CD₃OD, 400 MHz): δ 7.91 (m, 3H), 7.88 (m, 1H), 7.61 (m, 2H), 7.35 (t, 2H), 7.27 (d, 2H), 6.90 (d, 1H), 4.20 (s, 2H), 2.67 (s, 3H), 1.46 (s, 6H). MS (ESI): MH⁺=526.1. HPLC (Method B) $t_R$=2.53 min.

Example 177

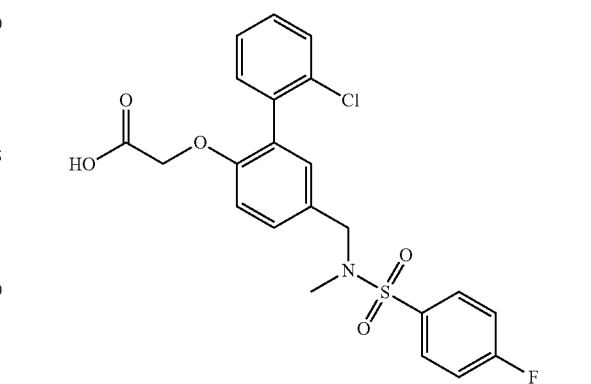

Example 177

$^1$HNMR (CD₃CN, 400 MHz): δ 7.89 (m, 2H), 7.50 (m, 1H), 7.28-7.39 (m, 6H), 7.09 (s, 1H), 6.95 (d, 1H), 4.61 (s,

2H), 4.14 (s, 2H), 2.64 (s, 3H). MS (ES-API): MH⁻=462.0. HPLC (Method A) $t_R$=2.26 min.

Example 178

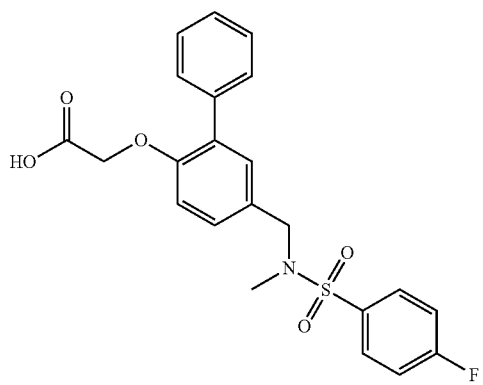

Example 178

¹HNMR (CD₃CN, 300 MHz): δ 7.90 (m, 2H), 7.58 (d, 2H), 7.30-7.48 (m, 5H), 7.23 (m, 2H), 6.94 (d, 1H), 4.69 (s, 2H), 4.17 (s, 2H), 2.64 (s, 3H). MS (ES-API): MH⁻=428.2. HPLC (Method A) $t_R$=2.11 min.

Example 179

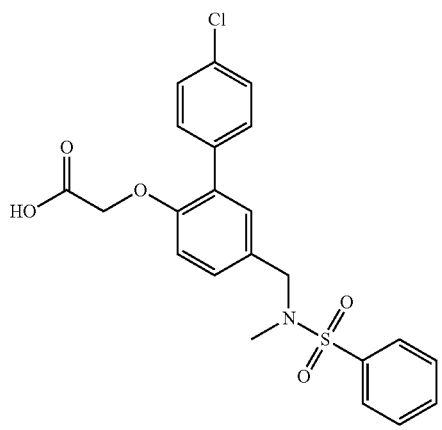

Example 179

¹HNMR (d-DMSO, 400 MHz): δ 13.05 (s, 1H), 7.83 (d, 2H), 7.70 (m, 3H), 7.55 (d, 2H), 7.45 (d, 2H), 7.23 (d, 1H), 7.19 (s, 1H), 6.98 (d, 1H), 4.72 (s, 2H), 4.12 (s, 2H), 2.56 (s, 3H). MS (ES-API): M+18=463.0. HPLC (Method A) $t_R$=2.08 min.

Example 180

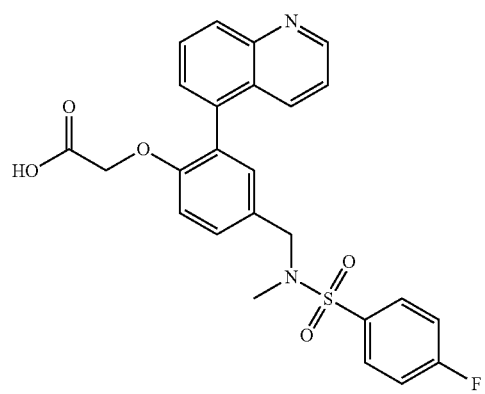

Example 180

¹HNMR (CD₃CN, 300 MHz): δ 9.10 (d, 1H), 8.70 (d, 1H), 8.36 (d, 1H), 8.12 (t, 1H), 7.75-7.90 (m, 4H), 7.45 (d, 1H), 7.32 (t, 2H), 7.22 (s, 1H), 7.03 (d, 1H), 4.60 (m, 2H), 4.21 (s, 2H), 2.68 (s, 3H). MS (ES-API): MH⁻=479.1. HPLC (Method A) $t_R$=1.56 min.

Example 181

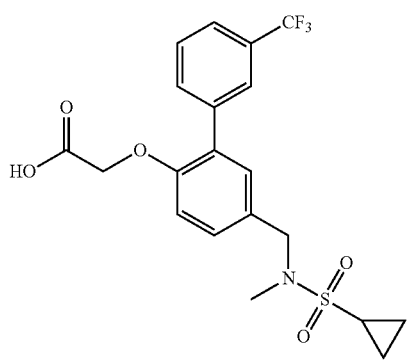

Example 181

¹HNMR (d-DMSO, 300 MHz): δ 13.10 (s, 1H), 7.99 (s, 1H), 7.87 (d, 1H), 7.70 (m, 2H), 7.35 (m, 2H), 7.09 (d, 1H), 4.79 (s, 2H), 4.30 (s, 2H), 2.72 (s, 3H), 2.65 (m, 1H), 1.00 (d, 4H). MS (ES-API): M+18=461.0. HPLC (Method A) $t_R$=2.02 min.
Example 182
Example 182
¹HNMR (CDCl₃, 300 MHz): δ 7.79 (s, 1H), 7.68 (d, 1H), 7.50 (m, 2H), 7.25 (m, 2H), 6.83 (d, 1H), 4.60 (s, 2H), 4.26 (s, 2H), 2.80 (s, 6H), 2.65 (s, 3H). MS (ES-API): MH⁻=445.1. HPLC (Method A) $t_R$=2.11 min.
Example 183
Example 183
¹HNMR (CD₃CN, 400 MHz): δ 9.69 (s, 1H), 7.90 (m, 2H), 7.70 (s, 1H), 7.60 (d, 1H), 7.31 (m, 4H), 7.20 (d, 2H), 6.95 (d,
1H), 6.50 (s, 1H), 4.60 (s, 2H), 4.14 (s, 2H), 2.65 (s, 3H). MS (ES-API): MH⁻=467.1. HPLC (Method A) $t_R$=1.59 min.
Example 184
Example 184
¹HNMR (CD₃CN, 300 MHz): δ 7.90 (m, 4H), 7.65 (m, 1H), 7.42 (d, 1H), 7.33 (t, 2H), 7.24 (s, 1H), 7.12 (m, 1H), 6.94 (d, 1H), 4.45 (s, 2H), 4.10 (s, 2H), 3.80 (s, 3H), 2.60 (s, 3H). MS (ES-API): MH⁻=482.1. HPLC (Method A) $t_R$=2.22 min.
Example 187
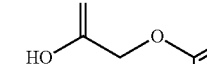
Example 187

¹HNMR (CD₃CN, 300 MHz): δ 8.00 (s, 1H), 7.80-7.95 (m, 4H), 7.35 (m, 4H), 7.03 (d, 1H), 4.78 (s, 2H), 4.19 (s, 2H), 2.65 (s, 3H). MS (ES-API): MH⁻=470.0. HPLC (Method A) t$_R$=2.16 min.

Example 188

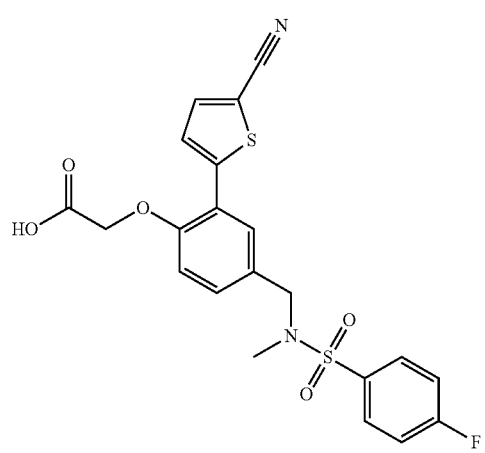

Example 188

¹HNMR (CD₃CN, 400 MHz): δ 7.90 (m, 2H), 7.74 (d, 1H), 7.66 (m, 2H), 7.35 (m, 3H), 7.03 (d, 1H), 4.88 (s, 2H), 4.17 (s, 2H), 2.63 (s, 3H). MS (ES-API): MH⁻=459.0. HPLC (Method A) t$_R$=2.07 min.

Example 186

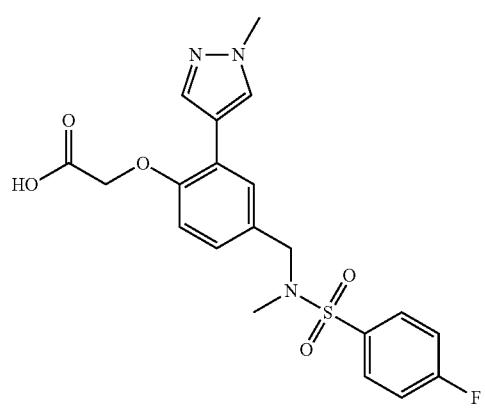

Example 186

¹HNMR (CD₃CN, 400 MHz): δ 8.19 (s, 1H), 7.93 (s, 1H), 7.90 (m, 2H), 7.49 (s, 1H), 7.36 (t, 2H), 7.12 (d, 1H), 6.91 (d, 1H), 4.77 (s, 2H), 4.12 (s, 2H), 3.90 (s, 3H), 2.61 (s, 3H). MS (ES-API): MH⁻=432.0. HPLC (Method A) t$_R$=1.87 min.

Example 185

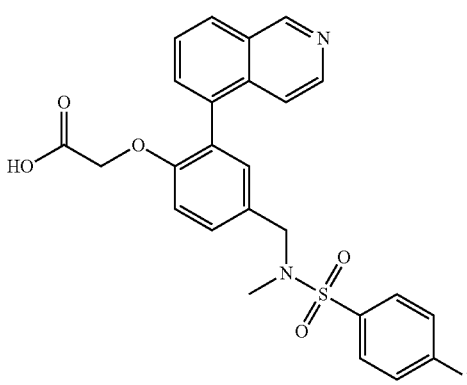

Example 185

¹HNMR (CD₃CN, 300 MHz): δ 9.59 (s, 1H), 8.42 (m, 2H), 7.99 (d, 2H), 7.95 (m, 1H), 7.38 (m, 2H), 7.45 (d, 1H), 7.32 (t, 2H), 7.24 (s, 1H), 7.07 (d, 1H), 4.61 (s, 2H), 4.21 (s, 2H), 2.68 (s, 3H). MS (ES-API): MH⁻=479.0. HPLC (Method A) t$_R$=1.998 min.

Example 189

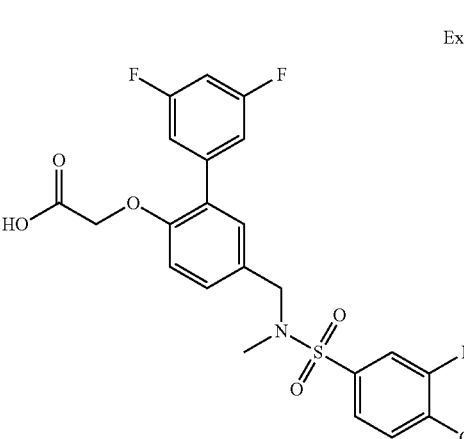

Example 189

¹HNMR (CD₃CN, 300 MHz): δ 7.61 (m, 2H), 7.20-7.35 (m, 5H), 6.99 (m, 2H), 4.72 (s, 2H), 4.17 (s, 2H), 3.95 (s, 3H), 2.63 (s, 3H). MS (ES-API): MH⁻=494.0. HPLC (WuXi) t$_R$=2.13 min.

Example 190

1H), 6.99 (d, 1H), 4.71 (s, 2H), 4.17 (s, 2H), 2.66 (s, 3H). MS (ES-API): MH⁻=492.9. HPLC (Method A) t$_R$=2.24 min.

Example 192

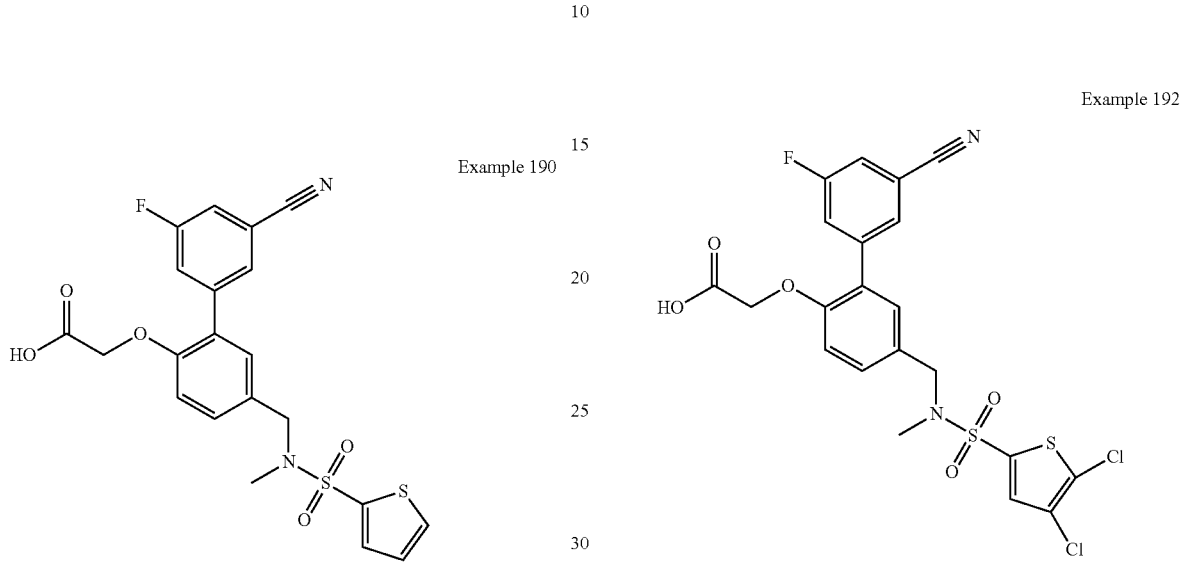

Example 190

Example 192

¹HNMR (CD₃CN, 300 MHz): δ 7.83(m, 2H), 7.75 (d, 1H), 7.65 (d, 1H), 7.50 (d, 1H), 7.36 (d, 1H), 7.31 (s, 1H), 7.23 (t, 1H), 7.01 (d, 1H), 4.75 (s, 2H), 4.19 (s, 2H), 2.69 (s, 3H). MS (ES-API): MH⁻=459.0. HPLC (Method A) t$_R$=2.21 min.

Example 191

¹HNMR (CD₃CN, 300 MHz): δ7.87(s, 1H), 7.75 (d, 1H), 7.51 (m, 2H), 7.38 (d, 1H), 7.31 (s, 1H), 7.01 (d, 1H), 4.76 (s, 2H), 4.22 (s, 2H), 2.73 (s, 3H). MS (ES-API): MH⁻=526.9. HPLC (Method A) t$_R$=2.32 min.

Example 193

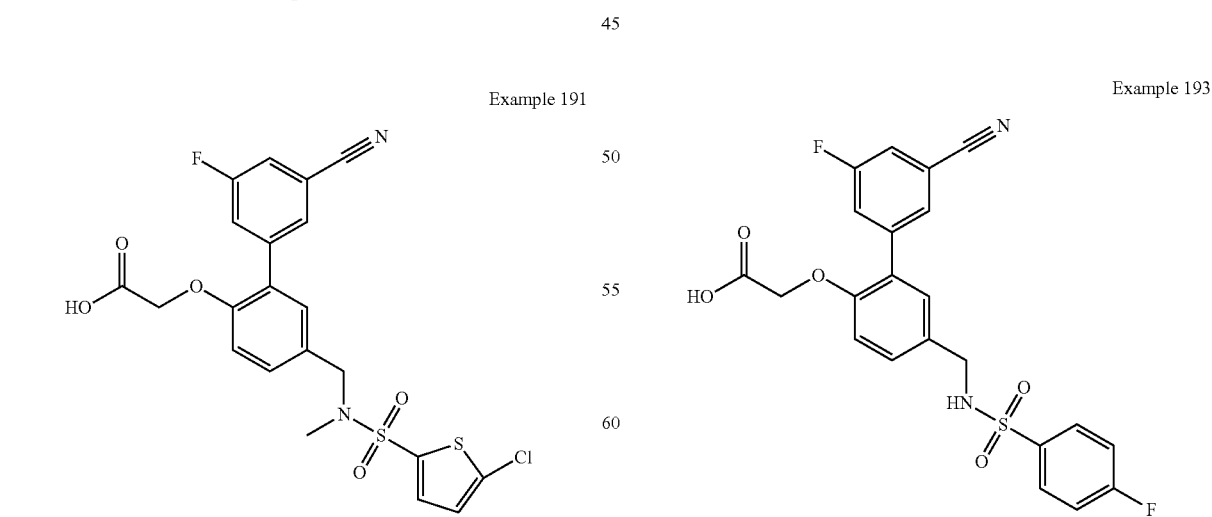

Example 191

Example 193

¹HNMR (CD₃CN, 300 MHz): δ7.80 (s, 1H), 7.71 (d, 1H), 7.48 (d, 1H), 7.41 (d, 1H), 7.32 (d, 1H), 7.28 (s, 1H), 7.11 (d,

¹HNMR (CD₃CN, 300 MHz): δ7.80(m, 3H), 7.68 (d, 1H), 7.50 (d, 1H), 7.21 (m, 3H), 7.12 (s, 1H), 6.91 (d, 1H), 6.10 (t,

1H), 4.71 (s, 2H), 4.12 (d, 2H). MS (ES-API): MH⁻=457.0. HPLC (Method A) $t_R$=2.05 min.

Example 194

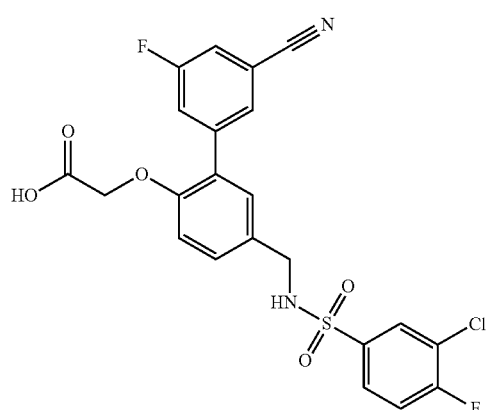

Example 194

¹HNMR (CD₃CN, 300 MHz): δ 7.79(m, 2H), 7.65 (m, 2H), 7.50 (d, 1H), 7.29 (d, 1H), 7.23 (m, 1H), 7.10 (s, 1H), 6.90 (d, 1H), 6.20 (t, 1H), 4.71 (s, 2H), 4.17 (d, 2H). MS (ES-API): MH⁻=491.0. HPLC (Method A) $t_R$=2.12 min.

Example 195

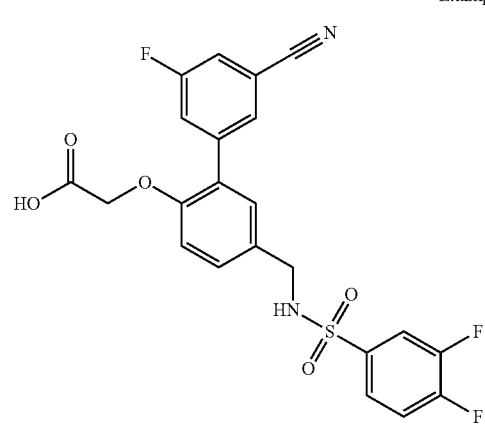

Example 195

¹HNMR (CD₃CN, 300 MHz): δ 7.79(s, 1H), 7.68 (m, 2H), 7.57 (m, 1H), 7.51 (d, 1H), 7.35 (m, 1H), 7.22 (d, 1H), 7.15 (s,

1H), 6.91 (d, 1H), 6.19 (t, 1H), 4.71 (s, 2H), 4.14 (d, 2H). MS (ES-API): MH⁻=475.0. HPLC (Method A) $t_R$=2.08 min.

Example 196

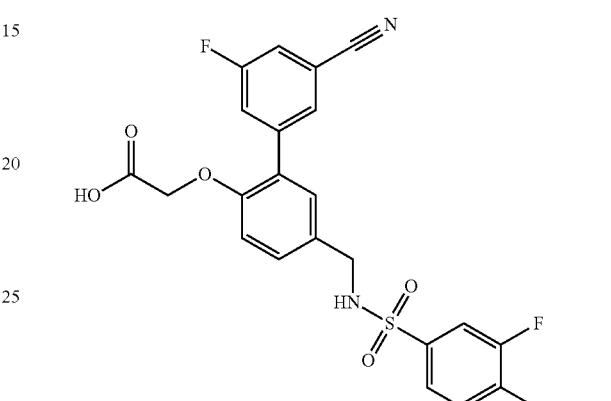

Example 196

¹HNMR (CD₃CN, 300 MHz): δ 7.77(s, 1H), 7.68 (m, 1H), 7.49 (m, 3H), 7.25 (m, 1H), 7.13 (m, 2H), 6.93 (d, 1H), 6.05 (t, 1H), 4.71 (s, 2H), 4.11 (d, 2H), 3.90 (s, 3H). MS (ES-API): MH⁻=487.0. HPLC (Method A) $t_R$=2.03 min.

Example 197

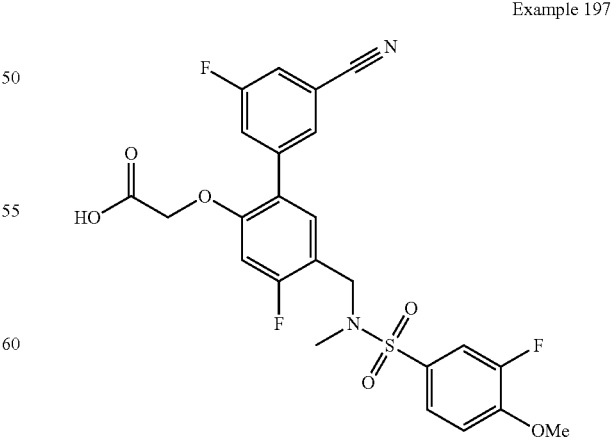

Example 197

¹HNMR (CD₃CN, 300 MHz): δ 7.81(s, 1H), 7.70 (d, 1H), 7.60 (m, 2H), 7.51 (d, 1H), 7.33 (d, 1H), 7.28 (t, 1H), 6.85 (d,

1H), 4.75 (s, 2H), 4.24 (s, 2H), 3.97 (s, 3H), 2.70 (s, 3H). MS (ES-API): M+18=538.5.0. HPLC (Method A) $t_R$=2.79 min.

Example 207

$^1$HNMR (CD$_3$CN, 300 MHz): δ 7.94(d, 2H), 7.87 (m, 2H), 7.75 (s, 1H), 7.35 (t, 3H), 7.26 (s, 1H), 7.00 (d, 1H), 4.73 (s, 2H), 4.16 (s, 2H), 2.64 (s, 3H). MS (ES-API): MH$^-$=487.0. HPLC (Method A) $t_R$=2.12 min.

Example 208

$^1$HNMR (CD$_3$CN, 300 MHz): δ 7.90(m, 2H), 7.81 (s, 1H), 7.71 (d, 1H), 7.51 (d, 1H), 7.33 (m, 3H), 6.86 (d, 1H), 4.75 (s,

2H), 4.24 (s, 2H), 2.69 (s, 3H). MS (ES-API): M=302.0 (main fragment) HPLC (Method A) $t_R$=2.79 min.

Example 209

$^1$HNMR (CD$_3$CN, 300 MHz): δ 7.95 (d, 1H), 7.80(m, 2H), 7.71 (m, 1H), 7.51 (m, 1H), 7.45 (m, 1H), 7.31 (m, 1H), 6.86 (d, 1H), 4.75 (s, 2H), 4.26 (s, 2H), 2.73 (s, 3H). MS (ES-API): M+23=547.0 HPLC (Method A) $t_R$=2.86 min.

Example 210

$^1$HNMR (CD$_3$CN, 300 MHz): δ 7.82(m, 3H), 7.70 (m, 2H), 7.64 (m, 1H), 7.50 (m, 1H), 7.20 (d, 1H), 6.86 (d, 1H), 4.75 (s, 2H), 4.27 (s, 2H), 2.72 (s, 3H). MS (ES-API): M=302.0 (main fragment) HPLC (Method A) $t_R$=2.84 min.

Example 211

Example 211

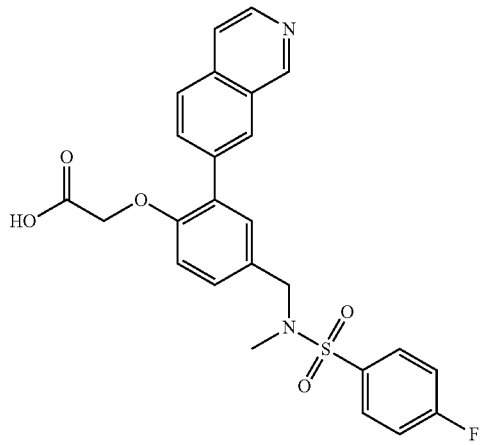

$^1$HNMR (CD$_3$CN, 300 MHz): δ 7.94(s, 1H), 7.75 (s, 1H), 7.72 (m, 3H), 7.52 (m, 1H), 7.30 (d, 1H), 6.86 (d, 1H), 4.75 (s, 2H), 4.30 (s, 2H), 2.79 (s, 3H). MS (ES-API): M=302.0 (main fragment) HPLC (Method A) $t_R$=2.91 min.

Example 212

PS16911

Example 212

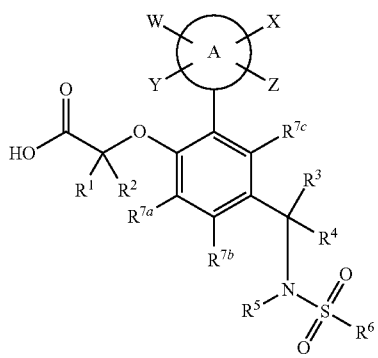

$^1$HNMR (CD$_3$CN, 300 MHz): δ 9.60(s, 1H), 8.57(m, 2H), 8.43(d, 1H), 8.32 (d, 1H), 8.22 (d, 1H), 7.90 (m, 2H), 7.38 (m, 4H), 7.06 (d, 1H), 4.78 (s, 2H), 4.18 (s, 2H), 2.68 (s, 3H). MS (ES-API): MH$^+$=481.0 HPLC (Method A) $t_R$=2.56 min.

Example 213

PS17051

Example 213

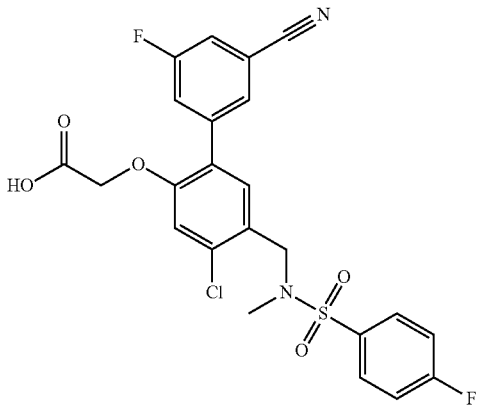

$^1$HNMR (CD$_3$CN, 300 MHz): δ 7.90(m, 2H), 7.81 (s, 1H), 7.71 (m, 1H), 7.52 (m, 1H), 7.35 (m, 3H), 7.12 (s, 1H), 4.75 (s, 2H), 4.29 (s, 2H), 2.68 (s, 3H). MS (ES-API): M+23=528.9 HPLC (Method A) $t_R$=2.82 min.

The invention claimed is:
1. A compound of formula I or salt thereof
wherein
$R^1$, $R^2$, $R^3$ and $R^4$ are each independently selected from hydrogen and (C$_1$-C$_6$) alkyl;
$R^5$ is selected from hydrogen, (C$_1$-C$_6$) alkyl and (C$_3$-C$_8$) cycloalkyl;
$R^6$ is selected from:
  a. (C$_1$-C$_4$) alkyl,
  b. (C$_3$-C$_8$) cycloalkyl,
  c. dialkylamino,
  d. alkylamino, and
  e. aryl, heteroaryl and arylalkyl, each optionally substituted with one to four substituents independently selected from halogen, cyano, (C$_1$-C$_6$) haloalkyl, (C$_1$-C$_6$) alkoxy, (C$_1$-C$_6$) haloalkoxy, (C$_1$-C$_6$) alkyl, and (C$_1$-C$_6$) alkylsulfonyl;

$R^{7a}$ is selected from hydrogen and fluoro;

$R^{7b}$ is selected from hydrogen, fluoro and chloro;

$R^{7c}$ is selected from hydrogen, fluoro and chloro;

A is selected from aryl and heteroaryl; and

W, X, Y and Z are each independently selected from hydrogen, $(C_1-C_6)$ alkyl, halogen, $(C_1-C_6)$ haloalkyl, $(C_1-C_6)$ haloalkoxy, hydroxy, $(C_1-C_6)$ alkoxyalkyl, $(C_1-C_6)$ alkylsulfonyl, $(C_1-C_6)$ alkylaminosulfonyl, carboxamido, cyano, $(C_1-C_6)$ alkoxy, $(C_1-C_6)$ alkoxycarbonyl, aminosulfonyl, dialkylaminosulfonyl, alkylaminocarbonyl, dialkylaminocarbonyl, heterocyclylcarbonyl, heterocyclylacyl, heterocyclylalkyl, and heterocyclyl optionally substituted with $(C_1-C_6)$ alkyl;

with the proviso that, when A is phenyl or pyridinyl substituted at the ortho position, any of W, X, Y and Z at said ortho position are each independently selected from hydrogen and halogen.

2. A compound or salt according to claim 1 wherein $R^1$, $R^2$, $R^3$ and $R^4$ are each independently selected from hydrogen and methyl.

3. A compound or salt according to claim 1, wherein $R^5$ is selected from hydrogen, methyl, ethyl, propyl and isopropyl.

4. A compound or salt according to claim 1, wherein $R^6$ is selected from aryl and heteroaryl, each optionally substituted with one to four substituents independently selected from halogen, cyano, $(C_1-C_6)$ haloalkyl, $(C_1-C_6)$ alkoxy, $(C_1-C_6)$ haloalkoxy, $(C_1-C_6)$ alkyl, and $(C_1-C_6)$ alkylsulfonyl.

5. A compound or salt according to claim 4, wherein $R^6$ is

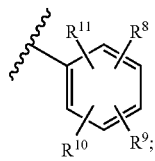

$R^8$ is selected from hydrogen, halogen, $(C_1-C_6)$ alkyl, cyano, $(C_1-C_6)$ haloalkyl, and $(C_1-C_6)$ alkoxy;

$R^9$ is selected from hydrogen, halogen, $(C_1-C_6)$ alkyl, $(C_1-C_6)$ haloalkoxy, $(C_1-C_6)$ alkoxy, cyano, $(C_1-C_6)$ haloalkyl and $(C_1-C_6)$ alkylsulfonyl;

$R^{10}$ is selected from hydrogen, halogen, $(C_1-C_6)$ alkoxy and $(C_1-C_6)$ alkyl; and $R^{11}$ is selected from hydrogen, halogen, alkoxy and $(C_1-C_6)$ alkyl.

6. A compound or salt according to claim 5 wherein $R^6$ is

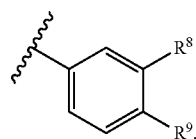

7. A compound or salt according to claim 6, wherein $R^8$ is selected from hydrogen, methyl, fluoro, chloro, cyano, —$CF_3$ and methoxy; and $R^9$ is selected from hydrogen, fluoro, chloro, methyl, methoxy, cyano, —$CF_3$ and —$SO_2CH_3$.

8. A compound or salt according to claim 7 wherein $R^8$ and $R^9$ are each independently selected from fluoro, chloro, methoxy and hydrogen.

9. A compound or salt according to claim 5 wherein $R^6$ is

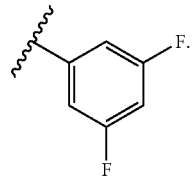 [SMILES: *c1cc(F)cc(F)c1]

10. A compound or salt according to claim 4 wherein $R^6$ is selected from naphthyl, pyridinyl and quinolinyl, each optionally substituted with one to four substituents independently selected from halogen, cyano, $(C_1-C_6)$ haloalkyl, $(C_1-C_6)$ alkoxy, $(C_1-C_6)$ haloalkoxy, $(C_1-C_6)$ alkyl and alkylsulfonyl.

11. A compound or salt according to claim 1, wherein $R^{7a}$ and $R^{7b}$ are each hydrogen.

12. A compound or salt according to claim 1, wherein A is selected from phenyl, pyridinyl, benzimidazolyl, quinolinyl, indolyl, pyrimidinyl and imidazopyridinyl.

13. A compound or salt according to claim 12, wherein A is phenyl or pyridinyl.

14. A compound or salt according to claim 13, wherein

W is selected from hydrogen, $(C_1-C_6)$ alkyl, halogen and haloalkyl;

X is selected from hydrogen, $(C_1-C_6)$ alkyl, halogen, haloalkyl, haloalkoxy, alkoxy, aminosulfonyl, alkoxycarbonyl, heterocyclylcarbonyl, hydroxy, alkoxyalkyl, alkylsulfonyl, alkylaminosulfonyl, carboxamido, cyano, and heterocyclyl optionally substituted with $(C_1-C_6)$ alkyl; and Y and Z are both hydrogen.

15. A compound or salt according to claim 14, wherein

W is selected from hydrogen, fluoro, chloro, methyl and trifluoromethyl; and

X is selected from hydrogen, trifluoromethyl, chloro, fluoro, bromo, methoxy, hydroxy, trifluoromethoxy, propyl, ethyl, methyl, methoxymethyl, cyano, carboxamido, heterocyclylcarbonyl, methylsulfonyl, ethylsulfonyl, propoxy, ethoxy, methoxy, methylaminocarbonyl, dimethylaminocarbonyl, dimethoxycarbonyl, aminosulfonyl, methylaminosulfonyl and dimethylaminosulfonyl.

16. A compound or salt according to claim 15 wherein W and X are in the meta positions in relation to the attachment of the ring A.

17. A compound or salt according to claim 15 wherein W is substituted in the meta position and X is substituted in the para position in relation to the attachment of the ring A.

18. A compound or salt according to claim 1, wherein $R^1$, $R^2$, $R^3$ and $R^4$ are each hydrogen;

$R^5$ is methyl;

$R^6$ is phenyl optionally substituted with one to four substituents independently selected from halogen, cyano, $(C_1-C_6)$ haloalkyl, $(C_1-C_6)$ haloalkoxy, $(C_1-C_6)$ alkoxy, $(C_1-C_6)$ alkyl and $(C_1-C_6)$ alkylsulfonyl;

$R^{7a}$ is hydrogen;

$R^{7b}$ is selected from hydrogen, fluoro and chloro;

$R^{7c}$ is hydrogen; and

A is selected from phenyl and pyridinyl.

19. A compound or salt according to claim 18, wherein $R^6$ is

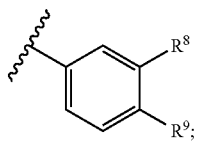

$R^8$ is selected from hydrogen, fluoro, chloro, methyl, cyano, —CF$_3$ and methoxy;
$R^9$ is selected from hydrogen, fluoro, chloro, methyl, methoxy, cyano, —CF$_3$, and —SO$_2$CH$_3$;
W is selected from hydrogen, (C$_1$-C$_6$) alkyl, halogen, and haloalkyl;
X is selected from hydrogen, (C$_1$-C$_6$) alkyl, halogen, haloalkyl, haloalkoxy, hydroxy, alkoxy, alkoxyalkyl, alkylsulfonyl, alkylaminosulfonyl, carboxamido, cyano, and heterocyclylalkyl; and
Y and Z are each hydrogen.

20. A compound or salt according to claim 19, wherein
$R^8$ is selected from hydrogen, fluoro, chloro and methyl;
A is phenyl;
W is selected from hydrogen and fluoro and is in the meta position in relation to the attachment of the ring A; and
X is selected from alkylsulfonyl, fluoro, alkylaminosulfonyl and cyano and is in the meta position in relation to the attachment of the ring A.

21. A compound according to formula Ia

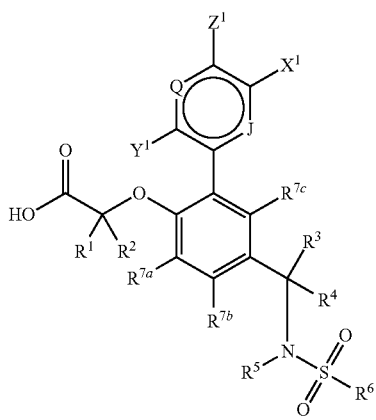

or salt thereof, wherein
$R^1$, $R^2$, $R^3$ and $R^4$ are each independently selected from hydrogen and (C$_1$-C$_6$) alkyl;
$R^5$ is selected from hydrogen, (C$_1$-C$_6$) alkyl, and cycloalkyl;
$R^6$ is selected from
 a. (C$_1$-C$_4$) alkyl,
 b. (C$_3$-C$_8$) cycloalkyl,
 c. dialkylamino,
 d. alkylamino, and
 e. aryl, heteroaryl and arylalkyl, each optionally substituted with one to four substituents independently selected from halogen, cyano, (C$_1$-C$_6$) haloalkyl, (C$_1$-C$_6$) alkoxy, (C$_1$-C$_6$) haloalkoxy, (C$_1$-C$_6$) alkyl, and (C$_1$-C$_6$) alkylsulfonyl;
$R^{7a}$ is selected from hydrogen and fluoro;
$R^{7b}$ is selected from hydrogen, fluoro, and chloro;
$R^{7c}$ is selected from hydrogen, fluoro, and chloro;
Q is selected from N and CX';
J is selected from N and CY', wherein both Q and J cannot be N;
$X^1$, X' and $Z^1$ are each independently selected from hydrogen, (C$_1$-C$_6$) alkyl, halogen, (C$_1$-C$_6$) haloalkyl, (C$_1$-C$_6$) haloalkoxy, hydroxy, (C$_1$-C$_6$) alkoxyalkyl, (C$_1$-C$_6$) alkylsulfonyl, (C$_1$-C$_6$) alkylaminosulfonyl, carboxamido, cyano, (C$_1$-C$_6$) alkoxy, (C$_1$-C$_6$) alkoxycarbonyl, aminosulfonyl, dialkylaminosulfonyl, alkylaminocarbonyl, dialkylaminocarbonyl, heterocyclylcarbonyl, heterocyclylacyl, heterocyclylalkyl, and heterocyclyl optionally substituted with (C$_1$-C$_6$) alkyl; and
$Y^1$ and Y' are each independently selected from hydrogen and halogen.

22. A compound or salt according to claim 21 wherein $R^1$, $R^2$, $R^3$ and $R^4$ are each independently selected from hydrogen and methyl.

23. A compound or salt according to claim 21, wherein $R^5$ is selected from hydrogen, methyl, ethyl, propyl and isopropyl.

24. A compound or salt according to claim 21, wherein $R^6$ is selected from aryl and heteroaryl, each optionally substituted with one to four substituents independently selected from halogen, cyano, (C$_1$-C$_6$) haloalkyl, (C$_1$-C$_6$) alkoxy, (C$_1$-C$_6$) haloalkoxy, (C$_1$-C$_6$) alkyl, and (C$_1$-C$_6$) alkylsulfonyl.

25. A compound or salt according to claim 24, wherein $R^6$ is

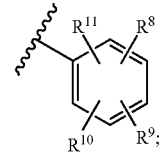

$R^8$ is selected from hydrogen, halogen, (C$_1$-C$_6$) alkyl, cyano, (C$_1$-C$_6$) haloalkyl, and (C$_1$-C$_6$) alkoxy;
$R^9$ is selected from hydrogen, halogen, (C$_1$-C$_6$) alkyl, (C$_1$-C$_6$) alkoxy, cyano, (C$_1$-C$_6$) haloalkoxy, (C$_1$-C$_6$) haloalkyl, and (C$_1$-C$_6$) alkylsulfonyl;
$R^{10}$ is selected from hydrogen, halogen, (C$_1$-C$_6$) alkoxy, and (C$_1$-C$_6$) alkyl; and
$R^{11}$ is selected from hydrogen, halogen, (C$_1$-C$_6$) alkoxy, and (C$_1$-C$_6$) alkyl.

26. A compound or salt according to claim 25, wherein $R^6$ is

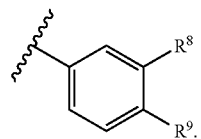

27. A compound or salt according to claim 26, wherein
$R^8$ is selected from hydrogen, methyl, fluoro, chloro, cyano, —CF$_3$, and methoxy; and
$R^9$ is selected from hydrogen, fluoro, chloro, methyl, methoxy, cyano, —CF$_3$, and —SO$_2$CH$_3$.

28. A compound or salt according to claim 25, wherein $R^6$ is

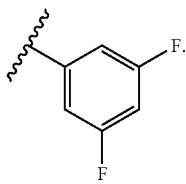 [SMILES: *c1cc(F)cc(F)c1]

29. A compound or salt according to claim 24, wherein $R^6$ is selected from naphthyl, pyridinyl and quinolinyl, each optionally substituted with one to four substituents independently selected from halogen, cyano, $(C_1-C_6)$ haloalkyl, $(C_1-C_6)$ haloalkoxy, $(C_1-C_6)$ alkoxy, $(C_1-C_6)$ alkyl, and $(C_1-C_6)$ alkylsulfonyl.

30. A compound or salt according to claim 21, wherein $R^{7a}$ and $R^{7c}$ are each hydrogen.

31. A compound or salt according to claim 21, wherein Q is CX' and J is CY'.

32. A compound or salt according to claim 31, wherein X' is selected from hydrogen, $(C_1-C_6)$ alkyl, halogen and haloalkyl; and Y' is hydrogen.

33. A compound or salt according to claim 21, wherein $Z^1$ is selected from hydrogen, $(C_1-C_6)$ alkyl, $(C_1-C_6)$ alkylsulfonyl, halogen, and haloalkyl.

34. A compound or salt according to claim 24, wherein
$R^1$, $R^2$, $R^3$ and $R^4$ are each hydrogen;
$R^5$ is methyl; and
$R^6$ is phenyl optionally substituted with one to four substituents independently selected from halogen, cyano, haloalkyl, $(C_1-C_6)$ haloalkoxy, alkoxy, $(C_1-C_6)$ alkyl, and alkylsulfonyl.

35. A compound or salt according to claim 34, wherein $R^6$ is

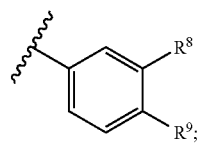

$R^8$ is selected from hydrogen, fluoro, chloro, methyl, cyano, —$CF_3$, and methoxy;
$R^9$ is selected from hydrogen, fluoro, chloro, methyl, methoxy, cyano, —$CF_3$, and —$SO_2CH_3$;
Q is CX';
X' is selected from hydrogen, $(C_1-C_6)$ alkyl, halogen, and haloalkyl; and
$X^1$ is selected from hydrogen, $(C_1-C_6)$ alkyl, halogen, haloalkyl, haloalkoxy, hydroxy, alkoxy, alkoxyalkyl, alkylsulfonyl, alkylaminosulfonyl, carboxamido, cyano, and heterocyclylalkyl.

36. A compound or salt according to claim 35, wherein $R^8$ is selected from hydrogen, fluoro, chloro and methyl;
J is CY';
X' is selected from hydrogen and fluoro;
$X^1$ is selected from alkoxy, alkylsulfonyl, fluoro, alkylaminosulfonyl and cyano; and
$Z^1$ is selected from hydrogen, fluoro, chloro, $(C_1-C_6)$ alkyl, alkylsulfonyl, and haloalkyl.

37. A compound or salt according to claim 21, wherein Q is N and J is CY'.

38. A pharmaceutical composition comprising a pharmaceutically acceptable carrier and a therapeutically effective amount of a compound or pharmaceutically acceptable salt thereof according to claim 1.

39. A method of ameliorating a disorder responsive to inhibition of chemoattractant receptor-homologous molecule expressed on T helper 2, which comprises administering to a subject in need of such treatment a therapeutically effective amount of a compound or pharmaceutically acceptable salt thereof of claim 1.

40. A method according to claim 39, wherein said disorder is selected from the group consisting of an inflammatory disorder, a respiratory disorder, and a skin disorder.

41. A method according to claim 39, wherein said disorder is selected from the group consisting of asthma, rhinitis, chronic obstructive pulmonary disease, bronchitis, nasal polyposis, nasal congestion, farmer's lung, fibroid lung, cough, dermatitis, cutaneous eosinophilias, Lichen planus, urticaria, psoriasis, pruritus, angiodermas, corneal ulcers, chronic skin ulcers, conjunctivitis, vasculitides, uveitis, erythemas, osteoarthritis, rheumatoid arthritis, pain, and inflammatory bowel disease.

42. A method according to claim 39, wherein said subject is a human.

43. The compound of claim 1 selected from the group consisting of
2-(3-cyano-5-fluorophenyl)-4-((3-fluoro-4-methoxy-N-methylphenylsulfonamido)methyl)phenoxyacetic acid,
2-(3-methoxy-5-fluorophenyl)-4-((4-fluoro-N-methylphenylsulfonamido)methyl)phenoxyacetic acid,
2-(3-cyano-5-fluorophenyl)-4-((3,4-difluoro-N-methylphenylsulfonamido)methyl)phenoxyacetic acid,
2-(3-fluoro-5-methoxyphenyl)-4-((3-chloro-4-fluoro-N-methylphenylsulfonamido)methyl)phenoxyacetic acid,
2-(3-N-methylsulfamoylphenyl)-4-((3-chloro-4-fluoro-N-methylphenylsulfonamido)methyl)phenoxyacetic acid,
2-(3-methylsulfonylphenyl)-4-((3-chloro-4-fluoro-N-methylphenylsulfonamido)methyl)phenoxyacetic acid,
2-(3-cyano-5-fluorophenyl)-4-((3,4-difluoro-phenylsulfonamido)methyl)phenoxyacetic acid,
2-(3-trifluoromethylphenyl)-4-((3-chloro-4-fluoro-N-methylphenylsulfonamido)methyl)phenoxyacetic acid,
2-(3-cyano-5-fluorophenyl)-4-((3-chloro-N-methylphenylsulfonamido)methyl)phenoxyacetic acid,
2-(3-N-methylsulfamoylphenyl)-4-((4-fluoro-N-methylphenylsulfonamido)methyl)phenoxyacetic acid,
2-(3-fluoro-5-methoxyphenyl)-4-((3,4-difluoro-N-methylphenylsulfonamido)methyl)phenoxyacetic acid,
2-(3-cyanophenyl)-4-((3-chloro-5-fluoro-N-methylphenylsulfonamido)methyl)phenoxyacetic acid,
2-(3-fluoro-5-methoxyphenyl)-4-((3-fluoro-4-methoxy-N-methylphenylsulfonamido)methyl)phenoxyacetic acid,
2-(3-cyanophenyl)-4-((4-fluoro-N-methylphenylsulfonamido)methyl)-5-chlorophenoxyacetic acid,
2-(3-N-methylsulfamoylphenyl)-4-((3,4-difluoro-N-methylphenylsulfonamido)methyl)phenoxyacetic acid,
2-(3-cyanophenyl)-4-((3,5-difluoro-N-methylphenylsulfonamido)methyl)phenoxyacetic acid,
2-(3,5-difluorophenyl)-4-((3,4-dichloro-N-methylphenylsulfonamido)methyl)phenoxyacetic acid,
2-(3-cyano-5-fluorophenyl)-4-((2,3-dichloro-N-methylthiophene-5-sulfonamido)methyl)phenoxyacetic acid,
2-(3-cyanophenyl)-4-((3-fluoro-N-methylphenylsulfonamido)methyl)-5-chlorophenoxyacetic acid, 2-(4-fluoro-3-(methylsulfonyl)phenyl)-4-((4-fluoro-N-methylphenylsulfonamido)methyl)phenoxyacetic acid,
2-(3-cyano-5-fluorophenyl)-4-((3-chloro-4-fluoro-N-methylphenylsulfonamido)methyl)phenoxyacetic acid,
2-(3-cyanophenyl)-4-((3-fluoro-4-chloro-N-methylphenylsulfonamido)methyl)phenoxyacetic acid,
2-(3-methylsulfonylphenyl)-4-((3-fluoro-N-methylphenylsulfonamido)methyl)phenoxyacetic acid,
2-(3-methylsulfonylphenyl)-4-((3,4-difluoro-N-methylphenylsulfonamido)methyl)phenoxyacetic acid,
2-(3-ethylsulfonylphenyl)-4-((3,4-difluoro-N-methylphenylsulfonamido)methyl)phenoxyacetic acid,
2-(3,5-difluorophenyl)-4-((3-fluoro-4-methoxy-N-methylphenylsulfonamido)methyl)phenoxyacetic acid,
2-(3-methylsulfonylphenyl)-4-((4-methyl-N-methylphenylsulfonamido)methyl)phenoxyacetic acid,
2-(5-benzo[c][1,2,5]oxadiazolyl)-4-((4-fluoro-N-methylphenylsulfonamido)methyl)phenoxyacetic acid,
2-(3-cyano-5-fluorophenyl)-4-((2-chloro-N-methylthiophene-5-sulfonamido)methyl)phenoxyacetic acid,
2-(3-cyano-5-fluorophenyl)-4-((3-fluoro-N-methylphenylsulfonamido)methyl)phenoxyacetic acid,
2-(3-cyanophenyl)-4-((3-fluoro-4-methyl-N-methylphenylsulfonamido)methyl)phenoxyacetic acid,
2-(3-cyanophenyl)-4-((3,4-difluoro-N-methylphenylsulfonamido)methyl)phenoxyacetic acid,
2-(3-cyano-5-fluorophenyl)-4-((4-fluoro-N-methylphenylsulfonamido)methyl)phenoxyacetic acid,
2-(3-cyanophenyl)-4-((3-methyl-4-fluoro-N-methylphenylsulfonamido)methyl)phenoxyacetic acid,
2-(3,5-difluorophenyl)-4-((3-chloro-4-fluoro-N-methylphenylsulfonamido)methyl)phenoxyacetic acid,
2-(3-methylsulfonyl-5-pyridinyl)-4-((4-fluoro-N-methylphenylsulfonamido)methyl)phenoxyacetic acid,
2-(3,5-difluorophenyl)-4-((3-chloro-N-methylphenylsulfonamido)methyl)phenoxyacetic acid,
2-(3-cyano-5-fluorophenyl)-4-((N-methylthiophene-2-sulfonamido)methyl)phenoxyacetic acid,
2-(3-cyanophenyl)-4-((3-chloro-4-fluoro-N-methylphenylsulfonamido)methyl)-5-fluorophenoxyacetic acid,
2-(3-methylsulfonylphenyl)-4-((4-methoxy-N-methylphenylsulfonamido)methyl)phenoxyacetic acid,
2-(3-aminosulfonylphenyl)-4-((4-fluoro-N-methylphenylsulfonamido)methyl)phenoxyacetic acid,
2-(3-cyanophenyl)-4-((3-chloro-N-methylphenylsulfonamido)methyl)phenoxyacetic acid,
2-(3-cyanophenyl)-4-((3,4-dichloro-N-methylphenylsulfonamido)methyl)phenoxyacetic acid,
2-(3-cyanophenyl)-4-((3-fluoro-4-methoxy-N-methylphenylsulfonamido)methyl)phenoxyacetic acid,
2-(3-methylsulfonylphenyl)-4-((4-fluoro-N-methylphenylsulfonamido)methyl)phenoxyacetic acid,
2-(3-methylsulfonylphenyl)-4-((3,5-difluoro-N-methylphenylsulfonamido)methyl)phenoxyacetic acid,
2-(3-cyanophenyl)-4-((N-methylphenylsulfonamido)methyl)-5-chlorophenoxyacetic acid,
2-(3-cyano-5-fluorophenyl)-4-((4-fluoro-phenylsulfonamido)methyl)phenoxyacetic acid,
2-(3-cyanophenyl)-4-((3-chloro-4-fluoro-N-methylphenylsulfonamido)methyl)phenoxyacetic acid,
2-(3-cyanophenyl)-4-((4-fluoro-N-methylphenylsulfonamido)methyl)-5-fluorophenoxyacetic acid,
2-(3-N,N-dimethylsulfamoylphenyl)-4-((4-fluoro-N-methylphenylsulfonamido)methyl)phenoxyacetic acid,
2-(3-methylsulfonylphenyl)-4-((N-methylphenylsulfonamido)methyl)phenoxyacetic acid,
2-(3-methylsulfonylphenyl)-4-((4-fluorophenylsulfonamido)methyl)phenoxyacetic acid,
2-(3-cyano-5-fluorophenyl)-4-((3-chloro-4-fluoro-phenylsulfonamido)methyl)phenoxyacetic acid,
2-(3-ethylsulfonylphenyl)-4-((4-fluoro-N-methylphenylsulfonamido)methyl)phenoxyacetic acid,
2-(3-cyanophenyl)-4-((4-fluorophenylsulfonamido)methyl)phenoxyacetic acid,
2-(3-methylsulfonyl-4-methyl-phenyl)-4-((4-fluoro-N-methylphenylsulfonamido)methyl)phenoxyacetic acid,
2-(3-cyanophenyl)-4-((4-fluoro-N-methylphenylsulfonamido)methyl)phenoxyacetic acid,
2-(3-methylsulfonylphenyl)-4-((4-cyano-N-methylphenylsulfonamido)methyl)phenoxyacetic acid,
2-(3-methylsulfonylphenyl)-4-((N-methylphenylsulfonamido)methyl)phenoxyacetic acid,
2-(3-cyanophenyl)-4-((3-fluoro-N-methylphenylsulfonamido)methyl)-5-fluorophenoxyacetic acid,
2-(3-cyano-5-fluorophenyl)-4-((3,4-dichloro-N-methylphenylsulfonamido)methyl)phenoxyacetic acid,
2-(3-trifluoromethyl-5-fluorophenyl)-4-((4-fluoro-N-methylphenylsulfonamido)methyl)phenoxyacetic acid,
2-(3-methylsulfonylphenyl)-4-((3-cyano-N-methylphenylsulfonamido)methyl)phenoxyacetic acid,
2-(1-methyl-indol-6-yl)-4-((4-fluoro-N-methylphenylsulfonamido)methyl)phenoxyacetic acid,
2-(2-cyanothiophen-5-yl)-4-((4-fluoro-N-methylphenylsulfonamido)methyl)phenoxyacetic acid,
2-(3-cyanophenyl)-4-((3-fluoro-N-methylphenylsulfonamido)methyl)phenoxyacetic acid,
2-(3,5-difluorophenyl)-4-((3-methyl-4-fluoro-N-methylphenylsulfonamido)methyl)phenoxyacetic acid,
2-(3,5-difluorophenyl)-4-((3,4-difluoro-N-methylphenylsulfonamido)methyl)phenoxyacetic acid,
2-(3-trifluoromethylphenyl)-4-((3,4-difluoro-N-methylphenylsulfonamido)methyl)phenoxyacetic acid,
2-(3-cyano-5-fluorophenyl)-4-((3,5-difluoro-N-methylphenylsulfonamido)methyl)phenoxyacetic acid,
2-(3-trifluoromethylphenyl)-4-(1-(3,4-difluoro-N-methylphenylsulfonamido)ethyl)phenoxyacetic acid,
2-(3-methylsulfonylphenyl)-4-((2-fluoro-N-methylphenylsulfonamido)methyl)phenoxyacetic acid,
2-(3-cyano-5-fluorophenyl)-4-((N-methylphenylsulfonamido)methyl)phenoxyacetic acid,
2-(3-cyanophenyl)-4-((N-methylphenylsulfonamido)methyl)-5-fluorophenoxyacetic acid,
2-(3-cyanophenyl)-4-((3-chloro-4-fluoro-N-methylphenylsulfonamido)methyl)-5-chlorophenoxyacetic acid,
2-(3-isopropoxy-5-fluorophenyl)-4-((4-fluoro-N-methylphenylsulfonamido)methyl)phenoxyacetic acid,
2-(3-trifluoromethylphenyl)-4-((4-fluoro-N-methylphenylsulfonamido)methyl)phenoxyacetic acid,
(S)-2-(2-(3-trifluoromethylphenyl)-4-((4-fluoro-N-methylphenylsulfonamido)methyl)phenoxy)propanoic acid,
2-(3-cyanophenyl)-4-((3-methoxy-4-fluoro-N-methylphenylsulfonamido)methyl)phenoxyacetic acid,
2-(3-methoxymethylphenyl)-4-((4-fluoro-N-methylphenylsulfonamido)methyl)phenoxyacetic acid,
2-(3-cyanophenyl)-4-((4-methoxy-N-methylphenylsulfonamido)methyl)phenoxyacetic acid,
2-(3-aminocarbonylphenyl)-4-((4-fluoro-N-methylphenylsulfonamido)methyl)phenoxyacetic acid,
2-(3-trifluoromethylphenyl)-4-((4-fluoro-N-methylphenylsulfonamido)methyl)phenoxyacetic acid,
2-(3-trifluoromethylphenyl)-4-((2,4-difluoro-N-methylphenylsulfonamido)methyl)phenoxyacetic acid, 2-(3-cyanophenyl)-4-((3-trifluoromethyl-N-methylphenylsulfonamido)methyl)phenoxyacetic acid,
2-(3-trifluoromethoxyphenyl)-4-((4-fluoro-N-methylphenylsulfonamido)methyl)phenoxyacetic acid,
2-(3-cyano-5-pyridinyl)-4-((4-fluoro-N-methylphenylsulfonamido)methyl)phenoxyacetic acid,
2-(2,5-difluorophenyl)-4-((4-fluoro-N-methylphenylsulfonamido)methyl)phenoxyacetic acid,
2-(3-trifluoromethylphenyl)-4-((4-chloro-N-methylphenylsulfonamido)methyl)phenoxyacetic acid,
2-(3-trifluoromethylphenyl)-4-((3-chloro-N-methylphenylsulfonamido)methyl)phenoxyacetic acid,
2-(3,5-difluorophenyl)-4-((4-fluoro-N-methylphenylsulfonamido)methyl)phenoxyacetic acid,
2-(3-ethoxy-5-fluorophenyl)-4-((4-fluoro-N-methylphenylsulfonamido)methyl)phenoxyacetic acid,
2-(3-trifluoromethylphenyl)-4-((3,4-difluoro-N-ethylphenylsulfonamido)methyl)phenoxyacetic acid,
2-(3-chloro-5-fluorophenyl)-4-((-N-methylphenylsulfonamido)methyl)phenoxyacetic acid,
2-(2-chloro-5-trifluoromethylphenyl)-4-((4-fluoro-N-methylphenylsulfonamido)methyl)phenoxyacetic acid,
2-(3-isopropylphenyl)-4-((4-fluoro-N-methylphenylsulfonamido)methyl)phenoxyacetic acid,
2-(3-trifluoromethylphenyl)-4-((4-cyano-N-methylphenylsulfonamido)methyl)phenoxyacetic acid,
2-(3-cyanophenyl)-4-((4-fluoro-N-methylphenylsulfonamido)methyl)-6-fluorophenoxyacetic acid,
2-(3-trifluoromethylphenyl)-4-((4-methoxy-N-methylphenylsulfonamido)methyl)phenoxyacetic acid,
2-(2,3-difluorophenyl)-4-((4-fluoro-N-methylphenylsulfonamido)methyl)phenoxyacetic acid,
2-(3-trifluoromethylphenyl)-4-(1-(4-fluoro-N-methylphenylsulfonamido)ethyl)phenoxyacetic acid,
2-(4-methylsulfonylphenyl)-4-((4-fluoro-N-methylphenylsulfonamido)methyl)phenoxyacetic acid,
2-(6-trifluoromethyl-2-pyridinyl)-4-((4-fluoro-N-methylphenylsulfonamido)methyl)phenoxyacetic acid,
2-(imidazo[1,2-a]pyridin-7-yl)-4-((4-fluoro-N-methylphenylsulfonamido)methyl)phenoxyacetic acid,
2-(3-(5-methyl-1,3,4-oxadiazol-2-yl)phenyl)-4-((4-fluoro-N-methylphenylsulfonamido)methyl)phenoxyacetic acid,
2-(3-fluorophenyl)-4-((4-fluoro-N-methylphenylsulfonamido)methyl)phenoxyacetic acid,
2-(3-trifluoromethylphenyl)-4-((N-methylphenylsulfonamido)methyl)phenoxyacetic acid,
2-(3-hydroxyphenyl)-4-((4-fluoro-N-methylphenylsulfonamido)methyl)phenoxyacetic acid,
2-(3-trifluoromethyl-5-pyridinyl)-4-((4-fluoro-N-methylphenylsulfonamido)methyl)phenoxyacetic acid,
2-(3-methoxyphenyl)-4-((4-fluoro-N-methylphenylsulfonamido)methyl)phenoxyacetic acid,
2-(3-trifluoromethylphenyl)-4-((4-methylsulfonyl-N-methylphenylsulfonamido)methyl)phenoxyacetic acid,
2-(3-trifluoromethylphenyl)-4-((N-methylpyridine-3-sulfonamido)methyl)phenoxyacetic acid,
2-(3-N-methylaminocarbonylphenyl)-4-((4-fluoro-N-methylphenylsulfonamido)methyl)phenoxyacetic acid,
2-(3-trifluoromethylphenyl)-4-((3,5-difluoro-N-methylphenylsulfonamido)methyl)phenoxyacetic acid,
2-(3,5-difluorophenyl)-4-((4-fluoro-N-methylphenylsulfonamido)methyl)-6-fluorophenoxyacetic acid,
2-(3-trifluoromethylphenyl)-4-((4-fluoro-N-ethylphenylsulfonamido)methyl)phenoxyacetic acid,
2-(3-methoxycarbonylphenyl)-4-((4-fluoro-N-methylphenylsulfonamido)methyl)phenoxyacetic acid,
2-(3-bromophenyl)-4-((4-fluoro-N-methylphenylsulfonamido)methyl)phenoxyacetic acid,
2-(3-trifluoromethylphenyl)-4-((3-fluoro-N-methylphenylsulfonamido)methyl)phenoxyacetic acid,
2-(3-trifluoromethylphenyl)-4-((N-methylquinoline-8-sulfonamido)methyl)phenoxyacetic acid,
2-(3,4-difluorophenyl)-4-((4-fluoro-N-methylphenylsulfonamido)methyl)phenoxyacetic acid,
2-(3-trifluoromethylphenyl)-4-((2-methoxy-N-methylphenylsulfonamido)methyl)phenoxyacetic acid,
2-(3-cyanophenyl)-4-((4-methyl-N-methylphenylsulfonamido)methyl)phenoxyacetic acid,
2-(3-pyridinyl)-4-((4-fluoro-N-methylphenylsulfonamido)methyl)phenoxyacetic acid,
2-(3-dimethylaminocarbonylphenyl)-4-((4-fluoro-N-methylphenylsulfonamido)methyl)phenoxyacetic acid,
2-(3-trifluoromethylphenyl)-4-((N-methylnaphthalene-1-sulfonamido)methyl)phenoxyacetic acid,
2-(3-trifluoromethylphenyl)-4-((N-methylnaphthalene-2-sulfonamido)methyl)phenoxyacetic acid,
2-(4-trifluoromethylphenyl)-4-((4-fluoro-N-methylphenylsulfonamido)methyl)phenoxyacetic acid,
2-(3-methylphenyl)-4-((4-fluoro-N-methylphenylsulfonamido)methyl)phenoxyacetic acid,
2-(3-trifluoromethylphenyl)-4-((3,4-difluoro-N-isopropylphenylsulfonamido)methyl)phenoxyacetic acid,
2-(3-trifluoromethylphenyl)-4-((3-methoxy-N-methylphenylsulfonamido)methyl)phenoxyacetic acid,
(R)-2-(2-(3-trifluoromethylphenyl)-4-((4-fluoro-N-methylphenylsulfonamido)methyl)phenoxy)propanoic acid,
2-(3,4-difluorophenyl)-4-((N-methylphenylsulfonamido)methyl)phenoxyacetic acid,
2-(3-chloro-4-fluorophenyl)-4-((4-fluoro-N-methylphenylsulfonamido)methyl)phenoxyacetic acid,
2-(3-trifluoromethylphenyl)-4-((4-fluoro-N-isopropylphenylsulfonamido)methyl)phenoxyacetic acid,
2-(4-trifluoromethyl-pyridinyl)-4-((4-fluoro-N-methylphenylsulfonamido)methyl)phenoxyacetic acid,
2-(3-trifluoromethylphenyl)-4-((N-methylbenzylsulfonamido)methyl)phenoxyacetic acid,
2-(isoquinolin-5-yl)-4-((4-fluoro-N-methylphenylsulfonamido)methyl)phenoxyacetic acid,
2-(3-trifluoromethylphenyl)-4-((N,3,5-trimethylisoxazole-4-sulfonamido)methyl)phenoxyacetic acid,
2-(3-trifluoromethylphenyl)-4-((4-fluoro-N-methylphenylsulfonamido)methyl)-6-fluorophenoxyacetic acid,
2-(3-chlorophenyl)-4-((4-fluoro-N-methylphenylsulfonamido)methyl)phenoxyacetic acid,
2-(pyrazinyl)-4-((4-fluoro-N-methylphenylsulfonamido)methyl)phenoxyacetic acid,
2-(4-methoxyphenyl)-4-((4-fluoro-N-methylphenylsulfonamido)methyl)phenoxyacetic acid,
2-(2,5-difluorophenyl)-4-((N-methylphenylsulfonamido)methyl)phenoxyacetic acid,
2-(3-chlorophenyl)-4-((N-methylphenylsulfonamido)methyl)phenoxyacetic acid,
2-(N-oxy-pyridine-3-yl)-4-((4-fluoro-N-methylphenylsulfonamido)methyl)phenoxyacetic acid,
2-phenyl-4-((N-methylphenylsulfonamido)methyl)phenoxyacetic acid,
2-(3-trifluoromethylphenyl)-4-((2-chloro-N-methylphenylsulfonamido)methyl)phenoxyacetic acid,
2-(3,5-dimethylisoxazol-4-yl)-4-((4-fluoro-N-methylphenylsulfonamido)methyl)phenoxyacetic acid,
2-(pyrimidin-5-yl)-4-((N-methylphenylsulfonamido)methyl)phenoxyacetic acid, 2-(3-trifluoromethylphenyl)-4-((N-methylpyridine-2-sulfonamido)methyl)phenoxyacetic acid,
2-((3-trifluoromethylphenyl)-4-((4-fluoro-N-methylphenylsulfonamido)methyl)phenoxy)-2-methylpropanoic acid,
2-(3-trifluoromethylphenyl)-4-((3,5-difluoro-N-isopropylphenylsulfonamido)methyl)phenoxyacetic acid,
2-(3-methyl-3H-benzo[d]imidazol-5-yl)-4-((4-fluoro-N-methylphenylsulfonamido)methyl)phenoxyacetic acid,
2-(3-morpholinocarbonylphenyl)-4-((4-fluoro-N-methylphenylsulfonamido)methyl)phenoxyacetic acid,
2-(4-chlorophenyl)-4-((4-fluoro-N-methylphenylsulfonamido)methyl)phenoxyacetic acid,
2-(2-chlorophenyl)-4-((4-fluoro-N-methylphenylsulfonamido)methyl)phenoxyacetic acid,
2-(4-chlorophenyl)-4-((N-methylphenylsulfonamido)methyl)phenoxyacetic acid,
2-(quinolin-5-yl)-4-((4-fluoro-N-methylphenylsulfonamido)methyl)phenoxyacetic acid,
2-(3-trifluoromethylphenyl)-4-((N-methylcyclopropanesulfonamido)methyl)phenoxyacetic acid,
2-(3-trifluoromethylphenyl)-4-((N-methyldimethylaminosulfonamido)methyl)phenoxyacetic acid,
2-phenyl-4-((4-fluoro-N-methylphenylsulfonamido)methyl)phenoxyacetic acid,
2-(1H-indol-6-yl)-4-((4-fluoro-N-methylphenylsulfonamido)methyl)phenoxyacetic acid,
2-(3-methoxyphenyl)-4-((-N-methylphenylsulfonamido)methyl)phenoxyacetic acid,
2-(1-methyl-1H-pyrazol-4-yl)-4-((4-fluoro-N-methylphenylsulfonamido)methyl)phenoxyacetic acid,
2-(3-cyano-5-fluorophenyl)-4-((3-fluoro-4-methoxyphenylsulfonamido)methyl)phenoxyacetic acid,
2-(3-cyano-5-fluorophenyl)-(5-fluoro-4-((3-fluoro-4-methoxy-N-methylphenylsulfonamido)methyl)phenoxy)acetic acid,
2-(3-cyano-5-chloro-phenyl)-4-((4-fluoro-N-methylphenylsulfonamido)methyl)phenoxyacetic acid,
2-(3-cyano-5-fluoro-phenyl)-4-((4-fluoro-N-methylphenylsulfonamido)methyl)-5-fluorophenoxyacetic acid,
2-(3-cyano-5-fluoro-phenyl)-4-((3-chloro-4-fluoro-N-methylphenylsulfonamido)methyl)-5-fluorophenoxyacetic acid,
2-(3-cyano-5-fluoro-phenyl)-4-((3-chloro-N-methylphenylsulfonamido)methyl)-5-fluorophenoxyacetic acid,
2-(3-cyano-5-fluoro-phenyl)-4-((3,4-dichloro-N-methylphenylsulfonamido)methyl)-5-fluorophenoxyacetic acid,
2-(3-cyano-5-fluoro-phenyl)-4-((4-fluoro-N-methylphenylsulfonamido)methyl)-5-chlorophenoxyacetic acid, and a salt thereof.

44. The compound of claim 1 selected from the group consisting of
2-(3-cyano-5-fluorophenyl)-4-((3-fluoro-4-methoxy-N-methylphenylsulfonamido)methyl)phenoxyacetic acid,
2-(3-methoxy-5-fluorophenyl)-4-((4-fluoro-N-methylphenylsulfonamido)methyl)phenoxyacetic acid,
2-(3-cyano-5-fluorophenyl)-4-((3,4-difluoro-N-methylphenylsulfonamido)methyl)phenoxyacetic acid,
2-(3-fluoro-5-methoxyphenyl)-4-((3-chloro-4-fluoro-N-methylphenylsulfonamido)methyl)phenoxyacetic acid,
2-(3-N-methylsulfamoylphenyl)-4-((3-chloro-4-fluoro-N-methylphenylsulfonamido)methyl)phenoxyacetic acid,
2-(3-methylsulfonylphenyl)-4-((3-chloro-4-fluoro-N-methylphenylsulfonamido)methyl)phenoxyacetic acid,
2-(3-cyano-5-fluorophenyl)-4-((3,4-difluoro-phenylsulfonamido)methyl)phenoxyacetic acid,
2-(3-cyano-5-fluorophenyl)-4-((3-chloro-N-methylphenylsulfonamido)methyl)phenoxyacetic acid,
2-(3-N-methylsulfamoylphenyl)-4-((4-fluoro-N-methylphenylsulfonamido)methyl)phenoxyacetic acid,
2-(3-fluoro-5-methoxyphenyl)-4-((3,4-difluoro-N-methylphenylsulfonamido)methyl)phenoxyacetic acid,
2-(3-cyanophenyl)-4-((3-chloro-5-fluoro-N-methylphenylsulfonamido)methyl)phenoxyacetic acid,
2-(3-fluoro-5-methoxyphenyl)-4-((3-fluoro-4-methoxy-N-methylphenylsulfonamido)methyl)phenoxyacetic acid,
2-(3-cyanophenyl)-4-((4-fluoro-N-methylphenylsulfonamido)methyl)-5-chlorophenoxyacetic acid,
2-(3-N-methylsulfamoylphenyl)-4-((3,4-difluoro-N-methylphenylsulfonamido)methyl)phenoxyacetic acid,
2-(3-cyanophenyl)-4-((3,5-difluoro-N-methylphenylsulfonamido)methyl)phenoxyacetic acid,
2-(3,5-difluorophenyl)-4-((3,4-dichloro-N-methylphenylsulfonamido)methyl)phenoxyacetic acid,
2-(3-cyano-5-fluorophenyl)-4-((2,3-dichloro-N-methylthiophene-5-sulfonamido)methyl)phenoxyacetic acid,
2-(3-cyanophenyl)-4-((3-fluoro-N-methylphenylsulfonamido)methyl)-5-chlorophenoxyacetic acid,
2-(4-fluoro-3-(methylsulfonyl)phenyl)-4-((4-fluoro-N-methylphenylsulfonamido)methyl)phenoxyacetic acid,
2-(3-cyano-5-fluorophenyl)-4-((3-chloro-4-fluoro-N-methylphenylsulfonamido)methyl)phenoxyacetic acid,
2-(3-cyanophenyl)-4-((3-fluoro-4-chloro-N-methylphenylsulfonamido)methyl)phenoxyacetic acid,
2-(3-methylsulfonylphenyl)-4-((3-fluoro-N-methylphenylsulfonamido)methyl)phenoxyacetic acid,
2-(3-methylsulfonylphenyl)-4-((3,4-difluoro-N-methylphenylsulfonamido)methyl)phenoxyacetic acid,
2-(3-ethylsulfonylphenyl)-4-((3,4-difluoro-N-methylphenylsulfonamido)methyl)phenoxyacetic acid,
2-(3,5-difluorophenyl)-4-((3-fluoro-4-methoxy-N-methylphenylsulfonamido)methyl)phenoxyacetic acid,
2-(3-methylsulfonylphenyl)-4-((4-methyl-N-methylphenylsulfonamido)methyl)phenoxyacetic acid,
2-(5-benzo[c][1,2,5]oxadiazolyl)-4-((4-fluoro-N-methylphenylsulfonamido)methyl)phenoxyacetic acid,
2-(3-cyano-5-fluorophenyl)-4-((2-chloro-N-methylthiophene-5-sulfonamido)methyl)phenoxyacetic acid,
2-(3-cyano-5-fluorophenyl)-4-((3-fluoro-N-methylphenylsulfonamido)methyl)phenoxyacetic acid,
2-(3-cyanophenyl)-4-((3-fluoro-4-methyl-N-methylphenylsulfonamido)methyl)phenoxyacetic acid,
2-(3-cyanophenyl)-4-((3,4-difluoro-N-methylphenylsulfonamido)methyl)phenoxyacetic acid,
2-(3-cyano-5-fluorophenyl)-4-((4-fluoro-N-methylphenylsulfonamido)methyl)phenoxyacetic acid,
2-(3-cyanophenyl)-4-((3-methyl-4-fluoro-N-methylphenylsulfonamido)methyl)phenoxyacetic acid,
2-(3,5-difluorophenyl)-4-((3-chloro-4-fluoro-N-methylphenylsulfonamido)methyl)phenoxyacetic acid,
2-(3-methylsulfonyl-5-pyridinyl)-4-((4-fluoro-N-methylphenylsulfonamido)methyl)phenoxyacetic acid,
2-(3,5-difluorophenyl)-4-((3-chloro-N-methylphenylsulfonamido)methyl)phenoxyacetic acid,
2-(3-cyano-5-fluorophenyl)-4-((N-methylthiophene-2-sulfonamido)methyl)phenoxyacetic acid,
2-(3-cyanophenyl)-4-((3-chloro-4-fluoro-N-methylphenylsulfonamido)methyl)-5-fluorophenoxyacetic acid, 2-(3-methylsulfonylphenyl)-4-((4-methoxy-N-methylphenylsulfonamido)methyl)phenoxyacetic acid,
2-(3-aminosulfonylphenyl)-4-((4-fluoro-N-methylphenylsulfonamido)methyl)phenoxyacetic acid,
2-(3-cyanophenyl)-4-((3-chloro-N-methylphenylsulfonamido)methyl)phenoxyacetic acid,
2-(3-cyanophenyl)-4-((3,4-dichloro-N-methylphenylsulfonamido)methyl)phenoxyacetic acid,
2-(3-cyanophenyl)-4-((3-fluoro-4-methoxy-N-methylphenylsulfonamido)methyl)phenoxyacetic acid,
2-(3-methylsulfonylphenyl)-4-((4-fluoro-N-methylphenylsulfonamido)methyl)phenoxyacetic acid,
2-(3-methylsulfonylphenyl)-4-((3,5-difluoro-N-methylphenylsulfonamido)methyl)phenoxyacetic acid,
2-(3-cyanophenyl)-4-((N-methylphenylsulfonamido)methyl)-5-chlorophenoxyacetic acid,
2-(3-cyano-5-fluorophenyl)-4-((4-fluoro-phenylsulfonamido)methyl)phenoxyacetic acid,
2-(3-cyanophenyl)-4-((3-chloro-4-fluoro-N-methylphenylsulfonamido)methyl)phenoxyacetic acid,
2-(3-cyanophenyl)-4-((4-fluoro-N-methylphenylsulfonamido)methyl)-5-fluorophenoxyacetic acid,
2-(3-N,N-dimethylsulfamoylphenyl)-4-((4-fluoro-N-methylphenylsulfonamido)methyl)phenoxyacetic acid,
2-(3-methylsulfonylphenyl)-4-((N-methylphenylsulfonamido)methyl)phenoxyacetic acid,
2-(3-methylsulfonylphenyl)-4-((4-fluorophenylsulfonamido)methyl)phenoxyacetic acid,
2-(3-cyano-5-fluorophenyl)-4-((3-chloro-4-fluoro-phenylsulfonamido)methyl)phenoxyacetic acid,
2-(3-ethylsulfonylphenyl)-4-((4-fluoro-N-methylphenylsulfonamido)methyl)phenoxyacetic acid,
2-(3-cyanophenyl)-4-((4-fluorophenylsulfonamido)methyl)phenoxyacetic acid,
2-(3-methylsulfonyl-4-methyl-phenyl)-4-((4-fluoro-N-methylphenylsulfonamido)methyl)phenoxyacetic acid,
2-(3-cyanophenyl)-4-((4-fluoro-N-methylphenylsulfonamido)methyl)phenoxyacetic acid,
2-(3-methylsulfonylphenyl)-4-((4-cyano-N-methylphenylsulfonamido)methyl)phenoxyacetic acid,
2-(3-methylsulfonylphenyl)-4-((N-methylphenylsulfonamido)methyl)phenoxyacetic acid,
2-(3-cyanophenyl)-4-((3-fluoro-N-methylphenylsulfonamido)methyl)-5-fluorophenoxyacetic acid,
2-(3-cyano-5-fluorophenyl)-4-((3,4-dichloro-N-methylphenylsulfonamido)methyl)phenoxyacetic acid,
2-(3-trifluoromethyl-5-fluorophenyl)-4-((4-fluoro-N-methylphenylsulfonamido)methyl)phenoxyacetic acid,
2-(3-methylsulfonylphenyl)-4-((3-cyano-N-methylphenylsulfonamido)methyl)phenoxyacetic acid,
2-(1-methyl-indol-6-yl)-4-((4-fluoro-N-methylphenylsulfonamido)methyl)phenoxyacetic acid,
2-(2-cyanothiophen-5-yl)-4-((4-fluoro-N-methylphenylsulfonamido)methyl)phenoxyacetic acid,
2-(3-cyanophenyl)-4-((3-fluoro-N-methylphenylsulfonamido)methyl)phenoxyacetic acid,
2-(3,5-difluorophenyl)-4-((3-methyl-4-fluoro-N-methylphenylsulfonamido)methyl)phenoxyacetic acid,
2-(3,5-difluorophenyl)-4-((3,4-difluoro-N-methylphenylsulfonamido)methyl)phenoxyacetic acid,
2-(3-trifluoromethylphenyl)-4-((3,4-difluoro-N-methylphenylsulfonamido)methyl)phenoxyacetic acid,
2-(3-cyano-5-fluorophenyl)-4-((3,5-difluoro-N-methylphenylsulfonamido)methyl)phenoxyacetic acid,
2-(3-trifluoromethylphenyl)-4-(1-(3,4-difluoro-N-methylphenylsulfonamido)ethyl)phenoxyacetic acid,
2-(3-methylsulfonylphenyl)-4-((2-fluoro-N-methylphenylsulfonamido)methyl)phenoxyacetic acid,
2-(3-cyano-5-fluorophenyl)-4-((N-methylphenylsulfonamido)methyl)phenoxyacetic acid,
2-(3-cyanophenyl)-4-((N-methylphenylsulfonamido)methyl)-5-fluorophenoxyacetic acid,
2-(3-cyanophenyl)-4-((3-chloro-4-fluoro-N-methylphenylsulfonamido)methyl)-5-chlorophenoxyacetic acid,
2-(3-isopropoxy-5-fluorophenyl)-4-((4-fluoro-N-methylphenylsulfonamido)methyl)phenoxyacetic acid,
2-(3-trifluoromethylphenyl)-4-((4-fluoro-N-methylphenylsulfonamido)methyl)phenoxyacetic acid,
2-(3-cyano-5-fluorophenyl)-4-((3-fluoro-4-methoxyphenylsulfonamido)methyl)phenoxyacetic acid,
2-(3-cyano-5-fluorophenyl)-(5-fluoro-4-((3-fluoro-4-methoxy-N-methylphenylsulfonamido)methyl)phenoxy)acetic acid,
and a salt thereof.

45. The compound of claim 1 selected from the group consisting of
(S)-2-(2-(3-trifluoromethylphenyl)-4-((4-fluoro-N-methylphenylsulfonamido)methyl)phenoxy)propanoic acid,
2-(3-cyanophenyl)-4-((3-methoxy-4-fluoro-N-methylphenylsulfonamido)methyl)phenoxyacetic acid,
2-(3-methoxymethylphenyl)-4-((4-fluoro-N-methylphenylsulfonamido)methyl)phenoxyacetic acid,
2-(3-cyanophenyl)-4-((4-methoxy-N-methylphenylsulfonamido)methyl)phenoxyacetic acid,
2-(3-aminocarbonylphenyl)-4-((4-fluoro-N-methylphenylsulfonamido)methyl)phenoxyacetic acid,
2-(3-trifluoromethylphenyl)-4-((4-fluoro-N-methylphenylsulfonamido)methyl)phenoxyacetic acid,
2-(3-trifluoromethylphenyl)-4-((2,4-difluoro-N-methylphenylsulfonamido)methyl)phenoxyacetic acid,
2-(3-cyanophenyl)-4-((3-trifluoromethyl-N-methylphenylsulfonamido)methyl)phenoxyacetic acid,
2-(3-trifluoromethoxyphenyl)-4-((4-fluoro-N-methylphenylsulfonamido)methyl)phenoxyacetic acid,
2-(3-cyano-5-pyridinyl)-4-((4-fluoro-N-methylphenylsulfonamido)methyl)phenoxyacetic acid,
2-(2,5-difluorophenyl)-4-((4-fluoro-N-methylphenylsulfonamido)methyl)phenoxyacetic acid,
2-(3-trifluoromethylphenyl)-4-((4-chloro-N-methylphenylsulfonamido)methyl)phenoxyacetic acid,
2-(3-trifluoromethylphenyl)-4-((3-chloro-N-methylphenylsulfonamido)methyl)phenoxyacetic acid,
2-(3,5-difluorophenyl)-4-((4-fluoro-N-methylphenylsulfonamido)methyl)phenoxyacetic acid,
2-(3-ethoxy-5-fluorophenyl)-4-((4-fluoro-N-methylphenylsulfonamido)methyl)phenoxyacetic acid,
2-(3-trifluoromethylphenyl)-4-((3,4-difluoro-N-ethylphenylsulfonamido)methyl)phenoxyacetic acid,
2-(3-chloro-5-fluorophenyl)-4-((-N-methylphenylsulfonamido)methyl)phenoxyacetic acid,
2-(2-chloro-5-trifluoromethylphenyl)-4-((4-fluoro-N-methylphenylsulfonamido)methyl)phenoxyacetic acid,
2-(3-isopropylphenyl)-4-((4-fluoro-N-methylphenylsulfonamido)methyl)phenoxyacetic acid,
2-(3-trifluoromethylphenyl)-4-((4-cyano-N-methylphenylsulfonamido)methyl)phenoxyacetic acid,
2-(3-cyanophenyl)-4-((4-fluoro-N-methylphenylsulfonamido)methyl)-6-fluorophenoxyacetic acid,
2-(3-trifluoromethylphenyl)-4-((4-methoxy-N-methylphenylsulfonamido)methyl)phenoxyacetic acid,
2-(2,3-difluorophenyl)-4-((4-fluoro-N-methylphenylsulfonamido)methyl)phenoxyacetic acid, 2-(3-trifluoromethylphenyl)-4-(1-(4-fluoro-N-methylphenylsulfonamido)ethyl)phenoxyacetic acid,
2-(4-methylsulfonylphenyl)-4-((4-fluoro-N-methylphenylsulfonamido)methyl)phenoxyacetic acid,
2-(6-trifluoromethyl-2-pyridinyl)-4-((4-fluoro-N-methylphenylsulfonamido)methyl)phenoxyacetic acid,
2-(imidazo[1,2-a]pyridin-7-yl)-4-((4-fluoro-N-methylphenylsulfonamido)methyl)phenoxyacetic acid,
2-(3-(5-methyl-1,3,4-oxadiazol-2-yl)phenyl)-4-((4-fluoro-N-methylphenylsulfonamido)methyl)phenoxyacetic acid,
2-(3-fluorophenyl)-4-((4-fluoro-N-methylphenylsulfonamido)methyl)phenoxyacetic acid,
2-(3-trifluoromethylphenyl)-4-((N-methylphenylsulfonamido)methyl)phenoxyacetic acid,
2-(3-hydroxyphenyl)-4-((4-fluoro-N-methylphenylsulfonamido)methyl)phenoxyacetic acid,
2-(3-trifluoromethyl-5-pyridinyl)-4-((4-fluoro-N-methylphenylsulfonamido)methyl)phenoxyacetic acid,
2-(3-methoxyphenyl)-4-((4-fluoro-N-methylphenylsulfonamido)methyl)phenoxyacetic acid,
2-(3-trifluoromethylphenyl)-4-((4-methylsulfonyl-N-methylphenylsulfonamido)methyl)phenoxyacetic acid,
2-(3-trifluoromethylphenyl)-4-((N-methylpyridine-3-sulfonamido)methyl)phenoxyacetic acid,
2-(3-N-methylaminocarbonylphenyl)-4-((4-fluoro-N-methylphenylsulfonamido)methyl)phenoxyacetic acid,
2-(3-trifluoromethylphenyl)-4-((3,5-difluoro-N-methylphenylsulfonamido)methyl)phenoxyacetic acid,
2-(3,5-difluorophenyl)-4-((4-fluoro-N-methylphenylsulfonamido)methyl)-6-fluorophenoxyacetic acid,
2-(3-trifluoromethylphenyl)-4-((4-fluoro-N-ethylphenylsulfonamido)methyl)phenoxyacetic acid,
2-(3-methoxycarbonylphenyl)-4-((4-fluoro-N-methylphenylsulfonamido)methyl)phenoxyacetic acid,
2-(3-bromophenyl)-4-((4-fluoro-N-methylphenylsulfonamido)methyl)phenoxyacetic acid,
2-(3-trifluoromethylphenyl)-4-((3-fluoro-N-methylphenylsulfonamido)methyl)phenoxyacetic acid,
2-(3-trifluoromethylphenyl)-4-((N-methylquinoline-8-sulfonamido)methyl)phenoxyacetic acid,
2-(3,4-difluorophenyl)-4-((4-fluoro-N-methylphenylsulfonamido)methyl)phenoxyacetic acid,
2-(3-trifluoromethylphenyl)-4-((2-methoxy-N-methylphenylsulfonamido)methyl)phenoxyacetic acid,
2-(3-cyanophenyl)-4-((4-methyl-N-methylphenylsulfonamido)methyl)phenoxyacetic acid,
2-(3-pyridinyl)-4-((4-fluoro-N-methylphenylsulfonamido)methyl)phenoxyacetic acid,
2-(3-dimethylaminocarbonylphenyl)-4-((4-fluoro-N-methylphenylsulfonamido)methyl)phenoxyacetic acid,
2-(3-trifluoromethylphenyl)-4-((N-methylnaphthalene-1-sulfonamido)methyl)phenoxyacetic acid, and
2-(3-trifluoromethylphenyl)-4-((N-methylnaphthalene-2-sulfonamido)methyl)phenoxyacetic acid,
or a salt thereof.

46. The compound of claim 1 selected from the group consisting of
2-(4-trifluoromethylphenyl)-4-((4-fluoro-N-methylphenylsulfonamido)methyl)phenoxyacetic acid,
2-(3-methylphenyl)-4-((4-fluoro-N-methylphenylsulfonamido)methyl)phenoxyacetic acid,
2-(3-trifluoromethylphenyl)-4-((3,4-difluoro-N-isopropylphenylsulfonamido)methyl)phenoxyacetic acid,
2-(3-trifluoromethylphenyl)-4-((3-methoxy-N-methylphenylsulfonamido)methyl)phenoxyacetic acid,
(R)-2-(2-(3-trifluoromethylphenyl)-4-((4-fluoro-N-methylphenylsulfonamido)methyl)phenoxy)propanoic acid,
2-(3,4-difluorophenyl)-4-((N-methylphenylsulfonamido)methyl)phenoxyacetic acid,
2-(3-chloro-4-fluorophenyl)-4-((4-fluoro-N-methylphenylsulfonamido)methyl)phenoxyacetic acid,
2-(3-trifluoromethylphenyl)-4-((4-fluoro-N-isopropylphenylsulfonamido)methyl)phenoxyacetic acid,
2-(4-trifluoromethyl-pyridinyl)-4-((4-fluoro-N-methylphenylsulfonamido)methyl)phenoxyacetic acid,
2-(3-trifluoromethylphenyl)-4-((N-methylbenzylsulfonamido)methyl)phenoxyacetic acid,
2-(isoquinolin-5-yl)-4-((4-fluoro-N-methylphenylsulfonamido)methyl)phenoxyacetic acid,
2-(3-trifluoromethylphenyl)-4-((N,3,5-trimethylisoxazole-4-sulfonamido)methyl)phenoxyacetic acid,
2-(3-trifluoromethylphenyl)-4-((4-fluoro-N-methylphenylsulfonamido)methyl)-6-fluorophenoxyacetic acid,
2-(3-chlorophenyl)-4-((4-fluoro-N-methylphenylsulfonamido)methyl)phenoxyacetic acid,
2-(pyrazinyl)-4-((4-fluoro-N-methylphenylsulfonamido)methyl)phenoxyacetic acid,
2-(4-methoxyphenyl)-4-((4-fluoro-N-methylphenylsulfonamido)methyl)phenoxyacetic acid,
2-(2,5-difluorophenyl)-4-((N-methylphenylsulfonamido)methyl)phenoxyacetic acid,
2-(3-chlorophenyl)-4-((N-methylphenylsulfonamido)methyl)phenoxyacetic acid,
2-(N-oxy-pyridine-3-yl)-4-((4-fluoro-N-methylphenylsulfonamido)methyl)phenoxyacetic acid,
2-phenyl-4-((N-methylphenylsulfonamido)methyl)phenoxyacetic acid,
2-(3-trifluoromethylphenyl)-4-((2-chloro-N-methylphenylsulfonamido)methyl)phenoxyacetic acid,
2-(3,5-dimethylisoxazol-4-yl)-4-((4-fluoro-N-methylphenylsulfonamido)methyl)phenoxyacetic acid,
2-(pyrimidin-5-yl)-4-((N-methylphenylsulfonamido)methyl)phenoxyacetic acid,
2-(3-trifluoromethylphenyl)-4-((N-methylpyridine-2-sulfonamido)methyl)phenoxyacetic acid,
2-((3-trifluoromethylphenyl)-4-((4-fluoro-N-methylphenylsulfonamido)methyl)phenoxy)-2-methylpropanoic acid,
2-(3-trifluoromethylphenyl)-4-((3,5-difluoro-N-isopropylphenylsulfonamido)methyl)phenoxyacetic acid,
2-(3-methyl-3H-benzo[d]imidazol-5-yl)-4-((4-fluoro-N-methylphenylsulfonamido)methyl)phenoxyacetic acid,
2-(3-morpholinocarbonylphenyl)-4-((4-fluoro-N-methylphenylsulfonamido)methyl)phenoxyacetic acid,
2-(4-chlorophenyl)-4-((4-fluoro-N-methylphenylsulfonamido)methyl)phenoxyacetic acid,
2-(2-chlorophenyl)-4-((4-fluoro-N-methylphenylsulfonamido)methyl)phenoxyacetic acid,
2-(4-chlorophenyl)-4-((N-methylphenylsulfonamido)methyl)phenoxyacetic acid,
2-(quinolin-5-yl)-4-((4-fluoro-N-methylphenylsulfonamido)methyl)phenoxyacetic acid,
2-(3-trifluoromethylphenyl)-4-((N-methylcyclopropanesulfonamido)methyl)phenoxyacetic acid,
2-(3-trifluoromethylphenyl)-4-((N-methyldimethylaminosulfonamido)methyl)phenoxyacetic acid,
2-phenyl-4-((4-fluoro-N-methylphenylsulfonamido)methyl)phenoxyacetic acid,
2-(1H-indol-6-yl)-4-((4-fluoro-N-methylphenylsulfonamido)methyl)phenoxyacetic acid,
2-(3-methoxyphenyl)-4-((-N-methylphenylsulfonamido)methyl)phenoxyacetic acid, 2-(1-methyl-1H-pyrazol-4-yl)-4-((4-fluoro-N-methylphenylsulfonamido)methyl)phenoxyacetic acid, 2-(3-cyano-5-chloro-phenyl)-4-((4-fluoro-N-methylphenylsulfonamido)methyl)phenoxyacetic acid, 2-(3-cyano-5-fluoro-phenyl)-4-((4-fluoro-N-methylphenylsulfonamido)methyl)-5-fluorophenoxyacetic acid, 2-(3-cyano-5-fluoro-phenyl)-4-((3-chloro-4-fluoro-N-methylphenylsulfonamido)methyl)-5-fluorophenoxyacetic acid, 2-(3-cyano-5-fluoro-phenyl)-4-((3-chloro-N-methylphenylsulfonamido)methyl)-5-fluorophenoxyacetic acid, 2-(3-cyano-5-fluoro-phenyl)-4-((3,4-dichloro-N-methylphenylsulfonamido)methyl)-5-fluorophenoxyacetic acid, 2-(isoquinolin-7-yl)-4-((4-fluoro-N-methylphenylsulfonamido)methyl)phenoxyacetic acid, 2-(3-cyano-5-fluoro-phenyl)-4-((4-fluoro-N-methylphenylsulfonamido)methyl)-5-chlorophenoxyacetic acid, and a salt thereof.

* * * * *

UNITED STATES PATENT AND TRADEMARK OFFICE
CERTIFICATE OF CORRECTION

| | | |
|---|---|---|
| PATENT NO. | : 8,822,467 B2 | Page 1 of 2 |
| APPLICATION NO. | : 13/715754 | |
| DATED | : September 2, 2014 | |
| INVENTOR(S) | : Brian F. McGuinness | |

It is certified that error appears in the above-identified patent and that said Letters Patent is hereby corrected as shown below:

On the Title Page

In column 2 (page 1, item 56) at line 8, References Cited Under Other Publications, change "Restricing Rold" to --Restricting Role--.

In column 2 (page 2, item 56) at line 7, References Cited Under Other Publications, change "(Th 2)" to --(Th2)--.

In the Specification

In column 1 at line 52, Change "thromboxan" to --thromboxane--.

In column 4 at line 36, Change "angiodermas," to --angioedemas,--.

In column 4 at line 51 (approx.), Change "angiodermas," to --angioedemas,--.

In column 10 at line 50, Change "X'" to --$X^1$--.

In column 10 at line 61, Change "X'" to --$X^1$--.

In column 11 at line 7, Change "Z'" to --$Z^1$--.

In column 11 at line 34, Change "X'" to --$X^1$--.

In column 13 at line 66, Change "pyrrolindinyl," to --pyrrolidinyl,--.

In column 14 at line 12, Change "thiamorpholinyl," to --thiomorpholinyl,--.

In column 14 at line 13, Change "thiamorpholinylsulfoxide," to --thiomorpholinylsulfoxide,--.

In column 14 at line 13, Change "thiamorpholinylsulfone," to --thiomorpholinylsulfone,--.

In column 14 at line 17, Change "aminopenthyl," to --aminopentyl,--.

In column 16 at line 8, Change "teoclatic," to --thiolactic,--.

In column 16 at line 19, Change "stereoisometric" to --stereoisomeric--.

In column 22 at line 5, Change "inhibitor," to --inhibitor.--.

In column 22 at line 20, Change "fumatrate" to --fumarate--.

Signed and Sealed this
Twenty-eighth Day of July, 2015

Michelle K. Lee
*Director of the United States Patent and Trademark Office*

CERTIFICATE OF CORRECTION (continued)
U.S. Pat. No. 8,822,467 B2

In column 22 at line 21, Change "β$_2$-adrenoreceptor" to --B$_2$-adrenoreceptor--.

In column 22 at line 37, Change "amelexanox," to --amlexanox,--.

In column 22 at line 58, Change "chromoglycate," to --cromoglycate,--.

In column 23 at line 57, Change "angiodermas," to --angioedemas,--.

In column 32 at line 64 (approx., Structure), Change "2,6-lutidene" to --2,6-lutidine--.

In column 33 at line 16, Change "2,6-lutidene" to --2,6-lutidine--.

In column 65 at line 34 (approx.), Change "MH+=" to --MH$^+$=--.

In column 68 at line 49, Change "MH+=" to --MH$^+$=--.

In column 69 at line 36, Change "(ChembridgeSoft" to --(CambridgeSoft--.

In column 69 at line 40, Change "G-TPγS" to --GTPγS--.

In column 70 at line 35 (approx.), Change "Pharmacology." to --Pharmacology--.

In column 74 at line 4 (approx., Table 2-continued), Change "2 (3-N-" to --2-(3-N- --.

In column 94 at line 6 (approx., Table 2-continued), Change "4-((3-chloro4-" to --4-((3-chloro-4- --.

In column 132 at line 19 (approx., Table 2-continued), Change "((-N-" to --((N- --.

In column 176 at line 11 (approx., Table 2-continued), Change "((-N-"to --((N- --.

In column 250 at line 38, Change "§" to --δ--.

In column 250 at line 66 (approx.), Change "§" to --δ--.

In column 251 at line 35, Change "§" to --δ--.

In column 251 at line 66, Change "§" to --δ--.

In column 252 at line 28 (approx.), Change "§" to --δ--.

In the Claims

In column 257 at line 29 (approx.), In Claim 34, change "claim 24," to --claim 21,--.

In column 258 at line 19, In Claim 41, change "angiodermas," to --angioedemas,--.

In column 261 at line 19, In Claim 43, change "((-N-" to --((N- --.

In column 263 at line 29, In Claim 43, change "((-N-" to --((N- --.

In column 264 at line 3, In Claim 44, below "acid," Insert --2-(3-trifluoromethylphenyl)-4-((3-chloro-4 fluoro-N-methylphenylsulfonamido)methyl)phenoxyacetic acid,--.

In column 266 at line 54, In Claim 45, change "((-N-" to --((N- --.

In column 268 at line 66, In Claim 46, change "((-N-" to --((N- --.